US008716557B2

(12) United States Patent
Dickey et al.

(10) Patent No.: US 8,716,557 B2
(45) Date of Patent: *May 6, 2014

(54) COMPOSITIONS AND METHODS FOR INHIBITION OF FUCOSYLTRANSFERASE AND XYLOSYLTRANSFERASE EXPRESSION IN PLANTS

(75) Inventors: Lynn F. Dickey, Cary, NC (US); Kevin M. Cox, Raleigh, NC (US); Charles G. Peele, Apex, NC (US); Ming-Bo Wang, Canberra (AU)

(73) Assignee: Synthon Biopharmaceuticals B.V., Nijmegen (NL)

( * ) Notice: Subject to any disclaimer, the term of this patent is extended or adjusted under 35 U.S.C. 154(b) by 349 days.

This patent is subject to a terminal disclaimer.

(21) Appl. No.: 11/624,158

(22) Filed: Jan. 17, 2007

(65) Prior Publication Data
US 2008/0060092 A1   Mar. 6, 2008

Related U.S. Application Data

(60) Provisional application No. 60/759,298, filed on Jan. 17, 2006, provisional application No. 60/790,373, filed on Apr. 7, 2006, provisional application No. 60/791,178, filed on Apr. 11, 2006, provisional application No. 60/812,702, filed on Jun. 9, 2006, provisional application No. 60/836,998, filed on Aug. 11, 2006, provisional application No. 60/860,358, filed on Nov. 21, 2006.

(51) Int. Cl.
C12N 15/82 (2006.01)
C07H 21/04 (2006.01)
A01H 5/00 (2006.01)

(52) U.S. Cl.
USPC ........... 800/285; 800/278; 800/286; 800/288; 800/295; 800/298; 536/23.6; 536/24.5; 536/23.1; 536/22.1; 435/320.1

(58) Field of Classification Search
None
See application file for complete search history.

(56) References Cited

U.S. PATENT DOCUMENTS

| | | | |
|---|---|---|---|
| 6,506,559 B1 | 1/2003 | Fire et al. | |
| 6,573,099 B2 | 6/2003 | Graham | |
| 7,019,195 B1 | 3/2006 | Heifetz et al. | |
| 7,326,681 B2 | 2/2008 | Gerngross | |
| 7,884,264 B2 * | 2/2011 | Dickey et al. | 800/285 |
| 2002/0160393 A1 | 10/2002 | Symonds et al. | |
| 2003/0051263 A1 | 3/2003 | Fire et al. | |
| 2003/0055020 A1 | 3/2003 | Fire et al. | |
| 2003/0056235 A1 | 3/2003 | Fire et al. | |
| 2003/0108923 A1 | 6/2003 | Tuschi et al. | |
| 2003/0157108 A1 | 8/2003 | Presta | |
| 2003/0175783 A1 | 9/2003 | Waterhouse et al. | |
| 2003/0175965 A1 | 9/2003 | Lowe et al. | |
| 2004/0072290 A1 | 4/2004 | Umana et al. | |
| 2004/0073968 A1 * | 4/2004 | Stomp et al. | 800/278 |
| 2004/0086884 A1 | 5/2004 | Beach et al. | |
| 2004/0121325 A1 | 6/2004 | Glössl et al. | |
| 2004/0175703 A1 | 9/2004 | Kreutzer et al. | |
| 2004/0194166 A1 | 9/2004 | Abdennebi-Najar et al. | |
| 2004/0214330 A1 | 10/2004 | Waterhouse et al. | |
| 2004/0259150 A1 | 12/2004 | Nakamura et al. | |
| 2005/0074843 A1 | 4/2005 | Umana et al. | |
| 2005/0079605 A1 | 4/2005 | Umana et al. | |
| 2005/0143564 A1 | 6/2005 | Seki et al. | |
| 2005/0144670 A1 | 6/2005 | Fujiyama et al. | |
| 2005/0234007 A1 | 10/2005 | Tuschi et al. | |
| 2005/0245475 A1 | 11/2005 | Khvorova et al. | |
| 2005/0255487 A1 | 11/2005 | Khvorova et al. | |
| 2005/0262593 A1 | 11/2005 | Kanda et al. | |
| 2005/0272916 A1 | 12/2005 | Hanai et al. | |
| 2005/0276805 A1 | 12/2005 | Hanai et al. | |
| 2006/0024800 A1 | 2/2006 | Hanai et al. | |
| 2006/0029604 A1 | 2/2006 | Gerngross et al. | |
| 2006/0063254 A1 | 3/2006 | Kanda et al. | |
| 2006/0064781 A1 | 3/2006 | Kanda et al. | |
| 2006/0078963 A1 | 4/2006 | Gerngross | |
| 2006/0078990 A1 | 4/2006 | Kanda et al. | |
| 2006/0078991 A1 | 4/2006 | Kanda et al. | |
| 2007/0134759 A1 | 6/2007 | Nishiya et al. | |
| 2008/0066200 A1 * | 3/2008 | Dickey et al. | 800/276 |
| 2009/0199306 A1 | 8/2009 | Altmann et al. | |

FOREIGN PATENT DOCUMENTS

| | | |
|---|---|---|
| CA | 2 362 964 | 8/2000 |
| EP | 1 772 518 A2 | 4/2000 |
| EP | 0 458 367 B1 | 10/2001 |

(Continued)

OTHER PUBLICATIONS

Waterhouse et al. Exploring plant genomes by RNA-induced gene silencing. (2003) Nature Review / Genetics; vol. 4; pp. 29-38.*

(Continued)

Primary Examiner — Cathy Kingdon Worley
(74) Attorney, Agent, or Firm — Alston & Bird LLP

(57) ABSTRACT

Methods for altering the N-glycosylation pattern of proteins in higher plants are provided. The methods comprise introducing into the plant a recombinant RNAi construct that provides for the inhibition of expression of α1,3-fucosyltransferase (FucT) and β1,2-xylosyltransferase (XylT) in a plant. Use of these RNAi constructs to inhibit or suppress expression of both of these enzymes, and isoforms thereof, advantageously provides for the production of endogenous and heterologous proteins having a "humanized" N-glycosylation pattern without impacting plant growth and development. Stably transformed higher plants having this protein N-glycosylation pattern are provided. Glycoprotein compositions, including monoclonal antibody compositions, having substantially homogeneous glycosylation profiles, and which are substantially homogeneous for the G0 glycoform, are also provided.

117 Claims, 59 Drawing Sheets

(56) References Cited

FOREIGN PATENT DOCUMENTS

| | | |
|---|---|---|
| EP | 1 176 195 A1 | 1/2002 |
| EP | 1 331 266 A1 | 7/2003 |
| EP | 0 983 370 B1 | 9/2003 |
| EP | 1 352 963 A1 | 10/2003 |
| EP | 1 498 491 A1 | 1/2005 |
| EP | 1 080 208 B1 | 3/2005 |
| EP | 1 516 931 A2 | 3/2005 |
| EP | 1 555 317 A1 | 7/2005 |
| EP | 1 263 968 B1 | 12/2005 |
| EP | 1 621 633 A2 | 2/2006 |
| EP | 1 624 060 A2 | 2/2006 |
| EP | 1 642 979 A1 | 4/2006 |
| EP | 1 228 231 B1 | 6/2007 |
| EP | 1 878 747 A1 | 1/2008 |
| JP | 2003-235561 | 8/2003 |
| WO | WO 94/01550 | 1/1994 |
| WO | WO 97/01952 | 1/1997 |
| WO | WO 98/53083 | 11/1998 |
| WO | WO 99/32619 | 7/1999 |
| WO | WO 99/49029 | 9/1999 |
| WO | WO 99/53050 | 10/1999 |
| WO | WO 99/54342 | 10/1999 |
| WO | WO 99/61631 | 12/1999 |
| WO | WO 00/34490 | 6/2000 |
| WO | WO 00/44914 | 8/2000 |
| WO | WO 00/49035 | 8/2000 |
| WO | WO 00/49153 | 8/2000 |
| WO | WO 01/29242 | 4/2001 |
| WO | WO 01/31045 | 5/2001 |
| WO | WO 01/64901 A1 | 9/2001 |
| WO | WO 02/057468 A2 | 7/2002 |
| WO | WO 02/070672 A2 | 9/2002 |
| WO | WO 03/011878 A2 | 2/2003 |
| WO | WO 03/035835 A2 | 5/2003 |
| WO | WO 03/056914 A1 | 7/2003 |
| WO | WO 2004/050838 A2 | 6/2004 |
| WO | WO 2004/057002 A | 7/2004 |
| WO | WO 2004/074458 A2 | 9/2004 |
| WO | WO 2004/074499 | 9/2004 |
| WO | WO 2005/030931 A2 | 4/2005 |
| WO | WO 2005/035778 A1 | 4/2005 |
| WO | WO 2006/014679 A1 | 2/2006 |
| WO | WO 2006/071280 | 7/2006 |
| WO | WO 2007/028144 | 3/2007 |
| WO | WO 2007/084672 A2 | 7/2007 |
| WO | WO 2007/084922 A2 | 7/2007 |

OTHER PUBLICATIONS

Chrispeels et al. The production of recombinant glycoproteins with defined non-immunogenic glycans. (1996) in Owen MRL, Pen J. (eds) Transgenic plants: a production system for industrial and pharmaceutical proteins. John Wiley Pub. UK, pp. 99-113.*

IDEC BLA97-0260; fda.gov/cder/biologics/review/ritugen112697, on the World Wide Web.

Shinkawa et al., "The Absence of Fucose But Not the Presence of Galactose or Bisecting N-Acetylglucosamine of Human IgG1 Complex-Type Oligosaccharides Shows the Critical Role of Enhancing Antibody-Dependent Cellular Cytotoxicity," 2003, *The Journal of Biological Chemistry*, pp. 3466-3473, vol. 278, No. 5.

Antoine et al., "Ammonium Chloride, Methylamine and Chloroquine Reversibly Inhibit Antibody Secretion by Plasma Cells," *Biol. Cell*, 1985, pp. 41-54, vol. 55.

Aoki et al., "Species-Specific β-N-Acetylgalactosaminylation of Serum IgG Proteins," *Biochimica et Biophysica Acta*, 1997, pp. 207-213, vol. 1334, Great Britain.

Bobrowicz et al., "Engineering of an Artificial Glycosylation Pathway Blocked in Core Oligosaccharide Assembly in the Yeast *Pichia pastoris*: Production of Complex Humanized Glycoproteins with Terminal Galactose," *Glycobiology*, 2004, pp. 757-766, vol. 14(9), Great Britain.

Boyd et al., "The Effect of the Removal of Sialic Acid, Galactose and Total Carbohydrate on the Functional Activity of Campath-1H," *Molecular Immunology*, 1995, pp. 1311-1318, vol. 32 (17/18), Great Britain.

Cameron et al., "Inhibition of Gene Expression by a Short Sense Fragment," *Nucleic Acids Research*, 1991, pp. 469-475, vol. 19(3).

Chrispeels et al., "The Production of Recombinant Glycoproteins with Defined Non-Immunogenic Glycans," *Transgenic Plants: a Production System for Industrial and Pharmaceutical Proteins*, 1996, pp. 99-113.

Cox et al., "Glycan Optimization of a Human Monoclonal Antibody in the Aquatic Plant *Lemna minor*," *Nature Biotechnology*, 2006, pp. 1591-1597, vol. 24(12), U.S.A.

Gerngross, "Advances in the Production of Human Therapeutic Proteins in Yeasts and Filamentous Fungi," *Nature Biotechnology*, 2004, pp. 1409-1414, vol. 22(11), U.S.A.

Hamilton et al., "Production of Complex Human Glycoproteins in Yeast," *Science, American Association for the Advancement of Science*, 2003, pp. 1244-1246, vol. 301, No. 5637, www.sciencemag.org, U.S.A.

Huether et al., "Glyco-Engineering of Moss Lacking Plant-Specific Sugar Residues," *Plant Biology*, 2005, pp. 292-299, vol. 7(3).

Koprivova, et al., "N-Glycosylation in the Moss *Physcomitrella patens* Is Organized Similarly to that in Higher Plants," *Plant Biology*, 2003, pp. 582-591, vol. 5(6).

Koprivova et al., "Targeted Knockouts of *Physcomitrella* Lacking Plant-Specific Immunogenic N-Glycans," *Plant Biotechnology Journal*, 2004, pp. 517-523, vol. 2(6), Great Britain.

Krotkiewski et al., "The Carbohydrate Structures of a Mouse Monoclonal IgG Antibody OKT3," *The Journal of Biological Chemistry*, 1990, pp. 20195-20201, vol. 265(33).

Lerouge et al., "N-Linked Oligosaccharide Processing Is Not Necessary for Glycoprotein Secretion in Plants," *The Plant Journal*, 1996, pp. 713-719, vol. 10(4).

Lerouge et al., "N-Glycoprotein Biosynthesis In Plants: Recent Developments and Future Trends," *Plant Molecular Biology*, 1998, pp. 31-48(38).

Li et al., "Optimization of Humanized IgGs in Glycoengineered *Pichia pastoris*," *Nature Biotechnology*, 2006, pp. 210-215, vol. 24(2), U.S.A.

Lifely et al., "Glycosylation and Biological Activity of CAMPATH-1H Expressed in Different Cell Lines and Grown Under Different Culture Conditions," *Glycobiology*, 1995, pp. 813-822, vol. 5(8).

McCarthy, "Biolex, Inc.: Pharmaceutical Production in Plants," *Chemistry and Biology, Current Biology*, 2005, pp. 141-142, vol. 12(2), Great Britain.

Okafo et al., "Simple Differentiation Between Core-Fucosylated and Nonfucosylated Glycans by Capillary Electrophoresis," *Analytical Biochemistry*, 1996, pp. 68-74, vol. 240.

Prati et al., "Antisense Strategies for Glycosylation Engineering of Chinese Hamster Ovary (CHO) Cells," *Biotechnology and Bioengineering*, 1998, pp. 445-450, vol. 59(4).

Ripka et al., "Lectin-Resistant CHO Cells: Selection of Four New Pea Lectin-Resistant Phenotypes," *Somatic Cell and Molecular Genetics*, 1986, pp. 51-62, vol. 12(1).

Ripka et al, "Two Chinese Hamster Ovary Glycosylation Mutants Affected in the Conversion of GDP-Mannose to GDP-Fucose," *Archives of Biochemistry and Biophysics*, 1986, pp. 533-545, vol. 249(2).

Rothman, "Glycosylation of IgG Secreted by Murine Hybridomas: Its Response and Influence Upon Antibody Dependent Cytotoxicity Mediated by Natural Killer Lymphocytes," *A Dissertation in Molecular Biology Presented to the Faculties of the University of Pennyslvania in Partial Fulfillment of the Requirements for the Degree of Doctor of Philosophy*, 1988.

Rothman et al., "Antibody-Dependent Cytotoxicity Mediated by Natural Killer Cells Is Enhanced by Castanospermine-Induced Alterations of IgG Glycosylation," *Molecular Immunology*, 1989, pp. 1113-1123, vol. 26(12), Great Britain.

Shitara et al., "A New Vector for the High Level Expression of Chimeric Antibodies in Myeloma Cells," *Journal of Immunological Methods*, 1994, pp. 271-278, vol. 167.

(56) References Cited

OTHER PUBLICATIONS

Sijen et al., "RNA-Mediated Virus Resistance: Role of Repeated Transgenes and Delineation of Targeted Regions," *The Plant Cell*, 1996, pp. 2277-2294, vol. 8.

Sourrouille, "Inactivation de l'α(1,3)-fucosyltransférase et de la β(1,2)-xylosyltransférase, en Vue de la Production de Protéines Recombinantes d'Intérêt Thérapeutique Chez la Luzerne," *Thesis*, 2005, pp. 1-164.

Stam et al., "Post-Transcriptional Silencing of Chalcone Synthase in *Petunia* by Inverted Transgene Repeats," *The Plant Journal*, 1997, pp. 63-82, vol. 12(1).

Stanley, "Chinese Hamster Ovary Cell Mutants with Multiple Glycosylation Defects for Production of Glycoproteins with Minimal Carbohydrate Heterogeneity," *Molecular and Cellular Biology*, 1989, pp. 377-383, vol. 9(2).

Strasser et al. "Generation of *Arabidopsis thaliana* Plants with Complex N-Glycans Lacking β1,2-Linked Xylose and Core α1,3-Linked Fucose," *FEBS Letters*, 2004, pp. 132-136, vol. 561(1-3), The Netherlands.

Van Blokland et al, "Transgene-Mediated Suppression of Chalcone Synthase Expression in *Petunia hybrida* Results from an Increase in RNA Turnover," *The Plant Journal*, 1994, pp. 861-877, vol. 6(6).

Von Schaewen et al., "Isolation of a Mutant *Arabidopsis* Plant that Lacks N-Acetyl Glucosaminyl Transferase I and Is Unable to Synthesize Golgi-Modified Complex N-Linked Glycans," *Plant Physiology*, 1993, pp. 1109-1118, vol. 102.

Wilson et al., "Cloning and Expression of cDNAs Encoding α1,3-fucosyltransferase Homologues from *Arabidopsis thaliana*," *Biochimica et Biophysica Acta*, 2001, pp. 88-96, vol. 1527(1-2).

Yamane-Ohnuki et al., "Establishment of *FUT8* Knockout Chinese Hamster Ovary Cells: An Ideal Host Cell Line for Producing Completely Defucosylated Antibodies with Enhanced Antibody-Dependent Cellular Cytotoxicity," *Biotechnology and Bioengineering*, 2004, pp. 614-622, vol. 87(5).

Sourrouille et al., Medicago Sativa Clone MS1-3FTb alpha 1,3 fucosyltransferase mRNA, complete eds. (2005) GenBank Accession AY082445; pp. 1-3.

Martinez-Duncker et al., *Hordeum vulgare* mRNA for putative glycoprotein 3-alpha-L-fucosyltransferase (core3ft gene), 2003, GenBank Accession AJ582181, pp. 1-2.

\* cited by examiner

DNA and amino acid sequence information

*Lemna minor* alpha 1-3 fucosyltransferase:

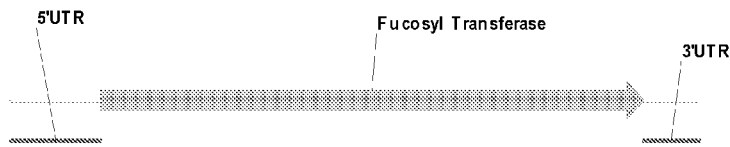

L. minor RACE PCR fucosyltransferase
1865 bp

FucT isoform #1 cDNA sequence: (UTR's in standard font, coding region in bold)
acgcggggggaagtggttgagtagctcagtggaaaattggaaatgtctattagaggggaagagggagggatccgagggg
aacgaggaagtgtgccgaattctcgtagatttcttcaattcctgcagatctcgtcttctctctgatttcttcccgagctc
cgcccgtaggaactcaatcggactcgatccaagttgacgaggcctacgaggaaggcgattttccgaagccctgcgatcga
**tggccacctctgctgctggtgctctcaacgccggtggcagggtcggggcaggaggagttggggtcagattgcttcccttct
ttgtgttgatgctggtggtaggggagatctggttcctcgggcggctggatgtggtcaagaacgccgctatggttcaaaact
ggacttcctcccacttgtttttcttaccagtttcttcctacacgtggtccgagaccgtcaaggaggaagaggattgcaagg
actggctggaaagagtagatgcggtcgattacaagagagatttccgtgtggaacccgttctggtaaatgacgctgaacagg
attggagttcatgttcagtgggctgtaagttcggatcattccccggaagaacgcctgatgctacatttggtttctctcaga
atccatcaacagtcagtgtccatcgatccatggaatcatcccattattatttggagaataatcttgataatgcacgacgga
aaggctatcaaattgtgatgacaactagtctcttgtcagatgtgcctgtcggttatttctcatgggctgaatatgatatca
tggcgcctcttcagccgaaaactgctggtgcacttgctgctgcatttatatctaattgcggagcacgtaatttccgcttgc
aggcccttgatatgctcgaaaagtcgaatattaagattgattcatatggtgcttgccatcgcaaccaagacggtaaagtgg
acaaggtacaaactttgaagcggtataagttcagcttagcttttgaaaactcgaacgaggatgactatgttactgagaagt
tcttt caatctcttgtcgctggagctattcctgttgtcgtcggagcccccaacattcaaaattttgcgccatcttctgatt
caattctgcacatcaggggagcccaaggatgtcagttcagtcgctgagagaatgaaatttctcgcttcaaatccgaagcat
ataaccaatcactgaggtggaagtttgagggccctctaactccttcaaagccctggtggacatggcagcagttcactcct
cctgccgcctatgcattcacattgccaccaagatcagagagaaggaagagagaaacccgaatttcaagactcgcccttgca
agtgcaccgcaatgggtctaccttatatcacttatacgcccgcgaaagaggcacctttgacttcttatcaatcttcatga**
gatcggataatctatcactgaaagcgctggggtcaacagttcttgagaaattcagttcttttgaagcacgtgccgatttgga
agaaggagaggccagagagtctgaaaggagggagcaagctggatcttacagaatctatccagtgggcattactcagagag
aagctctcttctctttccagttcaacactgacaaagaacttcaaatctaccttgaatcccatccatgtgcgaagtttgaag
tcatctttatttgatccctgaggtaattaggtcacgaattcagctaatttggttaattatgcttcaagcccacatggtatt
tcatatcattaattgaaggcatagttagttgatattgacattttcgtctaggatcattctaaagtctatccaatgaactt
aa

FucT isoform #1 predicted amino acid sequence:
matsaagalnaggrvggrrswvrllpffvlmlvvgeiwflgrldvvknaamvqnwtsshlfflpvssytwsetvkeeedck
dwlervdavdykrdfrvepvlvndaeqdwsscsvgckfgsfpgrtpdatfgfsqnpstvsvhrsmesshyylennldnarr
kgyqivmttsllsdvpvgyfswaeydimaplqpktagalaaafisncgarnfrlqaldmleksnikidsygachrnqdgkv
dkvqtlkrykfslafensneddyvtekffqslvagaipvvvgapniqnfapssdsilhirepkdvssvaermkflasnpea
ynqslrwkfegpsnsfkalvdmaavhsscrlcihiatkirekeernpnfktrpckctrngstlyhlyarergtfdflsifm
rsdnlslkalgstvlekfsslkhvpiwkkerpeslkggskldlyriypvgitqrealfsfqfntdkelqiyleshpcakfe
vifi*

FIG. 1

**Amino acid sequence alignment of alpha 1,3 fucosyltransferase from *Lemna minor* and other higher plants**

Total alignment positive – 89.2%
Total alignment identity – 41.1%

*Triticum aestivum*: Genbank accession# AJ582182.1
*Hordeum vulgare*: Genbank accession# AJ582181.1
*Oryza sativa*: Genbank accession# XM_482907.1
*Medicago sativa*: Genbank accession# AY082444.1
*Arabidopsis thaliana*: Genbank accession# AY184990.1

```
                                      1                                    35
          Lemna minor  FucT    (1)  ------------------M  S AGALN GGRVG
     Triticum aestivum FucT    (1)  -----------------MK   Q     Q
       Hordeum vulgare FucT    (1)  -----------------M    L     Q
          Oryza sativa FucT    (1)  ---------------MK   O O O OSC
        Medicago sativa FucT   (1)  MGLVSRT---------TTTTTQEGLPV V VSTTV
    Arabidopsis thaliana FucT  (1)  MGVFSNLRGPRAGATHDEFP  NGSPS S SP
                Consensus      (1)                      GSHS S S A  AAS 36                                   70
          Lemna minor  FucT   (17)  G  SWVR  PFFVL L     WI GR   V    M
     Triticum aestivum FucT   (13)          LPL VG  F GE IAFLGRLD
       Hordeum vulgare FucT   (12)          LPLLVG  F GE IAFLGRLD
          Oryza sativa FucT   (18)          LPL VG AAFLA  AFLGRLD
        Medicago sativa FucT  (27)  P   WSNL F FV   V   AEIAFLGRLD     M
    Arabidopsis thaliana FucT (36)  I   LSNL F C  V   AEI FLGRLDKVALVDT
                Consensus     (36)  RRRRCGWLLPLLVGLAVIAEIAFLGRLDMAKNAAA 71                                  105
          Lemna minor  FucT   (52)    Q    LFFLPVSS-----------YTW   TVK
     Triticum aestivum FucT   (48)         R  TW ---------------
       Hordeum vulgare FucT   (47)         R  TW ---------------
          Oryza sativa FucT   (53)        APS APARDGKAAVVVPGADAL
        Medicago sativa FucT  (62)   ADLFYRSR VEGDD------------FGL
    Arabidopsis thaliana FucT (71)    TD F  SP     -----------------
                Consensus     (71)  VESWTTSFYALSS  G              ADAPP 106                                 140
          Lemna minor  FucT   (76)  ----------    KW LERVD D KR  PV
     Triticum aestivum FucT   (69)        -------D     ERL PD V  P
       Hordeum vulgare FucT   (68)        -------D     ERLEPD V  P F
          Oryza sativa FucT   (88)    EVVEEDG IPLC ERL P  V  P
        Medicago sativa FucT  (81)   VGGDKNLEL P TC   LE  VT  N
    Arabidopsis thaliana FucT (87)   RSDRKKIGLFT  SC  WLM    VT SP TK
                Consensus    (106)  GSG        DDEECEEWLEREDAVPYDRDFEKD
```

FIG. 2A

```
                               141                               175
        Lemna minor FucT (100) PVLVNLAEQDWSSCSVGCKFGSFPCRKTPDATFGFA
    Triticum aestivum FucT (97) PVLVGGAEKDWNRCSVGCEFGFPASKTPDATFGIA
       Hordeum vulgare FucT (96) PVLVGGAEKDWNRCSVGCEFGFPASKTPDATFGIA
          Oryza sativa FucT (123) PVLVGGAEKDWNRCSVGCEFGFSATKTPDATFGIA
        Medicago sativa FucT (116) PVFVSGAEDEWKSCSVGCKFGFNSDKPEAAFGSP
    Arabidopsis thaliana FucT (122) PITISGGEKDQWCSVDCTFGDSGKRPAAFGSG
                  Consensus (141) PVLVGGAEKDWNRCSVGCEFGF ASKTPDATFGIA 176                               210
        Lemna minor FucT (135) QNDSTVSVHRSMESGHYYLENGRDNARRGYQIVM
    Triticum aestivum FucT (132) PDPSVESILRSMESSQYYSENGKNAARGKGYQIVM
       Hordeum vulgare FucT (131) PDPSVESILRSMESSQYYSENGKNAARGKGYQIVM
          Oryza sativa FucT (158) PDPTVESILRSMESSQYYSEDGKVAPGKCYKIVM
        Medicago sativa FucT (151) QQAGTASVLPSMESAQYYAENKDMARRGYHIVM
    Arabidopsis thaliana FucT (157) QKGTLSLRSMESSQYYPENDLRQALRGYDIVM
                  Consensus (176) QDPSVESILRSMESSQYYSENNIA ARRRGYQIVM 211                               245
        Lemna minor FucT (170) TTSLLSDVPVGYFSWAEYDIMAPIQPKTAGALAAA
    Triticum aestivum FucT (167) TTSLSSDVPVGYFSWAEYDIMAPVPPKTEEALAAA
       Hordeum vulgare FucT (166) TTSLSSDVPVGYFSWAEYDIMAPVPPKTEEALAAA
          Oryza sativa FucT (193) TTSLSSDVPVGYFSWAEYDIMAPVPPKTEEALAAA
        Medicago sativa FucT (186) TTSLSSDVPVGYFSWAEYDIMAPKPFTEKALAAA
    Arabidopsis thaliana FucT (192) TTSLSSDVPVGYFSWAEYDIMSPQPKTERAIAAA
                  Consensus (211) TTSLSSDVPVGYFSWAEYDIMAPVPPKTEEALAAA 246                               280
        Lemna minor FucT (205) FISNCGARNFRLQALDMLEKSNIKIDSYGACHRNQ
    Triticum aestivum FucT (202) FISNCGARNFRLQALEMLESLDVKIDSYGSCHRNR
       Hordeum vulgare FucT (201) FISNCGARNFRLQALEMLESLDVKIDSYGSCHRNR
          Oryza sativa FucT (228) FISNCGARNFRLQALEMLESLDVKIDSYGSCHRNH
        Medicago sativa FucT (221) FISNCGARNFRLQALEALKTNKSIDSYGSCHRNR
    Arabidopsis thaliana FucT (227) FISNCGARNFRLQALEALMKTNKKIDSYGCCHRNR
                  Consensus (246) FISNCGARNFRLQALEMLESLNIKIDSYGSCHRNR 281                               315
        Lemna minor FucT (240) DGKVDKVQTLKRYKFSLAFENSIEDYVTEKFFQS
    Triticum aestivum FucT (237) DGKVDKVETLKRYKFSLAFENSGEDYVTEKFFQS
       Hordeum vulgare FucT (236) DGKVDKVETLKGYKFSLAFENSNEDYVTEKFFQS
          Oryza sativa FucT (263) DGKVDKVETLKRYKFSLAFENSNEDYVTEKFFQS
        Medicago sativa FucT (256) DGKVDKDELTRYKFSLAFENSNEEDYVTEKFFQS
    Arabidopsis thaliana FucT (262) DGKVDKVEALKRYKFSLAFENSNEEDYVTEKFFQS
                  Consensus (281) DGKVDKVETLKRYKFSLAFENSNEEDYVTEKFFQS 316                               350
        Lemna minor FucT (275) IVAGAIPVVGAPNIQNFAPSSKTLHIRELPIDVS
    Triticum aestivum FucT (272) LVTGAIPVVVGAPNIQEFSPCEGAILHIKELDLVI
       Hordeum vulgare FucT (271) LVTGAIPVVVGAPNIQEFSPCEGAILHIKELDLVI
          Oryza sativa FucT (298) LVTGAIPVVTGAPNIQEFSPCEGAILHIKELDVP
        Medicago sativa FucT (291) LVAGTIPVVVGPPNIQDFAPSPGFLHIKELBDVE
    Arabidopsis thaliana FucT (297) LVAGSIPVVVGPPNIEEFAPASQTFLHIKTMDVE
                  Consensus (316) LVTGAIPVVVGAPNIQEFAPGEDAILHIKELDDV
```

FIG. 2B

```
            351                                    385
Lemna minor FucT       (310) SVAERMKF A NPEA NQSLRWK  GPSNSFKAL
Triticum aestivum FucT (307) SVAKTMK   A  EDA NQSLRWK  GPS SFKAL
Hordeum vulgare FucT   (306) SVAKTMK   A NEDA NQSLRWK  GPSDSFKAL
Oryza sativa FucT      (333) S AKTMK   A NQEA NQSLRWK  GPSDSFKAL
Medicago sativa FucT   (326) SVAK    A ENPEA N SLRWK  GPSDSFKAL
Arabidopsis thaliana FucT (332) P AKR    A AA   SLRW   GPSDSFKAL
Consensus              (351) SVAKTMKHIASNPEAFNQSLRWKYDGPSDSFKALI 386                                    420
Lemna minor FucT       (345) DMAAVHSSCRLCIH AT   EKEE NPNFKTK CK
Triticum aestivum FucT (342) DMAAVHSSCPLCIH AT  HEKEE  PKFMNRSC
Hordeum vulgare FucT   (341) DMAAVHSSCPLCIH AT  HEKEE T PKFMNRSC
Oryza sativa FucT      (368) DMAAVHSSCPLCIH AT  HEKEE  PKFMNR C
Medicago sativa FucT   (361) DMAAVHSSCPLCIH AT  SREKEE   PDFKKF CK
Arabidopsis thaliana FucT (367) DMAAVHSSCRLCIF AT  R  EQEEE PNFKKF CK
Consensus              (386) DMAAVHSSCRLCIHIATKIREKEERTPKFMNRPCS 421                                    455
Lemna minor FucT       (380) C RN-GS   Y HL  A ER GT DFLS   SDNL LK
Triticum aestivum FucT (377) C S K-RGTV HLFVRER    KTESIYL  SDQLTLG
Hordeum vulgare FucT   (376) C S  -RGTV HL VRER    KTESIYL  SDQLT G
Oryza sativa FucT      (403) C S  -RGK  HL VRER    KTESI L  SDQLT
Medicago sativa FucT   (396) C RG-SE   Y HL VRE GT EMESI LK  SN LT E
Arabidopsis thaliana FucT (402) C RGGSD  Y   VRE G  EMES  L RGKS  QE
Consensus              (421) CSSK RGTVYHLFVRERGRFKTESIFLRSDQLTLG 456                                    490
Lemna minor FucT       (414) A G T  EK   SL H    WKKE PE    GGSKL D
Triticum aestivum FucT (411) A     VH  K RSLK H    WK ERPSS  RGG     
Hordeum vulgare FucT   (410) A  SAVHDK  SLK HV    WK ERPSS  RGGDE  
Oryza sativa FucT      (437) A ESAVI  K RSLN VE   WK ERPPS  RGGDE  V
Medicago sativa FucT   (430)  FK AVLTK F SLN VE   WK PERPEI  GGDKI   
Arabidopsis thaliana FucT (437) A    AV  K F S L  HEA  WK  ERPGN  GDK   
Consensus              (456) ALESAVLAKFSSLKHVPVWKDERP SIKGGDELKV 491                                    525
Lemna minor FucT       (449) Y  I P GI TQREA  SP  NT K  QI   SH PCA
Triticum aestivum FucT (446) Y  I P  GLTER  AL KF QFSDDAE  ARYIKGH PCA
Hordeum vulgare FucT   (445) Y  I P  GLTER  AL KF QFSDDAE  ARYIKGH PCA
Oryza sativa FucT      (472) Y  I P  GLTQR  ALY QFR  DA    KYIKDH PCA
Medicago sativa FucT   (465) Y  I PAGLTQ  AL T QFNG V  FRSH  ESN PCA
Arabidopsis thaliana FucT (472) Y  I P GLTQ  AL N  FEGN   SH QNN PCA
Consensus              (491) YKIYPIGLTQRQALY FQF DDAELARYIK HPCA 526
Lemna minor FucT       (484) K E V F -
Triticum aestivum FucT (481) K  EVFV-
Hordeum vulgare FucT   (480) K  EVFV-
Oryza sativa FucT      (507) K  EVFV-
Medicago sativa FucT   (500) KFE V FV-
Arabidopsis thaliana FucT (507) KFE V FV-
Consensus              (526) KLEVIFV
```

FIG. 2C

***Lemna minor* beta 1-2 xylosyltransferase:**

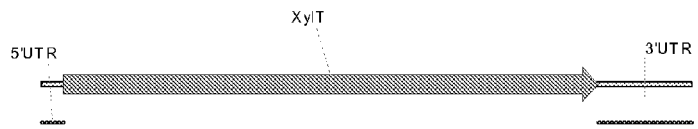

Lemna minor beta 1-2 xylosyltransferase
1860 bp

XylT isoform #1 cDNA sequence: (UTR's in standard font, coding region in bold)
ggcttccaaccggaggatctcgagctgaagaatcttcatgactgaagaattcatgtgatccc**atggctttggtgaactcgc
gagggagcagggtcagacgcatcgcgaagcccaccttcgttttcctcttgatcaacgtagtctgtctcctgtacttttcc
gtcagaacccctaatcccattcccgacgcttgtcttcacggggaatgcgacaaaccccgatttagtgactccccggcgat
ggaacttgaagccatgccgattcttccttcctttctgccatgggtgccgagctcccaccctgcccagggctcctgcgaag
cctacttcggcaacagcttcaaccgccggacggagatgctgaagaaggtagagggaagaggatggttccagtgcctgtaca
gcgatactcttcgaagttctgtttgccagggagggaatttgcggatggacccggaaaggattaggatgtcgaaaggggggg
aagatctagaggaggtgatgaagagagaggaggaagaagaattgcccaaattcgaggaggggtcgttccagattgaatctg
gttatggaagcggaggggaagttggagagagaattgcgactgacgaggtcctcgataatgttgtgccgaaaggcgctgttc
atgtacataccatgcgcaatctcatcagttcgattcagattgttggtcccgggcatcttcaatgctctcagtggatcgacg
aaccggttcttcttgtcacacgcttcgaatacgccaatctctttcacaccgtcaccgactggtacagcgcctacgaagct
cgaggattgccaacttgccttctcgccctcacttaattttcgtcgatggccattgcagggcggaacagttagaggacatgt
ggagagccctgttctcgaccgtccgatactccaagaacttctcccagccaatctgcttccgccacgtcgtcctctcacctc
tgggctatgagacggctctcttcaaaggcctatcagagagcttcagctgtgagggagctccggccaatcggctcaaagtca
accccgatgaccagaagactgcaagactggctgaattcggagagatgatcagagccgcctttgacttcctgtcgttgacc
cgtccattgacccgttgaccaaatccatcctcttcgtgcggcgggaagattacgtggcgcaccaccgccacagtgggagag
tggagtcgcggctgaccaacgagcaagaggtgtttgacttctgcacaattgggcaagtcatcacagaggcaggtgcaaca
tcagtatggtcaacgggcttttcgcgcacatgggaatgaaggaacagttgaaggcgattatggaagcttcggtggtggtgg
gggcccacggggctggtttgacccatctggtggcagcaaggtcaacgacagttgttcttgagattctgagtagtcaatacc
gtagaccgcactttcaactgatttctcggtggaaagggttggactaccatgcaattaatcttgccgggtcatttgctgacc
ctcgggaggtggtcgagaaattgactggcatagttgacaggcttggatgttga**agagaagtgaaagtcaacatttggaatt
ttaactttaaggggtggttaacaattgagcggcattgtcaacgggtttggatgctgggaaaagtgaaaatcaacacttgga
gttctgacattgaaggcaagacgtggaattttgatggtgttgaggatatttggatgtggagttctgatgaattaaagcagg
ggttgatcatttgccagtggaattatgttggtgtaagagagaaggggggagaataaacagtgttagagagctatgctgg

XylT isoform #1 predicted amino acid sequence:
malvnsrgsrvrriakptfvfllinvvcllyffrqnpnpipdaclhgecdkppilvtprrwnlkpwpilpsflpwvpsshp
aqgsceayfgnsfnrrtemlkkvegrgwfqclysdtlrssvcqggnlrmdperirmskggedleevmkreeeeelpkfeeg
sfqiesgygsggevgeriatdevldnvvpkgavhvhtmrnlissiqivgpghlqcsqwidepvllvtrfeyanlfhtvtdw
ysayassrianlpsrphlifvdghcraeqledmwralfstvrysknfsqpicfrhvvlsplgyetalfkglsesfscegap
anrlkvnpddqktarlaefgemiraafdfpvvdpsidpltksilfvrredyvahprhsgrvesrltneqevfdflhnwash
hrgrcnismvnglfahmgmkeqlkaimeasvvvgahgaglthlvaarsttvvleilssqyrrphfqlisrwkgldyhainl
agsfadprevvekltgivdrlgc*

FIG. 3

**Amino acid sequence alignment of beta 1,2 xylosyltransferase from *Lemna minor* and other higher plants**

Total alignment positive – 76.6%
Total alignment identity – 33.7%

*Medicago sativa*: Genbank accession# AY302251.1
*Oryza sativa*: Genbank accession# XM_483221.1
*Arabidopsis thaliana*: Genbank accession# AJ272121.1
Saccharum officinarum: Genbank accession# AJ864704.1
*Nicotiana tabacum*: Genbank accession# AJ627182.1

```
                               1                                    35
       Lemna minor XylT    (1) ----------MALVNSRGSRV    A PTFVF L
     Medicago sativa XylT  (1) -------------------MN KQ  LF  I
       Oryza sativa XylT   (1) MMPVRTYHHHHHHNNSNNH  R I P  LA
 Arabidopsis thaliana XylT (1) -----------------MS RNP      Y L
Saccharum officinarum XylT (1) ---MMAGRAHGHRN-----  R L P   L
   Nicotiana tabacum XylT  (1) -------------------  N K  F  S
                Consensus  (1)                      RL RKILKILL LFAI 36                                   70
       Lemna minor XylT   (25)   V   LY  RQNFNPIPDACLHGECDKPPILV PR
     Medicago sativa XylT (15)    F  C   H    FLNPTPSPN-- -DIKIF KD
       Oryza sativa XylT  (36) Y   FAA  LR Q PHPHPHPAADPERDAVDAAGG
 Arabidopsis thaliana XylT(19)   F I   F   SFSPEQSQ---  PHIYHV VN
Saccharum officinarum XylT(28) Y  FA    L  PQSESHHQSPPD TPRTEARDG
   Nicotiana tabacum XylT (16)    Y  SS   DHFRHKSPQNHF NTQNHY LS
                Consensus (36) NSVSL IYFL HSS          P           S 71                                  105
       Lemna minor XylT   (60) R-------------WNL               VP  H
     Medicago sativa XylT (47) SPFRRPF--IEKHK HIL           SF  QP N
       Oryza sativa XylT  (71) GGGGGAVDRVRVEA SSQ              S  V
 Arabidopsis thaliana XylT(51) N-----------Q AIQ             PW PFQR
Saccharum officinarum XylT(63) VG---------AP YSH           C   VY  A
   Nicotiana tabacum XylT (51) ENHHDNF--HSSVT QYT             Q-NP
                Consensus (71)               S    KPWPILPSYLPWS SS 106                                 140
       Lemna minor XylT   (81) PAQ--G                         KVE--------
     Medicago sativa XylT (80) ST -LR                      S  RAE-------
       Oryza sativa XylT (106) RP PKH                         RG--------
 Arabidopsis thaliana XylT(74) NL -TG                  DF  P------RIGG
Saccharum officinarum XylT(88) PP---H                       P GR--------
   Nicotiana tabacum XylT (83) NVS-LR                  L       SPELHQKFGE
                Consensus(106)    P    SCEGYFGNGFTRRVDVLKA
```

FIG. 4A

```
                                    141                                175
        Lemna minor XylT    (106)  -----GRGWFQCLYSDTLRSSVCQGGNLPMDPDRI
     Medicago sativa XylT   (107)  ---GRGGGWFRCNYSETLRSSVCGGGRVPMVVERI
        Oryza sativa XylT   (133)  ---GGGGGWFRCHYSETLSSSICEGGRVLDEGLI
Arabidopsis thaliana XylT   (102)  ---GGEGSWFRCFYSETLQSSICEGRNLPVEDRI
Saccharum officinarum XylT  (112)  ---GGGGGWFRCHYSETLGSSICEAEKRLDEALI
   Nicotiana tabacum XylT   (117)  NTVSGDGGWFRCFYCETLQSSICEGGAIRNNEEI
             Consensus      (141)     GGGGGWFRCFYSETLRSSICEGGRVRMDPDRI 176                                210
        Lemna minor XylT    (136)  RMSRGGEDLREVMKREEEEPLFEEEGSFQLESGY
     Medicago sativa XylT   (139)  KMARGGESLGEVIGREEEDELPLEEDGAEEVDGGV
        Oryza sativa XylT   (165)  AMSRGGEPLEQVMGRAEEEELPEALEQVEA-A
Arabidopsis thaliana XylT   (134)  VMSRGGEKLESVMGRKEEEELPAERQGAPEVAEEV
Saccharum officinarum XylT  (144)  AMSRGGEPLEQVMGREEEELPEKEPSAIQVEGPA
   Nicotiana tabacum XylT   (152)  LMSRGGEKLESVIGREEEDELPVEKNGAFQLKVTD
             Consensus      (176)    MSRGGE LEEVMGRAEEEELPKFE GAFQVEG 211                                245
        Lemna minor XylT    (171)  GSGGE----------------VGERIATEVLDNVK
     Medicago sativa XylT   (174)  GFEGG----------------KMVVEGFLDRE
        Oryza sativa XylT   (199)  AKETGP----------------LVEAGELDAV
Arabidopsis thaliana XylT   (169)  SSELGFKRHRRFGGGEGGSAVSRELVNDEMLNEM
Saccharum officinarum XylT  (179)  AGETAP----------------LVDAGELNDV
   Nicotiana tabacum XylT   (187)  KLEIG----------------KRLVGEKILNKV
             Consensus      (211)  A K G                KRLVDDGFLN YV 246                                280
        Lemna minor XylT    (191)  RKGAHVHTMRNLLSSQLVGPGHLCCSQWIEEPV
     Medicago sativa XylT   (192)  RRGEMEHTMRDLLGKMEVGRKEFKCDKWIEEPI
        Oryza sativa XylT   (216)  RTGGGMHTMRSIDSGRVVPSGPEHCSQWIEEPT
Arabidopsis thaliana XylT   (204)  QEGGDEHTMRDLVASRAVDTNEFVCEEWIEEPT
Saccharum officinarum XylT  (196)  PNGARMHTMRALLESAREVPRGEEHLSQWIEEPT
   Nicotiana tabacum XylT   (205)  REAESEHTMRELLDSIQEVGADEFHCSEWIEEPR
             Consensus      (246)  P GGI RHTMRDLIDSIRVVGPGELHCSQWIEEPT 281                                315
        Lemna minor XylT    (226)  LLVTRFEYANLFHTVTDWYSAYASSEANLPSPPH
     Medicago sativa XylT   (227)  LLVTRFEYANLFHTVTDWYSAYVSSRTGLPSPPH
        Oryza sativa XylT   (251)  LLVTRFEYANLFHTVTDWYSAYVSSRVDLPNKPN
Arabidopsis thaliana XylT   (239)  LLVTRFEYANLFHTVTDWYSAYVSSRVTGLPNKPH
Saccharum officinarum XylT  (231)  LLVTRFEYANLFHTVTDWYSAYVGSRVTNLPDRPN
   Nicotiana tabacum XylT   (240)  LLVTRFEYANLFHTVTDWYSAYVACRVTGLPSRPH
             Consensus      (281)  LLVTRFEYANLFHTVTDWYSAYVSSRVTGLPSRPH 316                                350
        Lemna minor XylT    (261)  NLVFVDGHCKEQLEDMRALFSTVRYSKNFSQPVC
     Medicago sativa XylT   (262)  NLFVDGHCKAP-LEETWKALFSSVRYAKNFTGTVC
        Oryza sativa XylT   (286)  WVFVDGHCKAS-LEQTWEALFSNTYVKNFSGPVC
Arabidopsis thaliana XylT   (274)  NEFVDGHCTTE-LEETWTALFSGRYAKNFTKEVC
Saccharum officinarum XylT  (266)  WVFVDGHCKAP-LEQTWEALFSNTYIKSFSGPVC
   Nicotiana tabacum XylT   (275)  NLFVDGHCETE-LEETWKALFSSVTYNFSGPVC
             Consensus      (316)  LVFVDGHCKAQ LEETWKALFSSVTYAKNFSGPVC
```

FIG. 4B

```
                                  351                              385
     Lemna minor XylT      (296)  FRHV LSPLGYETALFKGL SES SCEGA PA RLKV
     Medicago sativa XylT  (296)  FR A LSPLGYETALFKGL ED FCD ASA QE R
     Oryza sativa XylT     (320)  FR A LSPLGYETALFKGL SE F CE A A AESLRE
Arabidopsis thaliana XylT  (308)  FR A LSPLGYETALFKGL GE DCKGD AHNL Q
Saccharum officinarum XylT (300)  FR A LSPLGYETALFKGL SES CE ASA QSLR
    Nicotiana tabacum XylT (309)  FP A LSPLGYETALFKGL ET DCNGA AHDL Q
               Consensus   (351)  FRHAILSPLGYETALFKGLSESISCEGASAQ LWQ 386                              420
     Lemna minor XylT      (331)   PD QKTAR  EFGEMI AA FD   VDPS DPL K
     Medicago sativa XylT  (331)  KPDNE TAR SEFGEMI A F GI NLNH G PIF
     Oryza sativa XylT     (355)  KPDH QTAR SEFGEMI LA FD LR DILSS- S
Arabidopsis thaliana XylT  (343)   PD  RTAR SEFGEMI AA F GL NRHRSLE PL
Saccharum officinarum XylT (335)  RPDH QTAR SEFGEMI IA FD LE GIVPS  S
    Nicotiana tabacum XylT (344)   PD KRTAR SEFGEMI AA F G  RQN PRTV
               Consensus   (386)  NPDDQKTARLSEFGEMIRAAFGLPVD   I KKTS 421                              455
     Lemna minor XylT      (366)   --------- LFVRREDY AHPRHSG V SRL
     Medicago sativa XylT  (366)  G ------- H ALFVRREDY AHPRHGG V SRL
     Oryza sativa XylT     (389)  N ------- L  LFVRREDY AHPRHSGK V SRL
Arabidopsis thaliana XylT  (378)   SSSSSASVY  LFVRREDY AHPRHGG VQSRLI
Saccharum officinarum XylT (370)   ------- LK LFV RREDY AHPRHSGKV SRL
    Nicotiana tabacum XylT (379)  G---P-----   LFVRREDY AHPRHGG VQSRL
               Consensus   (421)  SG         NVLFVRREDYLAHPRHSGKVESRLS 456                              490
     Lemna minor XylT      (391)  NEQ V  F HN A HHR-- - CN SM  GL AHM
     Medicago sativa XylT  (394)  NEA V  S KSW AN----YKG KIN V GL AHM
     Oryza sativa XylT     (417)  NEK V DA EGW K-----  Q KIN V GL AHM
Arabidopsis thaliana XylT  (413)  NEE V DS HHW A TGSTGLT CGIN V GL AHM
Saccharum officinarum XylT (398)  NEQ V GA EK W KK---- Q KIN V GL AHM
    Nicotiana tabacum XylT (406)  NEEQ V  KSW ALN----HSE  IN  GL AHM
               Consensus   (456)  NE EVFDSL  WAA    G KCKINVVNGLFAHM 491                              525
     Lemna minor XylT      (423)  GM K Q RA TM ASV  GAHGAGLTH V ARST  
     Medicago sativa XylT  (425)   MK Q RAI QDASV  GAHGAGLTH V SAL K
     Oryza sativa XylT     (447)  NMK Q RAI  ASV  GAHGAGLTH V SA D K
Arabidopsis thaliana XylT  (448)   MK Q RAIQDASV  GAHGAGLTH V SA N
Saccharum officinarum XylT (429)   MK Q QAI L ASV  GAHGAGLTH V SA D K
    Nicotiana tabacum XylT (437)   MK Q RAI QDASV  GAHGAGLTH V SAA KA
               Consensus   (491)  SMKEQLRAIQDASVIIGAHGAGLTHIVSATP TVI 526                              560
     Lemna minor XylT      (458)   EI  S QT P HFQ   RWKGLEYHAINLAG  A
     Medicago sativa XylT  (460)   EI  S QF P HF Y  RWKGLEYHAINLD  AN
     Oryza sativa XylT     (482)   EI S MY R P F    HWKGLEYHAINLP  AR
Arabidopsis thaliana XylT  (483)  FEI SVE QRPHFE    WKGLEYHA NLANSRA
Saccharum officinarum XylT (464)   EI  S FY RPHFA   HWKA EYHAINLP SYAS
    Nicotiana tabacum XylT (472)   EI  S E YRPHFA   QWKGLEYHP YLE  A
               Consensus   (526)  LEIISS YRRPHFALIARWKGLEYHAINL GSYAD
```

FIG. 4C

```
                                     561              578
        Lemna minor XylT      (493) PR  K  GI DR  -
     Medicago sativa XylT     (495) ET  NALVS  K  R  -
       Oryza sativa XylT      (517) VT  NE  NI  GF  -
Arabidopsis thaliana XylT     (518) TA    TE    LGC-
Saccharum officinarum XylT    (499) IP  TSE  NI  G  -
    Nicotiana tabacum XylT    (507) PV     SS     -
                Consensus     (561) P DVIEKLS ILKSLGC
```

FIG. 4D

FucT RNAi design (single gene KO):

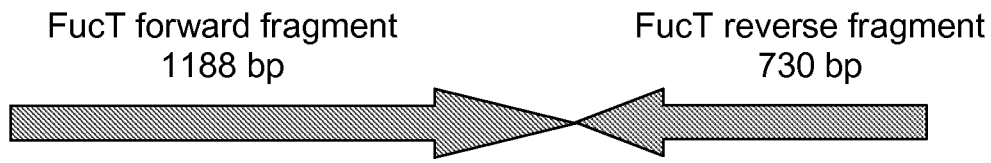

FucT forward fragment
1188 bp

FucT reverse fragment
730 bp

- Fucosyltransferase (FucT) RNAi expression cassette was designed to express a hairpin RNA with 730 bp of double-stranded RNA sequence and a 458 bp spacer sequence. The RNAi expression cassette comprises a FucT forward fragment (nt 255-985 of SEQ ID NO:1), the spacer sequence (nt 986-1444 of SEQ ID NO:1), and the FucT reverse fragment (antisense version of nt 255-985 of SEQ ID NO:1).

FIG. 5

XylT RNAi design (single gene KO):

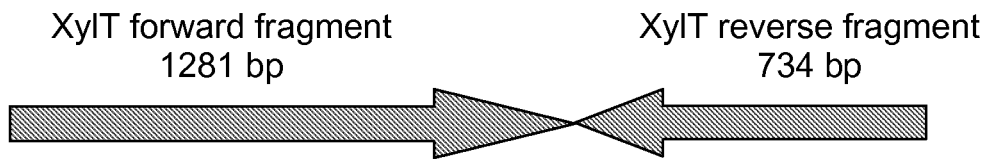

- Xylosyltransferase (XylT) RNAi expression cassette was designed to express a hairpin RNA with 734 bp of double-stranded RNA sequence and a 547 bp spacer sequence. The RNAi expression cassette comprises the XylT forward fragment (nt 318-1052 of SEQ ID NO:4), the spacer sequence (nt 1053-1599 of SEQ ID NO:4), and the XylT reverse fragment (antisense version of nt 318-1052 of SEQ ID NO:4).

FIG. 6

FucT + XylT chimeric RNAi design:

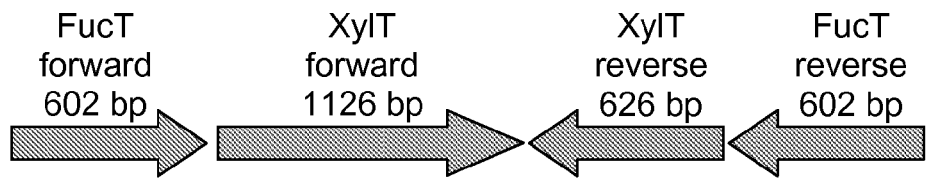

- Chimeric FucT + XylT RNAi expression cassette was designed to express a hairpin RNA with 602 bp of double-stranded FucT sequence, 626 bp of double-stranded XylT sequence, and a 500 bp spacer sequence. The RNAi expression cassette comprises in the 5' to 3' direction and operably linked: the FucT forward fragment (nt 254-855 of SEQ ID NO:1), the XylT forward fragment (nt 318-943 of SEQ ID NO:4), a spacer sequence (nt 944-1443 of SEQ ID NO:4), the XylT reverse fragment (antisense version of nt 318-943 of SEQ ID NO:4), and the FucT reverse fragment (antisense version of nt 254-855 of SEQ ID NO:1).

FIG. 7

XylT RNAi expression cassette

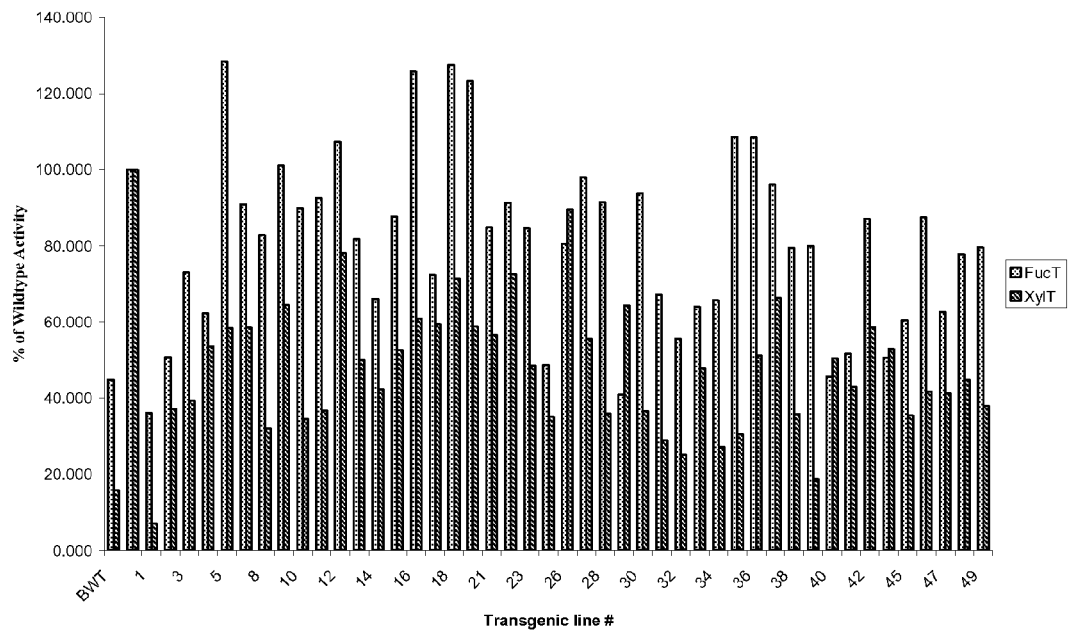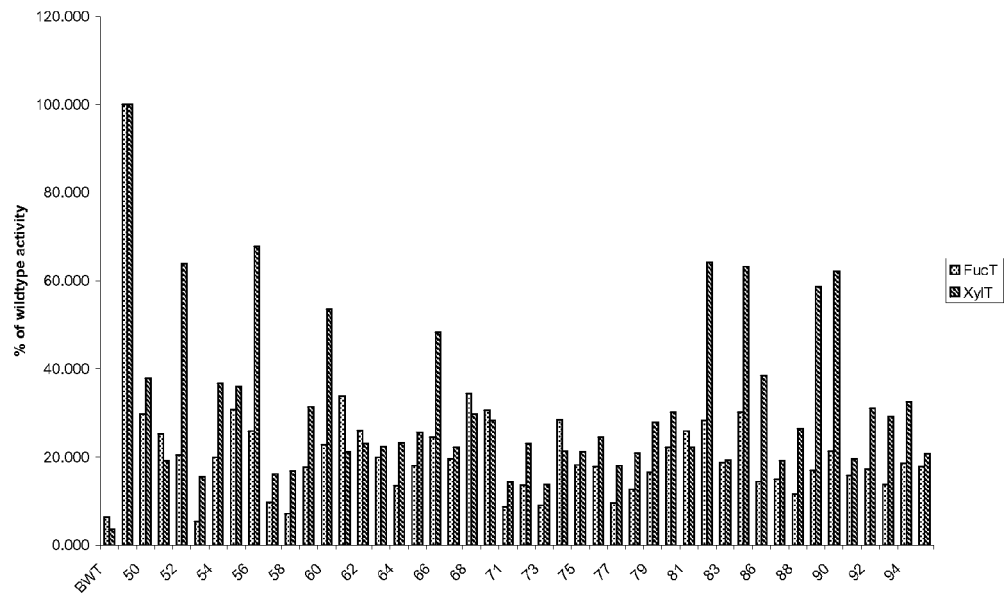
FIG. 15

Structure and molecular weight of derivatized wild-type *L. minor* mAb N-glycans.
2-AA-GnGn
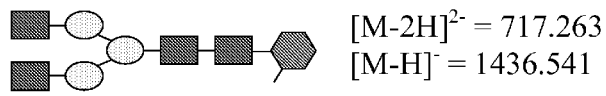
$[M-2H]^{2-} = 717.263$
$[M-H]^{-} = 1436.541$
2-AA-GnGnX
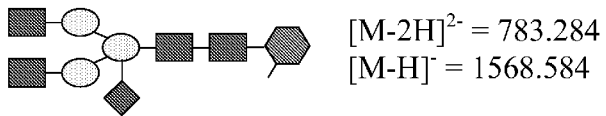
$[M-2H]^{2-} = 783.284$
$[M-H]^{-} = 1568.584$
2-AA-GnGnXF
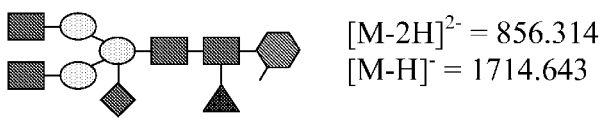
$[M-2H]^{2-} = 856.314$
$[M-H]^{-} = 1714.643$
Legend
■ = N-acetylglucosamine
◯ = Mannose
◆ = Xylose
▲ = Fucose
FIG. 18

MALDI analysis of mAbI01(WT) N-glycans
confirms the LC-MS results

*Possible design 1 (For targeting individual genes; applicable for both sequences):* first clone the full-length sequence in the antisense orientation, then clone the 3' half of the sequence downstream of the full-length sequence but in the sense orientation. In this way, the 3' half of the sequence (e.g. nt 950-nt1860) will form the dsRNA stem in the hpRNA, and the 5' half of the sequence will act as a spacer. The 3' region is chosen as this region is relatively conserved among different plant species (especially for FucT) compared with the 5' region.

*Possible design 2 (for targeting both genes):* Fuse a ~500 bp sequence from FucT with a ~500 bp sequence from XylT, and then use the fusion sequence to prepare the hpRNA constructs shown below. The sequence between nt700 to nt 1400 represents a region (especially for FucT) that is relatively conserved among different species of plants and is thus representative of one potentially good target. Both of the two versions shown below can be prepared for use together to potentially maximize silencing as preliminary results show that the sequence adjacent to the spacer appears to give better silencing than the distal sequence in the hpRNA construct.

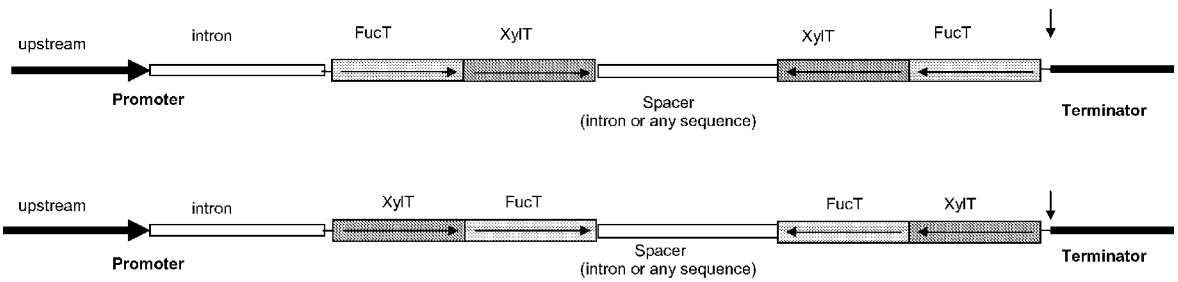

FIG. 28

| N-GLYCAN STRUCTURE | LEGEND |
|---|---|
| 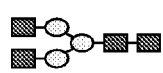 <br> G0 or GnGn or <br> GlcNAc$_2$Man$_3$GlcNAc$_2$ | ■ N-acetylglucosamine <br><br> ○ Mannose <br><br> ◆ Xylose <br><br> ▲ Fucose |
| 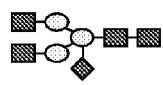 <br> G0X or GnGnX | |
| 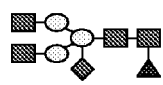 <br> G0XF$^3$ or GnGnXF | |
            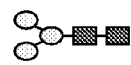
MGn or                          GnM or                     Man$_3$GlcNAc$_2$
GlcNAc$_1$Man$_3$GlcNAc$_2$     GlcNAc$_1$Man$_3$GlcNAc$_2$
(attached to 1,3 Mannose arm)   (attached to 1,6 Mannose arm)
FIG. 30

*Lemna minor* beta 1-2 xylosyltransferase (isoform 2)

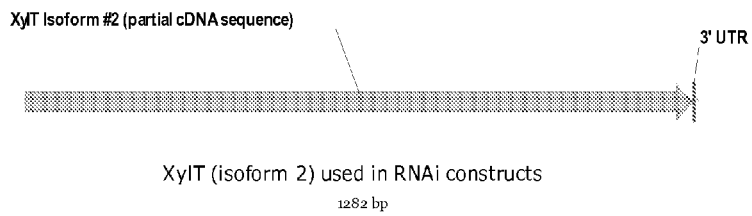

XylT (isoform 2) used in RNAi constructs
1282 bp

XylT isoform #2 partial cDNA sequence (coding sequence in bold font, 3'UTR sequence in standard font):

**tgcgaagcctacttcggcaacagcttcaaccgccggacggagatgctgaagaaggtagagggaagaggatggttccagtgcctgtaca
gcgatactcttcgaagttctgtttgccagggagggaatttgcggatggacccggaaaggattaggatgtcgaaaggggggggaagatcta
gaggaggtgatgaagagagaggaggaagaagaattgcccaaattcgaggaggggtcgttccagattgaatctggttatggaagcgga
ggggaagttggagagagaattgcgactgacgaggtcctcgataatgttgtgccgaaaggcgctgttcatgtacataccatgcgcaatctc
atcagttcgattcagattgttggtcccgggcatcttcaatgctctcagtggatcgacgaaccggttcttcttgtcacacgcttcgaatacgcc
aatctctttcacaccgtcaccgactggtacagcgcctacgcaagctcgaggattgccaacttgccctctcgccctcacttgatttcgtcgat
ggccattgcagggcagaacagttagaggacacgtggcgagccctgttctcaaccgtccgatacgccaagaacttctcccagccagtctgc
ttccgccacgccgtcctctcccctcttggctatgagacagctctcttcaaaggcctatcagagagcttcagctgtgagggagtgccggccaa
tcagctcaaagtcaaccctgatgaccagaagactgcgagactggctgaattcggagagatgatcagggctgcctttgactttcctgtcgtt
gacccgccgttgacccgttgaccaaatccatcctctttgtgcggcgggaagattacgtggcgcacccacgccacagtgggagagtggag
tcgcggttgaccaatgagcaagaggtgtttgactttctgcacaaatgggcaagtcaacacagaagcaggtgcaacgtcagtgtggtcaac
gggcttttcgcgcacatgggaatgaaggaacaggtgaaggcaattatggaagcttcggtggtggtcggggcccacggggctggtttgact
catctggtggcagcaaggtcaacgacagttgttcttgagattctgagcagtcaatatcgtagaccgcactttcaactgatttcacggtggaa
agggttggactaccacgcaattaatcttgccgggtcgtatgctgatcctcgggaggtggtcgagaaattgactggcatagtcgatgggctt
ggatgttgaagataag**

XylT isoform #2 predicted amino acid sequence (partial sequence):
ccayfgnsfnrrtcmlkkvcgrgwfqclysdtlrssvcqggnlrmdpcrirmskggedlccvmkrccccelpkfccgsfqicsgygsggcv
gcriatdcvldnvvpkgavhvhtmrnlissiqivgpghlqcsqwidcpvllvtrfcyanlfhtvtdwysayassrianlpsrphlifvdghcrac
qledtwralfstvryaknfsqpvcfrhavlsplgyetalfkglsesfscegvpanqlkvnpddqktarlaefgemiraafdfpvvdppvdpltks
ilfvrredyvahprhsgrvesrltneqevfdflhkwasqhrsrcnvsvvnglfahmgmkeqvkaimeasvvvgahgaglthlvaarsttvvl
eilssqyrrphfqlisrwkgldyhainlagsyadprevvekltgivdglgc*

FIG. 31

| | | 1 | 40 |
|---|---|---|---|
| LmXylT Isoform#1 | (1) | MALVNSRGSRVRRIAKPTFVFLLINVVCLLYFFRQNPNPI | |
| LmXylT Isoform #2 | (1) | ---------------------------------------- | |

| | | 41 | 80 |
|---|---|---|---|
| LmXylT Isoform#1 | (41) | PDACLHGECDKPPILVTPRRWNLKPWPILPSFLPWVPSSH | |
| LmXylT Isoform #2 | (1) | ---------------------------------------- | |

| | | 81 | 120 |
|---|---|---|---|
| LmXylT Isoform#1 | (81) | PAQGSCEAYFGNSFNPPTEMLKKVEGRGWFQCLYSDTLRS | |
| LmXylT Isoform #2 | (1) | -----CEAYFGNSFNPPTEMLKKVEGRGWFQCLYSDTLRS | |

| | | 121 | 160 |
|---|---|---|---|
| LmXylT Isoform#1 | (121) | SVCQGGNLRMDPERIRMSEGGEDLEEVMKREEEEELPKFE | |
| LmXylT Isoform #2 | (36) | SVCQGGNLRMDPERIRMSEGGEDLEEVMKREEEEELPKFE | |

| | | 161 | 200 |
|---|---|---|---|
| LmXylT Isoform#1 | (161) | EGSFQIESGYGSGGEVGERIATDEVLDNVVPKGAVHVHTM | |
| LmXylT Isoform #2 | (76) | EGSFQIESGYGSGGEVGERIATDEVLDNVVPKGAVHVHTM | |

| | | 201 | 240 |
|---|---|---|---|
| LmXylT Isoform#1 | (201) | RNLISSIQIVGPGHLQCSQWIDEPVLLVTPFEYANLFHTV | |
| LmXylT Isoform #2 | (116) | RNLISSIQIVGPGHLQCSQWIDEPVLLVTPFEYANLFHTV | |

| | | 241 | 280 |
|---|---|---|---|
| LmXylT Isoform#1 | (241) | TDWYSAYASSPIANLPSRPHLIFVDGHCRAEQLEDMNRAL | |
| LmXylT Isoform #2 | (156) | TDWYSAYASSPIANLPSRPHLIFVDGHCRAEQLEDTWRAL | |

| | | 281 | 320 |
|---|---|---|---|
| LmXylT Isoform#1 | (281) | FSTVRYKNFSQPKCFPHVVLSPLGYETALFKGLSESFSC | |
| LmXylT Isoform #2 | (196) | FSTVRIKNFSQPKCFPHAVLSPLGYETALFKGLSESFSC | |

| | | 321 | 360 |
|---|---|---|---|
| LmXylT Isoform#1 | (321) | EGAPANRLKVNPDDQKTARLAEFGEMIPAAFDFPVVDPS | |
| LmXylT Isoform #2 | (236) | EGVPANQLKVNPDDQKTARLAEFGEMIPAAFDFPVVDPP | |

| | | 361 | 400 |
|---|---|---|---|
| LmXylT Isoform#1 | (361) | DPLTKSILFVRREDYVAHPRHSGRVESKLTNEQEVFDFLH | |
| LmXylT Isoform #2 | (276) | DPLTKSILFVRREDYVAHPRHSGRVESKLTNEQEVFDFLH | |

| | | 401 | 440 |
|---|---|---|---|
| LmXylT Isoform#1 | (401) | NWASHHPGKCNSWVNGLFAHMGMKEQKAIMEASVVVGA | |
| LmXylT Isoform #2 | (316) | KWASQHRSRCNSWVNGLFAHMGMKEQKAIMEASVVVGA | |

| | | 441 | 480 |
|---|---|---|---|
| LmXylT Isoform#1 | (441) | HGAGLTHLVAAPSTTVVLEILSSQYRPPHFQLISPWKGLD | |
| LmXylT Isoform #2 | (356) | HGAGLTHLVAAPSTTVVLEILSSQYRPPHFQLISPWKGLD | |

| | | 481 | 510 |
|---|---|---|---|
| LmXylT Isoform#1 | (481) | YHAINLAGSKADPREVVEKLTGIVDRLGC- | |
| LmXylT Isoform #2 | (396) | YHAINLAGSKADPREVVEKLTGIVDGLG-- | |

FIG. 32

XylT RNAi design (single gene KO):

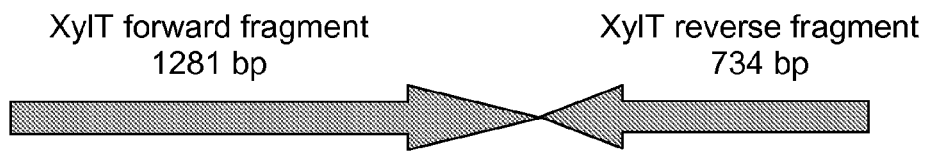

XylT forward fragment
1281 bp

XylT reverse fragment
734 bp

• Xylosyltransferase (XylT) RNAi expression cassette was designed to express a hairpin RNA with 734 bp of double-stranded RNA sequence and a 547 bp spacer sequence, based on the XylT isoform #2 partial DNA sequence. The RNAi expression cassette comprises the XylT forward fragment (nt 1-734 of SEQ ID NO:19), the spacer sequence (nt 735-1282 of SEQ ID NO:19), and the XylT reverse fragment (antisense version of nt 1-734 of SEQ ID NO:19).

FIG. 33

FucT + XylT chimeric RNAi design:

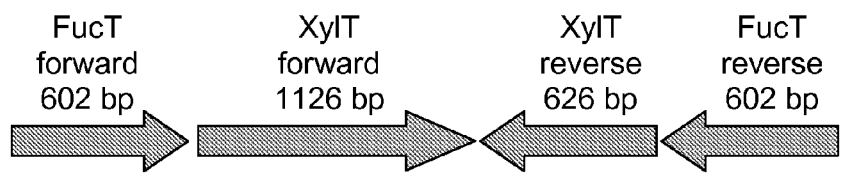

- Chimeric FucT + XylT RNAi expression cassette was designed to express a hairpin RNA with 602 bp of double-stranded FucT sequence, 626 bp of double-stranded XylT sequence, and a 500 bp spacer sequence. The RNAi cassette encompasses in the 5' to 3' direction and operably linked: the FucT forward fragment (nt 254-855 of SEQ ID NO:1), the XylT forward fragment from isoform #2 (nt 1-626 of SEQ ID NO:19, a spacer sequence (nt 627-1126 of SEQ ID NO:19), the XylT reverse fragment (antisense version of nt 1-626 of SEQ ID NO:19), and the FucT reverse fragment (antisense version of nt 254-855 of SEQ ID NO:1).

FIG. 34

COMPOSITIONS AND METHODS FOR INHIBITION OF FUCOSYLTRANSFERASE AND XYLOSYLTRANSFERASE EXPRESSION IN PLANTS

CROSS-REFERENCE TO RELATED APPLICATIONS

This application claims the benefit of U.S. Provisional Application Nos. 60/759,298, filed Jan. 17, 2006; 60/790,373, filed Apr. 7, 2006; 60/791,178, filed Apr. 11, 2006; 60/812,702, filed Jun. 9, 2006; 60/836,998, filed Aug. 11, 2006; and 60/860,358, filed Nov. 21, 2006; the contents of each of which are hereby incorporated herein in their entirety by reference.

FIELD OF THE INVENTION

The present invention is related to the field of plant molecular biology, more particularly to the field of recombinant mammalian protein production in plants.

BACKGROUND OF THE INVENTION

A number of plant species have been targeted for use in "molecular farming" of mammalian proteins of pharmaceutical interest. These plant expression systems provide for low cost production of biologically active mammalian proteins and are readily amenable to rapid and economical scale-up (Ma et al. (2003) *Nat. Rev. Genet.* 4:794-805; Raskin et al. (2002) *Trends Biotechnol.* 20:522-531). Large numbers of mammalian and plant proteins require post-translational processing for proper folding, assembly, and function. Of these modifications, the differences in glycosylation patterns between plants and mammals offer a challenge to the feasibility of plant expression systems to produce high quality recombinant mammalian proteins for pharmaceutical use.

As peptides move through the endoplasmic reticulum (ER) and Golgi subcellular compartments, sugar residue chains, or glycans, are attached, ultimately leading to the formation of glycoproteins. The linkage between the sugar chains and the peptide occurs by formation of a chemical bond to only one of four protein amino acids: asparagine, serine, threonine, and hydroxlysine. Based on this linkage pattern, two basic types of sugar residue chains in glycoproteins have been recognized: the N-glycoside-linked sugar chain (also referred to as N-linked glycan or N-glycan), which binds to asparagine residues on the peptide; and the O-glycoside-linked sugar chain, which binds to serine, threonine, and hydroxylysine residues on the peptide.

The N-glycoside-linked sugar chains, or N-glycans, have various structures (see, for example, Takahashi, ed. (1989) *Biochemical Experimentation Method 23—Method for Studying Glycoprotein Sugar Chain* (Gakujutsu Shuppan Center), but share a common oligomannosidic core (see FIG. 29A). The initial steps in the glycosylation pathway leading to the formation of N-glycans are conserved in plants and animals. However, the final steps involved in complex N-glycan formation differ (Lerouge et al. (1998) *Plant Mo. Biol.* 38:31-48; Steinkellner and Strasser (2003) *Ann. Plant Rev.* 9:181-192). Plants produce glycoproteins with complex N-glycans having a core bearing two N-acetylglucosamine (GlcNAc) residues that is similar to that observed in mammals. However, in plant glycoproteins this core is substituted by a β1,2-linked xylose residue (core xylose), which residue does not occur in humans, Lewis$^a$ epitopes, and an α1,3-linked fucose (core α[1,3]-fucose) instead of an α1,6-linked core fucose as in mammals (see, for example, Lerouge et al. (1998) *Plant Mol. Biol.* 38:31-48 for a review) (see also FIG. 29B). Both the α(1,3)-fucose and β(1,2)-xylose residues reportedly are, at least partly, responsible for the immunogenicity of plant glycoproteins in mammals (see, for example, Ree et al. (2000) *J. Biol. Chem.* 15:11451-11458; Bardor et al. (2003) *Glycobiol.* 13:427-434; Garcia-Casado et al. (1996) *Glycobiol.* 6:471-477). Therefore removal of these potentially allergenic sugar residues from mammalian glycoproteins recombinantly produced in plants would overcome concerns about the use of these proteins as pharmaceuticals for treatment of humans.

A number of recombinantly produced glycoproteins currently serve as therapeutics or are under clinical investigation. Examples include the interferons (IFNs), erythropoietin (EPO), tissue plasminogen activator (tPA), antithrombin, granulocyte-macrophage colony stimulating factor (GM-CSF), and therapeutic monoclonal antibodies (mABs). The oligosaccharide component of the N-glycan structures of glycoproteins can influence their therapeutic efficacy, as well as their physical stability, resistance to protease attack, pharmacokinetics, interaction with the immune system, and specific biological activity. See, for example, Jenkins et al. (1996) *Nature Biotechnol.* 14:975-981.

Methods are needed to alter the glycosylation pattern in plant expression systems, specifically to inhibit plant-specific glycosylation of the eukaryotic core structure, to advantageously produce recombinant mammalian proteins with a humanized glycosylation pattern.

BRIEF SUMMARY OF THE INVENTION

Methods for altering the N-glycosylation pattern of proteins in higher plants are provided. The methods comprise stably transforming the plant with at least one recombinant nucleotide construct that provides for the inhibition of expression of α1,3-fucosyltransferase (FucT) and β1,2-xylosyltransferase (XylT) in a plant. Use of these constructs to inhibit or suppress expression of one or both of these enzymes, and isoforms thereof, advantageously provides for the production of endogenous and heterologous proteins having a "humanized" N-glycosylation pattern without impacting plant growth and development. Stably transformed higher plants having this protein N-glycosylation pattern are provided. In some embodiments, the plant is a crop plant that is a member of the dicots, such as pea, alfalfa, and tobacco; in other embodiments, the plant is a crop plant that is a monocot, such as rice or maize. In yet other embodiments, the plant is a member of the Lemnaceae family, for example, a *Lemna* sp.

The transgenic plants of the invention have the ability to produce recombinant mammalian proteins having an N-glycosylation pattern that is more similar to that of the mammalian host. Thus, in some embodiments, the recombinantly produced mammalian proteins are glycoproteins comprising complex N-glycans having a reduction in the attachment of the plant-specific α(1,3)-fucose and β(1,2)-xylose residues. In other embodiments, these recombinantly produced glycoproteins comprise complex N-glycans that are devoid of these plant-specific residues. In yet other embodiments, these recombinantly produced glycoproteins have GlcNAc$_2$Man$_3$GlcNAc$_2$ as the single glycan species attached to the asparagine glycosylation site(s) within the glycoprotein.

In some embodiments, the recombinantly produced glycoprotein is a monoclonal antibody. In this manner, the present invention provides transgenic plants that are capable of producing glycan-optimized monoclonal antibodies that specifically bind a target protein of interest, including monoclonal antibodies having increased effector function. Thus, in some embodiments, the recombinantly produced glycan-optimized monoclonal antibodies comprise complex N-glycans that have a reduction in the attachment of α(1,3)-linked fucose residues, thereby increasing ADCC activity of these antibodies. In other embodiments, the recombinantly produced monoclonal antibodies comprise complex N-linked glycans that are devoid of these plant-specific fucose residues. In this manner, the present invention provides for the production of a monoclonal antibody composition, wherein at least 90% or more of the intact antibody is represented by a single glycoform, more particularly, the G0 glycoform. Thus, in some embodiments of the invention, the recombinantly produced monoclonal antibodies have increased effector function, wherein the ADCC activity is increased and/or the ratio of ADCC/CDC activity is increased. In some of these embodiments, the recombinantly produced monoclonal antibodies have decreased CDC activity, which can advantageously reduce the potential for adverse side effects related to CDC activation upon administration. These glycan-optimized monoclonal antibodies advantageously can be used to alter current routes of administration and current therapeutic regimens, as their increased effector function means they can be dosed at lower concentrations and with less frequency, thereby reducing the potential for antibody toxicity and/or development of antibody tolerance. Furthermore, their improved effector function yields new approaches to treating clinical indications that have been previously been resistant or refractory to treatment with the corresponding monoclonal antibody produced in other recombinant host systems.

Compositions for practicing the methods of the invention are provided. The compositions comprise novel isolated polynucleotides and polypeptides encoding a *Lemna minor* α1,3-fucosyltransferase and β1,2-xylosyltransferase, and variants and fragments thereof. Recombinant nucleotide constructs that target expression of these two proteins, or expression of variants thereof, are also provided, as are plant cells, plant tissues, plants, and seeds comprising these recombinant constructs.

BRIEF DESCRIPTION OF THE FORMAL DRAWINGS

FIG. 1 sets forth the DNA (SEQ ID NO:1; coding sequence set forth in SEQ ID NO:2) and amino acid (SEQ ID NO:3) sequences for the *Lemna minor* α1,3-fucosyltransferase (FucT). The coding sequence is shown in bold. Nucleotides denoted by the single underline (—) correspond to the FucT forward fragment within the RNAi expression cassette designed to inhibit expression of FucT (see FIG. 5); nucleotides denoted by the double underline (=) correspond to the spacer sequence within this RNAi expression cassette. The FucT reverse fragment of the RNAi expression cassette is the antisense of the FucT forward fragment shown here.

FIG. 2 sets forth an alignment of the *Lemna minor* FucT of SEQ ID NO:3 with α1,3-fucosyltransferases from *Triticum aestivum* (set forth in SEQ ID NO: 30), *Hordeum vulgare* (set forth in SEQ ID NO: 31), *Oryza sativa* (set forth in SEQ ID NO: 32), *Medicago sativa* (set forth in SEQ ID NO: 33), and *Arabidopsis thaliana* (set forth in SEQ ID NO: 34). The consensus sequence of the six sequences is set forth in SEQ ID NO: 34.

FIG. 3 sets forth the DNA (SEQ ID NO:4; coding sequence set forth in SEQ ID NO:5) sequence for the *Lemna minor* β1,2-xylosyltransferase (XylT) isoform #1 and the encoded amino acid (SEQ ID NO:6) sequence. Nucleotides denoted by the single underline (—) correspond to the XylT forward fragment within the RNAi expression cassette designed to inhibit expression of XylT (see FIG. 6); nucleotides denoted by the double underline (=) correspond to the spacer sequence within this RNAi expression cassette. The XylT reverse fragment of the RNAi expression cassette is the antisense of the XylT forward fragment shown here.

FIG. 4 sets forth an alignment of the *Lemna minor* XylT of SEQ ID NO:6 with β1,2-xylosyltransferases from *Medicago sativa* (set forth in SEQ ID NO: 36), *Oryza sativa* (set forth in SEQ ID NO: 37), *Arabidopsis thaliana* (set forth in SEQ ID NO: 38), *Saccharum officinarum* (set forth in SEQ ID NO: 39), and *Nicotiana tabacum* (set forth in SEQ ID NO: 40). The consensus sequence of the six sequences is set forth in SEQ ID NO: 41.

FIG. 5 sets forth one strategy for designing a single-gene RNAi knockout of *Lemna minor* FucT.

FIG. 6 sets forth one strategy for designing a single-gene RNAi knockout of *Lemna minor* XylT based on the DNA sequence for XylT isoform #1.

FIG. 7 sets forth one strategy for designing a double-gene RNAi knockout of *Lemna minor* FucT and XylT where the XylT portion of the RNAi knockout is based on the DNA sequence for XylT isoform #1.

FIG. 8 shows the Fuc02 construct comprising an RNAi expression cassette designed for single-gene RNAi knockout of *Lemna minor* FucT. Expression of the FucT inhibitory sequence (denoted by FucT forward and FucT reverse arrows; see FIG. 5) is driven by an operably linked expression control element (denoted as AocsAocsAocsAmasPmas) comprising three upstream activating sequences (Aocs) derived from the *Agrobacterium tumefaciens* octopine synthase gene operably linked to a promoter derived from an *Agrobacterium tumefaciens* mannopine synthase gene (AmasPmas). RbcS leader, rubisco small subunit leader sequence; ADH1, intron of maize alcohol dehydrogenase 1 gene; nos-ter, *Agrobacterium tumefacians* nopaline synthetase (nos) terminator sequence.

FIG. 9 shows the Xyl02 construct comprising an RNAi expression cassette designed for single-gene RNAi knockout of *Lemna minor* XylT. Expression of the XylT inhibitory sequence (denoted by XylT forward and XylT reverse arrows; see FIG. 6) is driven by the operably linked AocsAocsAocsAmasPmas expression control element. RbcS leader, rubisco small subunit leader sequence; ADH1, intron of maize alcohol dehydrogenase 1 gene; nos-ter, *Agrobacterium tumefacians* nopaline synthetase (nos) terminator sequence.

FIG. 10 shows the XF02 construct comprising a chimeric RNAi expression cassette designed for double-gene RNAi knockout of *Lemna minor* FucT/XylT. The hairpin RNA is expressed as a chimeric sequence (a chimeric hairpin RNA), where fragments of the two genes are fused together and expressed as one transcript. Expression of the FucT/XylT inhibitory sequence (denoted by FucT and XylT forward arrows and XylT and FucT reverse arrows; see FIG. 7) is driven by the operably linked AocsAocsAocsAmasPmas expression control element. RbcS leader, rubisco small subunit leader sequence; ADH1, intron of maize alcohol dehydrogenase 1 gene; nos-ter, *Agrobacterium tumefacians* nopaline synthetase (nos) terminator sequence.

FIG. 11 shows the XF03 construct comprising an RNAi expression cassette designed for double-gene RNAi knockout of *Lemna minor* FucT/XylT. The cassette expresses two RNAi hairpins, one targeting expression of FucT, the other targeting expression of XylT. Expression of the FucT inhibitory sequence (denoted by FucT forward and FucT reverse arrows; see FIG. 5) is driven by an operably linked expression control element comprising the *Lemna minor* ubiquitin promoter plus 5' UTR (LmUbq promoter) and intron (LmUbq intron) (see SEQ ID NO:7). Expression of the XylT inhibitory sequence (denoted by XylT forward and XylT reverse arrows; see FIG. 6) is driven by the operably linked AocsAocsAocsAmasPmas expression control element. RbcS leader, rubisco small subunit leader sequence; ADH1, intron of maize alcohol dehydrogenase 1 gene; nos-ter, *Agrobacterium tumefacians* nopaline synthetase (nos) terminator sequence.

FIG. 12 shows the mAbI04 construct that provides for co-expression of an IgG1 monoclonal antibody (referred to herein as mAbI) and the double-gene knockout of *Lemna minor* FucT and XylT, wherein a chimeric hairpin RNA targeting expression of the FucT and XylT is expressed. Expression of the FucT/XylT inhibitory sequence (denoted by FucT and XylT forward arrows and XylT and FucT reverse arrows; see FIG. 7) is driven by an operably linked expression control element comprising the *Spirodella polyrrhiza* ubiquitin promoter plus 5' UTR (SpUbq promoter) and intron (SpUbq intron) (see SEQ ID NO: 8). Expression of the IgG1 light chain is driven by an operably linked expression control element comprising the *L. minor* ubiquitin promoter plus 5' UTR (LmUbq promoter) and intron (LmUbq intron). Expression of the IgG1 heavy chain is driven by the operably linked AocsAocsAocsAmasPmas expression control element. RbcS leader, rubisco small subunit leader sequence; ADH1, intron of maize alcohol dehydrogenase 1 gene; nos-ter, *Agrobacterium tumefacians* nopaline synthetase (nos) terminator sequence.

FIG. 13 shows the mAbI05 construct that provides for co-expression of mAbI and the double-knockout of *Lemna minor* FucT and XylT, wherein two hairpin RNAs are expressed, one targeting expression of FucT, the other targeting expression of the XylT. Expression of the FucT inhibitory sequence (denoted by FucT forward and FucT reverse arrows; see FIG. 5) is driven by an operably linked expression control element comprising the *S. polyrrhiza* ubiquitin promoter plus 5' UTR (SpUbq promoter) and intron (SpUbq intron). Expression of the XylT inhibitory sequence (denoted by XylT forward and XylT reverse arrows; see FIG. 6) is driven by an operably linked expression control element comprising the *Lemna aequinoctialis* ubiquitin promoter plus 5' UTR (LaUbq promoter) and intron (LaUbq intron) (see SEQ ID NO:9). Expression of the IgG1 light chain is driven by an operably linked expression control element comprising the *L. minor* ubiquitin promoter plus 5' UTR (LmUbq promoter) and intron (LmUbq intron). Expression of the IgG1 heavy chain is driven by the operably linked AocsAocsAocsAmasPmas expression control element. RbcS leader, rubisco small subunit leader sequence; ADH1, intron of maize alcohol dehydrogenase 1 gene; nos-ter, *Agrobacterium tumefacians* nopaline synthetase (nos) terminator sequence.

FIG. 14 shows the mAbI01 construct that provides for expression of mAbI, where FucT and XylT expression are not suppressed. Expression of the IgG1 light chain and IgG1 heavy chain are independently driven by the operably linked AocsAocsAocsAmasPmas expression control element. RbcS leader, rubisco small subunit leader sequence; ADH1, intron of maize alcohol dehydrogenase 1 gene; nos-ter, *Agrobacterium tumefacians* nopaline synthetase (nos) terminator sequence. mAbI01 is referred to as the "wild-type" mAbI01 construct as the expressed m-AbI exhibits the glycosylation profile of wild-type *L. minor*.

FIGS. 15 and 16 show the primary screening data for transgenic RNAi *L. minor* plant lines comprising the XF02 construct of FIG. 10.

FIG. 17 shows primary screening data for transgenic RNAi *L. minor* plant lines comprising the mAbI04 construct of FIG. 12 and mAbI05 construct of FIG. 13.

FIG. 18 shows the structure and molecular weight of derivatized wild-type *L. minor* mAb N-glycans. "GnGn" represents the $GlcNAc_2Man_3GlcNAc_2$ N-glycan species, also referred to as a G0 N-glycan species. "GnGnX" represents the $GlcNAc_2Man_3GlcNAc_2$ N-glycan species with the plant-specific β(1,2)-xylose residue attached. "GnGnXF" represents the $GlcNAc_2Man_3GlcNAc_2$ N-glycan species with the plant-specific β(1,2)-xylose residue and plant-specific α(1,3)-fucose residue attached.

FIG. 19 shows that the wild-type mAbI01 construct (shown in FIG. 15) providing for expression of the mAbI monoclonal IgG1 antibody in *L. minor*, without RNAi suppression of *L. minor* FucT and XylT, produces an N-glycosylation profile with three major N-glycan species, including one species having the β1,2-linked xylose and one species having both the β1,2-linked xylose and core α1,3-linked fucose residues; this profile is confirmed with liquid chromatography mass spectrometry (LC-MS) (FIG. 20) and MALDI (FIG. 21) analysis.

FIG. 22 shows an overlay of the relative amounts of the various N-glycan species of mAbI produced in the wild-type *L. minor* line comprising the mAbI01 construct (no suppression of FucT or XylT) and in the two transgenic *L. minor* lines comprising the mAbI04 construct of FIG. 12 (providing for coexpression of mAbI and the chimeric RNAi construct targeting both *L. minor* FucT and XlT). Note the enrichment of the GnGn (i.e., G0) glycan species, with no β1,2-linked xylose or core α1,3-linked fucose residues attached, and the absence of the species having the β1,2-linked xylose or both the β1,2-linked xylose and core α1,3-linked fucose residues. "MGn" represents an N-glycan precursor, wherein the trimannose core structure, $Man_3GlcNAc_2$, has one N-acetylglucosamine attached to the 1,3 mannose arm. "GnM" represents an N-glycan precursor, wherein the trimannose core structure, $Man_3GlcNAc_2$, has one N-acetylglucosamine attached to the 1,6 mannose arm. These N-glycan precursors represent a trace amount of the total N-glycans present in the sample. This profile is confirmed with mass spec (LC-MS) (FIG. 23) and MALDI (FIG. 24) analysis.

FIG. 25 shows intact mass analysis of mAbI compositions produced in wild-type *L. minor* (line 20) comprising the mAbI01 construct. When XylT and FucT expression are not suppressed in *L. minor*, the recombinantly produced mAbI composition is heterogeneous, comprising at least 9 different glycoforms, with the $G0XF^3$ glycoform being the predominate species present. Note the very minor peak representing the G0 glycoform.

FIG. 26 shows intact mass analysis of mAbI compositions produced in transgenic *L. minor* (line 15) comprising the mAbI04 construct of FIG. 12. When XylT and FucT expression are suppressed in *L. minor* using this chimeric RNAi construct, the intact mAbI composition is substantially homogeneous for G0 N-glycans, with only trace amounts of precursor N-glycans present (represented by the GnM and MGn precursor glycan species). In addition, the mAbI composition is substantially homogeneous for the G0 glycoform, wherein both glycosylation sites are occupied by the G0 N-glycan species, with three minor peaks reflecting trace amounts of precursor glycoforms (one peak showing mAbI having an Fc region wherein the $C_H2$ domain of one heavy chain has a G0 glycan species attached to Asn 297, and the $C_H2$ domain of the other heavy chain is unglycosylated; another peak showing mAbI having an Fc region wherein the $C_H2$ domain of one heavy chain has a G0 glycan species attached to Asn 297, and the $C_H2$ domain of the other heavy chain has the GnM or MGn precursor glycan attached to Asn 297; and another peak showing mAbI having an Fc region wherein the Asn 297 glycosylation site on each of the $C_H2$ domains has a G0 glycan species attached, with a third G0 glycan species attached to an additional glycosylation site within the mAbI structure).

FIG. 27 shows intact mass analysis of the mAbI compositions produced in transgenic *L. minor* (line 72) comprising the mAbI05 construct of FIG. 13. When XylT and FucT expression are suppressed in *L. minor* using this construct, the intact mAbI composition is substantially homogeneous for G0 N-glycans, with only trace amounts of precursor N-glycan species present (represented by the GnM and MGn precursor glycan species). In addition, the mAbI composition is substantially homogeneous (at least 90%) for the G0 glycoform, with the same three minor peaks reflecting precursor glycoforms as obtained with the mAbI04 construct.

FIG. 28 summarizes two possible designs for targeting expression of individual FucT and XylT genes.

FIG. 29A shows the common oligomannosidic core structure of complex N-glycans of glycoproteins produced in plants and animals. In mammals, the core structure can include a fucose residue in which 1-position of the fucose is bound to 6-position of the N-acetylgucosamine in the reducing end through an a bond (i.e., $\alpha(1,6)$-linked fucose). FIG. 29B shows the plant-specific modifications to these N-glycans. The mammalian R groups can be one of the following: (a) R=GlcNAcβ(1,2); (b) R=Galβ(1,4)-GlcNAcβ(1,2); (c) R=NeuAcα(2,3)-Galβ(1,4)-GlcNAcβ(1,2); (d) R=NeuGcα(2,3)-Galβ(1,4)-GlcNAcβ(1,2); and (e) R=Galα(1,3)-Galβ(1,4)-GlcNAcβ(1,2). The plant R groups can be one of the following: (a) R=null; (b) R=GlcNAcβ(1,2);

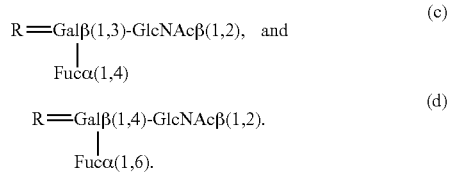

Abbreviations: Man, mannose; GlcNAc, N-acetylglucosamine; Xyl, xylose; Fuc, fucose; Gal, galactose; NeuAc (neuraminic acid (sialic acid);*, reducing end of sugar chain that binds to asparagine.

FIG. 30 shows the G0, G0X, and G0XF$^3$ species of N-linked glycans of glycoproteins referred to in the description and claims of the present invention, along with the alternate nomenclature used herein.

FIG. 31 sets forth the partial cDNA (SEQ ID NO: 19; coding sequence set forth in SEQ ID NO:20) sequence for the *Lemna minor* β1,2-xylosyltransferase (XylT) isoform #2, and partial amino acid (SEQ ID NO:21) sequence encoded thereby. Nucleotides denoted by the single underline (—) correspond to the XylT forward fragment within the RNAi expression cassette designed to inhibit expression of XylT (see FIG. 33); nucleotides denoted by the double underline (=) correspond to the spacer sequence within this RNAi expression cassette. The XylT reverse fragment of the RNAi expression cassette is the antisense of the XylT forward fragment shown here.

FIG. 32 sets forth an alignment of the *Lemna minor* XylT isoform #1 of SEQ ID NO:6 with the *Lemna minor* partial-length XylT isoform #2 of SEQ ID NO:21.

FIG. 33 sets forth one strategy for designing a single-gene RNAi knockout of *Lemna minor* XylT based on the partial DNA sequence for XylT isoform #2.

FIG. 34 sets forth one strategy for designing a double-gene RNAi knockout of *Lemna minor* FucT and XylT, where the XylT portion of the RNAi knockout is based on the partial DNA sequence for XylT isoform #2.

Figure 39:
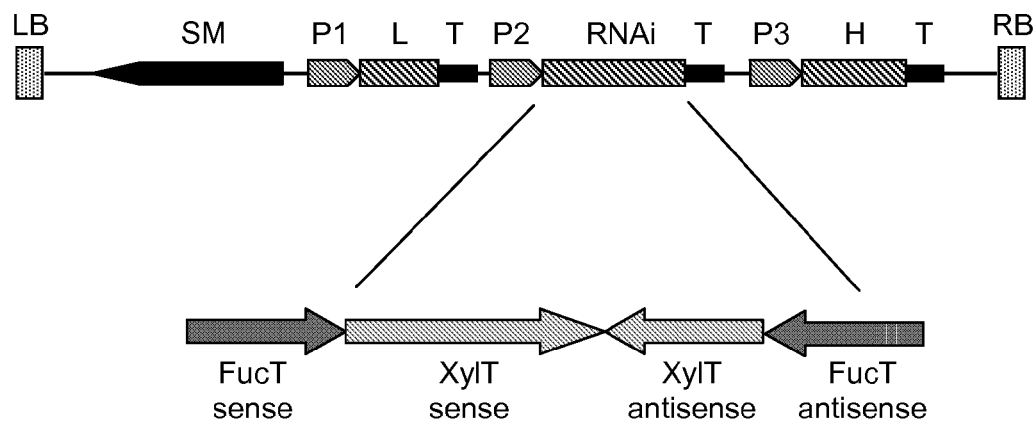

FIG. 39 shows a diagram of the MDXA04 binary expression vector for RNAi silencing of FucT and XylT activity in *Lemna*. Hatched regions show the position of the heavy (H) and light (L) chain variable region gene sequences of fully human mAb1 kappa antibody MDX-060 and the chimeric hairpin RNA (RNAi) designed to target silencing of endogenous *Lemna* genes encoding FucT and XylT. Promoters: P1, P2, and P3; terminator: T; selectable marker: SM; left border: LB; right border, RB. The MDXA01 expression vector used to express the MDX-060 mAb in wild-type *Lemna* did not contain the hairpin RNA region.

Figure 40:
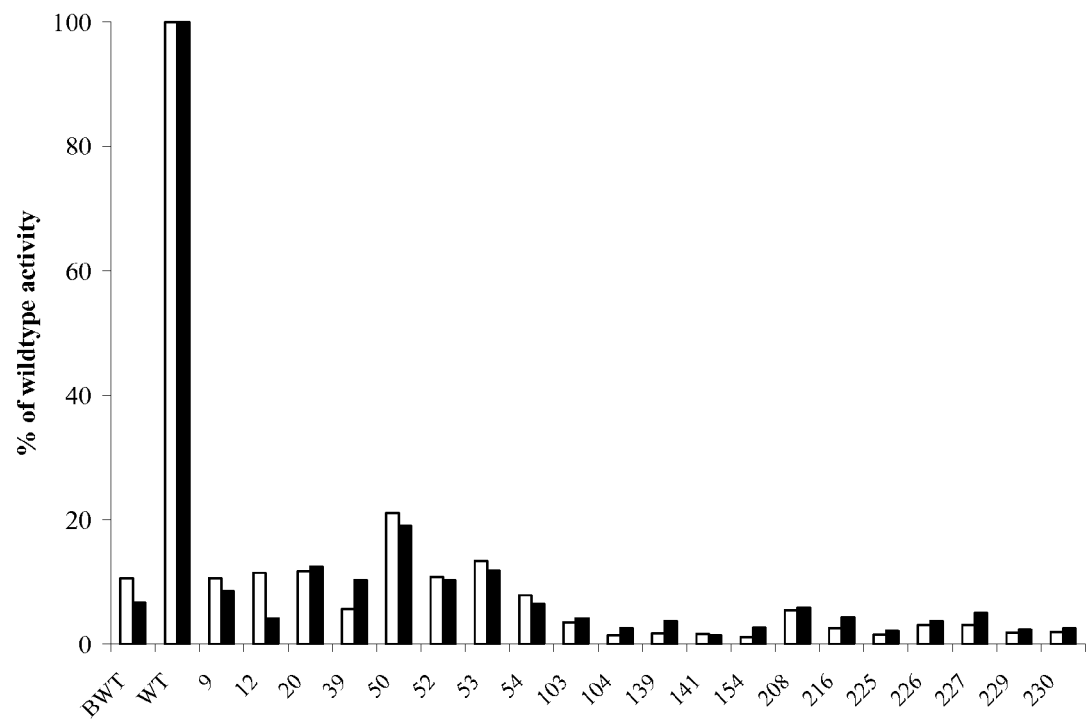

FIG. 40 shows glycosyltransferase activity in *Lemna* wild-type and MDX-060 LEX$^{Opt}$ RNAi lines. Microsomal membranes from wild-type (WT) and MDX-060 LEX$^{Opt}$ RNAi (line numbers are indicated) plants were incubated in the presence of a reaction buffer containing GDP-Fuc, UDP-Xyl and GnGn-dabsyl-peptide acceptor. Mass peaks corresponding to fucosylated (white bars) or xylosylated (black bars) products synthesized by microsomes from each line were measured by positive reflectron mode MALDI-TOF MS and normalized, in percent, to the WT positive control. Boiled wildtype membranes (BWT) indicate background ion counts.

Figure 41B:
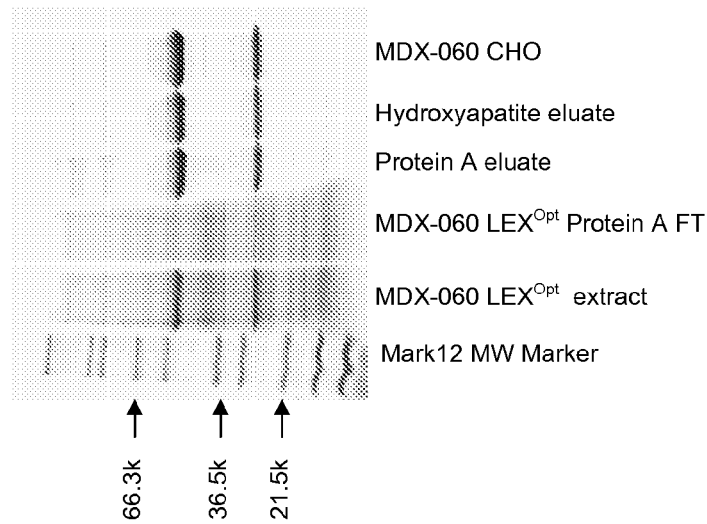
Figure 41A:
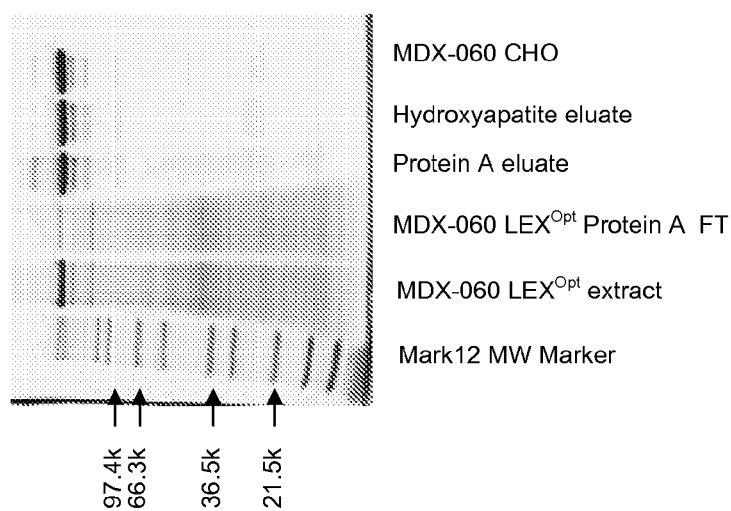

FIG. 41 shows SDS-PAGE of plant extracts and protein A or hydroxyapatite purified samples from MDX-060 LEX$^{Opt}$ under non-reducing (FIG. 41A) and reducing (FIG. 41B) conditions, respectively. MAb purified from a CHO cell line (MDX-060 CHO) was used as a positive control. Mark12 molecular weight markers were included on the gels. Gels were stained with Colloidal Blue.

Figure 42:
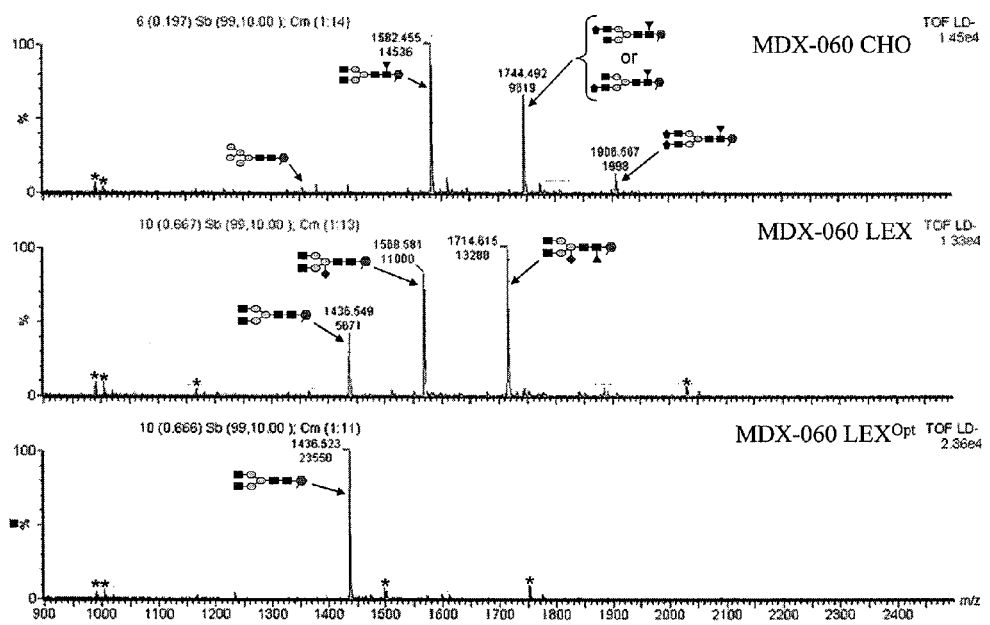

FIG. 42 shows the spectra obtained from negative, reflectron mode MALDI-TOF mass spectrometric analysis of 2-AA labeled N-glycans released from MDX-060 mAbs expressed in CHO (MDX-060 CHO), wild-type *Lemna* (MDX-060 LEX), or *Lemna* transformed with the XylT/FucT RNAi construct (MDX-060 LEX$^{Opt}$). Significant peaks are identified by the corresponding mass ([M−H]$^-$). The * indicates the location of matrix artefacts.

Figure 43:
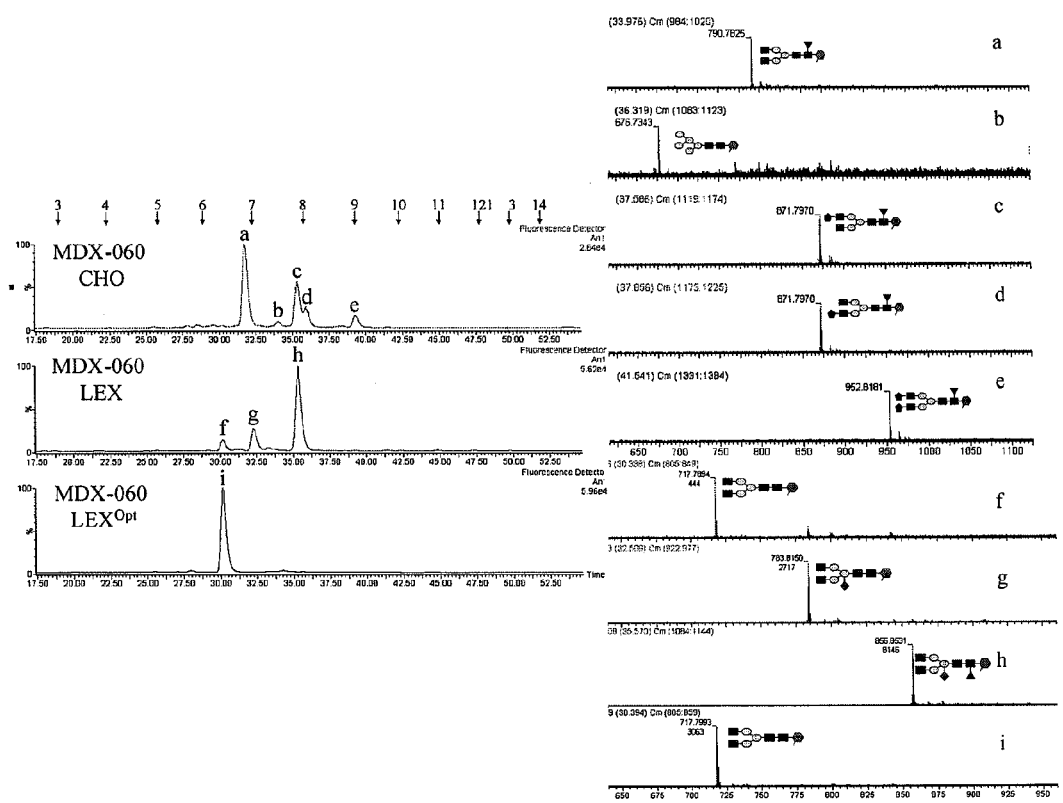

FIG. 43 shows the spectra obtained from NP-HPLC-QTOF MS analysis of 2-AA labeled N-glycans released from MDX-060 mAbs expressed in CHO (MDX-060 CHO), wild-type *Lemna* (MDX-060 LEX), or *Lemna* transformed with the XylT/FucT RNAi construct (MDX-060 LEX$^{Opt}$). 2-AA labeled N-glycans were separated by normal phase chromatography and detected by fluorescence. The most abundant peaks from each sample (labeled a-i) were characterized by on-line negative mode QTOF MS and their corresponding QTOF mass spectra ([M−2H]$^{2-}$) are shown.

Figure 44:
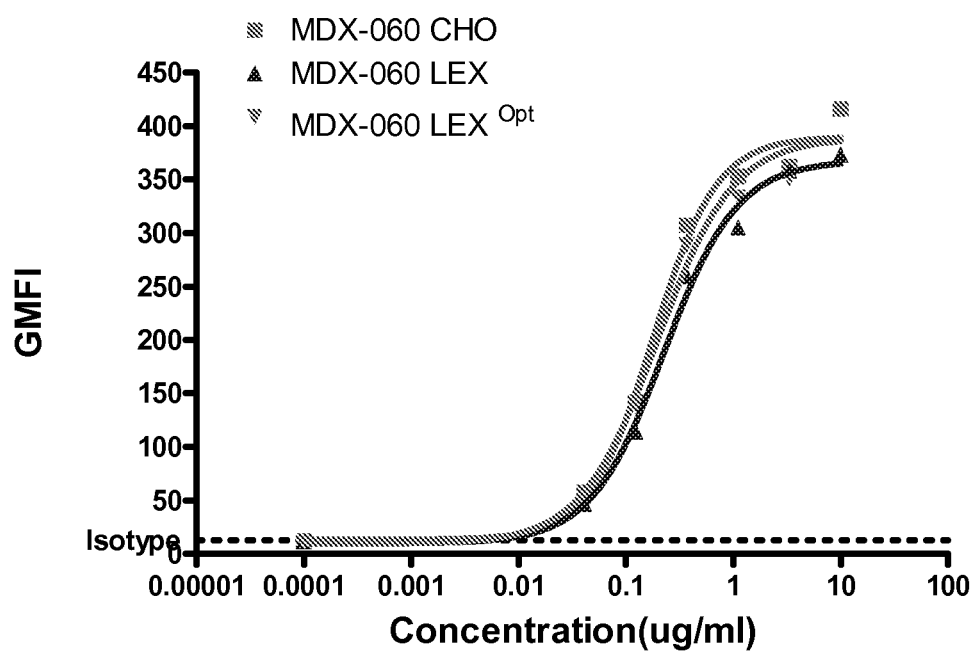

FIG. 44 shows in vitro activity of MDX-060 mAbs as measured by flow cytometric analysis of MDX-060 CHO, LEX, or glyco-optimized LEX$^{Opt}$ mAb binding to CD30 expressed on L540 cells. L540 cells were incubated with increasing concentrations of the indicated antibody as outlined in Example 6 herein below. Geo Mean Fluorescence Intensity (GMFI) is plotted against the various concentrations of mAb used. ■: MDX-060 CHO; ▲: MDX-060 LEX; ▼: MDX-060 LEX$^{opt}$.

Figure 45:
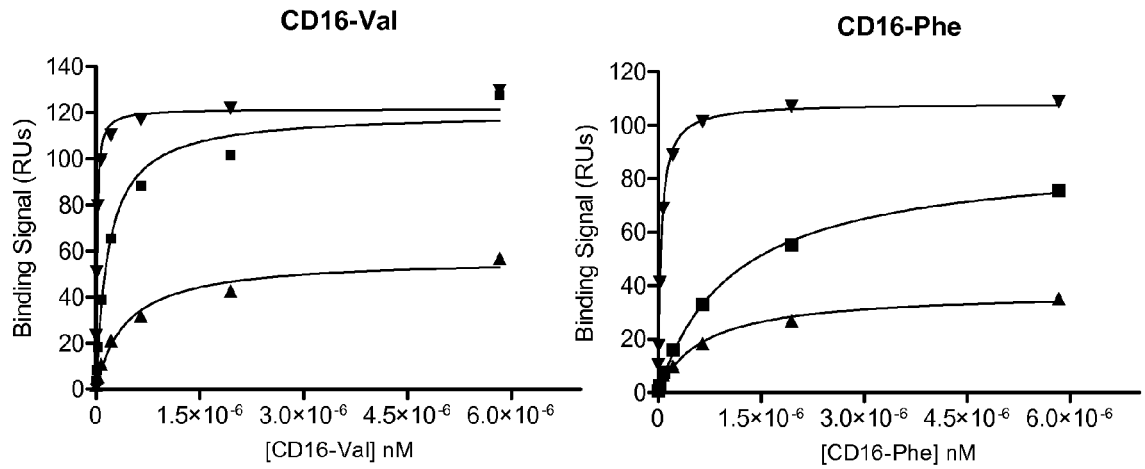

FIG. 45 shows equilibrium binding of glyco-optimized and wild-type mAb to two different human FcRγIIIa allotypes (Val$^{158}$ or Phe$^{158}$). The binding signal as a function of FcRγIIIa was fit to a one-site binding model. ■: MDX-060 CHO; ▲: MDX-060 LEX; ▼: MDX-060 LEX$^{opt}$.

Figure 46:
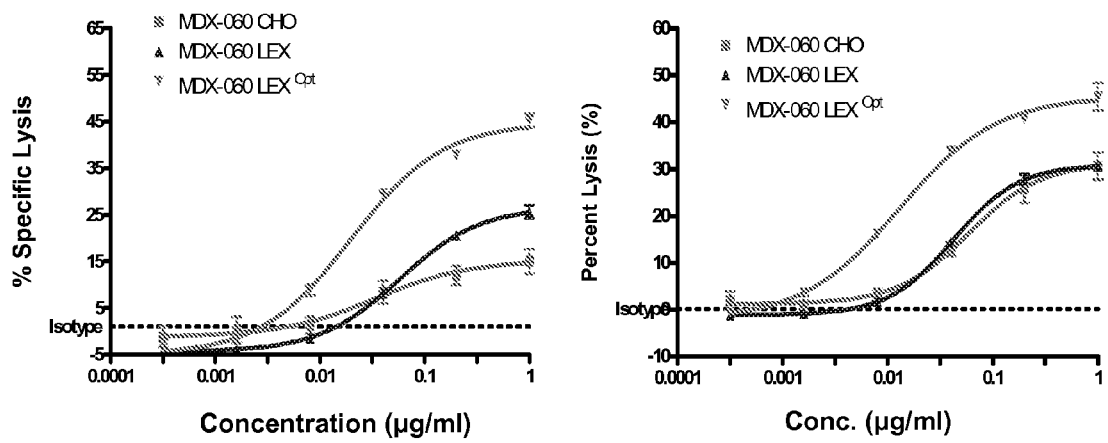

FIG. 46 shows ADCC activity of MDX-060 mAb derived from CHO, LEX (wild-type Lemna glycosylation), or LEX$^{Opt}$ (RNAi transgenic Lemna). Human effector cells from a FcγRIIIaPhe$^{158}$ homozygote donor and a FcγRIIaPhe/Val$^{158}$ heterozygote donor were incubated with BATDA-labeled L540 cells at an effector:target ratio of 50:1 in the presence of increasing concentrations of the indicated antibodies. Specific percent lysis at each mAb concentration is plotted. Human mAb1 not recognizing antigen on L540 cells was used as an isotype control in all experiments. EC$_{50}$ values (μg/mL), binding constants and maximal percent lysis were calculated using GraphPad Prism 3.0 software. ■: MDX-060 CHO; ▲: MDX-060 LEX; ▼: MDX-060 LEX$^{opt}$.

Figure 47:
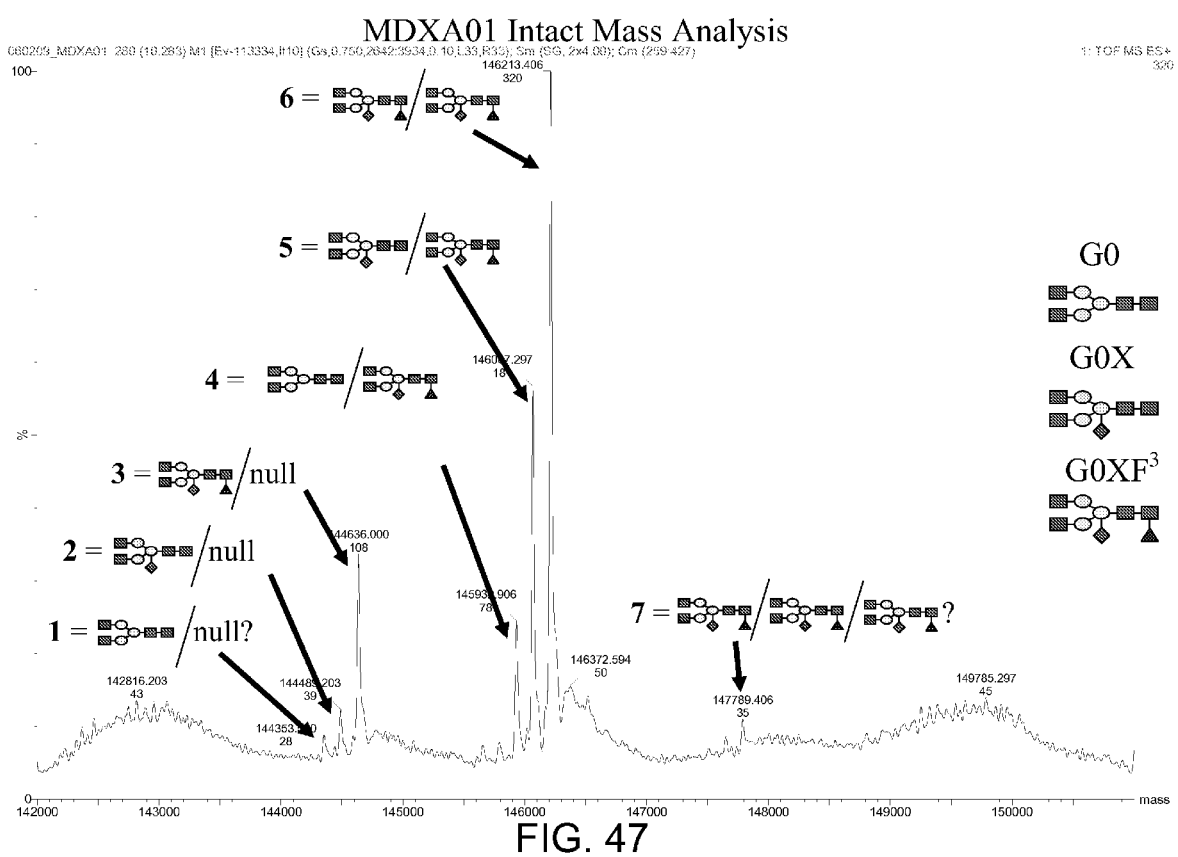

FIG. 47 shows intact mass analysis of the MDX-060 LEX mAb compositions produced in wild-type L. minor comprising the MDXA01 construct. When XylT and FucT expression are not suppressed in L. minor, the recombinantly produced MDX-060 LEX mAb composition comprises at least 7 different glycoforms, with the G0XF$^3$ glycoform being the predominate species present. Note the absence of a peak representing the G0 glycoform.

Figure 48:
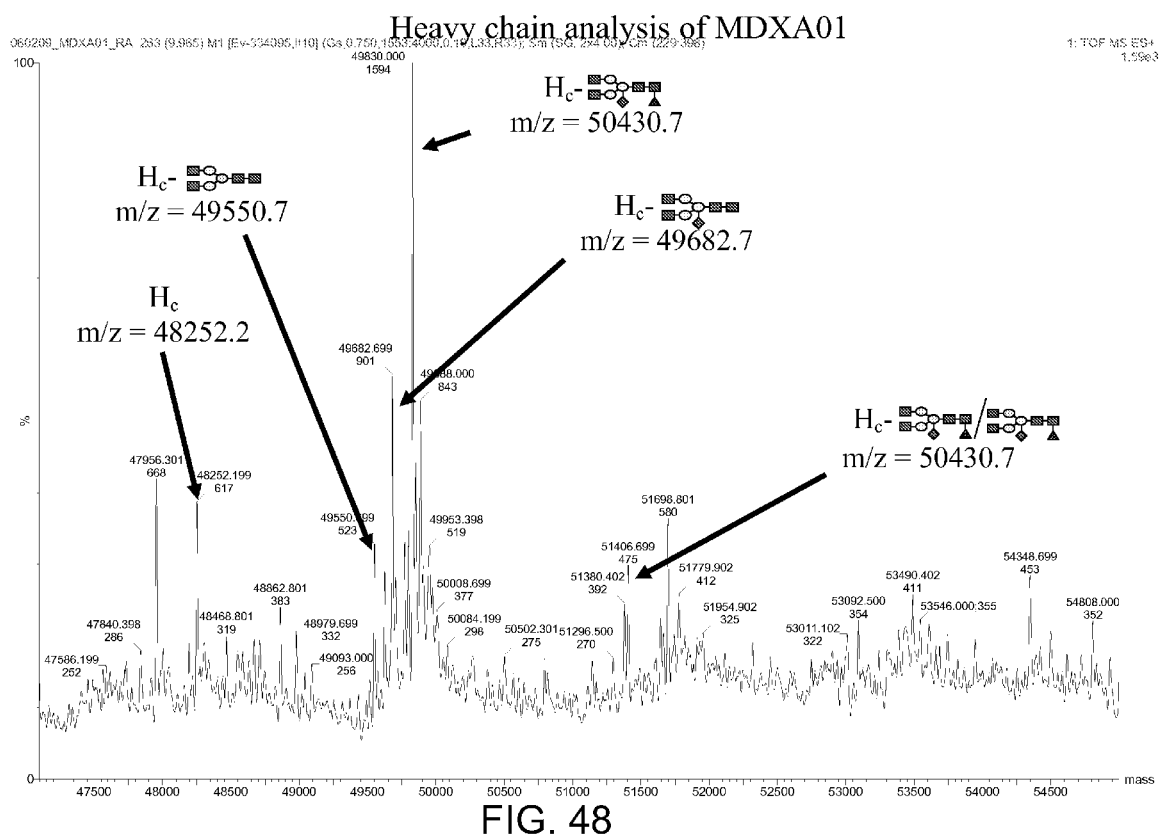

FIG. 48 shows glycan mass analysis of the heavy chain of the MDX-060 LEX mAb produced in wild-type L. minor comprising the MDXA01 construct. When XylT and FucT expression are not suppressed in L. minor, the predominate N-glycan species present is G0XF$^3$, with additional major peaks reflecting the G0X species. Note the minor presence of the G0 glycan species.

Figure 49:
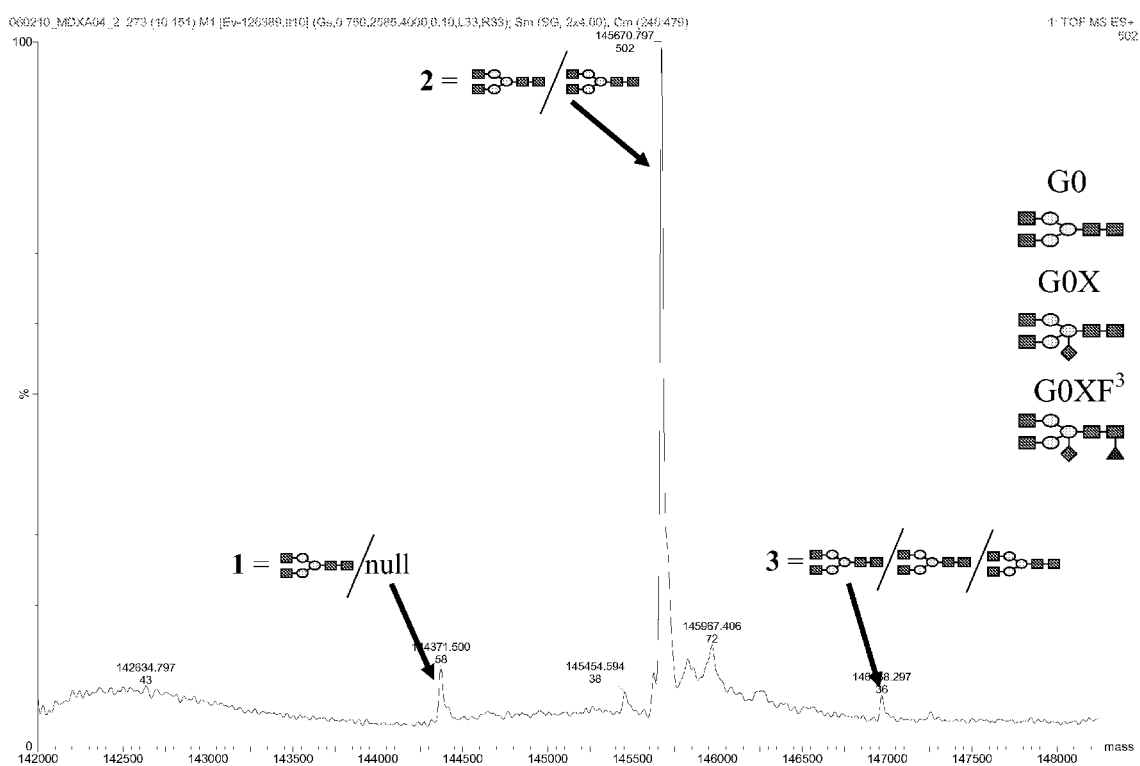

FIG. 49 shows intact mass analysis of the MDX-060 LEX$^{Opt}$ mAb compositions produced in transgenic L. minor comprising the MDXA04 construct. When XylT and FucT expression are suppressed in L. minor, the intact mAb composition contains only G0 N-glycans. In addition, the composition is substantially homogeneous for the G0 glycoform (peak 2), wherein both glycosylation sites are occupied by the G0 N-glycan species, with two minor peaks reflecting trace amounts of precursor glycoforms (peak 1, showing mAb having an Fc region wherein the C$_H$2 domain of one heavy chain has a G0 glycan species attached to Asn 297, and the C$_H$2 domain of the other heavy chain is unglycosylated; and peak 3, showing mAb having an Fc region wherein the Asn 297 glycosylation site on each of the C$_H$2 domains has a G0 glycan species attached, with a third G0 glycan species attached to an additional glycosylation site within the mAb structure).

Figure 50:
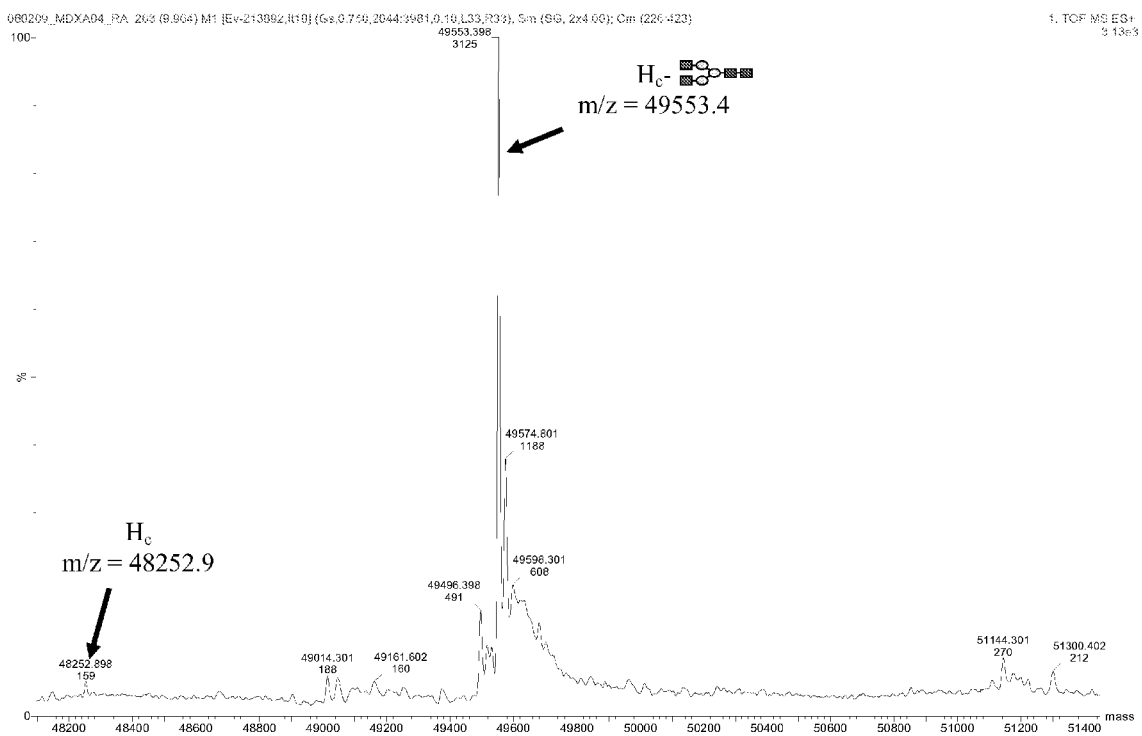

FIG. 50 shows glycan mass analysis of the heavy chain of the MDX-060 LEX$^{Opt}$ mAb produced in transgenic L. minor comprising the MDXA04 construct. When XylT and FucT expression are suppressed in L. minor, the only readily detectable N-glycan species attached to the Asn 297 glycosylation sites of the C$_H$2 domains of the heavy chains is G0.

Figure 51A:
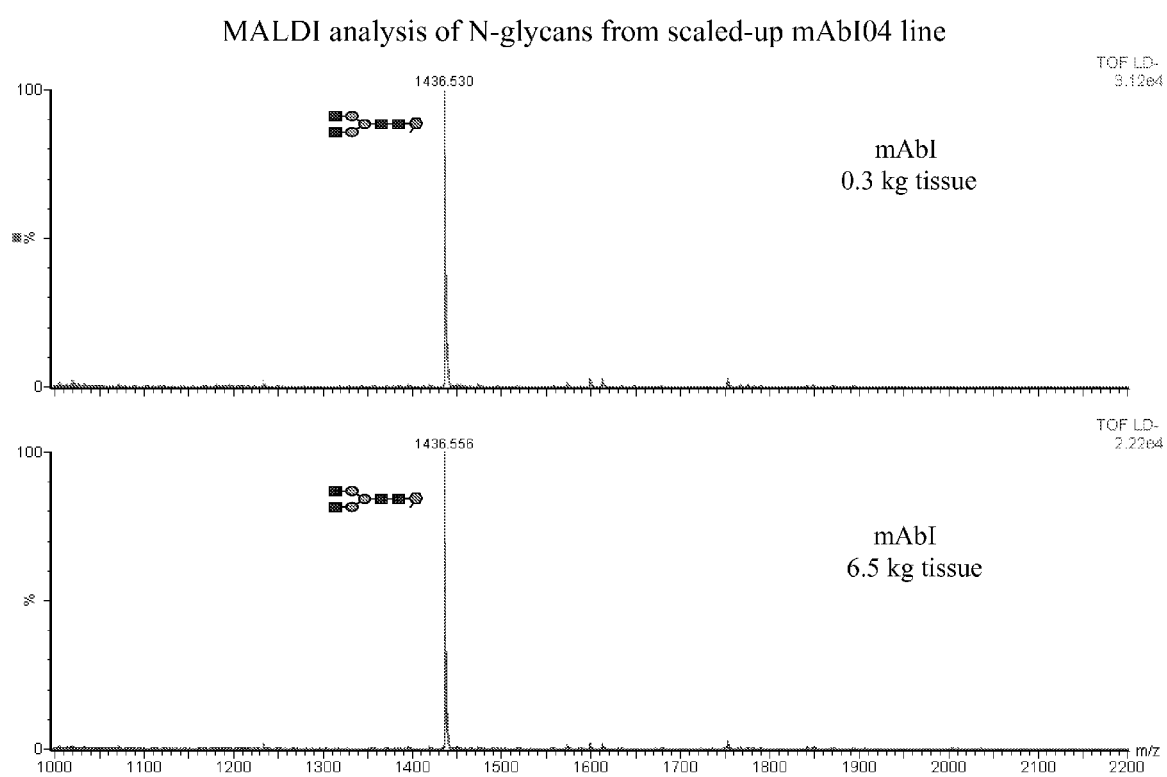
Figure 51B:
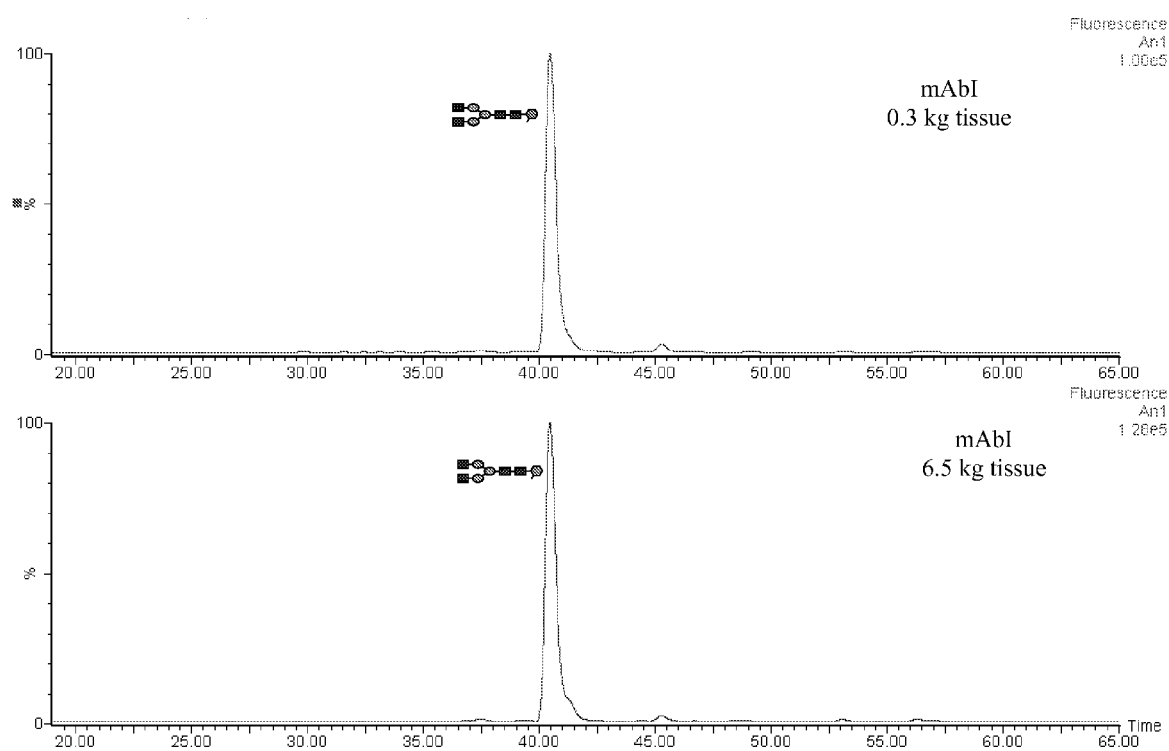

FIGS. 51A (MALDI analysis) and 51B (HPLC analysis) show that the homogeneous glycosylation profile exhibited by mAbI produced in transgenic L. minor (line 24) comprising the mAbI04 RNAi construct was consistently observed with scaled-up production. This glycosylation profile was consistent over the 8-month period of continuous maintenance of the transgenic line via clonal expansion.

Figure 12:
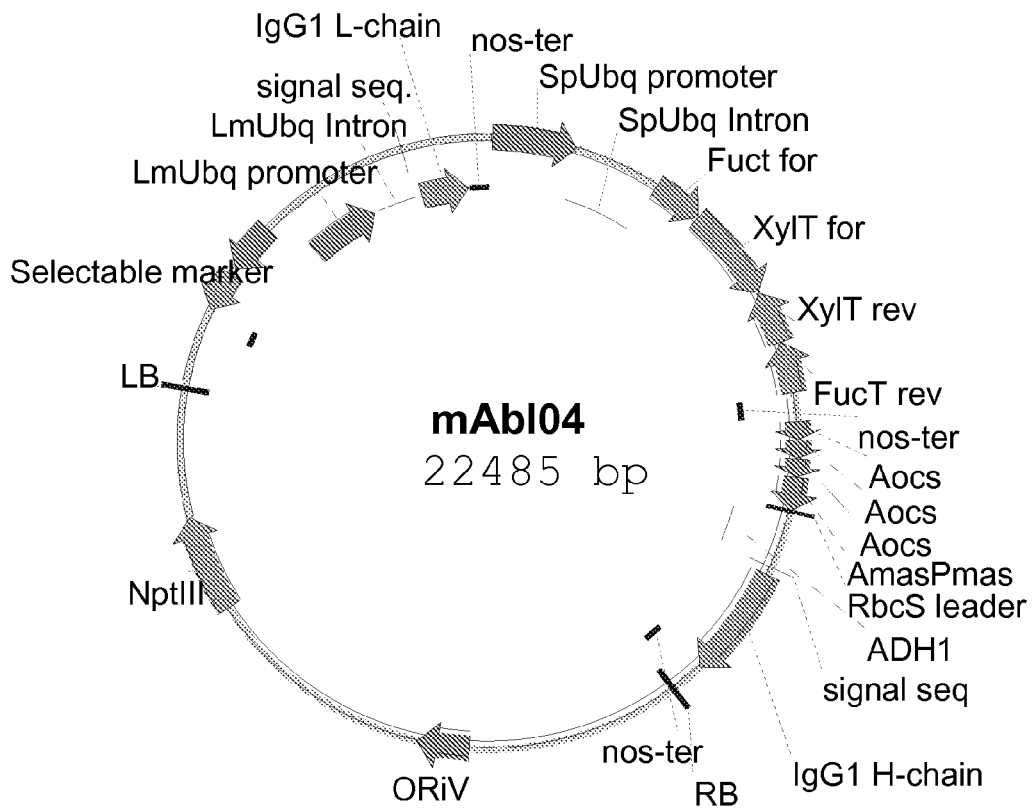
Figure 52:
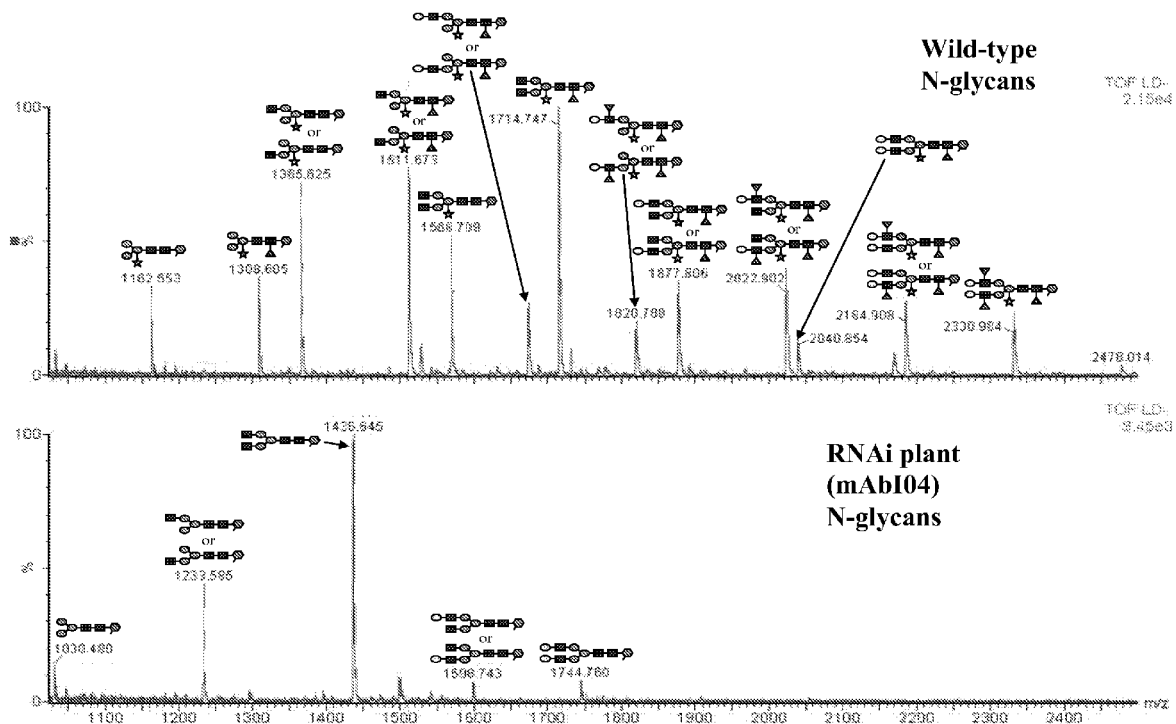

FIG. 52 shows that suppression of FucT and XylT expression using the chimeric RNAi mAbI04 construct of FIG. 12 results in endogenous glycoproteins having a homogeneous glycosylation pattern consistent with that observed for recombinant glycoproteins. For this figure, the β1,2-linked xylose residue attached to the trimannose core structure is designated by the star symbol.

Figure 53:
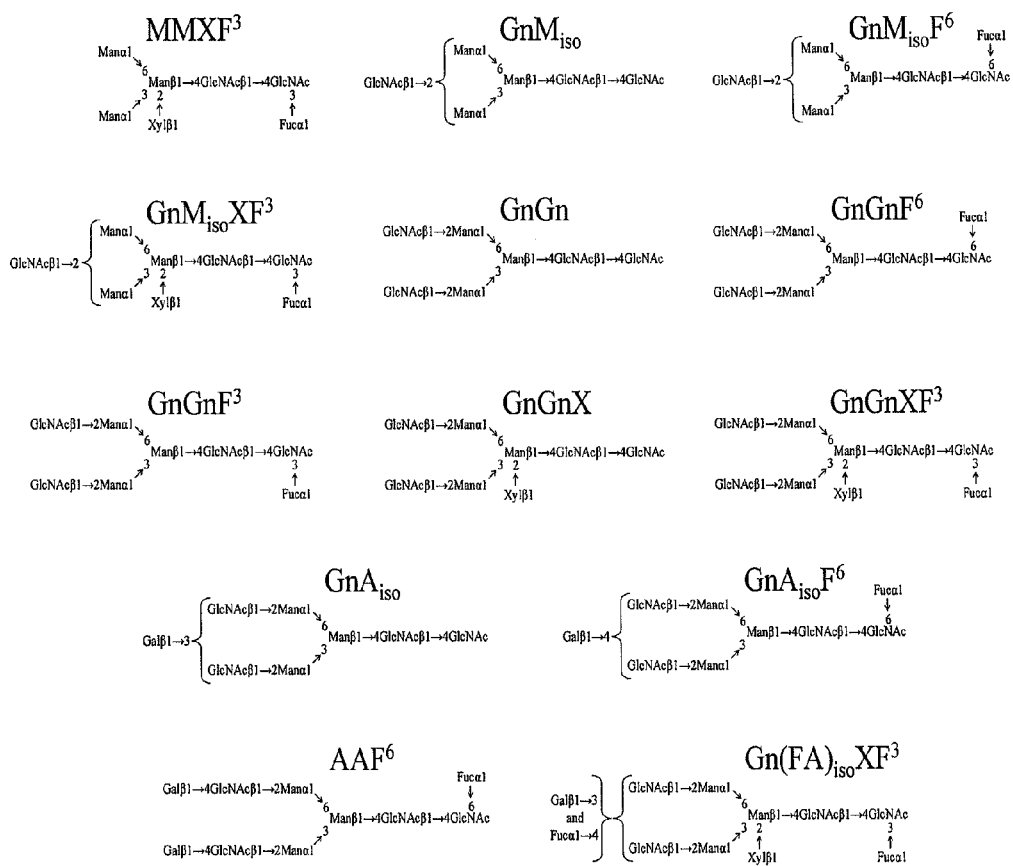

FIG. 53 shows the structure of complex N-glycans described in Example 6 below. M=mannose; Gn=N-acetylglucosamine; A=galactose; X=xylose; F=fucose.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides compositions and methods for altering the N-glycosylation pattern of homologous and heterologous polypeptides produced in a plant, particularly a plant that serves as an expression system for recombinant proteins of interest. The methods comprise the use of nucleotide constructs comprising one or more sequences that are capable of inhibiting expression of α1,3-fucosyltransferase (FucT) and β1,2-xylosyltransferase (XylT) in a plant. Compositions for use in practicing the methods of the invention, and compositions comprising glycoproteins having a substantially homologous glycosylation profile, including glycan-optimized monoclonal antibodies with improved effector function, are also provided.

Definitions

"Polypeptide" refers to any monomeric or multimeric protein or peptide.

"Biologically active polypeptide" refers to a polypeptide that has the capability of performing one or more biological functions or a set of activities normally attributed to the polypeptide in a biological context. Those skilled in the art will appreciate that the term "biologically active" includes polypeptides in which the biological activity is altered as compared with the native protein (e.g., suppressed or enhanced), as long as the protein has sufficient activity to be of interest for use in industrial or chemical processes or as a therapeutic, vaccine, or diagnostics reagent. Biological activity can be determined by any method available in the art. For example, the biological activity of members of the interferon family of proteins can be determined by any of a number of methods including their interaction with interferon-specific antibodies, their ability to increase resistance to viral infection, or their ability to modulate the transcription of interferon-regulated gene targets. In like manner, biological activity of monoclonal antibodies can be determined by any of a number of methods including, but not limited to, assays for measuring binding specificity and effector function, for example, using assays for antibody-dependent cellular cytotoxicity (ADCC) and complement-dependent cytotoxicity (CDC) activity.

By "host cell" is intended a cell that comprises a heterologous nucleic acid sequence of the invention. Though the nucleic acid sequences of the invention, and fragments and variants thereof, can be introduced into any cell of interest, of particular interest are plant host cells. In some embodiments, the plant host cells are cells of a plant that serves as a host for expression of recombinant proteins, for example, a plant expression system for production of recombinant mammalian proteins of interest as noted herein below.

By "heterologous polypeptide of interest" is intended a polypeptide that is not expressed by the host cells in nature. Conversely, a "homologous polypeptide" is intended a polypeptide that is naturally produced within the cells of the host. Heterologous and homologous polypeptides that undergo post-translational N-glycosylation are referred to herein as heterologous or homologous glycoproteins. In accordance with the methods of the present invention, the N-glycosylation pattern of both heterologous and homologous glycoproteins is altered within the cells of a plant host so that these glycoproteins have an N-glycosylation pattern that is more similar to that observed with mammalian hosts.

Exemplary heterologous polypeptide and heterologous nucleotide sequences of interest include, but are not limited to, sequences that encode mammalian polypeptides, such as insulin, growth hormone, α-interferon, β-interferon, β-glucocerebrosidase, β-glucoronidase, retinoblastoma protein, p53 protein, angiostatin, leptin, erythropoietin (EPO), granulocyte macrophage colony stimulating factor, plasminogen, tissue plasminogen activator, blood coagulation factors, for example, Factor VII, Factor VIII, Factor IX, and activated protein C, alpha 1-antitrypsin, monoclonal antibodies (mAbs), Fab fragments, single-chain antibodies, cytokines, receptors, hormones, human vaccines, animal vaccines, peptides, and serum albumin.

For purposes of the present invention, the terms "N-glycan," "N-linked glycan," and "glycan" are used interchangeably and refer to an N-linked oligosaccharide, e.g., one that is or was attached by an N-acetylglucosamine (GlcNAc) residue linked to the amide nitrogen of an asparagine residue in a protein. The predominant sugars found on glycoproteins are glucose, galactose, mannose, fucose, N-acetylgalactosamine (GalNAc), N-acetylglucosamine (GlcNAc), and sialic acid (e.g., N-acetyl-neuraminic acid (NeuAc)). The processing of the sugar groups occurs cotranslationally in the lumen of the ER and continues in the Golgi apparatus for N-linked glycoproteins.

Figure 29A:
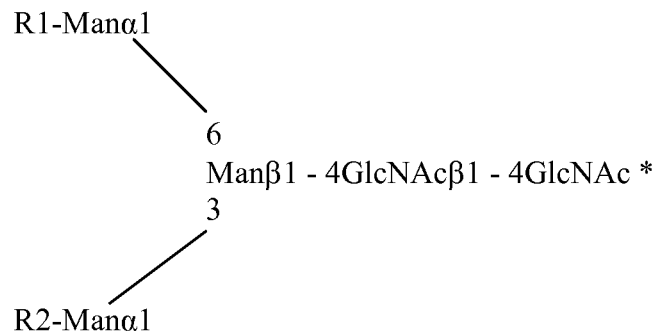
Figure 29B:
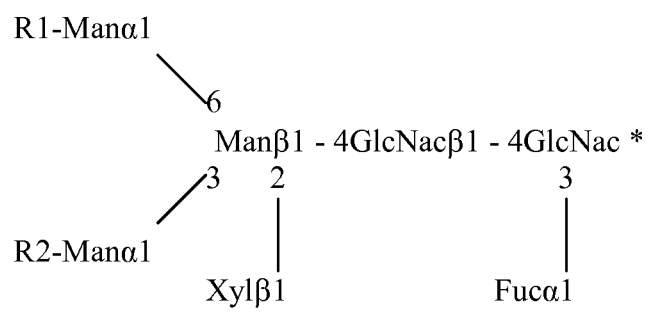

By "oligomannosidic core structure" or "trimannose core structure" of a complex N-glycan is intended the core structure shown in FIG. 29A, wherein the core comprises three mannose (Man) and two N-acetylglucosamine (GlcNAc) monosaccharide residues that are attached to the asparagine residue of the glycoprotein. The asparagine residue is generally within the conserved peptide sequence Asn-Xxx-Thr or Asn-Xxx-Ser, where Xxx is any residue except proline, aspartate, or glutamate. Subsequent glycosylation steps yield the final complex N-glycan structure. The trimannose core structure is denoted herein as "$Man_3GlcNAc_2$."

The N-glycans attached to glycoproteins differ with respect to the number of branches (antennae) comprising peripheral sugars (e.g., GlcNAc, galactose, fucose, and sialic acid) that are added to the trimannose core structure. N-glycans are commonly classified according to their branched constituents (e.g., complex, high mannose, or hybrid). A "complex" type N-glycan typically has at least one GlcNAc attached to the 1,3 mannose arm and at least one GlcNAc attached to the 1,6 mannose arm of a "trimannose" core. Where one GlcNAc is attached to each mannose arm, the species of N-linked glycan is denoted herein as "$GlcNAc_2Man_3GlcNAc_2$" or "GnGn." Where only one GlcNac is attached, the N-glycan species is denoted herein as "$GlcNAc_1Man_3GlcNAc_2$", wherein the GlcNac is attached to either the 1,3 mannose arm (denoted "MGn" herein) or the 1,6 mannose arm (denoted "GnM" herein) (see FIG. 30). Complex N-glycans may also have galactose ("Gal") or N-acetylgalactosamine ("GalNAc") sugar residues that are optionally modified with sialic acid or derivatives (e.g., "NeuAc," where "Neu" refers to neuraminic acid and "Ac" refers to acetyl). Where a galactose sugar residue is attached to each GlcNAc on each mannose arm, the species of N-linked glycan is denoted herein as "$Gal_2GlcNAc_2Man_3GlcNAc_2$." Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "high mannose" type N-glycan has five or more mannose residues. A "hybrid" N-glycan has at least one GlcNAc on the terminal of the 1,3 mannose arm of the trimannose core and zero or more mannoses on the 1,6 mannose arm of the trimannose core.

The terms "G0 glycan" and "G0 glycan structure" and "G0 glycan species" are used interchangeably and are intended to mean the complex N-linked glycan having the $GlcNAc_2Man_3GlcNAc_2$ structure, wherein no terminal sialic acids (NeuAcs) or terminal galactose (Gal) sugar residues are present. If a G0 glycan comprises a fucose ("Fuc") residue attached to the trimannose core structure, it is referred to herein as a "$G0F^3$ glycan" (having the plant-specific α1,3-linked fucose residue) or "$G0F^6$ glycan" (having the mammalian α1,6-linked fucose residue). In plants, a G0 glycan comprising the plant-specific β1,2-linked xylose residue attached to the trimannose core structure is referred to herein as a "G0X glycan," and a G0 glycan comprising both the plant-specific β1,2-linked xylose residue and plant-specific α1,3-linked fucose residue attached to the trimannose core structure is referred to herein as a "$G0XF^3$ glycan."

The terms "G1 glycan" and "G1 glycan structure" and "G1 glycan species" are used interchangeably and are intended to mean the complex N-linked glycan having the $GlcNAc_2Man_3GlcNAc_2$ structure, wherein one terminal galactose (Gal) residue is attached to either the 1,3 mannose or 1,6 mannose arm, and no terminal sialic acids are present. The terms "G2 glycan" and "G2 glycan structure" and "G2 glycan species" are used interchangeably and are intended to mean the complex N-linked glycan having the $GlcNAc_2Man_3GlcNAc_2$ structure, wherein a terminal galactose (Gal) residue is attached to the 1,3 mannose arm and the 1,6 mannose arm, and no terminal sialic acids are present.

The term "glycoform" as used herein refers to a glycoprotein containing a particular carbohydrate structure or structures. Thus, for example, a "G0 glycoform" refers to a glycoprotein that comprises only G0 glycan species attached to its glycosylation sites. It is recognized that a glycoprotein having more than one glycosylation site can have the same glycan species attached to each glycosylation site, or can have different glycan species attached to different glycosylation sites. In this manner, different patterns of glycan attachment yield different glycoforms of a glycoprotein.

The term "glycosylation profile" is intended to mean the characteristic "fingerprint" of the representative N-glycan species that have been released from a glycoprotein composition or glycoprotein product, either enzymatically or chemically, and then analyzed for their carbohydrate structure, for example, using LC-HPLC, or MALDI-TOF MS, and the like. See, for example, the review in *Current Analytical Chemistry*, Vol. 1, No. 1 (2005), pp. 28-57; herein incorporated by reference in its entirety.

The terms "substantially homogeneous," "substantially uniform," and "substantial homogeneity" in the context of a glycosylation profile for a glycoprotein composition or glycoprotein product are used interchangeably and are intended to mean a glycosylation profile wherein at least 80%, at least 85%, at least 90%, 91%, 92%, 93%, 94%, 95%, 96%, 97%, 98%, or at least 99% of the total N-glycan species within the profile are represented by one desired N-glycan species, with a trace amount of precursor N-glycan species appearing in the profile. By "trace amount" is intended that any given precursor N-glycan species that is present in the glycosylation profile is present at less than 5%, preferably less than 4%, less than 3%, less than 2%, less than 1%, and even less than 0.5% or even less than 0.1% of the total amount of N-glycan species appearing in the profile. By "precursor" N-glycan species is intended an N-glycan species that is incompletely processed. Examples of precursor N-glycan species present in trace amounts in the glycoprotein compositions or glycoprotein products of the invention, and thus appearing in the glycosylation profiles thereof, are the Man3GlcNAc2, MGn (GlcNac1Man3GlcNAc2 wherein GlcNac1 is attached to the 1,3 mannose arm), and GnM (GlcNac1Man3GlcNAc2 wherein GlcNac1 is attached to the 1,6 mannose arm) precursor N-glycan species described above.

Thus, for example, where the desired N-glycan species within a glycoprotein product or composition is G0, a substantially homogeneous glycosylation profile for that product or composition would be one wherein at least 80%, at least 85%, at least 90%, 91%, 92%, 93%, 94%, 95%, 96%, 97%, 98%, or at least 99% of the total amount of N-glycan species appearing in the glycosylation profile for the product or composition is represented by the G0 glycan species, with a trace amount of precursor N-glycan species appearing in the glycosylation profile. For such a composition, a representative precursor N-glycan species appearing in its glycosylation profile would be the Man3GlcNAc2, MGn (GlcNac1Man3GlcNAc2 wherein GlcNac1 is attached to the 1,3 mannose arm), and GnM (GlcNac1Man3GlcNAc2 wherein GlcNac1 is attached to the 1,6 mannose arm) precursor N-glycan species described above.

The terms "substantially homogeneous," "substantially uniform," and "substantial homogeneity" in the context of a glycoprotein composition or glycoprotein product are used interchangeably and are intended to mean the glycoprotein product or glycoprotein composition wherein at least 80%, at least 85%, at least 90%, 91%, 92%, 93%, 94%, 95%, 96%, 97%, 98%, or at least 99% of the glycoprotein present in the product or composition is represented by one desired glycoform, with a trace amount of precursor or undesired glycoforms being present in the composition. By "trace amount" is intended that any given precursor or undesired glycoform that is present in the glycoprotein product or composition is present at less than 5%, preferably less than 4%, less than 3%, less than 2%, less than 1%, and even less than 0.5% or even less than 0.1% of the total glycoprotein. By "precursor" glycoform is intended a glycoform wherein at least one glycosylation site is either unglycosylated, or is occupied by an N-glycan species that represents a precursor of the desired N-glycan species, or a glycoform wherein one or more additional glycosylation sites is present, relative to the desired glycoform, and is occupied by (i.e., has attached thereto) the desired N-glycan species or an undesired N-glycan species.

Thus, for example, a substantially homogeneous glycoprotein composition or product comprising the G0 glycoform is a composition or product wherein at least 80%, 80%, at least 85%, at least 90%, 91%, 92%, 93%, 94%, 95%, 96%, 97%, 98%, or at least 99% of the glycoprotein present in the product or composition is represented by the G0 glycoform, wherein all anticipated glycosylation sites are occupied by the G0 glycan species, with a trace amount of precursor or undesired glycoforms being present in the composition. In such a composition, a representative precursor glycoform would be one in which glycosylation sites are unoccupied, and an exemplary undesired glycoform would be a glycoform having a mixture of G0 glycan and G0X or G0XF3 glycan species attached to its glycosylation sites.

The term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. Antibodies represent one of the many glycoproteins contemplated by the methods and compositions of the present invention. Derivatives of antibodies are also contemplated by the present invention. Derivatives include fusion proteins comprising an immunoglobulin or portion thereof, such as an Fc region having a $C_H2$ domain.

The term "monoclonal antibody" as used herein refers to an antibody obtained from a population of substantially homogeneous antibodies, i.e., the individual antibodies comprising the population are identical except for possible naturally occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRS) or hypervariable regions both in the light-chain and the heavy-chain variable domains. The more highly conserved portions of variable domains are called the framework (FR) regions. The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991) *NIH Publ. No.* 91-3242, Vol. I, pages 647-669).

The constant domains are not involved directly in binding an antibody to an antigen, but exhibit various effecter functions, such as Fc receptor (FcR) binding, participation of the antibody in antibody-dependent cellular cytotoxicity (ADCC), opsonization, initiation of complement-dependent cytotoxicity (CDC activity), and mast cell degranulation.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8 (10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes mediate antibody-dependent cell-mediated cytotoxicity (ADCC) activity.

Immunoglobulins have conserved N-linked glycosylation of the Fc region of each of the two heavy chains. Thus, for example, immunoglobulins of the IgG type have glycosylated $C_H2$ domains bearing N-linked oligosaccharides at asparagine 297 (Asn-297). Different glycoforms of immunoglobulins exist depending upon the particular N-glycan species attached to each of these two glycosylation sites, and depending upon the degree to which both sites are glycosylated within an immunoglobulin composition.

"Nucleotide sequence of interest" as used herein with reference to expression of heterologous polypeptides refers to any polynucleotide sequence encoding a heterologous polypeptide intended for expression in a host, particularly a plant host, for example, in a higher plant, including members of the dicotyledonaceae and monocotyledonaceae. For example, polynucleotide sequences encoding therapeutic (e.g., for veterinary or medical uses) or immunogenic (e.g., for vaccination) polypeptides can be expressed using transformed plant hosts, for example, duckweed, according to the present invention.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The terms "inhibit," "inhibition," and "inhibiting" as used herein refer to any decrease in the expression or function of a target gene product, including any relative decrement in expression or function up to and including complete abrogation of expression or function of the target gene product. The term "expression" as used herein in the context of a gene product refers to the biosynthesis of that gene product, including the transcription and/or translation and/or assembly of the gene product. Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product.

The term "inhibitory sequence" encompasses any polynucleotide or polypeptide sequence that is capable of inhibiting the expression of a target gene product, for example, at the level of transcription or translation, or which is capable of inhibiting the function of a target gene product. Examples of inhibitory sequences include, but are not limited to, full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

It is recognized that inhibitory polynucleotides include nucleotide sequences that directly (i.e., do not require transcription) or indirectly (i.e., require transcription or transcription and translation) inhibit expression of a target gene product. For example, an inhibitory polynucleotide can comprise a nucleotide sequence that is a chemically synthesized or in vitro-produced small interfering RNA (siRNA) or micro RNA (miRNA) that, when introduced into a plant cell, tissue, or organ, would directly, though transiently, silence expression of the target gene product of interest. Alternatively, an inhibitory polynucleotide can comprise a nucleotide sequence that encodes an inhibitory nucleotide molecule that is designed to silence expression of the gene product of interest, such as sense-orientation RNA, antisense RNA, double-stranded RNA (dsRNA), hairpin RNA (hpRNA), intron-containing hpRNA, catalytic RNA, miRNA, and the like. In yet other embodiments, the inhibitory polynucleotide can comprise a nucleotide sequence that encodes a mRNA, the translation of which yields a polypeptide that inhibits expression or function of the target gene product of interest. In this manner, where the inhibitory polynucleotide comprises a nucleotide sequence that encodes an inhibitory nucleotide molecule or a mRNA for a polypeptide, the encoding sequence is operably linked to a promoter that drives expression in a plant cell so that the encoded inhibitory nucleotide molecule or mRNA can be expressed.

Inhibitory sequences are designated herein by the name of the target gene product. Thus, for example, an "α1,3-fucosyltransferase (FucT) inhibitory sequence" would refer to an inhibitory sequence that is capable of inhibiting the expression of a FucT, for example, at the level of transcription and/or translation, or which is capable of inhibiting the function of a FucT. Similarly, a "β1,2-xylosyltransferase (XylT) inhibitory sequence" would refer to an inhibitory sequence that is capable of inhibiting the expression of a XylT, at the level of transcription and/or translation, or which is capable of inhibiting the function of a XylT. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (i.e., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (i.e., inhibits expression or function of the target gene product).

The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations. In some embodiments, successive generations include progeny produced vegetatively (i.e., asexual reproduction), for example, with clonal propagation. In other embodiments, successive generations include progeny produced via sexual reproduction. A higher plant host that is "stably transformed" with at least one nucleotide construct that is capable of inhibiting expression of a FucT and/or XylT as described herein refers to a higher plant host that has the nucleotide construct(s) integrated into its genome, and is capable producing progeny, either via asexual or sexual reproduction, that also comprise the inhibitory nucleotide construct(s) stably integrated into their genome, and hence the progeny will also exhibit the desired phenotype of having an altered N-glycosylation pattern characterized by a reduction in the attachment of α1,3-fucose and/or β1,2-xylose residues to the N-glycans of homologous and heterologous glycoproteins produced therein.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, ovules, stems, fruits, leaves, roots, root tips, and the like originating in transgenic plants or their progeny previously transformed with a DNA molecule of the invention and therefore consisting at least in part of transgenic cells. As used herein, the term "plant cell" includes, without limitation, cells of seeds, embryos, meristematic regions, callus tissue, leaves, roots, shoots, gametophytes, sporophytes, pollen, and microspores.

The class of plants that can be used in the methods of the invention is generally as broad as the class of higher plants amenable to transformation techniques, including both monocotyledonous (monocot) and dicotyledonous (dicot)

plants. Examples of dicots include, but are not limited to, legumes including soybeans and alfalfa, tobacco, potatoes, tomatoes, and the like. Examples of monocots include, but are not limited to, maize, rice, oats, barley, wheat, members of the duckweed family, grasses, and the like. "Lower-order plants" refers to non-flowering plants including ferns, horsetails, club mosses, mosses, liverworts, hornworts, algae, for example, red, brown, and green algae, gametophytes, sporophytes of pteridophytes, and the like. In some embodiments, the plant of interest is a member of the duckweed family of plants.

The term "duckweed" refers to members of the family Lemnaceae. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*); genus *Wolfiella* (*Wl. caudata, Wl. denticulata, Wl. gladiata, Wl. hyalina, Wl. lingulata, Wl. repunda, Wl. rotunda,* and *Wl. neotropica*) and genus *Landoltia* (*L. punctata*). Any other genera or species of Lemnaceae, if they exist, are also aspects of the present invention. *Lemna* species can be classified using the taxonomic scheme described by Landolt (1986) *Biosystematic Investigation on the Family of Duckweeds: The family of Lemnaceae—A Monograph Study* (Geobatanischen Institut ETH, Stiftung Rubel, Zurich).

The term "duckweed nodule" as used herein refers to duckweed tissue comprising duckweed cells where at least about 50%, 55%, 60%, 65%, 70%, 75%, 80%, 85%, 90%, 95%, or 100% of the cells are differentiated cells. A "differentiated cell," as used herein, is a cell with at least one phenotypic characteristic (e.g., a distinctive cell morphology or the expression of a marker nucleic acid or protein) that distinguishes it from undifferentiated cells or from cells found in other tissue types. The differentiated cells of the duckweed nodule culture described herein form a tiled smooth surface of interconnected cells fused at their adjacent cell walls, with nodules that have begun to organize into frond primordium scattered throughout the tissue. The surface of the tissue of the nodule culture has epidermal cells connected to each other via plasmadesmata. Members of the duckweed family reproduce by clonal propagation, and thus are representative of plants that clonally propagate.

"Duckweed-preferred codons" as used herein refers to codons that have a frequency of codon usage in duckweed of greater than 17%.

"*Lemna*-preferred codons" as used herein refers to codons that have a frequency of codon usage in the genus *Lemna* of greater than 17%.

"*Lemna gibba*-preferred codons" as used herein refers to codons that have a frequency of codon usage in *Lemna gibba* of greater than 17% where the frequency of codon usage in *Lemna gibba* was obtained from the Codon Usage Database (GenBank Release 113,0; at http://www.kazusa.or.jp/codon/cgibin/showcodon.cgi?species=*Lemna+gibba*+[gbpln]).

"Translation initiation codon" refers to the codon that initiates the translation of the mRNA transcribed from the nucleotide sequence of interest.

"Translation initiation context nucleotide sequence" as used herein refers to the identity of the three nucleotides directly 5' of the translation initiation codon.

"Secretion" as used herein refers to translocation of a polypeptide across both the plasma membrane and the cell wall of a host plant cell.

"Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame.

Isolated Polynucleotides and Polypeptides

The present invention provides isolated polynucleotides and polypeptides that are involved in further modification of plant N-linked glycans (also referred to as "N-glycans"), particularly an α1,3-fucosyltransferase (FucT) and β1,2-xylosyltransferase (XylT) identified in *Lemna minor*, a member of the duckweed family, and variants and fragments of these polynucleotides and polypeptides. Inhibition of the expression of one or both of these proteins, or biologically active variants thereof, in a plant that expresses these proteins beneficially yields an N-glycosylation pattern that has a reduction in the attachment of α1,3-fucose and β1,2-xylose residues to glycoprotein N-glycans. In some embodiments of the invention, the methods disclosed herein provide for complete inhibition of expression of FucT and XylT, yielding an N-glycoslyation pattern of glycoproteins produced within a plant wherein the N-linked glycans are devoid of α1,3-fucose and β1,2-xylose residues.

The full-length cDNA sequence, including 5'- and 3'-UTR, for *L. minor* alpha 1-3 fucosyltransferase (FucT) is set forth in FIG. 1; see also SEQ ID NO:1 (open reading frame set forth in SEQ ID NO:2). The predicted amino acid sequence encoded thereby is set forth in SEQ ID NO:3. At least two isoforms of the *L. minor* FucT gene have been identified; the homology between the isoforms is about 90%. The encoded protein shares some similarity with other FucTs from other higher plants. See FIG. 2. For example, the *L. minor* FucT sequence shares approximately 50.1% sequence identity with the *Arabidopsis thaliana* FucT shown in FIG. 2.

The full-length cDNA sequence, including 5'- and 3'-UTR, for *L. minor* β1-2 xylosyltransferase (XylT) (isoform #1) is set forth in FIG. 3; see also SEQ ID NO:4 (ORF set forth in SEQ ID NO:5). The predicted amino acid sequence encoded thereby is set forth in SEQ ID NO:6. At least two isoforms of the *L. minor* XylT gene have been identified; the homology between the isoforms is about 90%. The encoded protein shares some similarity with other XylTs from other higher plants. See FIG. 4. For example, the *L. minor* XylT shares approximately 56.4% sequence identity with the *Arabidopsis thaliana* XylT shown in FIG. 4. A partial-length cDNA sequence, including 3'-UTR, for *L. minor* β1-2 xylosyltransferase (XylT) (isoform #2) is set forth in FIG. 31; see also SEQ ID NO:19 (ORF set forth in SEQ ID NO:20). The predicted amino acid sequence encoded thereby is set forth in SEQ ID NO:21. The partial-length XylT isoform #2 shares high sequence identity with the corresponding region of the full-length XylT isoform #1, as can be seen from the alignment shown in FIG. 32.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The coding sequence for the *L. minor* FucT gene is set forth as nucleotides (nt) 243-1715 of SEQ ID NO: 1 and as SEQ ID NO:2, and the amino acid sequence for the encoded FucT polypeptide is set forth in SEQ ID NO:3. The coding sequence for the *L. minor* XylT isoform #1 gene is set forth as nucleotides 63-1592 of SEQ ID NO:4 and as SEQ ID NO:5, and the amino acid sequence for the encoded XylT polypeptide is set forth in SEQ ID NO:6. The coding sequence for the partial-length *L. minor* XylT isoform #2 gene is set forth as nucleotides 1-1276 of SEQ ID NO:19 and as SEQ ID NO:20, and the amino acid sequence for the encoded partial-length XylT polypeptide is set forth in SEQ ID NO:21.

In particular, the present invention provides for isolated polynucleotides comprising nucleotide sequences encoding the amino acid sequences shown in SEQ ID NOS:3, 6, and 21. Further provided are polypeptides having an amino acid sequence encoded by a polynucleotide described herein, for example those set forth in SEQ ID NOS:1, 2, 4, 5, 19, and 20, and fragments and variants thereof. Nucleic acid molecules comprising the complements of these nucleotide sequences are also provided. It is recognized that the coding sequence for the FucT and/or XylT gene can be expressed in a plant for overexpression of the encoded FucT and/or XylT. However, for purposes of suppressing or inhibiting the expression of these proteins, the respective nucleotide sequences of SEQ ID NO:1, 2, 4, 5, 19, and 20 will be used to design constructs for suppression of expression of the respective FucT and/or XylT protein. Thus, polynucleotides, in the context of suppressing the FucT protein refers to the FucT coding sequences and to polynucleotides that when expressed suppress or inhibit expression of the FucT gene, for example, via direct or indirect suppression as noted herein below. Similarly, polynucleotides, in the context of suppressing or inhibiting the XylT protein refers to the XylT coding sequences and to polynucleotides that when expressed suppress or inhibit expression of the XylT gene, for example, via direct or indirect suppression as noted herein below.

Fragments and variants of the disclosed polynucleotides and proteins encoded thereby are also encompassed by the present invention. By "fragment" is intended a portion of the FucT or XylT polynucleotide or a portion of the FucT or XylT amino acid sequence encoded thereby. Fragments of a polynucleotide may encode protein fragments that retain the biological activity of the native protein and hence have FucT activity or XylT activity as noted elsewhere herein. Alternatively, fragments of a polynucleotide that are useful as hybridization probes generally do not encode fragment proteins retaining biological activity. Fragments of a FucT or XylT polynucleotide can also be used to design inhibitory sequences for suppression of expression of the FucT and/or XylT polypeptide. Thus, for example, fragments of a nucleotide sequence may range from at least about 15 nucleotides, 20 nucleotides, about 50 nucleotides, about 100 nucleotides, about 150 nucleotides, about 200 nucleotides, about 250 nucleotides, about 300 nucleotides, about 350 nucleotides, about 400 nucleotides, about 450 nucleotides, about 500 nucleotides, about 550 nucleotides, about 600 nucleotides, about 650 nucleotides, about 700 nucleotides, about 750 nucleotides, about 800 nucleotides, and up to the full-length polynucleotide encoding the proteins of the invention.

A fragment of a FucT polynucleotide that encodes a biologically active portion of a FucT protein of the invention will encode at least 15, 25, 30, 50, 100, 150, 200, 250, 300, 350, 400, 450, 475, 500 contiguous amino acids, or up to the total number of amino acids present in a full-length FucT protein of the invention (for example, 509 amino acids for SEQ ID NO:3). A fragment of a XylT polynucleotide that encodes a biologically active portion of a full-length XylT protein of the invention will encode at least 15, 25, 30, 50, 100, 150, 200, 250, 300, 350, 400, 450, 475 contiguous amino acids, or up to the total number of amino acids present in a full-length XylT protein of the invention (for example, 490 amino acids for SEQ ID NO:3). A fragment of a XylT polynucleotide that encodes a biologically active portion of a partial-length XylT protein of the invention will encode at least 15, 25, 30, 50, 100, 150, 200, 250, 300, 350, 400 contiguous amino acids, or up to the total number of amino acids present in a partial-length XylT protein of the invention (for example, 490 amino acids for SEQ ID NO:21)

Thus, a fragment of a FucT or XylT polynucleotide may encode a biologically active portion of a FucT or XylT protein, respectively, or it may be a fragment that can be used as a hybridization probe or PCR primer, or used to design inhibitory sequences for suppression, using methods disclosed below. A biologically active portion of a FucT or XylT protein can be prepared by isolating a portion of one of the FucT or XylT polynucleotides of the invention, respectively, expressing the encoded portion of the FucT or XylT protein (e.g., by recombinant expression in vitro), and assessing the activity of the encoded portion of the FucT or XylT polypeptide. Polynucleotides that are fragments of an FucT or XylT nucleotide sequence comprise at least 15, 20, 50, 75, 100, 150, 200, 250, 300, 350, 400, 450, 500, 550, 600, 650, 700, 800, 900, 1,000, 1,100, 1,200, 1,300, 1,400, or 1450 contiguous nucleotides, or up to the number of nucleotides present in a FucT or XylT polynucleotide disclosed herein (for example, 1865, 1473, 1860, 1530, 1282, or 1275 nucleotides for SEQ ID NOS:1, 2, 4, 5, 19, and 20, respectively).

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the FucT or XylT polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a FucT or XylT protein of the invention. Generally, variants of a particular polynucleotide of the invention (for example, SEQ ID NO:1, SEQ ID NO:2, SEQ ID NO:4, SEQ ID NO:5, SEQ ID NO:19, or SEQ ID NO:20, fragments thereof, and complements of these sequences) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the FucT or XylT polypeptide of SEQ ID NO:3, SEQ ID NO:6, or SEQ ID NO:21, respectively, is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein, that is, the enzymatic activity of attaching the α1,3-linked fucose residue (activity of FucT) or β1,2-linked xylose residue (activity of XylT) to glycoprotein N-glycans in plants as described herein. Such variants may result from, for example, genetic polymorphism or from human manipulation. Biologically active variants of a native FucT or XylT protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the FucT and XylT proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the polynucleotides of the invention include both the naturally occurring FucT and XylT sequences as well as mutant forms. Likewise, the proteins of the invention encompass both naturally occurring FucT and XylT proteins as well as variations and modified forms thereof. Such variants will continue to possess the desired activity. Thus, where expression of a functional protein is desired, the expressed protein will possess the desired FucT or XylT activity, i.e., the enzymatic activity of attaching the α1,3-linked fucose residue (activity of FucT) or β1,2-linked xylose residue (activity of XylT) to glycoprotein N-glycans in plants as described herein. Where the objective is inhibition of expression or function of the FucT and/or XylT polypeptide, the desired activity of the variant polynucleotide or polypeptide is one of inhibiting expression or function of the respective FucT and/or XylT polypeptide. Obviously, where expression of a functional FucT or XylT variant is desired, the mutations that will be made in the DNA encoding the variant must not place the sequence out of reading frame and optimally will not create complementary regions that could produce secondary mRNA structure. See, EP Patent Application Publication No. 75,444.

Where a functional protein is desired, the deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, including the assays for monitoring FucT and XylT activity described herein below in the Experimental section.

Variant polynucleotides and proteins also encompass sequences and proteins derived from a mutagenic and recombinogenic procedure such as DNA shuffling. With such a procedure, one or more different FucT or XylT coding sequences can be manipulated to create a new FucT or XylT protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the FucT or XylT gene of the invention and other known FucT or XylT genes, respectively, to obtain a new gene coding for a protein with an improved property of interest. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The comparison of sequences and determination of percent identity and percent similarity between two sequences can be accomplished using a mathematical algorithm. In a preferred embodiment, the percent identity between two amino acid sequences is determined using the Needleman and Wunsch (1970) *J. Mol. Biol.* 48:444-453 algorithm, which is incorporated into the GAP program in the GCG software package (available at www.accelrys.com), using either a BLOSUM62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a BLOSUM62 scoring matrix (see Henikoff et al. (1989) *Proc. Natl. Acad. Sci. USA* 89:10915) and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity limitation of the invention) is using a BLOSUM62 scoring matrix with a gap weight of 60 and a length weight of 3).

The percent identity between two amino acid or nucleotide sequences can also be determined using the algorithm of Meyers and Miller (1989) *CABIOS* 4:11-17 which has been incorporated into the ALIGN program (version 2.0), using a PAM 120 weight residue table, a gap length penalty of 12 and a gap penalty of 4.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al. (2001) *Molecular Cloning: A Laboratory Manual* (Cold Spring Harbor Laboratory Press, Cold Spring Harbor, NY) and Tijssen (1993) *Hybridization With Nucleic Acid Probes, Part I: Theory and Nucleic Acid Preparation* (Laboratory Techniques in Biochemistry and Molecular Biology, Elsevier Science Ltd., NY, N.Y.).

For purposes of the present invention, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

The FucT and XylT polynucleotides of the invention can be used as probes for the isolation of corresponding homologous sequences in other organisms, more particularly in other plant species. In this manner, methods such as PCR, hybridization, and the like can be used to identify such sequences based on their sequence homology to the sequences of the invention. See, for example, Sambrook et al. (1989) *Molecular Cloning: A Laboratory Manual* (2d ed., Cold Spring Harbor Laboratory Press, Plainview, N.Y.) and Innis et al. (1990), *PCR Protocols: A Guide to Methods and Applications* (Academic Press, New York). Polynucleotide sequences isolated based on their sequence identity to the entire FucT or XylT polynucleotides of the invention (i.e., SEQ ID NOS:1 and 2 for FucT; SEQ ID NOS:4 and 5 for XylT isoform #1 of SEQ ID NO:6; and SEQ ID NOS:19 and 20 for XylT isoform #2 of SEQ ID NO:21) or to fragments and variants thereof are encompassed by the present invention.

In a PCR method, oligonucleotides primers can be designed for use in PCR reactions for amplification of corresponding DNA sequences from cDNA or genomic DNA extracted from any organism of interest. Known methods of PCR include, but are not limited to, methods using paired primers, nested primers, single specific primers, degenerate primers, gene-specific primers, vector-specific primers, partially-mismatched primers, and the like. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In a hybridization method, all or part of a known nucleotide sequence can be used as a probe that selectively hybridizes to other corresponding polynucleotides present in a population of cloned genomic DNA fragments or cDNA fragments (i.e., cDNA or genomic libraries) from another organism of interest. The so-called hybridization probes may be genomic DNA fragments, cDNA fragments, RNA fragments, or other oligonucleotides, and may be labeled with a detectable group such as $^{32}P$, or any other detectable marker. Probes for hybridization can be made by labeling synthetic oligonucleotides based on the nucleotide sequence of interest, for example, the FucT or XylT polynucleotides of the invention. Degenerate primers designed on the basis of conserved nucleotides or amino acid residues in the known nucleotide or encoded amino acid sequence can additionally be used. Methods for construction of cDNA and genomic libraries, and for preparing hybridization probes, are generally known in the art and are disclosed in Sambrook et al. (1989) *Molecular Cloning: A Laboratory Manual* (2d ed., Cold Spring Harbor Laboratory Press, Plainview, N.Y.), herein incorporated by reference.

For example, all or part of the specific known FucT or XylT polynucleotide sequence may be used as a probe that selectively hybridizes to other FucT or XylT nucleotide and messenger RNAs. To achieve specific hybridization under a variety of conditions, such probes include sequences that are unique and are preferably at least about 10 nucleotides in length, and more optimally at least about 20 nucleotides in length. This technique may be used to isolate other corresponding FucT or XylT nucleotide sequences from a desired organism or as a diagnostic assay to determine the presence of a FucT or XylT coding sequences in an organism. Hybridization techniques include hybridization screening of plated DNA libraries (either plaques or colonies; see, for example, Innis et al., eds. (1990) *PCR Protocols: A Guide to Methods and Applications* (Academic Press, New York)).

Thus, in addition to the native FucT and XylT polynucleotides and fragments and variants thereof, the isolated polynucleotides of the invention also encompass homologous DNA sequences identified and isolated from other organisms by hybridization with entire or partial sequences obtained from the FucT or XylT polynucleotides of the invention or variants thereof. Conditions that will permit other DNA sequences to hybridize to the DNA sequences disclosed herein can be determined in accordance with techniques generally known in the art. For example, hybridization of such sequences may be carried out under various conditions of moderate, medium, high, or very high stringency as noted herein above.

Methods of the Invention

The present invention is directed to methods for altering protein glycosylation patterns in higher plants, particularly in higher plants that serve as hosts for production of recombinant proteins, particularly recombinant mammalian proteins of pharmaceutical interest. The methods find use in producing higher plants that are capable of producing recombinant proteins having an N-glycosylation pattern that more closely resembles that found in mammals. Compositions of the invention include higher plants that are stably transformed to comprise an altered N-glycosylation pattern of their endogenous (i.e., homologous) and recombinantly produced heterologous proteins. In some embodiments, the higher plants are transgenic plants that produce monoclonal antibodies (mAbs) to mammalian proteins that have enhanced ADCC activity relative to mAbs produced in a control plant that has not had the glycosylation machinery altered to reduce the plant-specific attachment of α1,3-fucose residues to the N-glycans of homologous and heterologous glycoproteins produced therein.

The methods of the invention target the suppression (i.e., inhibition) of the expression of one or both of the enzymes involved the production of complex glycoproteins in higher plants. Of particular interest is suppression of a fucosyltransferase or one or more isoforms thereof, suppression of a xylosyltransferase or one or more isoforms thereof, or suppression of expression of both of these proteins and one or more isoforms thereof. It is recognized that suppression of the fucosyltransferase and/or xylosyltransferase and one or more isoforms thereof can be accomplished transiently. Alternatively, by stably suppressing the expression of the fucosyltransferase and/or xylosyltransferase, it is possible to produce transgenic higher plants that carry over from generation to generation, either asexually or sexually, the ability to produce glycoproteins having an N-glycosylation pattern that more closely resembles that found in mammals, more particularly, in humans. This advantageously provides for the production of recombinant mammalian glycoproteins that have reduced attachment of the plant β1,2-linked xylose residue and/or α1,3-linked fucose residue to glycoprotein N-glycans.

Inhibition of the expression of one or advantageously both of these proteins in a plant, for example, a dicotyledonous or monocotyledonous plant, for example, a duckweed plant, can be carried out using any method known in the art. In this manner, a polynucleotide comprising an inhibitory sequence for FucT, XylT, or a combination thereof is introduced into the host cell of interest. For transient suppression, the FucT or XylT inhibitory sequence can be a chemically synthesized or in vitro-produced small interfering RNA (siRNA) or micro RNA (miRNA) that, when introduced into the host cell, would directly, though transiently, inhibit FucT, XylT, or a combination thereof, by silencing expression of these target gene product(s).

Alternatively, stable suppression of expression of FucT, XylT, or a combination thereof is desirable as noted herein above. Thus, in some embodiments, the activity of the FucT or the XylT polypeptide of the invention is reduced or eliminated by transforming a plant cell with an expression cassette that expresses a polynucleotide that inhibits the expression of the FucT or XylT, or both. The polynucleotide may inhibit the expression of the FucT or XylT, or both, directly, by preventing transcription or translation of the FucT or XylT messenger RNA, or indirectly, by encoding a polypeptide that inhibits the transcription or translation of a gene encoding the FucT or XylT, or both. Methods for inhibiting or eliminating the expression of a gene in a plant are well known in the art, and any such method may be used in the present invention to inhibit the expression of FucT or XylT, or both.

Thus, in some embodiments, expression of the FucT and/or XylT protein can be inhibited by introducing into the plant a nucleotide construct, such as an expression cassette, comprising a sequence that encodes an inhibitory nucleotide molecule that is designed to silence expression of the FucT and/or XylT gene product of interest, such as sense-orientation RNA, antisense RNA, double-stranded RNA (dsRNA), hairpin RNA (hpRNA), intron-containing hpRNA, catalytic RNA, miRNA, and the like. In other embodiments, the nucleotide construct, for example, an expression cassette, can comprise a sequence that encodes a mRNA, the translation of which yields a polypeptide of interest that inhibits expression or function of the FucT and/or XylT gene product of interest. Where the nucleotide construct comprises a sequence that encodes an inhibitory nucleotide molecule or a mRNA for a polypeptide of interest, the sequence is operably linked to a promoter that drives expression in a plant cell so that the encoded inhibitory nucleotide molecule or mRNA can be expressed.

In accordance with the present invention, the expression of a FucT or XylT gene is inhibited if the protein level of the FucT or XylT is statistically lower than the protein level of the same FucT or XylT in a plant that has not been genetically modified or mutagenized to inhibit the expression of that FucT or XylT. In particular embodiments of the invention, the protein level of the FucT or XylT, or both, in a modified plant according to the invention is less than 95%, less than 90%, less than 80%, less than 70%, less than 60%, less than 50%, less than 40%, less than 30%, less than 20%, less than 10%, or less than 5% of the protein level of the same FucT or XylT in a plant that is not a mutant or that has not been genetically modified to inhibit the expression of that FucT or XylT, or both the FucT or XylT. The expression level of the FucT or XylT, or both, may be measured directly, for example, by assaying for the level of FucT or XylT, or both, expressed in the plant cell or plant, or indirectly, for example, by observing the effect in a transgenic plant at the phenotypic level, i.e., by transgenic plant analysis, observed as a reduction, or even elimination, of the attachment of β1,2-xylose and/or α1,3-fucose residues to the glycoprotein N-glycans in the plant.

In other embodiments of the invention, the activity of FucT or XylT, or both, is reduced or eliminated by transforming a plant cell with an expression cassette comprising a polynucleotide encoding a polypeptide that inhibits the activity of FucT or XylT, or both. The activity of a FucT or XylT is inhibited according to the present invention if the activity of the FucT or XylT is statistically lower than the activity of the same FucT or XylT in a plant that has not been genetically modified to inhibit the activity of that FucT or XylT. In particular embodiments of the invention, the activity of the FucT or XylT in a modified plant according to the invention is less than 95%, less than 90%, less than 80%, less than 70%, less than 60%, less than 50%, less than 40%, less than 30%, less than 20%, less than 10%, or less than 5% of the activity of the same FucT or XylT in a plant that has not been genetically modified to inhibit the expression of that FucT or XylT. The activity of a FucT or XylT is "eliminated" according to the invention when it is not detectable by the assay methods described elsewhere herein.

In other embodiments, the activity of a FucT or XylT, or both, may be reduced or eliminated by disrupting the gene encoding the FucT or XylT, or both of these genes. The invention encompasses mutagenized plants, particularly plants that are members of the duckweed family, that carry mutations in a FucT or XylT gene, or mutations in both genes, where the mutations reduce expression of the FucT and/or XylT gene or inhibit the activity of the encoded FucT and/or XylT.

The methods of the invention can involve any method or mechanism known in the art for reducing or eliminating the activity or level of FucT and/or XylT in the cells of a higher plant, including, but not limited to, antisense suppression, sense suppression, RNA interference, directed deletion or mutation, dominant-negative strategies, and the like. Thus, the methods and compositions disclosed herein are not limited to any mechanism or theory of action and include any method where expression or function of FucT and/or XylT is inhibited in the cells of the higher plant of interest, thereby altering the N-glycosylation pattern of endogenous and heterologous glycoproteins produced in the plant.

For example, in some embodiments, the FucT inhibitory sequence or the XylT inhibitory sequence (or both) is expressed in the sense orientation, wherein the sense-oriented transcripts cause cosuppression of the expression of one or both of these enzymes. Alternatively, the FucT and/or XylT inhibitory sequence (e.g., full-length sequence, truncated sequence, fragments of the sequence, combinations thereof, and the like) can be expressed in the antisense orientation and thus inhibit endogenous FucT and/or XlyT expression or function by antisense mechanisms.

In yet other embodiments, the FucT and/or XylT inhibitory sequence or sequences are expressed as a hairpin RNA, which comprises both a sense sequence and an antisense sequence. In embodiments comprising a hairpin structure, the loop structure may comprise any suitable nucleotide sequence including for example 5' untranslated and/or translated regions of the gene to be suppressed, such as the 5' UTR and/or translated region of the FucT polynucleotide of SEQ ID NO:1 or 2, or the 5' UTR and/or translated region of the XylT polynucleotide of SEQ ID NO:4, 5, 19, or 20, and the like. In some embodiments, the FucT or XylT inhibitory sequence expressed as a hairpin is encoded by an inverted region of the FucT or XylT nucleotide sequence. In yet other embodiments, the FucT and/or XylT inhibitory sequences are expressed as double-stranded RNA, where one FucT and/or XylT inhibitory sequence is expressed in the sense orientation and another complementary sequence is expressed in the antisense orientation. Double-stranded RNA, hairpin structures, and combinations thereof comprising FucT nucleotide sequences, XylT nucleotide sequences, or combinations thereof may operate by RNA interference, cosuppression, antisense mechanism, any combination thereof, or by means of any other mechanism that causes inhibition of FucT and/or XylT expression or function.

Thus, many methods may be used to reduce or eliminate the activity of a FucT or XylT, or both of these proteins, and any isoforms thereof. By "isoform" is intended a naturally occurring protein variant of the FucT or XylT protein of interest, where the variant is encoded by a different gene. Generally, isoforms of a particular FucT or XylT protein of interest are encoded by a nucleotide sequence having at least 90% sequence identity to the nucleotide sequence encoding the FucT or XylT protein of interest. More than one method may be used to reduce or eliminate the activity of a single plant FucT or XylT, and isoforms thereof. Non-limiting examples of methods of reducing or eliminating the activity of a plant FucT or XylT are given below.

Polynucleotide-Based Methods:

In some embodiments of the present invention, a plant cell is transformed with an expression cassette that is capable of expressing a polynucleotide that inhibits the expression of FucT or XylT, or both. The term "expression" as used herein refers to the biosynthesis of a gene product, including the transcription and/or translation of the gene product. For example, for the purposes of the present invention, an expression cassette capable of expressing a polynucleotide that inhibits the expression of at least one FucT or XylT, or both, is an expression cassette capable of producing an RNA molecule that inhibits the transcription and/or translation of at least one FucT or XylT, or both. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a FucT or XylT, or both, are given below.

Sense Suppression/Cosuppression

In some embodiments of the invention, inhibition of the expression of FucT or XylT, or both, may be obtained by sense suppression or cosuppression. For cosuppression, an expression cassette is designed to express an RNA molecule corresponding to all or part of a messenger RNA encoding a FucT or XylT, or both, in the "sense" orientation. Overexpression of the RNA molecule can result in reduced expression of the native gene. Accordingly, multiple plant lines transformed with the cosuppression expression cassette are screened to identify those that show the greatest inhibition of FucT or XylT expression.

The polynucleotide used for cosuppression may correspond to all or part of the sequence encoding the FucT or XylT, all or part of the 5' and/or 3' untranslated region of a FucT or XylT transcript, or all or part of both the coding sequence and the untranslated regions of a transcript encoding FucT or XylT. In some embodiments where the polynucleotide comprises all or part of the coding region for the FucT or XylT protein, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin et al. (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91:3490-3496; Jorgensen et al. (1996) *Plant Mol. Biol.* 31:957-973; Johansen and Carrington (2001) *Plant Physiol.* 126:930-938; Broin et al. (2002) *Plant Cell* 14:1417-1432; Stoutjesdijk et al. (2002) *Plant Physiol.* 129:1723-1731; Yu et al. (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

Antisense Suppression

In some embodiments of the invention, inhibition of the expression of FucT or XylT, or both, may be obtained by antisense suppression. For antisense suppression, the expression cassette is designed to express an RNA molecule complementary to all or part of a messenger RNA encoding the FucT or XylT. Overexpression of the antisense RNA molecule can result in reduced expression of the native gene. Accordingly, multiple plant lines transformed with the antisense suppression expression cassette are screened to identify those that show the greatest inhibition of FucT or XylT expression.

The polynucleotide for use in antisense suppression may correspond to all or part of the complement of the sequence encoding the FucT or XylT, all or part of the complement of the 5' and/or 3' untranslated region of the FucT or XylT transcript, or all or part of the complement of both the coding sequence and the untranslated regions of a transcript encoding the FucT or XylT. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu et al. (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

Double-Stranded RNA Interference

In some embodiments of the invention, inhibition of the expression of a FucT or XylT, or both, may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of FucT or XylT expression. Methods for using dsRNA interference to inhibit the expression of endogenous plant genes are described in Waterhouse et al. (1998) *Proc. Natl. Acad. Sci. USA* 95:13959-13964, Liu et al. (2002) *Plant Physiol.* 129:1732-1743, and WO 99/49029, WO 99/53050, WO 99/61631, and WO 00/49035; each of which is herein incorporated by reference.

Hairpin RNA Interference and Intron-Containing Hairpin RNA Interference

In some embodiments of the invention, inhibition of the expression of FucT or XylT, or both, may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk et al. (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407: 319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407:319-320; Wesley et al. (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz et al. (2002) *PNAS* 99 (Suppl. 4): 16499-16506; Mette et al. (2000) *EMBO J* 19(19):5194-5201).

Expression cassettes that are designed to express an RNA molecule that forms a hairpin structure are referred to herein as RNAi expression cassettes. In some embodiments, the RNAi expression cassette is designed in accordance with a strategy outlined in FIG. 28. In such embodiments, an RNAi expression cassette can be designed to suppress the expression of the individual FucT and XylT genes (i.e., each cassette provides a single gene knockout), or can be designed to suppress the expression of both the FucT and XylT genes (i.e., a single RNAi expression cassette expresses an inhibitory molecule that provides for suppression of expression of both of these genes). Where the RNAi expression cassette suppresses expression of both the FucT and XylT genes, it is referred to herein as a "chimeric" RNAi expression cassette. The single-gene and chimeric RNAi expression cassettes can be designed to express larger hpRNA structures or, alternatively, small hpRNA structures, as noted herein below.

Thus, in some embodiments, the RNAi expression cassette is designed to express larger hpRNA structures having sufficient homology to the target mRNA transcript to provide for post-transcriptional gene silencing of one or both of a FucT and XylT gene. For larger hp RNA structures, the sense strand of the RNAi expression cassette is designed to comprise in the 5'-to-3' direction the following operably linked elements: a promoter of interest, a forward fragment of the FucT or XylT gene sequence comprising about 500 to about 800 nucleotides (nt) of a sense strand for FucT or XylT, respectively, a spacer sequence comprising about 100 to about 700 nt of any sequence as noted herein below, and a reverse fragment of the XylT or FucT gene sequence, wherein the reverse fragment comprises the antisense sequence complementary to the respective (i.e., FucT or XylT) forward fragment. Thus, for example, if a forward fragment is represented by nucleotides " . . . acttg . . . ", the corresponding reverse fragment is represented by nucleotides " . . . caagt . . . ", and the sense strand for such an RNAi expression cassette would comprise the following sequence: "5'- . . . acttg . . . nnnn . . . caagt . . . -3', where "nnnn" represents the spacer sequence.

It is recognized that the forward fragment can comprise a nucleotide sequence that is 100% identical to the corresponding portion of the sense strand for the target FucT or XylT gene sequence, or in the alternative, can comprise a sequence that shares at least 90%, at least 95%, or at least 98% sequence identity to the corresponding portion of the sense strand for the target FucT or XylT gene to be silenced. In like manner, it is recognized that the reverse fragment does not have to share 100% sequence identity to the complement of the forward fragment; rather it must be of sufficient length and sufficient complementarity to the forward fragment sequence such that when the inhibitory RNA molecule is expressed, the transcribed regions corresponding to the forward fragment and reverse fragment will hybridize to form the base-paired stem (i.e., double-stranded portion) of the hp RNA structure. By "sufficient length" is intended a length that is at least 10%, at least 15%, at least 20%, at least 30%, at least 40% of the length of the forward fragment, more frequently at least 50%, at least 75%, at least 90%, or least 95% of the length of the forward fragment. By "sufficient complementarity" is intended the sequence of the reverse fragment shares at least 90%, at least 95%, at least 98% sequence identity with the complement of that portion of the forward fragment that will hybridize with the reverse fragment to form the base-paired stem of the hp RNA structure. Thus, in some embodiments, the reverse fragment is the complement (i.e., antisense version) of the forward fragment.

In designing such an RNAi expression cassette, the lengths of the forward fragment, spacer sequence, and reverse fragments are chosen such that the combined length of the polynucleotide that encodes the hpRNA construct is about 650 to about 2500 nt, about 750 to about 2500 nt, about 750 to about 2400 nt, about 1000 to about 2400 nt, about 1200 to about 2300 nt, about 1250 to about 2100 nt, or about 1500 to about 1800. In some embodiments, the combined length of the expressed hairpin construct is about 650 nt, about 700 nt, about 750 nt, about 800 nt, about 850 nt, about 900 nt, about 950 nt, about 1000 nt, about 1050 nt, about 1100 nt, about 1150 nt, about 1200 nt, about 1250 nt, about 1300 nt, about 1350 nt, about 1400 nt, about 1450 nt, about 1500 nt, about 1550 nt, about 1600 nt, about 1650 nt, about 1700 nt, about 1750 nt, about 1800 nt, about 1850 nt, about 1900 nt, about 1950 nt, about 2000 nt, about 2050 nt, about 2100 nt, about 2150 nt, about 2200 nt, about 2250 nt, about 2300 nt, or any such length between about 650 nt to about 2300 nt.

In some embodiments, the forward fragment comprises about 500 to about 800 nt, for example, 500, 525, 550, 575, 600, 625, 650, 675, 700, 725, 750, 775, or 800 nt of a sense strand for FucT or XylT, for example, of the sense strand set forth in SEQ ID NO:1 or 2 (FucT) or SEQ ID NO:4, 5, 19, or 20 (XylT); the spacer sequence comprises about 100 to about 700 nt, for example, 100, 125, 150, 175, 200, 225, 250, 275, 300, 325, 350, 375, 400, 425, 450, 475, 500, 525, 550, 575, 600, 625, 650, 675, or 700 nt of any sequence as noted below, and the reverse fragment comprises the antisense strand for the forward fragment sequence, or a sequence having sufficient length and sufficient complementarity to the forward fragment sequence.

The spacer sequence can be any sequence that has insufficient homology to the target gene, i.e., FucT or XylT, and insufficient homology to itself such that the portion of the expressed inhibitory RNA molecule corresponding to the spacer region fails to self-hybridize, and thus forms the loop of the hairpin RNA structure. In some embodiments, the spacer sequence comprises an intron, and thus the expressed inhibitory RNA molecule forms an ihpRNA as noted herein above. In other embodiments, the spacer sequence comprises a portion of the sense strand for the FucT or XylT gene to be silenced, for example, a portion of the sense strand set forth in SEQ ID NO:1 or 2 (FucT) or SEQ ID NO:4, 5, 19, or 20 (XylT), particularly a portion of the sense strand immediately downstream from the forward fragment sequence.

The operably linked promoter can be any promoter of interest that provides for expression of the operably linked inhibitory polynucleotide within the plant of interest, including one of the promoters disclosed herein below. The regulatory region can comprise additional regulatory elements that enhance expression of the inhibitory polynucleotide, including, but not limited to, the 5' leader sequences and 5' leader sequences plus plant introns discussed herein below.

In one embodiment, the RNAi expression cassette is designed to suppress expression of the FucT polypeptide of SEQ ID NO:3, a biologically active variant of the FucT polypeptide of SEQ ID NO:3, or a FucT polypeptide encoded by a sequence having at least 75% sequence identity to the sequence of SEQ ID NO:1 or SEQ ID NO:2, for example, at least 75%, at least 80%, at least 85%, at least 90%, or at least 95% sequence identity to the sequence of SEQ ID NO:1 or SEQ ID NO:2. In this manner, the sense strand of the RNAi expression cassette is designed to comprise in the 5'-to-3' direction the following operably linked elements: a promoter of interest; a forward fragment of the FucT gene sequence, wherein the forward fragment comprises nt 255-985 of SEQ ID NO:1; a spacer sequence comprising about 100 to about 700 nt of any sequence as noted above; and a reverse fragment of the FucT gene sequence, wherein the reverse fragment comprises the complement (i.e., antisense version) of nt 255-985 of SEQ ID NO:1. In one such embodiment, the spacer sequence is represented by nt 986-1444 of SEQ ID NO:1, and the total length of that portion of the sense strand of the RNAi expression cassette corresponding to the coding sequence for the hpRNA structure is 1918 nt. Stably transforming a plant with a nucleotide construct comprising this RNAi expression cassette, for example, the vector shown in FIG. 8, effectively inhibits expression of FucT within the plant cells of the plant in which the hpRNA structure is expressed. In one embodiment, the plant of interest is a member of the duckweed family, for example, a member of the Lemnaceae, and the plant has been stably transformed with the vector shown in FIG. 8.

In other embodiments of the invention, the RNAi expression cassette is designed to suppress expression of the XylT polypeptide of SEQ ID NO:6 or SEQ ID NO:21, a biologically active variant of the XylT polypeptide of SEQ ID NO:6 or SEQ ID NO:21, or a XylT polypeptide encoded by a sequence having at least 75% sequence identity to the sequence of SEQ ID NO:4, SEQ ID NO:5, SEQ ID NO:19, or SEQ ID NO:20, for example, at least 75%, at least 80%, at least 85%, at least 90%, or at least 95% sequence identity to the sequence of SEQ ID NO:4, SEQ ID NO:5, SEQ ID NO:19, or SEQ ID NO:20. In this manner, the sense strand of the RNAi expression cassette is designed to comprise in the 5'-to-3' direction the following operably linked elements: a promoter of interest; a forward fragment of the XylT gene sequence, wherein the forward fragment comprises nt 318-1052 of SEQ ID NO:4; a spacer sequence comprising about 100 to about 700 nt of any sequence as noted above; and a reverse fragment of the XylT gene sequence, wherein the reverse fragment comprises the complement (i.e., antisense version) of nt 318-1052 of SEQ ID NO:4. In one such embodiment, the spacer sequence is represented by nt 1053-1599 of SEQ ID NO:4, and the total length of that portion of the sense strand of the RNAi expression cassette corresponding to the coding sequence for the hpRNA structure is 2015 nt. Stably transforming a plant with a nucleotide construct comprising this RNAi expression cassette, for example, the vector shown in FIG. 9, effectively inhibits expression of FucT within the plant cells of the plant in which the hpRNA structure is expressed. In one embodiment, the plant of interest is a member of the duckweed family, for example, a member of the Lemnaceae, and the plant has been stably transformed with the vector shown in FIG. 9.

In other embodiments, the sense strand of the RNAi expression cassette is designed to comprise in the 5'-to-3' direction the following operably linked elements: a promoter of interest; a forward fragment of the XylT gene sequence, wherein the forward fragment comprises nt 1-734 of SEQ ID NO:19; a spacer sequence comprising about 100 to about 700 nt of any sequence as noted above; and a reverse fragment of the XylT gene sequence, wherein the reverse fragment comprises the complement (i.e., antisense version) of nt 1-734 of SEQ ID NO:19. In one such embodiment, the spacer sequence is represented by nt 735-1282 of SEQ ID NO:19, and the total length of that portion of the sense strand of the RNAi expression cassette corresponding to the coding sequence for the hpRNA structure is 2015 nt. Stably transforming a plant with a nucleotide construct comprising this RNAi expression cassette, for example, the vector shown in FIG. 9, effectively inhibits expression of FucT within the plant cells of the plant in which the hpRNA structure is expressed. In one embodiment, the plant of interest is a member of the duckweed family, for example, a member of the Lemnaceae, and the plant has been stably transformed with the vector shown in FIG. 9.

In yet other embodiments, larger hpRNA structures can be designed such that the antisense and sense sequences are in opposite orientation. In this manner, the sense strand of the RNAi expression cassette is designed to comprise in the 5'-to-3' direction the following operably linked elements: a promoter of interest, the full-length FucT or XylT gene sequence in the antisense orientation, and a forward fragment of the FucT or XylT gene sequence comprising the 3'-half of the sequence in the sense orientation (see FIG. 28, design 1). In this type of construct, the 3'-half of the sequence forms the base-paired (i.e., double-stranded) stem of the hpRNA, and the 5'-half of the sequence acts as a spacer sequence. Without being bound by any theory or mechanism, the 3' region of the FucT or XylT sequence is chosen to form the double-stranded region of the hpRNA for for this construct because this region is relatively conserved among different plant species compared to the 5' region.

In one such embodiment, the RNAi expression cassette is designed to suppress expression of the FucT polypeptide of SEQ ID NO:3, a biologically active variant of the FucT polypeptide of SEQ ID NO:3, or a FucT polypeptide encoded by a sequence having at least 75% sequence identity to the sequence of SEQ ID NO:1 or SEQ ID NO:2, for example, at least 75%, at least 80%, at least 85%, at least 90%, or at least 95% sequence identity to the sequence of SEQ ID NO:1 or SEQ ID NO:2. In this manner, the sense strand of the RNAi expression cassette is designed to comprise in the 5'-to-3' direction the following operably linked elements: a promoter of interest; nucleotides 1-1865 of SEQ ID NO:1 in antisense orientation, and nucleotides 950-1865 of SEQ ID NO:1 in the sense orientation. Stably transforming a plant with a nucleotide construct comprising this RNAi expression cassette effectively inhibits expression of FucT within the plant cells of the plant in which the hpRNA structure is expressed. In one embodiment, the plant of interest is a member of the duckweed family, for example, a member of the Lemnaceae.

In another such embodiment, the RNAi expression cassette is designed to suppress expression of the XylT polypeptide of SEQ ID NO:6 or SEQ ID NO:21, a biologically active variant of the XylT polypeptide of SEQ ID NO:6 or SEQ ID NO:21, or a XylT polypeptide encoded by a sequence having at least 75% sequence identity to the sequence of SEQ ID NO:4, SEQ ID NO:5, SEQ ID NO:19, or SEQ ID NO:20, for example, at least 75%, at least 80%, at least 85%, at least 90%, or at least 95% sequence identity to the sequence of SEQ ID NO:5, SEQ ID NO:19, or SEQ ID NO:20. In this manner, the sense strand of the RNAi expression cassette is designed to comprise in the 5'-to-3' direction the following operably linked elements: a promoter of interest, nucleotides 1-1860 of SEQ ID NO:4 in antisense orientation, and nucleotides 950-1860 of SEQ ID NO:4 in the sense orientation. Stably transforming a plant with a nucleotide construct comprising this RNAi expression cassette effectively inhibits expression of XylT within the plant cells of the plant in which the hpRNA structure is expressed. In one embodiment, the plant of interest is a member of the duckweed family, for example, a member of the Lemnaceae.

Figure 8:
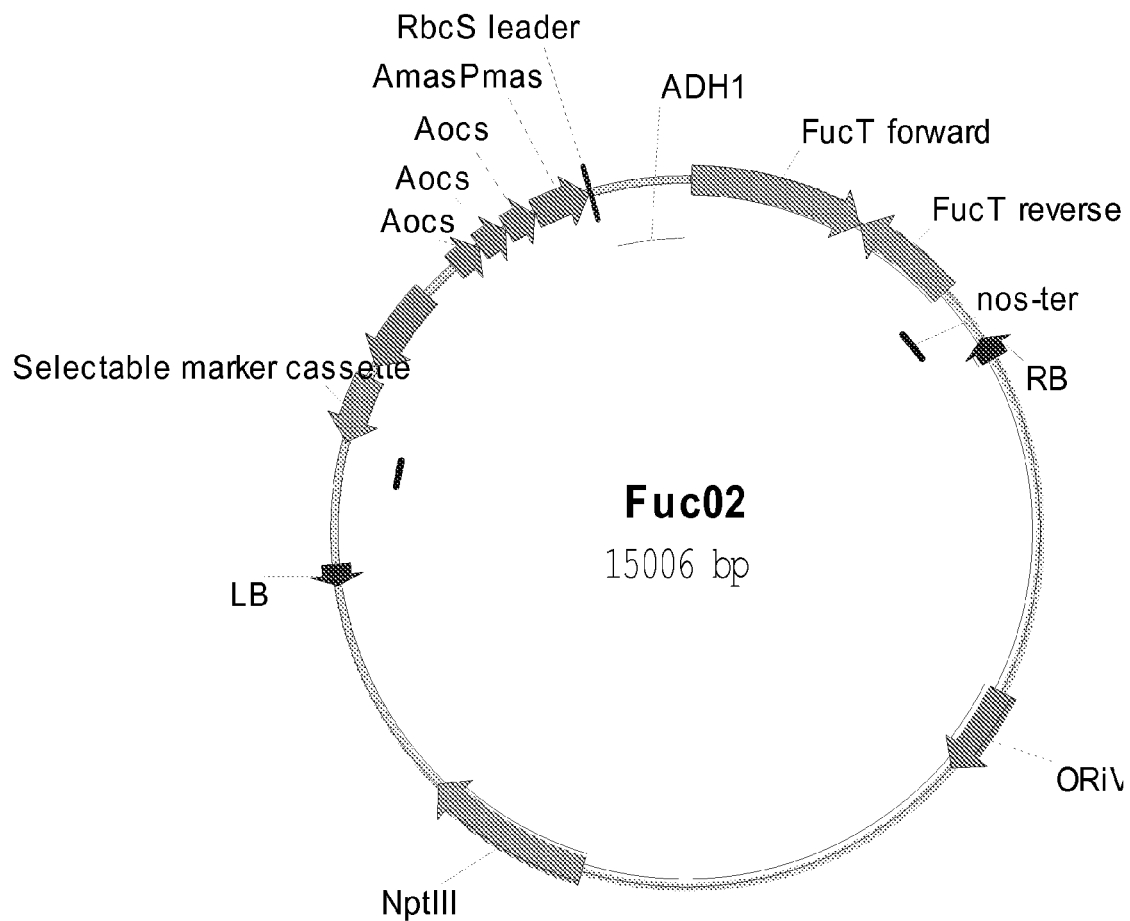
Figure 9:
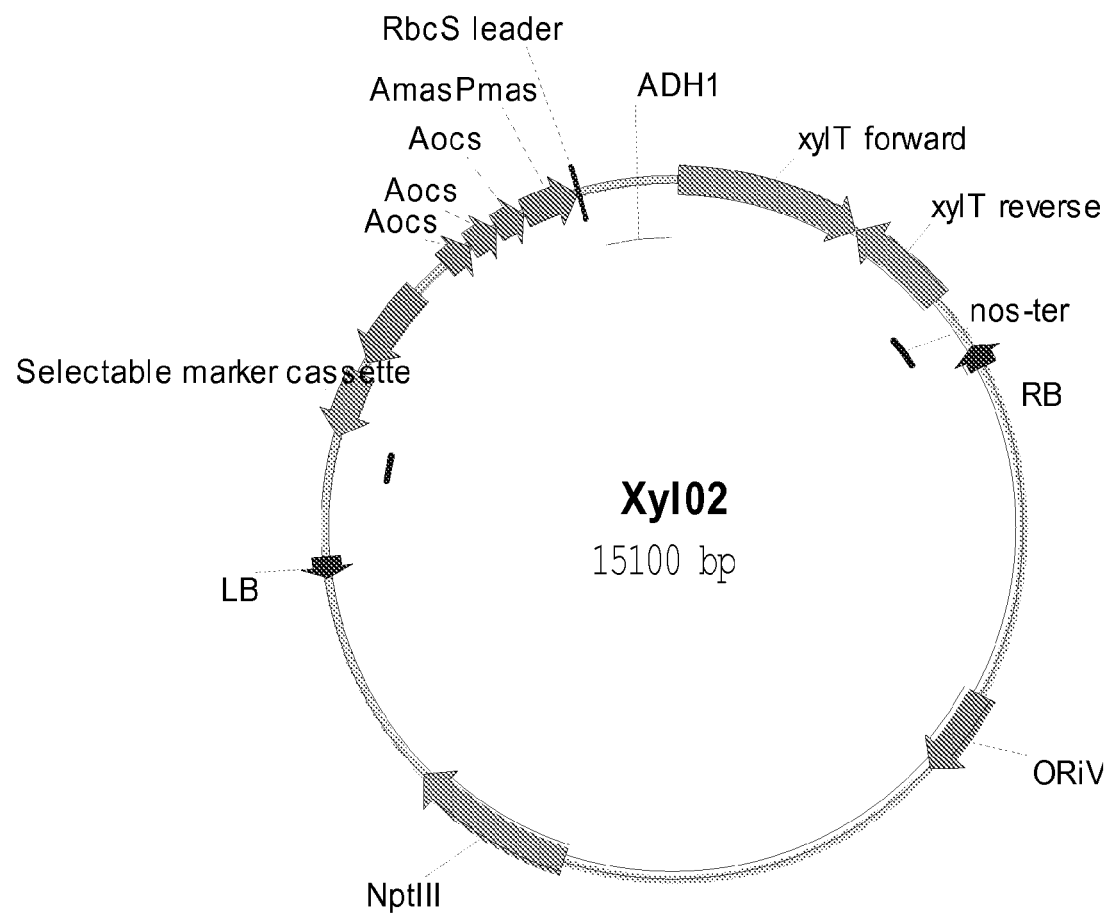
Figure 11:
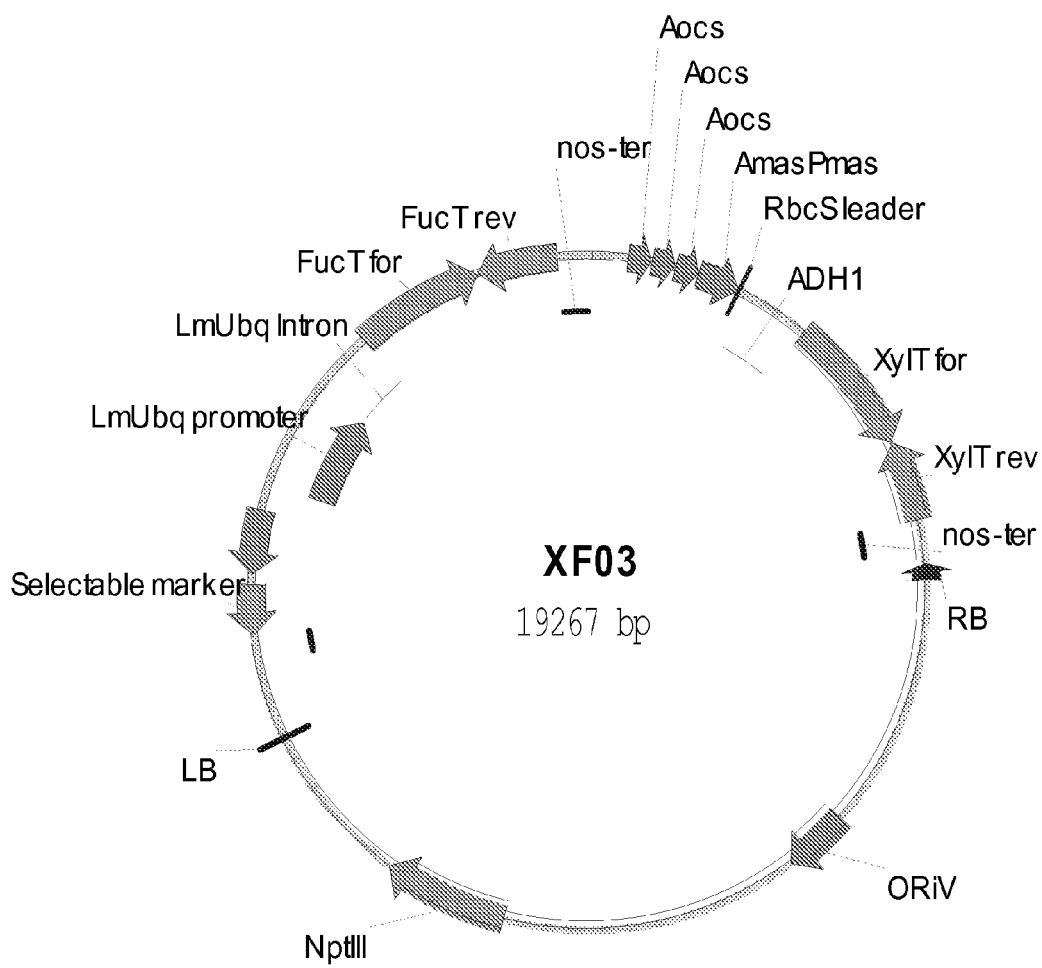

In another such embodiment, the sense strand of the RNAi expression cassette is designed to comprise in the 5'-to-3' direction the following operably linked elements: a promoter of interest, nucleotides 1-1282 of SEQ ID NO:19 in antisense orientation, and nucleotides 652-1282 of SEQ ID NO:19 in the sense orientation. Stably transforming a plant with a nucleotide construct comprising this RNAi expression cassette effectively inhibits expression of XylT within the plant cells of the plant in which the hpRNA structure is expressed. In one embodiment, the plant of interest is a member of the duckweed family, for example, a member of the Lemnaceae.

Where suppression of both the FucT and XylT proteins is desired, it can be achieved by introducing these single-gene RNAi expression cassettes into the plant in a single transformation event, for example, by assembling these single-gene RNAi expression cassettes within a single transformation vector, for example, a vector similar to that shown in FIG. 11, or as separate co-transformation events, for example, by assembling these single-gene RNAi expression cassettes within two transformation vectors, for example, vectors similar to those shown in FIGS. 8 and 9, using any suitable transformation method known in the art, including but not limited to the transformation methods disclosed elsewhere herein.

Alternatively, suppression of both the FucT and XylT proteins can be achieved by introducing into the higher plant of interest a chimeric RNAi expression cassette as noted herein above. Thus, in some embodiments of the invention, the sense strand of a chimeric RNAi expression cassette is designed to comprise in the 5'-to-3' direction the following operably linked elements: a promoter of interest; a chimeric forward fragment, comprising about 500 to about 650 nucleotides (nt) of a sense strand for FucT and about 500 to about 650 nt of a sense strand for XylT, wherein the FucT sequence and XylT sequence can be in either order; a spacer sequence comprising about 100 to about 700 nt of any sequence; and a reverse fragment of the chimeric forward fragment, wherein the reverse fragment comprises the antisense sequence complementary to the respective chimeric forward fragment.

As previously noted for the individual RNAi expression cassettes, it is recognized that the individual FucT or XlyT sequence within the chimeric forward fragment can comprise a nucleotide sequence that is 100% identical to the corresponding portion of the sense strand for the target FucT and XylT gene sequence, respectively, or in the alternative, can comprise a sequence that shares at least 90%, at least 95%, or at least 98% sequence identity to the corresponding portion of the sense strand for the target FucT or XylT gene to be silenced. In like manner, it is recognized that the reverse fragment does not have to share 100% sequence identity to the complement of the chimeric forward fragment; rather it must be of sufficient length and sufficient complementarity to the chimeric forward fragment sequence, as defined herein above, such that when the inhibitory RNA molecule is expressed, the transcribed regions corresponding to the chimeric forward fragment and reverse fragment will hybridize to form the base-paired stem (i.e., double-stranded portion) of the hpRNA structure.

In designing such a chimeric RNAi expression cassette, the lengths of the forward fragment, spacer sequence, and reverse fragments are chosen such that the combined length of the polynucleotide that encodes the hpRNA structure is about 1200 to about 3300 nt, about 1250 to about 3300 nt, about 1300 to about 3300 nt, about 1350 to about 3300 nt, about 1400 to about 3300 nt, about 1450 nt to about 3300 nt, about 1500 to about 3300 nt, about 2200 to about 3100 nt, about 2250 to about 2800 nt, or about 2500 to about 2700 nt. In some embodiments, the combined length of the expressed hairpin construct is about 1200 nt, about 1250 nt, about 1300 nt, about 1350 nt, about 1400 nt, about 1450 nt, about 1500 nt, about 1800 nt, about 2200 nt, about 2250 nt, about 2300 nt, about 2350 nt, about 2400 nt, about 2450 nt, about 2500 nt, about 2550 nt, about 2600 nt, about 2650 nt, about 2700 nt, about 2750 nt, about 2800 nt, about 2850 nt, about 2900 nt, about 2950 nt, about 3000 nt, about 3050 nt, about 3100 nt, about 3150 nt, about 3200 nt, about 3250 nt, about 3300 nt, or any such length between about 1200 nt to about 3300 nt.

In some embodiments, the chimeric forward fragment comprises about 500 to about 650 nt, for example, 500, 525, 550, 575, 600, 625, or 650 nt, of a sense strand for FucT, for example, of the sense strand set forth in SEQ ID NO:1 or 2, and about 500 to about 650 nt, for example, 500, 525, 550, 575, 600, 625, or 650 nt, of a sense strand for XylT, for example, of the sense strand set forth in SEQ ID NO:4, 5, 19, or 20, where the FucT and XylT sequence can be fused in either order; the spacer sequence comprises about 100 to about 700 nt, for example, 100, 200, 225, 250, 275, 300, 325, 350, 375, 400, 425, 450, 475, 500, 525, 550, 575, 600, 625, 650, 675, or 700 nt of any sequence of interest; and the reverse fragment comprises the antisense strand for the chimeric forward fragment sequence, or a sequence having sufficient length and sufficient complementarity to the chimeric forward fragment sequence.

As noted above for the single-gene RNAi expression cassettes, the spacer sequence can be any sequence that has insufficient homology to the target gene, i.e., FucT or XylT, and insufficient homology to itself such that the portion of the expressed inhibitory RNA molecule corresponding to the spacer region fails to self-hybridize, and thus forms the loop of the hpRNA structure. In some embodiments, the spacer sequence comprises an intron, and thus the expressed inhibitory RNA molecule forms an ihpRNA as noted herein above. In other embodiments, the spacer sequence comprises a portion of the sense strand for the FucT or XylT gene to be silenced, for example, a portion of the sense strand set forth in SEQ ID NO:1 or 2 (FucT) or SEQ ID NO:4, 5, 19, or 20 (XylT). In one embodiment, the chimeric forward fragment comprises the FucT and XylT sequence fused in that order, and the spacer sequence comprises a portion of the XylT sense strand immediately downstream from the XylT sequence contained within the chimeric forward fragment. In another embodiment, the chimeric forward fragment comprises the XylT and FucT sequence fused in that order, and the spacer sequence comprises a portion of the FucT sense strand immediately downstream from the FucT sequence contained within the chimeric forward fragment.

In some embodiments, the chimeric RNAi expression cassette is designed to suppress expression of the FucT polypeptide of SEQ ID NO:3, a biologically active variant of the FucT polypeptide of SEQ ID NO:3, or a FucT polypeptide encoded by a sequence having at least 75% sequence identity to the sequence of SEQ ID NO:1 or SEQ ID NO:2, for example, at least 75%, at least 80%, at least 85%, at least 90%, or at least 95% sequence identity to the sequence of SEQ ID NO:1 or SEQ ID NO:2, and to suppress expression of the XylT polypeptide of SEQ ID NO:6 or SEQ ID NO:21, a biologically active variant of the XylT polypeptide of SEQ ID NO:6 or SEQ ID NO:21, or a XylT polypeptide encoded by a sequence having at least 75% sequence identity to the sequence of SEQ ID NO:4, SEQ ID NO:5, SEQ ID NO:19, or SEQ ID NO:20, for example, at least 75%, at least 80%, at least 85%, at least 90%, or at least 95% sequence identity to the sequence of SEQ ID NO:4, SEQ ID NO:5, SEQ ID NO:19, or SEQ ID NO:20. For some of these embodiments, the FucT sequence within the chimeric forward fragment is chosen such that it corresponds to nt 700 to nt 1400 of SEQ ID NO:1 or SEQ ID NO:2, and/or the XylT sequence within the chimeric forward fragment is chosen such that it corresponds to nt 700 to nt 1400 of SEQ ID NO:4 or SEQ ID NO:5, or nt 383 to 1083 of SEQ ID NO:19 or 20. Without being bound by theory, it is believed that this region (particularly for FucT) is relatively conserved among different plant species, and therefore is a potentially good target.

In other embodiments, the sense strand of the chimeric RNAi expression cassette is designed to comprise in the 5'-to-3' direction the following operably linked elements: a promoter of interest; a chimeric forward fragment comprising nt 254-855 of SEQ ID NO:1 (FucT sequence) and nt 318-943 of SEQ ID NO:4 (XlyT sequence); a spacer sequence comprising about 100 to about 700 nt of any sequence as noted above;

and a reverse fragment comprising the complement (i.e., antisense version) of the chimeric forward fragment, i.e., comprising the complement of nt 318-943 of SEQ ID NO:4 and the complement of nt 254-855 of SEQ ID NO:1. In a particular embodiment, the spacer sequence within this chimeric RNAi expression cassette is represented by nt 944-1443 of SEQ ID NO:4, and the total length of that portion of the sense strand of the RNAi expression cassette corresponding to the coding sequence for the hpRNA structure is 2956 nt.

In another such embodiment, the sense strand of the chimeric RNAi expression cassette is designed to comprise in the 5'-to-3' direction the following operably linked elements: a promoter of interest; a chimeric forward fragment comprising nt 318-943 of SEQ ID NO:4 (XlyT sequence) and nt 254-855 of SEQ ID NO:1 (FucT sequence); a spacer sequence comprising about 100 to about 700 nt of any sequence as noted above; and a reverse fragment comprising the complement (i.e., antisense version) of the chimeric forward fragment, i.e., comprising the complement of nt 254-855 of SEQ ID NO:1 and the complement of nt 318-943 of SEQ ID NO:4. In a particular embodiment, the spacer sequence within this chimeric RNAi expression cassette is represented by nt 856-1355 of SEQ ID NO:1, and the total length of that portion of the sense strand of the RNAi expression cassette corresponding to the coding sequence for the hpRNA structure is 2956 nt.

In yet other embodiments, the sense strand of the chimeric RNAi expression cassette is designed to comprise in the 5'-to-3' direction the following operably linked elements: a promoter of interest; a chimeric forward fragment comprising nt 254-855 of SEQ ID NO:1 (FucT sequence) and nt 1-626 of SEQ ID NO:19 (XlyT sequence); a spacer sequence comprising about 100 to about 700 nt of any sequence as noted above; and a reverse fragment comprising the complement (i.e., antisense version) of the chimeric forward fragment, i.e., comprising the complement of nt 1-626 of SEQ ID NO:19 and the complement of nt 254-855 of SEQ ID NO:1. In a particular embodiment, the spacer sequence within this chimeric RNAi expression cassette is represented by nt 627-1126 of SEQ ID NO:19, and the total length of that portion of the sense strand of the RNAi expression cassette corresponding to the coding sequence for the hpRNA structure is 2956 nt.

In another such embodiment, the sense strand of the chimeric RNAi expression cassette is designed to comprise in the 5'-to-3' direction the following operably linked elements: a promoter of interest; a chimeric forward fragment comprising nt 1-626 of SEQ ID NO:19 (XlyT sequence) and nt 254-855 of SEQ ID NO:1 (FucT sequence); a spacer sequence comprising about 100 to about 700 nt of any sequence as noted above; and a reverse fragment comprising the complement (i.e., antisense version) of the chimeric forward fragment, i.e., comprising the complement of nt 254-855 of SEQ ID NO:1 and the complement of nt 1-626 of SEQ ID NO:19. In a particular embodiment, the spacer sequence within this chimeric RNAi expression cassette is represented by nt 856-1355 of SEQ ID NO:1, and the total length of that portion of the sense strand of the RNAi expression cassette corresponding to the coding sequence for the hpRNA structure is 2956 nt.

Figure 10:
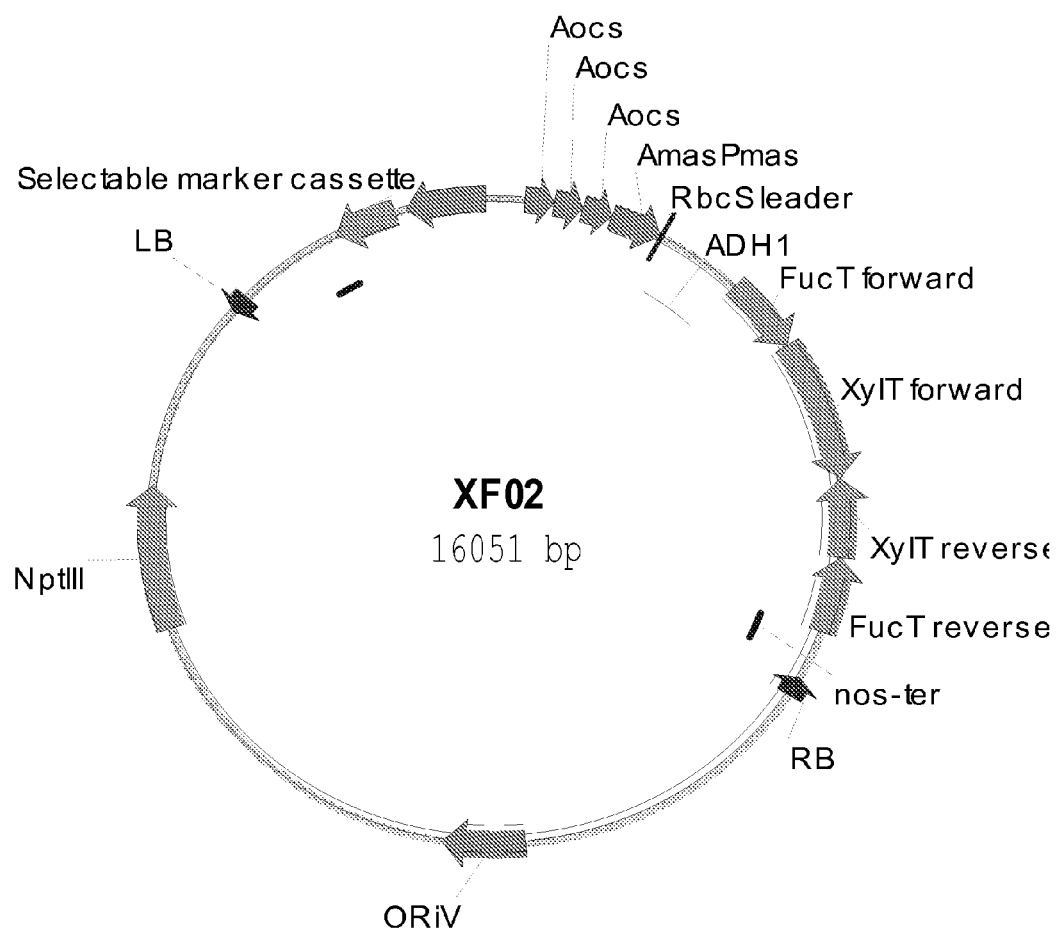

Stably transforming a plant with a nucleotide construct comprising a chimeric RNAi expression cassette described herein, for example, stable transformation with the vector shown in FIG. 10, effectively inhibits expression of both FucT and XylT within the plant cells of the plant in which the hpRNA structure is expressed. In one embodiment, the plant of interest is a member of the duckweed family, for example, a member of the Lemnaceae, and the plant has been stably transformed with the vector shown in FIG. 10.

It is recognized that the plant can be stably transformed with at least two of these chimeric RNAi expression cassettes to provide for very efficient gene silencing of the FucT and XylT proteins, including silencing of any isoforms of these two proteins. See, for example, the two orientations provided in "possible design 2" of FIG. 28. In this manner, the plant can be stably transformed with a first chimeric RNAi expression cassette wherein the chimeric forward fragment comprises the FucT and XylT sequence fused in that order, and the spacer sequence comprises a portion of the XylT sense strand immediately downstream from the XylT sequence contained within the chimeric forward fragment; and with a second chimeric RNAi expression cassette wherein the chimeric forward fragment comprises the XylT and FucT sequence fused in that order, and the spacer sequence comprises a portion of the FucT sense strand immediately downstream from the FucT sequence contained within the chimeric forward fragment.

The operably linked promoter within any of the RNAi expression cassettes encoding large hpRNA structures, or large ihpRNA structures can be any promoter of interest that provides for expression of the operably linked inhibitory polynucleotide within the plant of interest, including one of the promoters disclosed herein below. The regulatory region can comprise additional regulatory elements that enhance expression of the inhibitory polynucleotide, including, but not limited to, the 5' leader sequences and 5' leader sequences plus plant introns discussed herein below.

In yet other embodiments, the RNAi expression cassette can be designed to provide for expression of small hpRNA structures having a base-paired stem region comprising about 200 base pairs or less. Expression of the small hpRNA structure is preferably driven by a promoter recognized by DNA-dependent RNA polymerase III. See, for example, U.S. Patent Application No. 20040231016, herein incorporated by reference in its entirety.

In this manner, the RNAi expression cassette is designed such that the transcribed DNA region encodes an RNA molecule comprising a sense and antisense nucleotide region, where the sense nucleotide sequence comprises about 19 contiguous nucleotides having about 90% to about 100% sequence identity to a nucleotide sequence of about 19 contiguous nucleotides from the RNA transcribed from the gene of interest and where the antisense nucleotide sequence comprises about 19 contiguous nucleotides having about 90% to about 100% sequence identity to the complement of a nucleotide sequence of about 19 contiguous nucleotides of the sense sequence. The sense and antisense nucleotide sequences of the RNA molecule should be capable of forming a base-paired (i.e., double-stranded) stem region of RNA of about 19 to about 200 nucleotides, alternatively about 21 to about 90 or 100 nucleotides, or alternatively about 40 to about 50 nucleotides in length. However, the length of the base-paired stem region of the RNA molecule may also be about 30, about 60, about 70 or about 80 nucleotides in length. Where the base-paired stem region of the RNA molecule is larger than 19 nucleotides, there is only a requirement that there is at least one double-stranded region of about 19 nucleotides (wherein there can be about one mismatch between the sense and antisense region) the sense strand of which is "identical" (allowing for one mismatch) with 19 consecutive nucleotides of the target FucT or XylT polynucleotide of interest. The transcribed DNA region of this type of RNAi expression cassette may comprise a spacer sequence positioned between the sense and antisense encoding nucleotide region. The spacer sequence is not related to the targeted FucT or XylT polynucleotide, and can range in length from 3 to about 100 nucleotides or alternatively from about 6 to about 40 nucleotides. This type of RNAi expression cassette also comprises a terminator sequence recognized by the RNA polymerase III, the sequence being an oligo dT stretch, positioned downstream from the antisense-encoding nucleotide region of the cassette. By "oligo dT stretch" is a stretch of consecutive T-residues. It should comprise at least 4 T-residues, but obviously may contain more T-residues.

It is recognized that in designing the short hpRNA, the fragments of the targeted gene sequence (i.e., fragments of FucT or XylT gene sequence) and any spacer sequence to be included within the hpRNA-encoding portion of the RNAi expression cassette are chosen to avoid GC-rich sequences, particularly those with three consecutive G/C's, and to avoid the occurrence of four or more consecutive T's or A's, as the string "TTTT..." serves as a terminator sequence recognized by the RNA polymerase III.

Thus, where gene silencing with a short hpRNA is desired, the RNAi expression cassette can be designed to comprise in the 5'-to-3' direction the following operably linked elements: a promoter recognized by a DNA dependent RNA polymerase III of the plant cell, as defined herein below; a DNA fragment comprising a sense and antisense nucleotide sequence, wherein the sense nucleotide sequence comprises at least 19 contiguous nucleotides having about 90% to about 100% sequence identity to a nucleotide sequence of at least 19 contiguous nucleotides from the sense strand of the FucT or XylT gene of interest, and wherein the antisense nucleotide sequence comprises at least 19 contiguous nucleotides having about 90% to about 100% sequence identity to the complement of a nucleotide sequence of at least 19 contiguous nucleotides of the sense sequence, wherein the sense and antisense nucleotide sequence are capable of forming a double-stranded RNA of about 19 to about 200 nucleotides in length; and an oligo dT stretch comprising at least 4 consecutive T-residues.

In some embodiments of the invention, the RNAi expression cassette is designed to express a small hpRNA that suppresses expression of the FucT polypeptide of SEQ ID NO:3, a biologically active variant of the FucT polypeptide of SEQ ID NO:3, or a FucT polypeptide encoded by a sequence having at least 90% sequence identity to the sequence of SEQ ID NO:1 or SEQ ID NO:2. In this manner, the RNAi expression cassette can be designed to comprise in the 5'-to-3' direction the following operably linked elements: a promoter recognized by a DNA dependent RNA polymerase III of the plant cell, as defined herein below; a DNA fragment comprising a sense and antisense nucleotide sequence, wherein the sense nucleotide sequence comprises at least 19 contiguous nucleotides having about 90% to about 100% sequence identity to a nucleotide sequence of at least 19 contiguous nucleotides of SEQ ID NO:1, and wherein the antisense nucleotide sequence comprises at least 19 contiguous nucleotides having about 90% to about 100% sequence identity to the complement of a nucleotide sequence of at least 19 contiguous nucleotides of the sense sequence, wherein the sense and antisense nucleotide sequence are capable of forming a double-stranded RNA of about 19 to about 200 nucleotides in length; and an oligo dT stretch comprising at least 4 consecutive T-residues.

In other embodiments of the invention, the RNAi expression cassette is designed to express a small hpRNA that suppresses expression of the XylT polypeptide of SEQ ID NO:6 or SEQ ID NO:21, a biologically active variant of the XylT polypeptide of SEQ ID NO:6 or SEQ ID NO:21, or a XylT polypeptide encoded by a sequence having at least 90% sequence identity to the sequence of SEQ ID NO:4, SEQ ID NO:5, SEQ ID NO:19, or SEQ ID NO:20. In this manner, the RNAi expression cassette can be designed to comprise in the 5'-to-3' direction the following operably linked elements: a promoter recognized by a DNA dependent RNA polymerase III of the plant cell, as defined herein below; a DNA fragment comprising a sense and antisense nucleotide sequence, wherein the sense nucleotide sequence comprises at least 19 contiguous nucleotides having about 90% to about 100% sequence identity to a nucleotide sequence of at least 19 contiguous nucleotides of SEQ ID NO:4, and wherein the antisense nucleotide sequence comprises at least 19 contiguous nucleotides having about 90% to about 100% sequence identity to the complement of a nucleotide sequence of at least 19 contiguous nucleotides of the sense sequence, wherein the sense and antisense nucleotide sequence are capable of forming a double stranded RNA of about 19 to about 200 nucleotides in length; and an oligo dT stretch comprising at least 4 consecutive T-residues.

Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for FucT or XylT, or both). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

Ribozymes

In some embodiments, the polynucleotide expressed by the expression cassette of the invention is catalytic RNA or has ribozyme activity specific for the messenger RNA of FucT or XylT, or both. Thus, the polynucleotide causes the degradation of the endogenous messenger RNA, resulting in reduced expression of the FucT or XylT, or both. This method is described, for example, in U.S. Pat. No. 4,987,071, herein incorporated by reference.

Small Interfering RNA or Micro RNA

In some embodiments of the invention, inhibition of the expression of FucT or XylT, or both, may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425: 257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of FucT or XylT expression, the 22-nucleotide sequence is selected from a FucT or XylT transcript sequence and contains 22 nucleotides of said FucT or XylT sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

Polypeptide-Based Inhibition of Gene Expression

In one embodiment, the polynucleotide encodes a zinc finger protein that binds to a gene encoding a FucT or XylT, or both, resulting in reduced expression of the gene. In particular embodiments, the zinc finger protein binds to a regulatory region of a FucT or XylT gene. In other embodiments, the zinc finger protein binds to a messenger RNA encoding a FucT or XylT and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

Polypeptide-Based Inhibition of Protein Activity

In some embodiments of the invention, the polynucleotide encodes an antibody that binds to at least one FucT or XylT, and reduces the activity of the FucT or XylT. In another embodiment, the binding of the antibody results in increased turnover of the antibody-FucT or XylT complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

Gene Disruption

In some embodiments of the present invention, the activity of FucT or XylT, or both, is reduced or eliminated by disrupting the gene encoding the FucT or XylT, or both. The gene encoding the FucT or XylT, or both, may be disrupted by any method known in the art. For example, in one embodiment, the gene is disrupted by transposon tagging. In another embodiment, the gene is disrupted by mutagenizing plants using random or targeted mutagenesis, and selecting for plants that have reduced FucT and/or XylT activity.

Transposon Tagging

In one embodiment of the invention, transposon tagging is used to reduce or eliminate the activity of FucT or XylT, or both. Transposon tagging comprises inserting a transposon within an endogenous FucT or XylT gene to reduce or eliminate expression of the FucT or XylT. "FucT" or "XylT" gene is intended to mean the gene that encodes a FucT or XylT, respectively, according to the invention.

In this embodiment, the expression of FucT or XylT is reduced or eliminated by inserting a transposon within a regulatory region or coding region of the gene encoding the FucT or XylT. A transposon that is within an exon, intron, 5' or 3' untranslated sequence, a promoter, or any other regulatory sequence of a FucT or XylT, or both, gene may be used to reduce or eliminate the expression and/or activity of the encoded FucT or XylT.

Methods for the transposon tagging of specific genes in plants are well known in the art. See, for example, Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928). In addition, the TUSC process for selecting Mu insertions in selected genes has been described in Bensen et al. (1995) *Plant Cell* 7:75-84; Mena et al. (1996) *Science* 274:1537-1540; each of which is herein incorporated by reference.

The invention encompasses additional methods for reducing or eliminating the activity of FucT or XylT. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham et al. (1999) *Proc. Natl. Acad. Sci. USA* 96:8774-8778; each of which is herein incorporated by reference.

Thus inhibition of expression of FucT and/or XylT in a higher plant of interest can be accomplished by any of the foregoing methods in order to alter the N-glycosylation pattern of endogenous and heterologous glycoproteins produced within that plant such that these glycoproteins comprise complex N-glycans that have a reduction in the amount of $\beta1,2$-linked xylose residues and/or $\alpha1,3$-linked fucose residues. The extent to which attachment of the $\beta1,2$-linked xylose residue and/or $\alpha1,3$-linked fucose residue to glycoprotein N-glycans is reduced is governed by the degree of inhibition of expression of the respective XylT and FucT enzymes.

In some embodiments of the invention, recombinant glycoproteins produced in a plant host that is stably transformed using the methods described herein to target XylT expression have N-linked glycans comprising less than 50%, less than 40%, less than 30% of the $\beta1,2$-linked xylose residues occurring in the respective N-linked glycans of glycoproteins produced in a plant host that has not been genetically modified to inhibit expression of the XylT enzyme and isoforms thereof. In other embodiments, these recombinant glycoproteins have N-linked glycans comprising less than 25%, less than 20%, less than 15%, less than 10%, less than 5%, or less than 1% of the $\beta1,2$-linked xylose residues occurring in the respective N-linked glycans of glycoproteins produced in a plant host that has not been genetically modified to inhibit expression of the XylT enzyme and isoforms thereof. In yet other embodiments, the methods of the invention provide for complete silencing of the XylT gene and any isoforms thereof within the stably transformed plant, such that the recombinant glycoproteins produced within the plant have N-linked glycans that are devoid of $\beta1,2$-linked xylose residues.

In like manner, where a plant host has been stably transformed using the methods described herein to target FucT expression, recombinant glycoproteins produced within the plant have N-linked glycans comprising less than 50%, less than 40%, less than 30% of the $\alpha1,3$-linked fucose residues occurring in the respective N-linked glycans of glycoproteins produced in a plant host that has not been genetically modified to inhibit expression of the FucT enzyme and isoforms thereof. In other embodiments, these recombinant glycoproteins have N-linked glycans comprising less than 25%, less than 20%, less than 15%, less than 10%, less than 5%, or less than 1% of the $\alpha1,3$-linked fucose residues occurring in the respective N-linked glycans of glycoproteins produced in a plant host that has not been genetically modified to inhibit expression of the FucT enzyme and isoforms thereof. In yet other embodiments, the methods of the invention provide for complete silencing of the FucT gene and any isoforms thereof within the stably transformed plant, such that the recombinant glycoproteins produced within the plant have N-linked glycans that are devoid of $\alpha1,3$-linked fucose residues.

Where a plant host has been stably transformed using the methods described herein to target expression of both the XylT and FucT enzymes, and any isoforms thereof, recombinant glycoproteins produced within the plant have N-linked glycans comprising less than 50%, less than 40%, less than 30% of the β1,2-linked xylose residues and less than 50%, less than 40%, less than 30% of the α1,3-linked fucose residues occurring in the respective N-linked glycans of glycoproteins produced in a plant host that has not been genetically modified to inhibit expression of the XylT and FucT enzymes and isoforms thereof. In other embodiments, these recombinant glycoproteins have N-linked glycans comprising less than 25%, less than 20%, less than 15%, less than 10%, less than 5%, or less than 1% of the β1,2-linked xylose residues and 25%, less than 20%, less than 15%, less than 10%, less than 5%, or less than 1% of the α1,3-linked fucose residues occurring in the respective N-linked glycans of glycoproteins produced in a plant host that has not been genetically modified to inhibit expression of the XylT and FucT enzymes and isoforms thereof. In yet other embodiments, the methods of the invention provide for complete silencing of the XylT and FucT gene and any isoforms thereof within the stably transformed plant, such that the recombinant glycoproteins produced within the plant have N-linked glycans that are devoid of β1,2-linked xylose residues and α1,3-linked fucose residues.

In some embodiments of the present invention, a plant host that has been stably transformed using the methods described herein to target expression of both the XylT and FucT enzymes, and any isoforms thereof, is capable of producing recombinant glycoproteins wherein the N-linked glycans are substantially homogenous. By "substantially homogenous" is intended that the glycosylation profile reflects the presence of a single major peak corresponding to a desired N-glycan species, more particularly, the G0 glycan species, wherein at least 90% of the N-glycan structures present on said glycoproteins are of the G0 glycan species.

Methods for monitoring changes in the N-glycosylation pattern of glycoproteins, also referred to as glycosylation profiles, are well known in the art and include, but are not limited to, matrix-assisted laser desorption ionization time-of-flight (MALDI-TOF) mass spectrometry, for example, using the modified MALDI-TOF assay disclosed in Example 3 herein below, liquid chromatograph mass spectrometry (LC-MS), gas chromatography, anion-exchange chromatography, size-exclusion chromatography, high-concentration polyacrylaminde gel electrophoresis, nuclear magnetic resonance spectroscopy, and capillary electrophoresis and capillary gel electrophoresis, fluorescence labeling and detection by high-performance liquid chromatography (HPLC) and QTOF, and the like. In this manner, changes in the N-glycosylation pattern due to inhibition of the expression or function of XylT and/or FucT in a stably transformed plant of the invention can be monitored by subjecting a sample (for example, a leaf tissue sample) obtained from the stably transformed plant to total N-glycan analysis by MALDI-TOF mass spectrometry, and comparing the results with those obtained for a comparable sample from a control plant, wherein the control plant has not been genetically modified to inhibit expression or function of XylT and/or FucT. A reduction in the amount of xylose and/or fucose residues in the N-glycans can be monitored by a reduction of the mass of the respective peaks. See, for example, Strasser et al. (2004) *FEBS Letters* 561:132-136.

Similarly, the glycosylation profile of any given recombinantly produced glycoprotein is readily determined using standard techniques well known to those in the art. See, for example, the review provided in Morelle and Michalski (2005) *Curr. Anal. Chem.* 1:29-57; herein incorporated by reference in its entirety. Thus, glycoproteins that have been recombinantly produced in a host organism, including a plant host, can be analyzed for the ratio of the particular N-linked glycan structures attached thereto. In this manner, a sample comprising isolated recombinantly produced glycoprotein can be subjected to enzymatic or chemical reaction to release the individual glycan structures from the glycoprotein. Following this deglycosylation step, analysis of the glycosylation profile can be carried out using any of the analytical assays described herein above.

Recombinantly produced glycoprotein products typically exist as a diverse population of glycoforms carrying between one and several dozen different glycans in variable molar amounts at glycosylation sites with varying degrees of site occupancy. Depending upon the glycoprotein, different glycoforms can yield different functional profiles. Thus, in some embodiments of the invention, it is desirable to determine the glycosylation profile of the glycoprotein having the N-glycans intact. Any technique known in the art for determining the glycosylation profile of an intact glycoprotein can be used, including the mass spectrometry methods noted above and in the examples herein below.

By reducing or eliminating the expression or function of fucosyltransferase and/or xylosyltransferase in the manner set forth herein, either transiently or stably, it is possible to produce a transgenic higher plant having the ability to produce glycoproteins having an N-glycosylation profile with reduced heterogeneity relative to that normally observed for glycoproteins produced by this plant when expression or function of these enzymes has not been altered (i.e., the plant has the native or wild-type glycosylation machinery). Where expression or function of one or both of these enzymes is stably reduced or eliminated using one or more of the methods described herein above, the reduction in the heterogeneity of the N-glycosylation profile of glycoproteins produced by the transgenic plant can be maintained from plant generation to plant generation, including with asexual or sexual reproduction, and can be maintained across cultural conditions and with scale-up in production.

In this manner, the present invention provides a method for reducing heterogeneity of the N-glycosylation profile of a glycoprotein produced in a higher plant, for example, a dicotyledonous or monocotyledonous plant, for example, a duckweed plant. The method comprises introducing into the plant a nucleotide construct described herein such that the expression or function of fucosyltransferase and/or xylosyltransferase is reduced or eliminated within the plant. In some embodiments of the invention, the method for reducing heterogeneity of the N-glycosylation profile of a glycoprotein produced in a higher plant comprises introducing into the higher plant of interest at least one nucleotide construct described herein above, where the nucleotide construct(s) provides for suppression of the expression of fucosyltransferase and/or xylosyltransferase in the plant, for example, using one or more of the methods described herein above.

By "reducing heterogeneity of the N-glycosylation profile" it is intended that the N-glycosylation profile is characterized by a reduction in the total number of distinct N-glycan species that appear in the profile. Thus, for example, where a glycoprotein produced by a higher plant having the native or wild-type glycosylation machinery (and thus which has not been genetically modified to reduce or eliminate expression of fucosyltransferase and xylosyltransferase) produces a glycoprotein with an N-glycosylation profile characterized by the presence of a mixture of 5 N-glycan species, the methods of the invention can be used to reduce the number of N-glycan species appearing in the N-glycosylation profile. In this manner, when that higher plant is genetically modified in the manner set forth herein to reduce or eliminate expression or function of fucosyltransferase and/or xylosyltransferase, the N-glycosylation profile of this glycoprotein would be characterized by a reduction in the number of N-glycan species appearing in the profile, for example, a mixture of fewer than 5 N-glycan species, for example, 4, 3, or 2 N-glycan species, or even a single N-glycan species. Where heterogeneity of the N-glycosylation profile is reduced such that the profile is characterized by the presence of a single predominant N-glycan species, the N-glycosylation profile would be substantially homogeneous for that N-glycan species.

In some embodiments, the methods for reducing the heterogeneity of the N-glycosylation profile of a glycoprotein produced in a higher plant result in the produced glycoprotein having an N-glycosylation profile that is substantially homogeneous for the G0 glycan species. In such embodiments, the methods for reducing the heterogeneity of the N-glycosylation profile of a glycoprotein produced in a higher plant result in the produced glycoprotein having a substantially homogeneous N-glycosylation profile, wherein at least 80%, at least 85%, at least 90%, 91%, 92%, 93%, 94%, 95%, 96%, 97%, 98%, or at least 99% of the total amount of N-glycan species appearing in the N-glycosylation profile for the glycoprotein is represented by the G0 glycan species. In these embodiments, a trace amount of precursor N-glycan species may appear in the N-glycosylation profile as noted elsewhere herein, where any given precursor N-glycan species that is present in the N-glycosylation profile is present at less than 5%, preferably less than 4%, less than 3%, less than 2%, less than 1%, and even less than 0.5% or even less than 0.1% of the total amount of N-glycan species appearing in the profile.

The glycoprotein can be an endogenous glycoprotein of interest, or can be a heterologous glycoprotein that is produced by the higher plant of interest, for example, a mammalian glycoprotein, including, for example, the glycoproteins described elsewhere herein. In some embodiments, the glycoprotein is a monoclonal antibody. In other embodiments, the glycoprotein is selected from the group consisting of an interferon, erythropoietin (EPO), tissue plasminogen activator (tPA), plasminogen, granulocyte-macrophage colony stimulating factor (GM-CSF), and therapeutic immunoglobulins.

Using the methods of the present invention, it is possible to maintain the reduced heterogeneity within the N-glycosylation profile for a glycoprotein produced in the transgenic plant with scale-up in production, and thus the plant continues to produce the glycoprotein such that its N-glycosylation profile is characterized by a reduction in the number of N-glycan species appearing in the profile. By "scale-up in production" or "increase in production scale" is intended an increase in the amount of plant biomass that is present within a culture system (i.e., a culture vessel or culture container within which the plant is cultured) that is being used to produce a protein of interest, in this case, a glycoprotein of interest. Thus, scale-up in production occurs, for example, when scaling up production from a scale that is suitable for research purposes to one that is suitable for pilot production, and further up to a scale that is suitable for commercial production of the glycoprotein of interest.

In some embodiments, the transgenic higher plant is a monocotyledonous plant, for example, a duckweed plant, that serves as a host for recombinant production of a glycoprotein, and the reduced heterogeneity of the N-glycosylation profile of the recombinantly produced glycoprotein is maintained with an increase in production scale, where the production scale is increased by at least 300-fold, at least 500-fold, at least 700-fold, at least 1,000-fold, at least 1,500-fold or greater over the initial starting biomass. In some of these embodiments, the transgenic higher plant is a duckweed plant that recombinantly produces a glycoprotein of interest, and the reduced heterogeneity of the N-glycosylation profile is maintained with an increase in production scale, where the production scale is increased by at least 2,000-fold, at least 3,000-fold, at least 4,000-fold, at least 5,000-fold, at least 6,000-fold, at least 6,500-fold, or greater over the initial starting biomass. In one such embodiment, the higher plant is a duckweed plant that recombinantly produces a glycoprotein of interest, and the reduced heterogeneity of the N-glycosylation profile for that glycoprotein is maintained with an increase in production scale, where the production scale is increased by at least 7,000-fold, 8,000-fold, 9,000-fold, 10,000-fold, 12,500-fold, 15,000-fold, 17,500-fold, 20,000-fold, 23,000-fold, 26,000-fold, or greater over the initial starting biomass.

Furthermore, when the transgenic plant of interest is to be maintained by continuous clonal culture, the resulting transgenic line continues to produce glycoproteins that exhibit the reduced heterogeneity within their N-glycosylation profile. Continuous clonal culture can be achieved using any suitable method known in the art. In some embodiments, continuous clonal culture is achieved by periodically taking one or more subsamples of the plant culture and transferring the subsample(s) to fresh culture medium for further culture. Thus, for example, in some embodiments, the transgenic plant line that is maintained by continuous clonal culture is a duckweed transgenic plant line that has been genetically modified to reduce or eliminate expression or function of fucosyltransferase and/or xylosyltransferase. In this manner, the reduced heterogeneity of the N-glycosylation profile of glycoproteins produced in the transgenic plant line is maintained with continuous clonal culture of the transgenic plant line for at least 8 months, at least 10 months, at least 1 year, at least 1.5 years, at least 2 years, at least 2.5 years, at least 3 years, at least 3.5 years, at least 4 years, at least 4.5 years, at least 5 years, or longer, and can be maintained for as long as the transgenic plant line is maintained.

Heterologous Polypeptides and Glycoproteins

Higher plants, particularly higher plants that serve as expression systems for recombinant proteins for pharmaceutical use, that have been stably transformed to produce glycoproteins with an altered N-glycoslyation pattern using the methods described herein may be genetically modified to produce any recombinant protein of interest. Where the recombinant protein is one in which post-translational glycosylation is applicable, the methods of the invention advantageously provide a means to produce these glycoproteins with an N-glycosylation pattern that more closely reflects that of mammalian hosts, particularly a glycosylation pattern that is "humanized." Examples of recombinant proteins of interest include, but are not limited to, insulin, growth hormone, plasminogen, α-interferon, β-interferon, β-glucocerebrosidase, β-glucoronidase, retinoblastoma protein, p53 protein, angiostatin, leptin, monoclonal antibodies and fragments thereof, cytokines, for example, erythropoietin (EPO), granulocyte macrophage colony stimulating factor, tissue plaminogen activator, blood coagulation factors, for example, Factor VII, Factor VIII, Factor IX, and activated protein C, alpha 1-antitrypsin, receptors, hormones, human vaccines, animal vaccines, peptides, and serum albumin. Furthermore, the transgenic higher plants of the invention are capable of producing a glycoprotein product that has a substantially homogenous glycosylation profile for the G0 glycan species, and which is characterized by its substantial hoomogeniety for the G0 glycoform. This advantageously results in plant host expression systems that have increased production consistency, as well as reduced chemical, manufacturing, and control (CMC) risk associated with the production of these glycoprotein compositions.

The glycoprotein compositions produced in accordance with the methods of the present invention may be contained in a composition comprising a pharmaceutically acceptable carrier. Such compositions are useful in a method of treating a subject for a disease or disorder for which treatment with the glycoprotein will provide a therapeutic benefit. In this manner, glycoproteins that have been produced in a plant, for example, a duckweed plant, stably transformed in accordance with the methods of the present invention can be administered to a subject in need thereof.

The glycoprotein compositions of the invention comprise N-linked glycans that are predominately of the G0 glycan structure. In this manner, the present invention provides glycoprotein compositions that have glycosylation profiles that are "substantially homogeneous" or "substantially uniform" or have "substantial homogeneity" as defined herein above. Thus, in some embodiments, the glycoprotein compositions are substantially homogeneous for the G0 glycan species, and thus have a substantially homogeneous glycosylation profile, wherein at least 80%, at least 85%, at least 90%, 91%, 92%, 93%, 94%, 95%, 96%, 97%, 98%, or at least 99% of the total amount of N-glycan species appearing in the glycosylation profile for the composition is represented by the G0 glycan species, with a trace amount of precursor N-glycan species appearing in the glycosylation profile, i.e., any given precursor N-glycan species that is present in the glycosylation profile is present at less than 5%, preferably less than 4%, less than 3%, less than 2%, less than 1%, and even less than 0.5% or even less than 0.1% of the total amount of N-glycan species appearing in the profile. For such a composition, a representative precursor N-glycan species appearing in its glycosylation profile would be the Man3GlcNAc2, MGn (GlcNac1Man3GlcNAc2 wherein GlcNac1 is attached to the 1,3 mannose arm), and GnM (GlcNac1Man3GlcNAc2 wherein GlcNac1 is attached to the 1,6 mannose arm) precursor N-glycan species described above, where any single one or any combination of these precursor N-glycan species can be present.

In this manner, the invention provides "substantially homogeneous" or "substantially uniform" glycoprotein compositions or glycoprotein compositions having "substantial homogeneity" as defined herein above. In some embodiments, the invention provides substantially homogeneous glycoprotein compositions, wherein at least 80%, at least 85%, at least 90%, 91%, 92%, 93%, 94%, 95%, 96%, 97%, 98%, or at least 99% of the glycoprotein present in the composition is represented by the G0 glycoform, wherein all anticipated glycosylation sites are occupied by the G0 glycan species, with a trace amount of precursor or undesired glycoforms being present in the composition, i.e., the precursor glycoforms represent less than 5%, less than 4%, less than 3%, less than 2%, less than 1%, or even less than 0.5%, or less than 0.1% of the total glycoforms present within the composition. In such a composition, a representative precursor glycoform would be one in which glycosylation sites are unoccupied, and an exemplary undesired glycoform would be a glycoform having a mixture of G0 glycan and G0X or G0XF3 glycan species attached to its glycosylation sites.

In some embodiments of the invention, the plant host comprises one or more polynucleotides that provide for expression of an antibody that specifically binds to a mammalian protein of interest, particularly a human protein of interest. Thus, in one aspect, the invention provides methods for producing monoclonal antibodies in higher plants, wherein the monoclonal antibodies have an N-glycosylation pattern that reflects a reduction in the amount of $\beta1,2$-linked xylose residues and $\alpha1,3$-linked fucose residues within the N-linked glycans, and compositions comprising recombinant monoclonal antibodies produced using plant hosts genetically modified in the manner set forth herein. In some embodiments, the plant host of interest is a member of the duckweed family.

Monoclonal antibodies are increasingly being used as therapeutic agents to treat human disease, including, but not limited to, cancer and diseases having an autoimmune or inflammatory component. See, for example, King (1999) *Curr. Opin. Drug Discovery Dev.* 2:110-17; Vaswani and Hamilton (1998) *Ann. Allergy Asthma Immunol.* 81:105-19; and Holliger and Hoogenboom, *Nat. Biotechnology* 16:1015-16; each of which is herein incorporated by reference. Although some of these antibodies have therapeutic effects that result solely from antigen binding, for example antibodies that bind to a receptor or ligand to prevent ligand-receptor interactions, other antibodies need effector functions such as the recruitment of the immune system to kill target cells in order to be therapeutically active. See, for example, Clynes et al. (2000) *Nat. Med.* 6:443-46; Clynes et al. (1998) *Proc. Natl. Acad. Sci. U.S.A.* 95:652-56, and Anderson et al. (1997) *Biochem. Soc. Trans.* 25:705-8; each of which is herein incorporated by reference.

The antigen-recognition activities and effector functions of antibodies reside in different portions of the antibody molecule. The Fab' portion of the antibody provides antigen recognition activity, while the Fc portion provides effector functions such as the activation of accessory effector cells including phagocytic cells (macrophages and neutrophils), natural killer cells, and mast cells. Antibodies bind to cells via the Fc region, with an Fc receptor site on the antibody Fc region binding to an Fc receptor (FcR) on a cell. There are a number of Fc receptors that are specific for different classes of antibodies, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), initiation of complement-dependent cytotoxicity (CDC), release of inflammatory mediators, and control of immunoglobulin production. Methods for assaying effector function of antibodies are well known in the art and include those assaying for CDC, ADCC, and apoptosis. See, for example, Subbramanian et al. (2002) *J. Clin. Microbiol.* 40:2141-2146; Ahman et al. (1994) *J. Immunol. Methods* 36:243-254; Brezicka et al. (2000) *Cancer Immunol. Immunother.* 49:235-242; Gazzano-Santoro et al. (1997) *J. Immunol. Methods* 202:163-171; Prang et al. (2005) *British J. Cancer* 92:342-349; Shan et al. (1998) *Blood* 92:3756-3771; Ghetie et al. (2001) *Blood* 97:1392-1398; and, Mathas et al. (2000) *Cancer Research* 60:7170-7176; all of which are herein incorporated by reference.

It is known in the art that the glycosylation status of the Fc portion of an antibody molecule plays a key role in determining whether an antibody will have effector function. See, for example, Tao and Morrison (1987) *J. Immunol.* 143:2595-601; Wright and Morrison (1997) *Trends in Biotech.* 15:26-32; Wright and Morrison (1998) *J. Immunol.* 160:3393-402; Mimura et al. (2000) *Mol. Immunol.* 37:697-706; Jefferis and Lund (2002) Immunol. Lett. 82:57-65; Krapp et al. (2003) *J. Mol. Biol.* 325:979-89; and Jefferis (2005) *Biotechnol. Prog.* 21:11-16; each of which is herein incorporated by reference.

Glycosylation of recombinantly produced antibodies varies depending on the expression system used. See, for example, Raju et al. (2000) *Glycobiology* 10:477-86; Wright and Morrison (1997) *Trends in Biotech.* 15:26-32. Further, where the N-glycosylation pattern of a mammalian-produced monoclonal antibody is altered to reduce or deplete the α(1,6)-linked core fucose residue, the monoclonal antibody exhibits increased effector function, particularly increased ADCC activity. See, for example, U.S. Pat. No. 6,946,292. For some mammalian-produced monoclonal antibodies, where the N-glycosylation pattern is altered to reduce or deplete the β(1,4)-galactose residues attached to the 1,3 and/or 1,6 mannose arms, activation of complement-dependent cytotoxicity (CDC) against antigen-bearing target cells may be reduced without altering other functional activities of the antibody, including ADCC activity. See, for example, Boyd et al. (1995) *Mol. Immunol.* 32:1311-1318.

Antibodies having antigen recognition activity, and in some embodiments improved effector function, may be produced by a higher plant host, such as duckweed, that has been stably transformed in the manner set forth herein to alter its glycosylation machinery. Accordingly, the present invention provides methods for producing a recombinant monoclonal antibody, including a monoclonal antibody having improved effector function, wherein the antibody is recombinantly produced within a plant having an altered N-glycosylation pattern of endogenous and heterologous gylcoproteins produced therein such that these glycoproteins exhibit a reduction in the amount of the plant-specific β1,2-linked xylose residues and/or α1,3-linked fucose residues attached to the N-glycans thereof. Where the antibodies have reduced amounts α1,3-linked fucose residues attached to the N-glycans thereof, the antibodies may have increased ADCC activity relative to antibodies produced in a control plant that has not been genetically modified to inhibit expression or function of FucT.

Also encompassed are recombinant monoclonal antibodies having effector function, and in some embodiments, improved effector function, where the antibodies are produced in a duckweed expression system that has been genetically modified to inhibit expression or function of the FucT of SEQ ID NO:3 and/or the XylT of SEQ ID NO:6, and any isoforms thereof, for example, the XylT isoform #2 comprising the sequence set forth in SEQ ID NO:21 (encoded by SEQ ID NO:20). Thus, in some embodiments, the plant serving as the host for recombinant production of the monoclonal antibody is a member of the Lemnaceae as noted elsewhere herein, for example, a *Lemna* plant, comprising, for example, a XylT RNAi expression cassette and/or a FucT RNAi expression cassette described above stably integrated within its genome. In this manner, the present invention provides a method for producing a recombinant monoclonal antibody having an N-glycosylation pattern that more closely resembles that found in a mammalian host expression system, and with improved effector function, where the method comprises expressing one or more chains of the antibody in a duckweed plant, or duckweed cell or duckweed nodule, that has been genetically modified to alter the glycosylation machinery such that the recombinantly produced monoclonal antibody exhibits a reduction in the attachment of the plant β1,2-linked xylose residue and/or α1,3-linked fucose residue to the N-glycans thereof, and culturing the duckweed plant, or duckweed cell or duckweed nodule, under conditions suitable for expression of the monoclonal antibody.

Thus the present invention provides novel antibody compositions wherein the antibody comprises N-linked glycans that are predominately of the G0 glycan structure. In this manner, the present invention provides antibody compositions, for example, monoclonal antibody compositions, that have glycosylation profiles that are "substantially homogeneous" or "substantially uniform" or have "substantial homogeneity" as defined herein above. Thus, in some embodiments, the antibody compositions are substantially homogeneous for the G0 glycan species, and thus have a substantially homogeneous glycosylation profile, wherein at least 80%, at least 85%, at least 90%, 91%, 92%, 93%, 94%, 95%, 96%, 97%, 98%, or at least 99% of the total amount of N-glycan species appearing in the glycosylation profile for the composition is represented by the G0 glycan species, with a trace amount of precursor N-glycan species appearing in the glycosylation profile, i.e., any given precursor N-glycan species that is present in the glycosylation profile is present at less than 5%, preferably less than 4%, less than 3%, less than 2%, less than 1%, and even less than 0.5% or even less than 0.1% of the total amount of N-glycan species appearing in the profile. For such a composition, a representative precursor N-glycan species appearing in its glycosylation profile would be, for example, the Man3GlcNAc2, MGn (GlcNac1Man3GlcNAc2 wherein GlcNac1 is attached to the 1,3 mannose arm), and GnM (GlcNac1Man3GlcNAc2 wherein GlcNac1 is attached to the 1,6 mannose arm) precursor N-glycan species described above, where any single one or any combination of these precursor N-glycan species can be present.

In one such embodiment, the monoclonal antibody composition has a substantially homogeneous glycosylation profile, wherein 95.8% of the total amount of N-glycan species appearing in the glycosylation profile for the composition is represented by the G0 glycan species (GlcNAc$_2$Man$_3$GlcNAc$_2$), with the following precursor N-glycan species appearing in the glycosylation profile: Man$_3$GlcNAc$_2$ (0.67%), GlcNAcMan$_3$GlcNAc$_2$ (1.6%), GalGlcNAc$_2$Man$_3$GlcNAc$_2$ (1.2%), Man$_6$GlcNAc$_2$ (0.21%), Man$_7$GlcNAc$_2$ (0.30%), and Man$_8$GlcNAc$_2$ (0.28%). This can be compared with the monoclonal antibody composition obtained from the "wild-type" duckweed plant expression system wherein the same monoclonal antibody is expressed but where the glycosylation machinery of the duckweed plant has not been genetically modified to inhibit expression of XylT and FucT. Such a "wild-type"-derived monoclonal antibody composition has a more heterogeneous glycosylation profile that is characterized by two predominant N-glycan species, i.e., G0XF[3] and G0X, with several precursor N-glycan species represented in trace amounts. In one such embodiment, the "wild-type"-derived monoclonal antibody composition has a glycosylation profile with the following N-glycan species represented therein: G0 (GlcNAc$_2$Man$_3$GlcNAc$_2$) (8.4%); G0X (GlcNAc$_2$[Xyl]Man$_3$GlcNAc$_2$) (17.2%); G0XF[3] (GlcNAc$_2$[Xyl]Man$_3$[Fuc]GlcNAc$_2$) (67.4%); Man$_3$GlcNAc$_2$ (0.26%); GlcNAcMan$_3$GlcNAc$_2$ (0.40%); (Xyl)Man$_3$(Fuc)GlcNAc$_2$ (0.76%); GlcNAc$_2$Man$_3$(Fuc)GlcNAc$_2$ (2.1%); GlcNAc(Xyl)Man$_3$(Fuc)GlcNAc$_2$ (1.4%); Man$_6$GlcNAc$_2$ (0.21%); Man$_7$GlcNAc$_2$ (0.63%); Gal(Fuc)GlcNAc$_2$(Xyl)Man$_3$(Fuc)GlcNAc$_2$ (0.26%); Man$_8$GlcNAc$_2$ (0.61%); and Man$_9$GlcNAc$_2$ (0.40%).

In this manner, the invention provides "substantially homogeneous" or "substantially uniform" antibody compositions or antibody compositions having "substantial homogeneity" as defined herein above. In some embodiments, the invention provides substantially homogeneous antibody compositions, for example, monoclonal antibody compositions, wherein at least 80%, at least 85%, at least 90%, 91%, 92%, 93%, 94%, 95%, 96%, 97%, 98%, or at least 99% of the antibody present in the composition is represented by the G0 glycoform, wherein all anticipated glycosylation sites (for example, each of the Asn-297 residues of the $C_H2$ domains of the heavy chains of an IgG-type antibody) are occupied by the G0 glycan species, with a trace amount of precursor glycoforms being present in the composition. In one such composition, the precursor glycoforms are selected from the group consisting of an antibody having an Fc region wherein the $C_H2$ domain of one heavy chain has a G0 glycan species attached to Asn 297, and the $C_H{}^2$ domain of the other heavy chain is unglycosylated; an antibody having an Fc region wherein the $C_H{}^2$ domain of one heavy chain has a G0 glycan species attached to Asn 297, and the $C_H2$ domain of the other heavy chain has the GnM or MGn precursor glycan attached to Asn 297; and an antibody having an Fc region wherein the Asn 297 glycosylation site on each of the $C_H{}^2$ domains has a G0 glycan species attached, with a third G0 glycan species attached to an additional glycosylation site within the mAb structure; wherein a trace amount of these precursor glycoforms is present, i.e., the precursor glycoforms represent less than 5%, less than 4%, less than 3%, less than 2%, less than 1%, or even less than 0.5%, or less than 0.1% of the total glycoforms present within the antibody composition.

The substantially homogeneous antibody compositions of the invention wherein at least 80%, at least 85%, at least 90%, 91%, 92%, 93%, 94%, 95%, 96%, 97%, 98%, or at least 99% of the antibody present in the composition is represented by the G0 glycoform represent "glycan-optimized antibodies." By "glycan-optimized antibodies" is intended the antibodies of the invention have been genetically engineered in their glycosylation pattern such that they are substantially homogeneous for the G0 glycoform, which yields an antibody having improved Fc effector function. By "improved Fc effector function" is intended these antibodies have increased ADCC activity relative to same-sequence antibodies (i.e., antibodies that have the same amino acid sequence) that, as a result of the production process, have a more heterogeneous glycosylation profile. Thus, for example, antibodies produced in mammalian host expression systems, for example CHO cells, in insect host cells, in yeast cells, or in other plant host expression systems that have not been genetically altered to inhibit XylT and FucT expression tend to have more heterogeneous glycosylation profiles, and thus a mixture of glycoforms, that can effect overall effector function of the antibody product. The G0 glycoform of the antibody compositions of the present invention advantageously provides an antibody composition that has increased ADCC activity in association with the absence of fucose residues. In some embodiments, ADCC activity is increased by 25-fold, 50-fold, 75-fold, 100-fold, 150-fold, 200-fold, 250-fold, 300-fold, 400-fold, 500-fold, or even 1000-fold relative to same-sequence antibodies having a heterogeneous glycosylation profile (i.e., with multiple glycoforms present as major glycoforms in the antibody composition). Furthermore, the G0 glycoform lacks the terminal Gal residues present in antibodies having the G2 glycoform. As such, these substantially homogeneous antibody compositions of the invention having predominately the G0 glycoform have increased ADCC/CDC ratios. In addition, the substantially homogeneous antibody compositions of the invention having predominately the G0 glycoform have increased binding to the FcγRIII, for example, FcγRIIIa, wherein binding affinity is increased about 20-fold, 30-fold, 40-fold, 50-fold, 75-fold, up to 100-fold over that observed for same-sequence antibody compositions having a heterogeneous glycosylation profile, and thus a mixture of glycoforms. For oncology and autoimmune diseases, therapeutic antibodies having increased binding affinity for Fc receptors, for example, FcγRIII, has been strongly correlated with increased efficacy and improved response to treatment.

In some embodiments of the invention, the substantially homogeneous antibody compositions of the invention having predominately the G0 glycoform have altered CDC activity when compared to that observed for same-sequence antibody compositions having a heterogeneous glycosylation profile, and thus a mixture of glycoforms. For example, in one such embodiment, the substantially homogeneous antibody compositions of the invention have predominately the G0 glycoform and have decreased CDC activity when compared to that observed for same-sequence antibody compositions having a heterogeneous glycosylation profile, and thus a mixture of glycoforms. Thus, in some embodiments, the present invention provides substantially homogeneous antibody compositions having predominately the G0 glycoform and CDC activity that is decreased by as much as 5%, 10%, 15%, 20%, 25%, 30%, 35%, 40%, 45%, 50%, 55%, 60%, 65%, 70%, 75%, 80%, 85%, 90%, 95%, or even 100% when compared to same-sequence antibody compositions having a heterogeneous glycosylation profile. In some of these embodiments, the substantially homogeneous antibody compositions having predominately the G0 glycoform and decreased CDC activity are further characterized by having increased ADCC activity when compared to same-sequence antibody compositions having a heterogeneous glycosylation profile.

Without being bound by any theory or mechanism of action, a substantially homogeneous G0 glycoform antibody composition of the present invention having decreased CDC activity, and similar or increased ADCC activity in the manner described above, may advantageously provide for increased cytotoxicity against target cells while reducing potential adverse side effects that may be associated with complement activation following its administration. By reducing the potential for these adverse side effects, the substantially homogeneous antibody compositions having predominately the G0 glycoform can advantageously be administered at faster infusion rates, thereby reducing dosing time at any given administration, and/or can be dosed at higher initial concentrations if warranted, with reduced concern for triggering adverse side affects associated with complement activation.

For example, complement activation plays a pivotal role in the pathogenesis of moderate to severe first-dose side effects of treatment with the chimeric anti-CD20 monoclonal antibody IDEC-C2B8 (IDEC Pharmaceuticals Corp., San Diego, Calif.; commercially available under the tradename Rituxan®, also referred to as rituximab). See, for example, van der Kolk et al. (2001) *British J. Haematol.* 115:807-811. The rituximab antibody within the Rituxan® product is expressed within Chinese hamster ovary (CHO) cells, and thus the antibody composition comprises a heterogeneous glycosylation profile (i.e., a mixture of glycoforms). CDC activity of rituximab has been shown to be correlated with galactose content. In this manner, as the number of galactose residues increases from 0-2 moles/mole of heavy chain, the level of CDC activity increases from 80% (β-galactosidase treated to remove all β(1,4)-galactose residues from the 1,3 and 1,6 mannose arms of the N-glycans attached to Asn 297 of the $C_H2$ domains of the heavy chains) to 150% (UDP galactosyl transferase treated to ensure β(1,4)-galactose residues are attached to both the 1,3 and 1,6 mannose arms of the N-glycans attached to Asn 297 sites) of the maximum observed for the antibody having 1 mole galactose/mole of heavy chain (see, IDEC BLA 97-0260 at the website fda.gov/Cder/biologics/review/ritugen112697, available on the worldwide web). A substantially homogeneous anti-CD20 antibody composition comprising anti-CD20 antibody having the same sequence as rituximab and having predominately the G0 glycoform would advantageously have decreased CDC activity, thereby reducing the potential for adverse side effects normally associated with complement activation upon antibody administration when the antibody composition comprises a heterogenous glycosylation profile (i.e., a mixture of glycoforms).

Thus, a substantially homogeneous G0 glycoform antibody composition of the present invention having decreased CDC activity, and the same or increased ADCC activity, can advantageously be used in therapeutic applications that have heretofore been unsuitable, inadvisable, or inefficacious for one or more patient populations as a result of complications due to adverse side effects normally associated with complement activation upon administration of the same-sequence antibody composition that comprises a heterogeneous glycosylation profile (i.e., a mixture of glycoforms). Such side effects include, but are not limited to, moderate to severe side effects that can be associated with first-time and/or rapid administration of an antibody, including, for example, fever and/or chills, nausea, dyspnea, flushes, and the like. See, for example, van der Kolk et al. (2001) *British J. Haematol.* 115:807-811 and the references cited therein; Winkler et al. (1999) *Blood* 94:2217-2224). In this manner, the present invention provides a method for reducing one or more adverse side effects related to complement activation upon administration of an antibody, for example, a monoclonal antibody, the method comprising administering the antibody as a substantially homogeneous antibody composition as defined herein above, and thus at least 80%, at least 85%, at least 90%, 91%, 92%, 93%, 94%, 95%, 96%, 97%, 98%, or at least 99% of the antibody present in the composition is represented by the G0 glycoform, with a trace amount of precursor glycoforms being present in the composition. In some embodiments, at least 90%, at least 95%, or at least 99% of the antibody present in the composition is represented by the G0 glycoform, with a trace amount of precursor glycoforms being present in the composition.

As a result of their increased Fc effector function, the substantially homogenous antibody compositions of the invention having the predominately G0 glycoform provide the opportunities for new and improved routes of administration, for example, extending the possible routes of administration for known therapeutic antibodies to other routes of administration beyond infusion and intravenous administration, for example, to subcutaneous administration. Furthermore, as a result of their increased potency, the antibody compositions of the invention can be dosed at lower concentrations, or dosed at lower volumes, and dosed with less frequency. A reduction in the volume of the administered antibody composition is particularly advantageous in those instances where adverse events resulting from infusion reactions with a monoclonal antibody are volume-related. The increased potency of the antibody compositions of the invention also opens up new clinical indications for existing mAb targets that may not have been responsive to antibody therapy with more heterogenous glycoform antibody compositions, and provides the ability to revisit previously undeveloped mAb targets.

The monoclonal antibodies produced in accordance with the methods of the present invention may be contained in a composition comprising a pharmaceutically acceptable carrier. Such compositions are useful in a method of treating a subject in need of an antibody having effector function, and in some embodiments, improved effector function where FucT expression has been targeted for inhibition. In this manner, monoclonal antibodies produced in a plant, for example, a duckweed plant, stably transformed in accordance with the methods of the present invention can be administered to a subject in need thereof.

Any antibody may be produced within a plant host genetically modified according to the methods of the invention. In one embodiment, the antibody is a therapeutic antibody. Antibodies have been approved for the treatment of a number of disorders, and many additional therapeutic antibodies are in development. See, Brekke and Sandlie (2003) *Nat. Rev. Drug. Discov.* 2 (3):240, herein incorporated by reference. Examples of therapeutic antibodies that may be expressed by the methods of the invention include, but are not limited to, anti-CD3 antibodies targeting the CD3 antigen (e.g., OKT®3); anti-platelet gpIIb/IIIa antibodies (e.g. abciximab (previously known as c7E3 Fab), distributed as ReoPro®); anti-EpCAM antibodies (e.g., Panorex®); anti-CD20 antibodies targeting the CD20 antigen (e.g. rituximab, distributed as Rituxan®; see U.S. Pat. No. 5,736,137, herein incorporated by reference); anti IL-2 receptor (e.g. Zenapax®, Simulect®); anti-ERBB2 (e.g. trastuzumab, distributed as Herceptin®; see U.S. Pat. No. 6,165,464, herein incorporated by reference); anti-TNF-α (e.g., infliximab, distributed as Remicade®), anti-F-protein (e.g. Synagis®); anti-CD30 antibodies targeting the CD30 antigen (see, for example, the 5F11 antibody described in Borchmann et al. (2003) *Blood* 102:3737-3742 and in Example 6 herein below, see also WO 03/059282 and U.S. Patent Application Publication No. 2004/0006215, herein incorporated by reference; the SGN-30 antibody described in Wahl et al. (2002) *Cancer Res.* 62:3736-3742, a chimeric version of the AC10 anti-CD30 antibody, see also U.S. Patent Application Publication No. 20040018194 and U.S. Pat. No. 7,090,843, herein incorporated by reference); anti-CD33 antibodies targeting the CD33 antigen (e.g. Mylotarg®; see U.S. Pat. No. 5,733,001, herein incorporated by reference); anti-CD52 antibodies targeting the CD52 antigen (e.g., alemtuzumab, distributed as Campath®; see U.S. Pat. No. 5,846,534, herein incorporated by reference); anti-CD20 (e.g., Zevalin®); anti-IgE Fc (e.g., omalizumab, marketed under Xolair®); anti-VEGF (e.g., bevacizumab, distributed as Avastin®; see, Presta et al. (1997) *Cancer Res.* 57:4593-9; herein incorporated by reference); anti-EGF-R (e.g., cetuximab, distributed as Erbitux®)); anti-CD11a (e.g., efalizumab, distributed under Raptiva®), anti-IL-8; anti-C5; anti-TNF-α (e.g., adalimumab, distributed as Humira®); anti-TGF-β2; anti-IL2 receptor (e.g., daclizumab (*Zenapax*) and basiliximab (*Simulect*)); anti-α-4-integrin; anti-CD4; anti-CD2; anti-CD19 (e.g., MT103, a bispecific antibody); anti-CD22 antibody targeting the CD22 antigen (e.g., the monoclonal antibody BL-22); anti-CD23 antibody targeting the CD23 antigen on malignant B cells (e.g., IDEC-152); anti-CD80 antibody targeting the CD80 antigen (e.g., IDEC-114); anti-CD38 antibody targeting the CD38 antigen on malignant B cells; α-M-CSF antibody targeting macrophage colony stimulating factor; antibodies targeting the receptor activator of nuclear factor-kappaB (RANK) and its ligand (RANKL), which are overexpressed in multiple myeloma; anti-CD40 antibodies (e.g., SGN-40) targeting the CD40 antigen on malignant B cells; antibodies targeting tumor necrosis factor-related apoptosis-inducing ligand receptor 1 (TRAIL-R1) (e.g., the agonistic human monoclonal antibody HGS-ETR1) and TRAIL-R2 expressed on a number of solid tumors and tumors of hematopoietic origin) anti-HBV antibodies; or anti-MHC class II antibodies. Many of these antibodies are known to require effector activity for function, either CDC and/or ADCC, for example, Herceptin®, Rituxan®, Mylotarg®, and Campath®.

In some embodiments, the plant host that has been genetically modified to alter its glycosylation machinery in the manner set forth herein, for example, duckweed, may express biologically active α-2b-interferon, for example human α-2b-interferon precursor (NCBI Protein Accession No. AAB59402) or mature human α-2b-interferon (amino acids 24-188 of NCBI Protein Accession No. AAB9402) or biologically active variants thereof. Examples of biologically active variants of human α-2b-interferon are known in the art. See, for example, WO 2005/035767, disclosing truncated versions of α-2b-interferon; European patent EP211148B1; and U.S. Pat. Nos. 4,748,233, 4,801,685, 4,816,566, 4,973,479, 4,975,276, 5,089,400, 5,098,703, 5,231,176, and 5,869,293; herein incorporated by reference. In other embodiments, the plant host, for example, duckweed, may express biologically active mature human growth hormone with or without its accompanying signal peptide. The plant host may also express biologically active variants of human growth hormone. See, for example, WO 02/10414, directed to expression of biologically active polypeptides using a duckweed expression system.

In yet other embodiments, the plant host, for example, duckweed, may express plasminogen, microplasminogen, or biologically active variants thereof. The plasminogen or microplasminogen to be expressed in the plant host may be from any mammalian source. In some embodiments, the plasminogen or microplasminogen is human or porcine. See, for example, WO 2005/078109, directed to expression of these proteins using a duckweed expression system.

By "biologically active variant" of these heterologous polypeptides is intended a polypeptide derived from the native polypeptide by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variants of a heterologous polypeptide of interest encompassed by the present invention retain the biological activity of the native polypeptides.

For example, biologically active variants of α-2b-interferon continue to possess the desired biological activity of the native α-2b-interferon including the ability to increase resistance to viral infection, or the ability to modulate the transcription of α-2b-interferon-regulated gene targets. Such biologically active variants may result from, for example, genetic polymorphism or from human manipulation. Biologically active variants of a heterologous protein of interest will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the heterologous protein of interest. Thus, for example, a biologically active variant of native α-2b-interferon will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for human α-2b-interferon precursor (NCBI Protein Accession No. AAB59402) or mature human α-2b-interferon (amino acids 24-188 of NCBI Protein Accession No. AAB9402), where sequence identity is determined using the parameters identified herein above. Thus, a biologically active variant of a native heterologous protein of interest may differ from that protein by as few as 1-15 amino acid residues, as few as 1-10, such as 6-10, as few as 5, as few as 4, 3, 2, or even 1 amino acid residue.

In one embodiment, the plant host that has been genetically modified to alter its glycosylation machinery in the manner set forth herein is a stably transformed duckweed plant or duckweed cell or duckweed nodule that expresses biologically active polypeptides that cannot effectively be commercially produced by existing gene expression systems, because of cost or logistical constraints, or both. For example, some proteins cannot be expressed in mammalian systems because the protein interferes with cell viability, cell proliferation, cellular differentiation, or protein assembly in mammalian cells. Such proteins include, but are not limited to, retinoblastoma protein, p53, angiostatin, and leptin. The present invention can be advantageously employed to produce mammalian regulatory proteins; it is unlikely given the large evolutionary distance between higher plants and mammals that these proteins will interfere with regulatory processes in duckweed. Transgenic duckweed can also be used to produce large quantities of proteins such as serum albumin (in particular, human serum albumin), hemoglobin, and collagen, which challenge the production capabilities of existing expression systems.

Finally, higher plant systems can be engineered to produce biologically active multimeric proteins (e.g., monoclonal antibodies, hemoglobin, P450 oxidase, and collagen, and the like) far more easily than can mammalian systems. One exemplary approach for producing biologically active multimeric proteins in duckweed uses an expression vector containing the genes encoding all of the polypeptide subunits. See, e.g., During et al. (1990) *Plant Mol. Biol.* 15:281 and van Engelen et al. (1994) *Plant Mol. Biol.* 26:1701. The expression cassette comprising the XylT and/or FucT inhibitory polynucleotide can be introduced into such a vector. This vector is then introduced into duckweed cells using any known transformation method, such as a ballistic bombardment or *Agrobacterium*-mediated transformation. This method results in clonal cell lines that express all of the polypeptides necessary to assemble the multimeric protein, as well as the XylT and/or FucT inhibitory sequences that alter the glycosylation pattern of the N-glycans of glycoproteins. Accordingly, in some embodiments, the transformed duckweed contains one or more expression vectors encoding a heavy and light chain of a monoclonal antibody or Fab' antibody fragment, and an expression cassette comprising the XylT and/or FucT inhibitory polynucleotide, and the monoclonal antibody or antibody fragment is assembled in the duckweed plant from the expressed heavy and light chain.

A variation on this approach is to make single gene constructs, mix DNA from these constructs together, then deliver this mixture of DNAs into plant cells using ballistic bombardment or *Agrobacterium*-mediated transformation. As a further variation, some or all of the vectors may encode more than one subunit of the multimeric protein (i.e., so that there are fewer duckweed clones to be crossed than the number of subunits in the multimeric protein). In an alternative embodiment, each duckweed clone has been genetically modified to alter its glycosylation machinery and expresses at least one of the subunits of the multimeric protein, and duckweed clones secreting each subunit are cultured together and the multimeric protein is assembled in the media from the various secreted subunits. In some instances, it may be desirable to produce less than all of the subunits of a multimeric protein, or even a single protein subunit, in a transformed duckweed plant or duckweed nodule culture, e.g., for industrial or chemical processes or for diagnostic, therapeutic, or vaccination purposes.

In some embodiments of the invention, the transgenic plant host of interest is a "high expresser" of a glycoprotein described herein, including, for example, the glycoproteins comprising N-linked glycans that are predominately of the G0 glycan structure. By "high expresser" is intended the transgenic plant host that has been engineered to produce the glycoproteins described herein is capable of producing the glycoprotein of interest at a level such that the glycoprotein of interest represents at least 5% or more of the total soluble protein produced in the transgenic plant host. In some embodiments, a "high expresser" is a transgenic plant host that has been engineered to produce the glycoproteins described herein such that the glycoprotein of interest represents at least 5%, 6%, 7%, 8%, 9%, 10%, 11%, 12%, 13%, 14%, 15%, or more of the total soluble protein produced in the transgenic plant host. Thus, for example, in one embodiment, the transgenic plant host is a duckweed that has been modified to inhibit expression of XylT and FucT, and the transgenic duckweed is a high expresser of a glycoprotein described herein. In some of these embodiments, the transgenic duckweed is a high expresser of a glycan-optimized monoclonal antibody having the predominate G0 glycoform described herein above. In yet other embodiments, the transgenic duckweed expresses the glycan-optimized monoclonal antibody such that this glycoprotein represents about 5%, 6%, 7%, 8%, 9%, 10%, 11%, 12%, 13%, 14%, 15%, or greater, of the total soluble protein.

Further Humanization of Glycoproteins

In some embodiments, it may be desirable for the glycoproteins of the present invention to comprise complex N-glycans having the terminal β(1,4)-galactose residues attached to the 1,3 and/or 1,6 mannose arms. Without being bound by theory, these terminal galactose residues may contribute to the therapeutic function and/or pharmacokinetic activity of a glycoprotein. It is recognized that the methods of the present invention can be paired with other methods known in the art to further modify the glycoproteins of the invention such that one or more of the N-glycans attached thereto comprises one or more terminal galactose residues, i.e., wherein one or more of the N-glycans is represented by the G1 or G2 glycan species. In this manner, the glycoprotein compositions of the present invention, including the monoclonal antibodies described herein, can be modified, for example, enzymatically with use of a glycosyltransferase enzyme to obtain glycoproteins having a substantially homogenous glycosylation profile for the G1, preferably for the G2 glycan species. See, for example, U.S. Patent Application Publication No. 2004/0191256, herein incorporated by reference in its entirety, teaching galactosyltransferase modification of a substrate glycoprotein to obtain a glycoprotein wherein substantially all of the N-linked glycan species are of the G2 form. In this manner, the glycoprotein of interest can be reacted with an activated galactose in the presence of a galactosyltransferase and a metal salt. The galactosyltransferase can be a mammalian β1,4 galactosyltransferase (GalT), for example, human GalT, and the activated glactose can be, for example, UDP-galactose.

Alternatively, the transgenic plants of the invention having FucT and XylT expression silenced in the manner set forth herein can be further modified in their glycosylation machinery such that they express a galactosyltransferase and efficiently attach the terminal galactose residue to the N-glycans of endogenous and heterologous glycoproteins produced therein. In this manner, the transgenic plants of the invention can be further modified by introducing a nucleotide construct, for example, an expression cassette, that provides for the expression of a galactosyltransferase. The galactosyltransferase can be a mammalian β1,4 galactosyltransferase (GalT), for example, human GalT (see, for example, U.S. Pat. No. 6,998,267, herein incorporated by reference in its entirety) or a hybrid GalT (see, for example, WO 03/078637, herein incorporated by reference in its entirety) comprising at least a portion of a cytoplasmic tail-transmembrane-stem region of a first glycosyltransferase (e.g., a plant glycosyltransferase such as xylosyltransferase, N-acetylglycosaminlytransferase or fucosyltransferase) and at least a portion of a catalytic region of a second glycosyltransefersae (e.g., mammalian glycosyltrasferase, for example, human GalT). By silencing expression of XylT and FucT in a plant, for example, a duckweed, and providing for expression of GalT, for example, human GalT, or a hybrid enzyme comprising a portion of the catalytic domain of GalT, for example, human GalT, in this plant, for example, duckweed, it is possible to obtain transgenic plants producing glycoproteins, both endogenous and heterologous, that have an altered glycosylation pattern, wherein the N-linked glycans attached thereto have a reduction in the attachment of plant-specific xylose and plant-specific fucose residues and which comprise the terminal galactose residues (i.e., G2 glycan species). In this manner, glycoproteins that have a substantially homogeneous profile for the G2 glycan species, and/or which are substantially homogenous for the G2 glycoform can be obtained from transgenic plants of the invention.

In other embodiments, it may be desirable to further modify the glycosylation pattern of the glycoproteins of the invention, wherein the N-linked glycans attached thereto further comprise a terminal sialic acid residue attached to one or both of the galactose residues attached to the 1,3 and 1,6 mannose arms. The addition of the terminal sialic acid residue(s) may be required for the sustained stability, and in some cases function, of some therapeutic proteins.

Depending upon the transgenic plant system, natural sialylation of glycoproteins may occur. Thus, there have been reports in the literature that cultured *Arabidopsis*, tobacco, and *Medicago* cultured cells synthesize sialylated glycoproteins (Shah et al. (2003) *Nat. Biotech.* 21 (12):1470-1471; Joshi and Lopez (2005) *Curr. Opin. Plant Biol.* 8 (2):223-226). More recently, it was reported that Japanese rice express active sialyltransferase-like proteins (Takashima et al. (2006) *J. Biochem.* (*Tokyo*) 139 (2):279-287). Hence, there are now orthogonal reports that plants have the machinery required to sialylate glycoproteins.

Where further modification of the glycosylation pattern of the glycoproteins of the invention, wherein the N-linked glycans attached thereto further comprise a terminal sialic acid residue attached to one or both of the galactose residues attached to the 1,3 and 1,6 mannose arms, is desired, the transgenic plants of the invention can be modified to express a β-1,4 galactosyltransferase, for example, human β-1,4 galactosyltransferase, and to express or overexpress a sialyltransferase. Thus, for example, the transgenic plants can be further modified to express a sialyltransferase such as α-2,3- and/or α-2,6-sialyltransferase. See, for example WO 2004/071177; and Wee et al. (1998) *Plant Cell* 10: 1759-1768; herein incorporated by reference in their entirety. Alternatively, the transgenic plants of the invention can be modified to express a β-1,4 galactosyltransferase, for example, human β-1,4 galactosyltransferase, and to express any other enzymes that are deficient in the plant host's sialic acid pathway. The strategy(s) employed can be determined after an initial investigation of whether the particular plant host, for example, a duckweed, naturally expresses sialic acid-containing N-glycans on native or recombinantly produced glycoproteins. For example, if there is not evidence for the presence of the terminal sialic acid residues on N-glycans of glycoproteins produced within the transgenic plant host, particularly a transgenic plant host engineered to express a β-1,4 galactosyltransferase, then one or both of these strategies could be employed to achieve terminal sialylation of the N-glycans of glycoproteins produced within the transgenic plant host of interest.

Alternatively, the glycoprotein compositions of the invention that are substantially homologous for G2 glycan species or the G2 glycoform can be modified by in vitro enzymatic processing; see, for example, U.S. Patent Application Publication No. 20030040037; herein incorporated by reference in its entirety.

It is also recognized that for some glycoproteins produced in the transgenic plants of the invention, it may be desirable to have the mammalian α1-6 fucose residue attached to the trimannose core structure ($Man_3GlcNAc_2$) of the N-glycan species attached thereto. In such embodiments, the transgenic plants of the invention can be further genetically modified to express an α1-6 fucosyltransferase, for example, human α1-6 fucosyltransferase, using glycoengineering methods known in the art.

It is recognized that the glycoprotein compositions of the invention can be produced by engineering any host cell of interest, including the plant host cells exemplified and described herein. In this manner, other protein expression host systems in addition to plant hosts, including animal, insect, bacterial cells and the like may be used to produce glycoprotein compositions according to the present invention. Such protein expression host systems may be engineered or selected to express a predominant glycoform or alternatively may naturally produce glycoproteins having predominant glycan structures. Examples of engineered protein expression host systems producing a glycoprotein having a predominant glycoform include gene knockouts/mutations (Shields et al. (2002) *JBC* 277:26733-26740); genetic engineering (Umana et al. (1999) *Nature Biotech*. 17:176-180); or a combination of both. Alternatively, certain cells naturally express a predominant glycoform, for example, chickens, humans, and cows (Raju et al. (2000) *Glycobiology* 10:477-486). Thus, the expression of a glycoprotein, including an immunoglobulin such as a monoclonal antibody, or composition having predominantly one specific glycan structure according to the present invention can be obtained by one skilled in the art by selecting at least one of many expression host systems. Further expression host systems found in the art for production of glycoproteins include: CHO cells (see, for example, WO 9922764A1 and WO 03/035835A1); hybridroma cells (Trebak et al. (1999) *J. Immunol. Methods* 230:59-70); insect cells (Hsu et al. (1997) *JBC* 272:9062-970). See also, WO 04/074499A2 regarding additional plant host systems.

The glycoproteins produced in accordance with the methods of the present invention can be harvested from host cells in which they are recombinantly produced in order to obtain them in their isolated or purified form. In this manner, the recombinantly produced glycoproteins of the invention are isolated from the host cells using any conventional means known in the art and purified, for example, by chromatography, electrophoresis, dialysis, solvent-solvent extraction, and the like. Thus, the present invention also provides for purified glycoproteins, including monoclonal antibody compositions, where the glycoproteins have substantially homogeneous glycosylation profiles, and are substantially homogeneous for the G0 glycoform. These purified glycoproteins are substantially free of host cellular material, and include preparations of glycoprotein having less than about 30%, 20%, 10%, 5%, or 1% (by dry weight) of contaminating protein, as noted herein above. In some embodiments, these purified glycoproteins can include at least 0.001%, 0.005%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, or up to about 30% (by dry weight) of contaminating protein. Furthermore, for the recombinantly produced purified glycoproteins of the invention, optimally culture medium represents less than about 30%, 20%, 10%, 5%, or 1% (by dry weight) of chemical precursors or non-protein-of-interest chemicals within the purified glycoprotein preparation, as noted herein above. Thus, in some embodiments, culture medium components within these purified glycoproteins can represent at least 0.001%, 0.005%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, or up to about 30% (by dry weight) of chemical precursors or non-protein-of-interest chemicals within the purified glycoprotein preparation. In some embodiments, isolation and purification results in recovery of purified glycoprotein that is free of contaminating host protein, free of culture medium components, and/or free of both contaminating host protein and culture medium components.

Thus, in some embodiments, the protein expression host system is a plant, for example, a duckweed, and the purified glycoprotein obtained from the plant host is substantially free of plant cellular material, including embodiments where the preparations of glycoprotein have less than about 30%, 20%, 10%, 5%, or 1% (by dry weight) of contaminating plant protein. In other embodiments, the plant culture medium represents less than about 30%, 20%, 10%, 5%, or 1% (by dry weight) of chemical precursors or non-protein-of-interest chemicals within the purified glycoprotein.

In some embodiments, these purified glycoproteins obtained from the plant host can include at least 0.001%, 0.005%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, or up to about 30% (by dry weight) of contaminating plant protein. In other embodiments, plant culture medium components within in these purified glycoproteins can represent at least 0.001%, 0.005%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, or up to about 30% (by dry weight) of chemical precursors or non-protein-of-interest chemicals within the purified glycoprotein. In some embodiments, isolation and purification from the plant host results in recovery of purified glycoprotein that is free of contaminating plant protein, free of plant culture medium components, and/or free of both contaminating plant protein and plant culture medium components.

Expression Cassettes

According to the present invention, stably transformed higher plants, for example, stably transformed duckweed, are obtained by transformation with a polynucleotide of interest contained within an expression cassette. Depending upon the objective, the polynucleotide of interest can be one encoding a FucT or XylT polypeptide of interest, for example, encoding the polypeptide set forth in SEQ ID NO:3 (FucT) or SEQ ID NO:6 or 21 (XylT), or a variant thereof, thus providing for expression of these polypeptides in a cell, for example, a plant cell, or can be a FucT or XylT inhibitory polynucleotide that is capable of inhibiting expression or function of the FucT or XylT polypeptide when stably introduced into a cell, for example, a plant cell of interest.

Thus, in some embodiments, the FucT and/or XylT polynucleotides of the invention, including those set forth in SEQ ID NOS:1 and 2 (FucT) and SEQ ID NOS:4, 5, 19, and 20 (XylT) and fragments and variants thereof, are used to construct expression cassettes that comprise a FucT and/or XylT inhibitory polynucleotide as defined herein above. Stably introducing such an expression cassette into a plant or plant cell of interest can provide for inhibition of expression or function of the FucT and/or XylT polypeptides of the invention, including those set forth in SEQ ID NO:3 (FucT) and SEQ ID NO:6 or 21 (XylT) and variants thereof, thereby altering the N-glycan glycosylation pattern of endogenous and heterologous glycoproteins within a plant or plant cell stably transformed with the expression cassette.

In some embodiments, the plant or plant cell that is stably transformed with an expression cassette comprising a FucT and/or XylT inhibitory polynucleotide has also been stably transformed with an expression cassette that provides for expression of a heterologous polypeptide of interest, for example, a mammalian protein of interest, including the mammalian proteins of pharmaceutical interest as noted herein above. The expression cassette providing for expression of a heterologous polypeptide of interest can be provided on the same polynucleotide (for example, on the same transformation vector) for introduction into a plant, or on a different polynucleotide (for example, on different transformation vectors) for introduction into the plant or plant cell of interest at the same time or at different times, by the same or by different methods of introduction, for example, by the same or different transformation methods.

The expression cassettes of the present invention comprise expression control elements that at least comprise a transcriptional initiation region (e.g., a promoter) linked to the polynucleotide of interest, i.e., a polynucleotide encoding a FucT or XylT polypeptide of the invention, a FucT and/or XylT inhibitory polynucleotide, or a polynucleotide encoding a heterologous polypeptide of interest, for example, a mammalian protein. Such an expression cassette is provided with a plurality of restriction sites for insertion of the polynucleotide or polynucleotides of interest (e.g., one polynucleotide of interest, two polynucleotides of interest, etc.) to be under the transcriptional regulation of the promoter and other expression control elements. In particular embodiments of the invention, the polynucleotide to be transferred contains two or more expression cassettes, each of which encodes at least one polynucleotide of interest.

By "expression control element" is intended a regulatory region of DNA, usually comprising a TATA box, capable of directing RNA polymerase TI, or in some embodiments, RNA polymerase III, to initiate RNA synthesis at the appropriate transcription initiation site for a particular coding sequence. An expression control element may additionally comprise other recognition sequences generally positioned upstream or 5' to the TATA box, which influence (e.g., enhance) the transcription initiation rate. Furthermore, an expression control element may additionally comprise sequences generally positioned downstream or 3' to the TATA box, which influence (e.g., enhance) the transcription initiation rate.

The transcriptional initiation region (e.g., a promoter) may be native or homologous or foreign or heterologous to the host, or could be the natural sequence or a synthetic sequence. By foreign, it is intended that the transcriptional initiation region is not found in the wild-type host into which the transcriptional initiation region is introduced. By "functional promoter" is intended the promoter, when operably linked to a sequence encoding a protein of interest, is capable of driving expression (i.e., transcription and translation) of the encoded protein, or, when operably linked to an inhibitory sequence encoding an inhibitory nucleotide molecule (for example, a hairpin RNA, double-stranded RNA, miRNA polynucleotide, and the like), the promoter is capable of initiating transcription of the operably linked inhibitory sequence such that the inhibitory nucleotide molecule is expressed. The promoters can be selected based on the desired outcome. Thus the expression cassettes of the invention can comprise constitutive, tissue-preferred, or other promoters for expression in plants.

As used herein a chimeric gene comprises a coding sequence operably linked to a transcription initiation region that is heterologous to the coding sequence.

Any suitable promoter known in the art can be employed according to the present invention, including bacterial, yeast, fungal, insect, mammalian, and plant promoters. For example, plant promoters, including duckweed promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthorne et al. (1990) *Plant Mol. Biol.* 15:49). Other promoters from viruses that infect plants, preferably duckweed, are also suitable including, but not limited to, promoters isolated from Dasheen mosaic virus, Chlorella virus (e.g., the Chlorella virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Other suitable expression control elements are disclosed in the commonly owned and copending provisional application entitled "Expression Control Elements from the Lemnaceae Family," assigned U.S. Patent Application No. 60/759,308, filed Jan. 17, 2006, herein incorporated by reference in its entirety. The expression control elements disclosed in this copending application were isolated from ubiquitin genes for several members of the Lemnaceae family, and are thus referred to as "Lemnaceae ubiquitin expression control elements." SEQ ID NO:7 of the present application sets forth the full-length *Lemna minor* ubiquitin expression control element, including both the promoter plus 5' UTR (nucleotides 1-1625) and intron (nucleotides 1626-2160). SEQ ID NO:8 sets forth the full-length *Spirodella polyrrhiza* ubiquitin expression control element, including both the promoter plus 5' UTR (nucleotides 1-1041) and intron (nucleotides 1042-2021). SEQ ID NO:9 sets forth the full-length *Lemna aequinoctialis* ubiquitin expression control element, including both the promoter plus 5' UTR (nucleotides 1-964) and intron (nucleotides 965-2068). SEQ ID NO:10 sets forth the promoter plus 5' UTR portion of the *L. minor* ubiquitin expression control element (designated "LmUbq promoter" herein). SEQ ID NO:11 sets forth the promoter plus 5' UTR portion of the *S. polyrrhiza* ubiquitin expression control element (designated "SpUbq promoter" herein). SEQ ID NO:12 sets forth the promoter plus 5' UTR portion of the *L. aequinoctialis* ubiquitin expression control element (designated "LaUbq promoter" herein). SEQ ID NO:13 sets forth the intron portion of the *L. minor* ubiquitin expression control element (designated "LmUbq intron" herein). SEQ ID NO:14 sets forth the intron portion of the *S. polyrrhiza* ubiquitin expression control element (designated "SpUbq intron" herein). SEQ ID NO:15 sets forth the intron portion of the *L. aequinoctialis* ubiquitin expression control element (designated "LaUbq intron" herein). It is recognized that the individual promoter plus 5' UTR sequences set forth in SEQ ID NOs: 10-12, and biologically active variants and fragments thereof, can be used to regulate transcription of operably linked nucleotide sequences of interest in plants. Similarly, one or more of the intron sequences set forth in SEQ ID NOs:13-15, and biologically active fragments or variants thereof, can be operably linked to a promoter of interest, including a promoter set forth in SEQ ID NO:10, 11, or 12 in order to enhance expression of a nucleotide sequence that is operably linked to that promoter.

Fragments and variants of the disclosed expression control elements can also be used within expression cassettes to drive expression of the operably linked polynucleotide of interest. By "fragment of an expression control element" is intended a portion of the full-length expression control element, such as a portion of any one of the expression control elements set forth in SEQ ID NOs:7-9. Fragments of an expression control element retain biological activity and hence encompass fragments capable of initiating or enhancing expression of an operably linked polynucleotide of interest. Thus, for example, less than the entire expression control elements disclosed herein may be utilized to drive expression of an operably linked polynucleotide of interest. Specific, non-limiting examples of such fragments of an expression control element include the nucleotide sequences set forth in any one of SEQ ID NOs:10-12 (as described herein above), as well as 5' truncations of the *L. minor* ubiquitin expression control element (SEQ ID NO:7), such as nucleotides 1288-2160 of SEQ ID NO:7 (LmUbq truncated promoter No. 1) and nucleotides 1132-2160 of SEQ ID NO:1 (LmUbq truncated promoter No. 2). See the copending provisional application assigned U.S. Patent Application No. 60/759,308, herein incorporated by reference in its entirety.

The nucleotides of such fragments will usually comprise the TATA recognition sequence of the particular expression control element. Such fragments can be obtained by use of restriction enzymes to cleave the naturally occurring expression control elements disclosed herein; by synthesizing a nucleotide sequence from the naturally occurring sequence of the expression control element DNA sequence; or can be obtained through the use of polymerase chain reaction (PCR) technology. See particularly, Mullis et al. (1987) *Methods Enzymol.* 155:335-350, and Erlich, ed. (1989) *PCR Technology* (Stockton Press, New York).

Variants of expression control elements, such as those resulting from site-directed mutagenesis, can also be used in the expression cassettes of the present invention to provide expression of the operably linked polynucleotide of interest. By "variant of an expression control element" is intended sequences having substantial similarity with an expression control element disclosed herein (for example, the expression control element set forth in SEQ ID NO:7, 9, or 9), or with a fragment thereof (for example, the respective sequences set forth in SEQ ID NOs:10-15). Naturally occurring variants of expression control elements can be identified with the use of well-known molecular biology techniques, as, for example, with PCR and hybridization techniques as outlined above. Variant expression control elements also include synthetically derived nucleotide sequences, such as those generated, for example, by using site-directed mutagenesis. Generally, variants of a particular expression control element disclosed herein, including variants of SEQ ID NOs:7-15, will have at least 40%, 50%, 60%, 65%, 70%, generally at least 75%, 80%, 85%, preferably about 90%, 91%, 92%, 93%, 94%, to 95%, 96%, 97%, and more preferably about 98%, 99% or more sequence identity to that particular nucleotide sequence as determined by sequence alignment programs described herein above using default parameters.

Expression control elements, including promoters, can be chosen to give a desired level of regulation. For example, in some instances, it may be advantageous to use a promoter that confers constitutive expression (e.g, the mannopine synthase promoter from *Agrobacterium tumefaciens*). Alternatively, in other situations, for example, where expression of a heterologous polypeptide is concerned, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacteriur turefaciens* octopine synthase gene can enhance transcription from the *Agrobacteriur turefaciens* mannopine synthase promoter (see U.S. Pat. No. 5,955,646 to Gelvin et al.). In the present invention, the expression cassette can contain activating nucleotide sequences inserted upstream of the promoter sequence to enhance the expression of the nucleotide sequence of interest. In one embodiment, the expression cassette includes three upstream activating sequences derived from the *Agrobacteriur turefaciens* octopine synthase gene operably linked to a promoter derived from an *Agrobacterium tumefaciens* mannopine synthase gene (see U.S. Pat. No. 5,955,646, herein incorporated by reference).

Where the expression control element will be used to drive expression of an operably linked DNA sequence encoding a small hpRNA molecule, for example, within an RNAi expression cassette described herein above, it is advantageous to use an expression control element comprising a promoter recognized by the DNA dependent RNA polymerase III. As used herein, "a promoter recognized by the DNA dependent RNA polymerase III" is a promoter which directs transcription of the associated DNA region through the polymerase action of RNA polymerase III. These include genes encoding 5S RNA, tRNA, 7SL RNA, U6 snRNA and a few other small stable RNAs, many involved in RNA processing. Most of the promoters used by Pol III require sequence elements downstream of +1, within the transcribed region. A minority of pol III templates however, lack any requirement for intragenic promoter elements. These are referred to as type 3 promoters. By "type 3 Pol III promoters" is intended those promoters that are recognized by RNA polymerase III and contain all cis-acting elements, interacting with the RNA polymerase III upstream of the region normally transcribed by RNA polymerase III. Such type 3 Pol III promoters can be assembled within the RNAi expression cassettes of the invention to drive expression of the operably linked DNA sequence encoding the small hpRNA molecule.

Typically, type 3 Pol III promoters contain a TATA box (located between −25 and −30 in Human U6 snRNA gene) and a Proximal Sequence element (PSE; located between −47 and −66 in Human U6 snRNA). They may also contain a Distal Sequence Element (DSE; located between −214 and −244 in Human U6 snRNA). Type 3 Pol III promoters can be found, e.g., associated with the genes encoding 7SL RNA, U3 snRNA and U6 snRNA. Such sequences have been isolated from *Arabidopsis*, rice, and tomato. See, for example, SEQ ID NOs:1-8 of U.S. Patent Application Publication No. 20040231016.

Other nucleotide sequences for type 3 Pol III promoters can be found in nucleotide sequence databases under the entries for the *A. thaliana* gene AT7SL-1 for 7SL RNA (X72228), *A. thaliana* gene AT7SL-2 for 7SL RNA (X72229), *A. thaliana* gene AT7SL-3 for 7SL RNA (AJ290403), *Humulus lupulus* H17SL-1 gene (AJ236706), *Humulus lupulus* H17SL-2 gene (AJ236704), *Humulus lupulus* H17SL-3 gene (AJ236705), *Humulus lupulus* H17SL-4 gene (AJ236703), *A. thaliana* U6-1 snRNA gene (X52527), *A. thaliana* U6-26 snRNA gene (X52528), *A. thaliana* U6-29 snRNA gene (X52529), *A. thaliana* U6-1 snRNA gene (X52527), *Zea mays* U3 snRNA gene (Z29641), *Solanum tuberosum* U6 snRNA gene (Z17301; X 60506; S83742), tomato U6 smal nuclear RNA gene (X51447), *A. thaliana* U3C snRNA gene (X52630), *A. thaliana* U3B snRNA gene (X52629), *Oryza sativa* U3 snRNA promoter (X79685), tomato U3 small nuclear RNA gene (X14411), *Triticum aestivum* U3 snRNA gene (X63065), and *Triticum aestivum* U6 snRNA gene (X63066).

Other type 3 Pol III promoters may be isolated from other varieties of tomato, rice or *Arabidopsis*, or from other plant species using methods well known in the art. For example, libraries of genomic clones from such plants may be isolated using U6 snRNA, U3 snRNA, or 7SL RNA coding sequences (such as the coding sequences of any of the above mentioned sequences identified by their accession number and additionally the *Vicia faba* U6snRNA coding sequence (X04788), the maize DNA for U6 snRNA (X52315), or the maize DNA for 7SL RNA (X14661)) as a probe, and the upstream sequences, preferably the about 300 to 400 bp upstream of the transcribed regions may be isolated and used as type 3 Pol III promoters. Alternatively, PCR based techniques such as inverse-PCR or TAIL™-PCR may be used to isolate the genomic sequences including the promoter sequences adjacent to known transcribed regions. Moreover, any of the type 3 Pol III promoter sequences described herein, identified by their accession numbers and SEQ ID NOS, may be used as probes under stringent hybridization conditions or as source of information to generate PCR primers to isolate the corresponding promoter sequences from other varieties or plant species.

Although type 3 Pol III promoters have no requirement for cis-acting elements located with the transcribed region, it is clear that sequences normally located downstream of the transcription initiation site may nevertheless be included in the RNAi expression cassettes of the invention. Further, while type 3 Pol III promoters originally isolated from monocotyledonous plants can effectively be used in RNAi expression cassettes to suppress expression of a target gene in both dicotyledonous and monocotyledonous plant cells and plants, type 3 Pol III promoters originally isolated from dicotyledonous plants reportedly can only be efficiently used in dicotyledonous plant cells and plants. Moreover, the most efficient gene silencing reportedly is obtained when the RNAi expression cassette is designed to comprise a type 3 Pol III promoter derived from the same or closely related species. See, for example, U.S. Patent Application Publication No. 20040231016. Thus, where the plant of interest is a monocotyledonous plant, and small hpRNA interference is the method of choice for inhibiting expression of FucT and/or XylT, the type 3 Pol III promoter preferably is from another monocotyledonous plant, including the plant species for which the glycosylation pattern of N-linked glycans of a glycoprotein of interest is to be altered.

The expression cassette of the invention thus includes in the 5'-3' direction of transcription, an expression control element comprising a transcriptional and translational initiation region, a polynucleotide of interest, for example, a sequence encoding a heterologous protein of interest or a sequence encoding a FucT or XylT inhibitory sequence that, when expressed, is capable of inhibiting the expression or function of FucT and/or XylT, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence. Other suitable termination sequences will be apparent to those skilled in the art, including the oligo dT stretch disclosed herein above for use with type 3 Pol III promoters driving expression of a FucT and/or XlyT inhibitory polynucleotide that forms a small hpRNA structure.

Alternatively, the polynucleotide(s) of interest can be provided on any other suitable expression cassette known in the art.

Generally, the expression cassette will comprise a selectable marker gene for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) *EMBO J.* 6:2513; DeBlock et al. (1989) *Plant Physiol.* 91:691; Fromm et al. (1990) *BioTechnology* 8:833; Gordon-Kamm et al. (1990) *Plant Cell* 2:603. For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) CRC *Critical Reviews in Plant Science* 4: 1); cyanamide hydratase (Maier-Greiner et al. (1991) *Proc. Natl. Acad. Sci. USA* 88:4250); aspartate kinase; dihydrodipicolinate synthase (Perl et al. (1993) *BioTechnology* 11:715); bar gene (Toki et al. (1992) *Plant Physiol.* 100:1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761, 373 to Anderson et al.; Haughn et al. (1988) *Mol. Gen. Genet.* 221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to: gentamycin (e.g., aacC1, Wohlleben et al. (1989) *Mol. Gen. Genet.* 217:202-208); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Bio.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Bio.* 15:127); bromoxynil (Stalker et al. (1988) *Science* 242:419); 2,4-D (Streber et al. (1989) *BioTechnology* 7:811); phosphinothricin (DeBlock et al. (1987) EMBO J. 6:2513); spectinomycin (Bretagne-Sagnard and Chupeau, *Transgenic Research* 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff (1992) *Mol. Microbiol.* 6:2419; Barkley et al. (1980) *The Operon* 177-220; Hu et al. (1987) *Cell* 48:555; Brown et al. (1987) *Cell* 49:603; Figge et al. (1988) *Cell* 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al. (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes are not meant to be limiting. Any selectable marker gene can be used in the present invention.

Modification of Nucleotide Sequences for Enhanced Expression in a Plant Host

Where the plant of interest is also genetically modified to express a heterologous protein of interest, for example, a transgenic plant host serving as an expression system for recombinant production of a heterologous protein, the present invention provides for the modification of the expressed polynucleotide sequence encoding the heterologous protein of interest to enhance its expression in the host plant. Thus, where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing nucleotide sequences with plant-preferred codons. See, e.g., U.S. Pat. Nos. 5,380,831 and 5,436,391; Perlak et al. (1991) *Proc. Natl. Acad. Sci. USA* 15:3324; Tannacome et al. (1997) *Plant Mol. Biol.* 34:485; and Murray et al., (1989) *Nucleic Acids. Res.* 17:477, herein incorporated by reference.

In some embodiments of the invention, the plant host is a member of the duckweed family, and the polynucleotide encoding the heterologous polypeptide of interest, for example, a mammalian polypeptide, is modified for enhanced expression of the encoded heterologous polypeptide. In this manner, one such modification is the synthesis of the polynucleotide encoding the heterologous polypeptide of interest using duckweed-preferred codons, where synthesis can be accomplished using any method known to one of skill in the art. The preferred codons may be determined from the codons of highest frequency in the proteins expressed in duckweed. For example, the frequency of codon usage for *Lemna gibba* is found on the web page: http://www.kazusa.or.jp/codon/cgi-bin/showcodon.cgi?species=Lemna+gibba+[gbpln], and the frequency of codon usage for *Lemna minor* is found on the web page http://www.kazusa.or.jp/codon/cgibin/showcodon.cgi?species=Lemna+minor+[gbpln] and in Table 1. It is recognized that heterologous genes that have been optimized for expression in duckweed and other monocots, as well as other dicots, can be used in the methods of the invention. See, e.g., EP 0 359 472, EP 0 385 962, WO 91/16432; Perlak et al. (1991) *Proc. Natl. Acad. Sci. USA* 88:3324; lannacome et al. (1997) *Plant Mol. Biol.* 34:485; and Murray et al. (1989) *Nuc. Acids Res.* 17:477, and the like, herein incorporated by reference. It is further recognized that all or any part of the polynucleotide encoding the heterologous polypeptide of interest may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be duckweed-preferred codons. In one embodiment, between 90 and 96% of the codons are duckweed-preferred codons. The coding sequence of a polynucleotide sequence encoding a heterologous polypeptide of interest may comprise codons used with a frequency of at least 17% in *Lemna gibba*. In one embodiment, the modified nucleotide sequence is the human α-2B-interferon encoding nucleotide sequence shown in SEQ ID NO:16, which contains 93% duckweed preferred codons.

TABLE 1

*Lemna gibba*-preferred codons from GenBank Release 113

| | | | | | | | |
|---|---|---|---|---|---|---|---|
| UUU 2.2 | (4) | UCU 0.5 | (1) | UAU 2.2 | (4) | UGU 0.0 | (0) |
| UUC 50.5 | (92) | UCC 31.9 | (58) | UAC 40.1 | (73) | UGC 17.6 | (32) |
| UUA 0.0 | (0) | UCA 0.5 | (1) | UAA 3.8 | (7) | UGA 1.6 | (3) |
| UUG 2.7 | (5) | UCG 15.4 | (28) | UAG 0.0 | (0) | UGG 24.2 | (44) |
| CUU 0.5 | (1) | CCU 6.6 | (12) | CAU 0.5 | (1) | CGU 1.1 | (2) |
| CUC 39.0 | (71) | CCC 43.4 | (79) | CAC 6.6 | (12) | CGC 26.9 | (49) |
| CUA 1.1 | (2) | CCA 2.2 | (4) | CAA 4.4 | (8) | CGA 1.1 | (2) |
| CUG 22.5 | (41) | CCG 20.9 | (38) | CAG 26.9 | (49) | CGG 7.7 | (14) |
| AUU 0.0 | (0) | ACU 3.3 | (6) | AAU 1.1 | (2) | AGU 0.0 | (0) |
| AUC 33.5 | (61) | ACC 26.4 | (48) | AAC 37.9 | (69) | AGC 22.0 | (40) |
| AUA 0.0 | (0) | ACA 0.5 | (1) | AAA 0.0 | (0) | AGA 4.9 | (9) |
| AUG 33.5 | (61) | ACG 9.3 | (17) | AAG 57.1 | (104) | AGG 6.0 | (11) |
| GUU 9.3 | (17) | GCU 7.1 | (13) | GAU 1.6 | (3) | GGU 1.1 | (2) |

TABLE 1-continued

Lemna gibba-preferred codons from GenBank Release 113

| GUC 28.0 | (51) | GCC 73.6 | (134) | GAC 38.4 | (70) | GGC 46.7 | (85) |
| GUA 0.0 | (0) | GCA 5.5 | (10) | GAA 2.2 | (4) | GGA 1.1 | (2) |
| GUG 34.0 | (62) | GCG 20.9 | (38) | GAG 62.6 | (114) | GGG 27.5 | (50) |

Other modifications can also be made to the polynucleotide encoding the heterologous polypeptide of interest to enhance its expression in a plant host of interest, including duckweed. These modifications include, but are not limited to, elimination of sequences encoding spurious polyadenylation signals, exon-intron splice site signals, transposon-like repeats, and other such well characterized sequences which may be deleterious to gene expression. The G-C content of the sequence may be adjusted to levels average for a given cellular host, as calculated by reference to known genes expressed in the host cell. When possible, the polynucleotide encoding the heterologous polypeptide of interest may be modified to avoid predicted hairpin secondary mRNA structures.

There are known differences between the optimal translation initiation context nucleotide sequences for translation initiation codons in animals and plants and the composition of these translation initiation context nucleotide sequences can influence the efficiency of translation initiation. See, for example, Lukaszewicz et al. (2000) *Plant Science* 154:89-98; and Joshi et al. (1997); *Plant Mol. Biol.* 35:993-1001. In the present invention, the translation initiation context nucleotide sequence for the translation initiation codon of the polynucleotide nucleotide of interest, for example, the polynucleotide encoding a heterologous polypeptide of interest, may be modified to enhance expression in duckweed. In one embodiment, the nucleotide sequence is modified such that the three nucleotides directly upstream of the translation initiation codon of the nucleotide sequence of interest are "ACC." In a second embodiment, these nucleotides are "ACA."

Expression of a transgene in a host plant, including duckweed, can also be enhanced by the use of 5' leader sequences. Such leader sequences can act to enhance translation. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA,* 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthome et al. (1990) *J. Plant. Mol. Biol.* 15:49-58); and maize chlorotic mottle virus leader (MCMV; Lommel et al. (1991) Virology 81:382). See also, Della-Cioppa et al. (1987) *Plant Physiology* 84:965. Leader sequence comprising plant intron sequence, including intron sequence from the maize alcohol dehydrogenase 1 (ADH1) gene, the castor bean catalase gene, or the *Arabidopsis* tryptophan pathway gene PAT1 has also been shown to increase translational efficiency in plants (Callis et al. (1987) *Genes Dev.* 1:1183-1200; Mascarenhas et al. (1990) *Plant Mol. Biol.* 15:913-920). See also copending provisional application U.S. Patent Application No. 60/759,308, wherein leader sequence comprising a duckweed intron sequence selected from the group consisting of the introns set forth in SEQ ID NOs:13-15 provides for increased translational efficiency in duckweed.

In some embodiments of the present invention, nucleotide sequence corresponding to nucleotides 1222-1775 of the maize alcohol dehydrogenase 1 gene (ADH1; GenBank Accession Number X04049), or nucleotide sequence corresponding to the intron set forth in SEQ ID NO:13, 14, or 15, is inserted upstream of the polynucleotide encoding the heterologous polypeptide of interest or the FucT and/or XylT inhibitory polynucleotide to enhance the efficiency of its translation. In another embodiment, the expression cassette contains the leader from the *Lemna gibba* ribulose-bis-phosphate carboxylase small subunit 5B gene (RbcS leader; see Buzby et al. (1990) *Plant Cell* 2:805-814; also see SEQ ID NO:16, 17, or 18 of the present invention).

Figure 13:
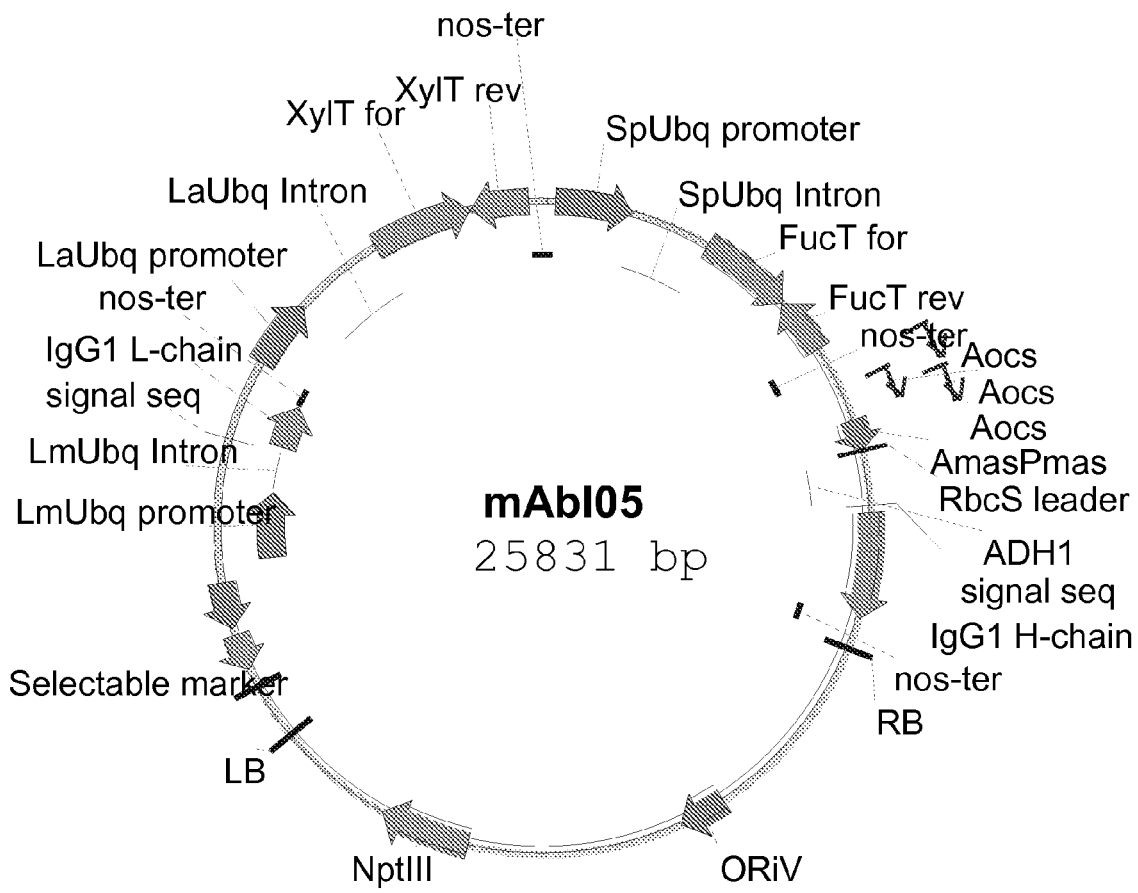
Figure 14:
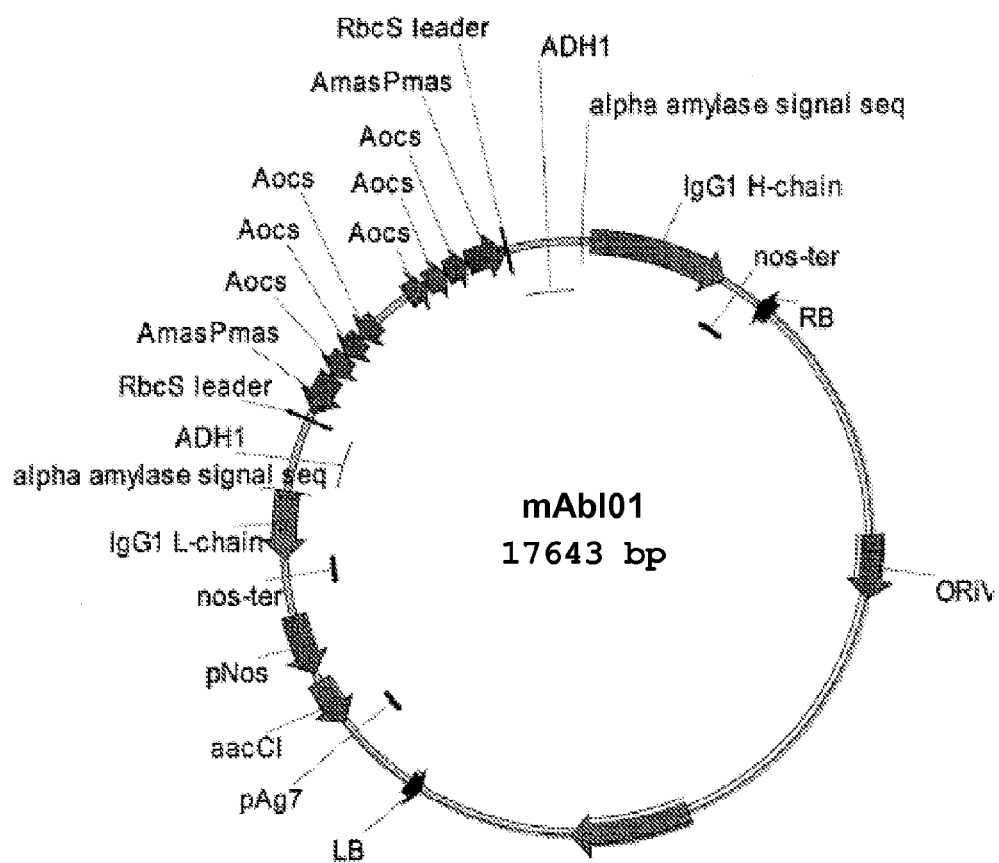

See also, by way of example only, the expression vectors disclosed in the figures herein, wherein the RbcS leader and ADH1 intron are included as upstream regulatory sequences within an expression cassette comprising the FucT inhibitory polynucleotide (FIG. 8), the XylT inhibitory polynucleotide (FIGS. 9 and 11), an expression cassette comprising the chimeric FucT/XylT inhibitory molecule (FIG. 10), or an expression cassette comprising the coding sequence for the heterologous polypeptide, the IgG1 heavy chain of a monoclonal antibody (FIGS. 12, 13, and 14) or the light chain of a monoclonal antibody (FIG. 14); wherein the LmUbq promoter and LmUbq intron are included as upstream regulatory sequences within an expression cassette comprising the FucT inhibitory polynucleotide (FIG. 11), or an expression cassette comprising the coding sequence for the heterologous polypeptide, the IgF1 light chain of a monoclonal antibody (FIG. 13); wherein the SpUbq promoter and SpUbq intron are included as upstream regulatory sequences within an expression cassette comprising the FucT inhibitory polynucleotide (FIG. 13), or an expression cassette comprising the chimeric FucT/XylT inhibitory polynucleotide (FIG. 12); and wherein the LaUbq promoter and LaUbq intron are included as upstream regulatory sequences in an expression cassette comprising the XylT inhibitory polynucleotide (FIG. 13).

It is recognized that any of the expression-enhancing nucleotide sequence modifications described above can be used in the present invention, including any single modification or any possible combination of modifications. The phrase "modified for enhanced expression" in a plant, for example, a duckweed plant, as used herein refers to a polynucleotide sequence that contains any one or any combination of these modifications.

Signal Peptides

It is recognized that the heterologous polypeptide of interest may be one that is normally or advantageously expressed as a secreted protein. Secreted proteins are usually translated from precursor polypeptides that include a "signal peptide" that interacts with a receptor protein on the membrane of the endoplasmic reticulum (ER) to direct the translocation of the growing polypeptide chain across the membrane and into the endoplasmic reticulum for secretion from the cell. This signal peptide is often cleaved from the precursor polypeptide to produce a "mature" polypeptide lacking the signal peptide. In an embodiment of the present invention, a biologically active polypeptide is expressed in the plant host of interest, for example, duckweed or other higher plant, from a polynucleotide sequence that is operably linked with a nucleotide sequence encoding a signal peptide that directs secretion of the polypeptide into the culture medium. Plant signal peptides that target protein translocation to the endoplasmic reticulum (for secretion outside of the cell) are known in the art. See, for example, U.S. Pat. No. 6,020,169 to Lee et al. In the present invention, any plant signal peptide can be used to target the expressed polypeptide to the ER.

In some embodiments, the signal peptide is the *Arabidopsis thaliana* basic endochitinase signal peptide (amino acids 14-34 of NCBI Protein Accession No. BAA82823), the extensin signal peptide (Stiefel et al. (1990) *Plant Cell* 2:785-793), the rice α-amylase signal peptide (amino acids 1-31 of NCBI Protein Accession No. AAA33885), or a modified rice α-amylase signal sequence (SEQ ID NO:17). In another embodiment, the signal peptide corresponds to the signal peptide of a secreted duckweed protein.

Alternatively, a mammalian signal peptide can be used to target recombinant polypeptides expressed in a genetically engineered plant of the invention, for example, duckweed or other higher plant of interest, for secretion. It has been demonstrated that plant cells recognize mammalian signal peptides that target the endoplasmic reticulum, and that these signal peptides can direct the secretion of polypeptides not only through the plasma membrane but also through the plant cell wall. See U.S. Pat. Nos. 5,202,422 and 5,639,947 to Hiatt et al. In one embodiment of the present invention, the mammalian signal peptide that targets polypeptide secretion is the human α-2b-interferon signal peptide (amino acids 1-23 of NCBI Protein Accession No. AAB59402).

In one embodiment, the nucleotide sequence encoding the signal peptide is modified for enhanced expression in the plant host of interest, for example, duckweed or other higher plant, utilizing any modification or combination of modifications disclosed above for the polynucleotide sequence of interest.

The secreted biologically active polypeptide can be harvested from the culture medium by any conventional means known in the art and purified by chromatography, electrophoresis, dialysis, solvent-solvent extraction, and the like. In this manner, purified polypeptides, as defined above, can be obtained from the culture medium.

Thus, in some embodiments, the protein expression host system is a plant, for example, a duckweed or other higher plant, and the secreted biologically active polypeptide is a glycoprotein of the invention, where the glycoprotein has a substantially homogeneous glycosylation profile, and is substantially homogeneous for the G0 glycoform. In such embodiments, any such glycoprotein that may remain within the plant material can optionally be isolated and purified as described above. The secreted glycoprotein can be obtained from the plant culture medium and purified using any conventional means in the art as noted above. In this manner, the purified glycoprotein obtained from the plant material is substantially free of plant cellular material, and includes embodiments where the preparations of glycoprotein have less than about 30%, 20%, 10%, 5%, or 1% (by dry weight) of contaminating plant protein. Where the purified glycoprotein is obtained from the plant culture medium, the plant culture medium represents less than about 30%, 20%, 10%, 5%, or 1% (by dry weight) of chemical precursors or non-protein-of-interest chemicals within the purified glycoprotein preparation.

In some embodiments, these purified glycoproteins obtained from the plant host can include at least 0.001%, 0.005%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, or up to about 30% (by dry weight) of contaminating plant protein. In other embodiments, where the glycoprotein is collected from the plant culture medium, the plant culture medium in these purified glycoproteins can include at least 0.001%, 0.005%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, 20%, 25%, or up to about 30% (by dry weight) of chemical precursors or non-protein-of-interest chemicals within the purified glycoprotein preparation. In some embodiments, isolation and purification from the plant host, and where secreted, from the culture medium, results in recovery of purified glycoprotein that is free of contaminating plant protein, free of plant culture medium components, and/or free of both contaminating plant protein and plant culture medium components.

Transformed Plants and Transformed Duckweed Plants and Duckweed Nodule Cultures

Transformation protocols as well as protocols for introducing nucleotide sequences into plants may vary depending on the type of plant or plant cell or nodule, that is, monocot or dicot, targeted for transformation. Suitable methods of introducing nucleotide sequences into plants or plant cells or nodules include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,563,055 and 5,981,840, both of which are herein incorporated by reference), direct gene transfer (Paszkowski et al. (1984) *EMBO J.* 3:2717-2722), ballistic particle acceleration (see, e.g., U.S. Pat. Nos. 4,945,050; 5,879,918; 5,886,244; and 5,932,782 (each of which is herein incorporated by reference); and Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926). The cells that have been transformed may be grown into plants in accordance with conventional ways. See, for example, McCormick et al. (1986) *Plant Cell Reports* 5:81-84.

The stably transformed duckweed utilized in this invention can be obtained by any method known in the art. In one embodiment, the stably transformed duckweed is obtained by one of the gene transfer methods disclosed in U.S. Pat. No. 6,040,498 to Stomp et al., herein incorporated by reference. These methods include gene transfer by ballistic bombardment with microprojectiles coated with a nucleic acid comprising the nucleotide sequence of interest, gene transfer by electroporation, and gene transfer mediated by *Agrobacterium* comprising a vector comprising the nucleotide sequence of interest. In one embodiment, the stably transformed duckweed is obtained via any one of the *Agrobacterium*-mediated methods disclosed in U.S. Pat. No. 6,040,498 to Stomp et al. The *Agrobacterium* used is *Agrobacterium tumefaciens* or *Agrobacterium rhizogenes*.

It is preferred that the stably transformed duckweed plants utilized in these methods exhibit normal morphology and are fertile by sexual reproduction. Preferably, transformed plants of the present invention contain a single copy of the transferred nucleic acid, and the transferred nucleic acid has no notable rearrangements therein. Also preferred are duckweed plants in which the transferred nucleic acid is present in low copy numbers (i.e., no more than five copies, alternately, no more than three copies, as a further alternative, fewer than three copies of the nucleic acid per transformed cell).

The following examples are offered by way of illustration and not by way of limitation.

EXPERIMENTAL

*Lemna*, a small aquatic plant, is a scalable and economically attractive expression platform for the manufacture of therapeutic proteins free of human pathogens and with a clear path towards regulatory approval. The *Lemna* expression system (LEX Systems<sup>SM</sup>) enables rapid clonal expansion of transgenic plants, secretion of transgenic proteins, high protein yields, ease of containment that is comparable to mammalian cell culture systems such as CHO cells, and has the additional advantage of low operating and capital costs (Gasdaska et al. (2003) *Bioprocessing J.* 50-56). In addition, this plant expression system offers the advantage of high protein yields (in the range of 6-8% of the total soluble protein (TSP)). These expression levels, in combination with *Lemna*'s high protein content and fast growth rate (36 hr doubling time), enable production of >1 g of mAb per kg biomass in a robust and well-controlled format.

The following examples demonstrate how humanization of the glycosylation profile of a mAb was accomplished by coexpression of the mAb with an interference RNA (RNAi) construct targeting the endogenous expression of α1,3-fucosyltransferase and β1,2-xylosyltransferase genes. The resultant mAb contained a single major N-glycan species (>95%) devoid of the plant specific α-1,3-linked fucose and β-1,2-linked xylose sugars. In receptor binding assays, this glycan optimized mAb exhibited enhanced effector cell receptor binding activity when compared to mAb produced in wild-type *Lemna* having the native glycosylation machinery and mAb produced in CHO cells.

Example 1

Isolation of *Lemna minor* Proteins Involved in N-Glycosylation of Proteins

In order to generate recombinant proteins with remodeled N-glycan, alpha 1-3 fucosyltransferase and β1-2 xylosyltransferase were selected as targets for RNAi gene silencing in *L. minor*. Initial results from cDNA sequencing efforts indicated that two or more isoforms were present for each of the target genes. Sequence homology between the isoforms was determined to be between 90% and 95%. Full length cDNA sequences for both target genes were retrieved and characterized. The full-length cDNA sequence, including 5'- and 3'-UTR, for *L. minor* α1-3 fucosyltransferase (FucT) is set forth in FIG. 1; see also SEQ ID NO:1 (open reading frame set forth in SEQ ID NO:2). The predicted amino acid sequence encoded thereby is set forth in SEQ ID NO:3. The encoded protein shares some similarity with other FucTs from other higher plants. See FIG. 2. For example, the *L. minor* FucT sequence shares approximately 50.1% sequence identity with the *Arabidopsis thaliana* FucT shown in FIG. 2.

The full-length cDNA sequence, including 5'- and 3'-UTR, for *L. minor* β1-2 xylosyltransferase (XylT) (isoform #1) is set forth in FIG. 3; see also SEQ ID NO:4 (ORF set forth in SEQ ID NO:5). The predicted amino acid sequence encoded thereby is set forth in SEQ ID NO:6. The encoded protein shares some similarity with other XylTs from other higher plants. See FIG. 4. For example, the *L. minor* XylT shares approximately 56.4% sequence identity with the *Arabidopsis thaliana* XylT shown in FIG. 4. A partial-length cDNA sequence, including 3'-UTR, for *L. minor* β1-2 xylosyltransferase (XylT) (isoform #2) is set forth in FIG. 31; see also SEQ ID NO:19 (ORF set forth in SEQ ID NO:20). The predicted amino acid sequence encoded thereby is set forth in SEQ ID NO:21. The partial-length XylT isoform #2 shares high sequence identity with the corresponding region of the full-length XylT isoform #1, as can be seen from the alignment shown in FIG. 32.

Example 2

RNAi Inhibition of Expression of *L. minor* FucT and XylT

Several RNAi strategies were undertaken to inhibit expression of the *L. minor* FucT and XylT isoforms. FIGS. 5-7, 33, and 34 outline these strategies. FIGS. 8-13 show maps of the various constructs that were made to achieve the desired knockout of expression of these two genes. A number of transgenic lines comprising the various knockout RNAi constructs were generated using standard transformation protocols described herein above.

The test antibody, designated herein as mAbI, was expressed in wild-type *Lemna* having the native glycosylation machinery, and transgenic *Lemna* lines expressing RNAi constructs designed to inhibit expression of *L. minor* XylT and FucT isoforms. Generally, three binary vectors were constructed for expression of mAbI in the *Lemna* system. Expression vector mAbI01 contained codon optimized genes encoding heavy (H) and light (L) chains of mAbI; vector mAbI04 contained codon optimized genes encoding mAbI H and L chains and a chimeric RNAi construct targeting expression of both XylT and FucT isoforms; and vector mAbI05 contained codon optimized genes encoding mAbI H and L chains, a single-gene RNAi construct targeting FucT gene expression, and a single-gene RNAi construct targeting XylT gene expression. Independent transgenic lines were generated for the mABI01, mAbI04, and mAbI05 expression vectors.

Optimized genes for mAbI H and L chains were designed to have *Lemna* preferred codon usage (63%-67% GC content) and contain the rice α-amylase signal sequence (GenBank M24286) fused to the 5' end of their coding sequences. Restriction endonuclease sites were added for cloning into *Agrobacterium* binary vectors (EcoRI (5')/SacI (3'), H-chain) and (SalI (5')/HindIII (3'), L-chain).

For the XF02 data presented in FIGS. 15-17 and the m-AbI04 data presented in FIGS. 22-24 and 26, described herein below, the RNAi strategy for inhibiting expression of the *L. minor* FucT and XylT isoforms employed the chimeric RNAi design shown in FIG. 34. For the mAbI05 data presented in FIG. 27, described herein below, the RNAi strategy for inhibiting expression of the *L. minor* FucT and XylT isoforms employed a double knockout of these genes using a combination of the single gene RNAi designs shown in FIG. 5 (FucT RNAi design) and FIG. 33 (XylT RNAi design).

Independent expression cassettes containing promoter, gene of interest, and Nos terminator were created for the optimized mAbI H and L chains and the single-gene or chimeric RNAi. Expression cassettes were cloned into a modification of the *Agrobacterium* binary vector pBMSP3 (obtained from Dr. Stan Gelvin, Purdue University) with the appropriate restriction sites. Depending upon the expression cassette, the L chain was fused to either the modified chimeric octopine and mannopine synthase promoter with *Lemna gibba* 5' RbcS leader (mAbI01, FIG. 14) or the high expression, constitutive *Lemna minor* polyubiquitin promoter (LmUbq) (mAbI04, FIG. 12; mAbI05; FIG. 13). The H-chain was fused to the modified chimeric octopine and mannopine synthase promoter with *Lemna gibba* 5' RbcS leader (mAbI04, mAbI05, and mAbI01). The chimeric RNAi cassette, taken from plasmid XF02 in T7-4, was fused to the high expression, constitutive *Spirodela polyrhiza* polyubiquitin promoter (SpUbq). The single-gene RNAi cassette for expression of the FucT inhibitory sequence was driven by the SpUbq promoter; and the single gene RNAi cassette for expression of the XylT inhibitory sequence was driven by an operably linked expression control element comprising the *Lemna aequinoctialis* ubiquitin promoter plus 5' UTR (LaUbq promoter). The H, L, and chimeric RNAi expression cassettes were cloned into the modified pBMSP3 binary vector in tandem orientation creating plasmid mAbI04. The H, L, and single-gene RNAi expression cassettes targeting FucT and XylT expression were cloned into the modified pBMSP3 binary vector creating plasmid mAbI05. The H and L expression cassettes were cloned into the modified pBMSP3 binary vector creating plasmid mAbI01.

Though any transformation protocol can be used as noted herein above, in some embodiments, the transformation protocol was as follows. Using *Agrobacterium tumefaciens* C58Z707, a disarmed, broad host range C58 strain (Hepburn et al. (1985) *J. Gen. Microbiol.* 131:2961-2969), transgenic plants representing individual clonal lines were generated from rapidly growing *Lemna minor* nodules according to the procedure of Yamamoto et al. (2001) *In Vitro Cell Dev. Biol. Plant* 37:349-353. For transgenic screening, individual clonal lines were preconditioned for 1 week at 150 to 200 μmol m-2s-2 in vented plant growth vessels containing SH media (Schenk and Hildebrandt (1972) *Can. J. Botany* 50:199-204) without sucrose. Fifteen to twenty preconditioned fronds were then placed into vented containers containing fresh SH media, and allowed to grow for two weeks. Tissue and media samples from each line were frozen and stored at −70° C.

A MALDI-TOF assay was developed to measure *L. minor* β-1,2-xylosyltransferase (XylT) and α-1,3-fucosyltransferase (FucT) activities (Example 3 below).

Figure 16:
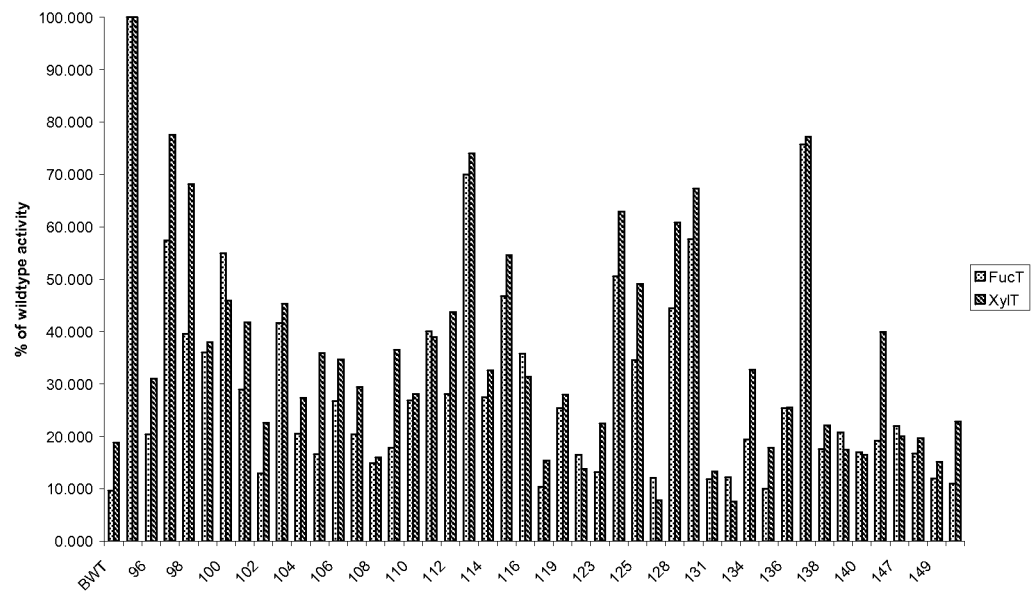
Figure 17:
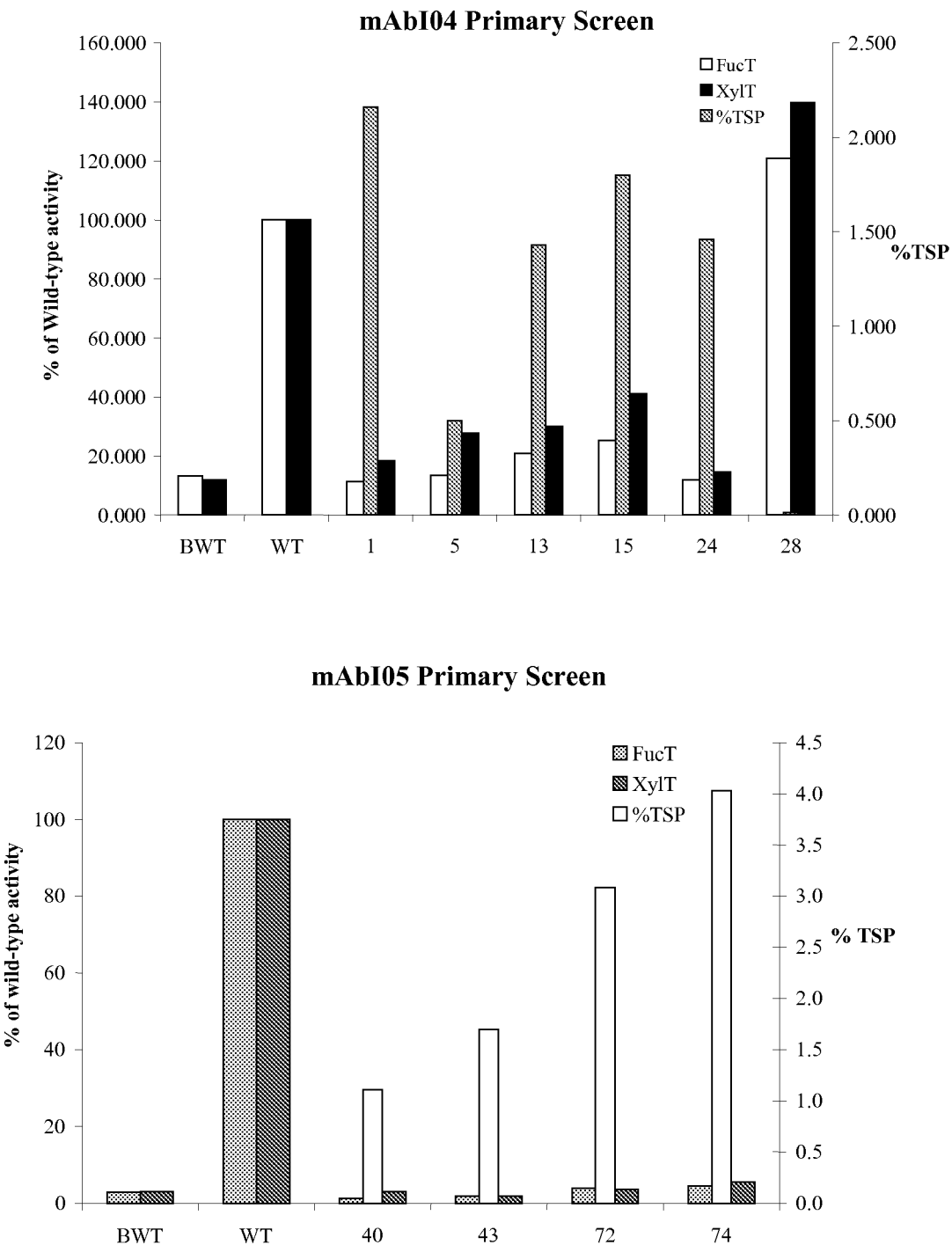

FIGS. 15-17 represent primary screening data for the XF02, mAbII04, and mAbI05 plants lines using the aforementioned assay. In this assay, WT (wild-type) represents the FucT and XylT activity in wild-type plants while BWT (boiled wild-type) represents their activity in boiled plant extracts. Boiled wild-type (BWT) plant extracts are representative of plant material in which FucT and XylT activity has been deactivated. This data set shows that several plant lines from each construct have a reduced level of FucT and XylT activity compared with wild-type plant lines (WT) and a comparable level of activity with boiled wild-type samples (BWT).

Specifically, primary screening data for transgenic RNAi *L. minor* plant lines comprising the XF02 construct of FIG. 10 are shown in FIGS. 15 and 16. The XF02 construct expresses a chimeric RNAi molecule that targets expression of both the *L. minor* FucT and XylT proteins, including the various isoforms of the respective proteins.

FIG. 17 shows primary screening data for transgenic RNAi *L. minor* plant lines comprising the mAbI04 construct of FIG. 12 and mAbI05 construct of FIG. 13.

Example 3

MALDI-TOF Assay for N-glycan
β-1,2-xylosyltransferase (XylT) and
α-1,3-fucosyltransferase (FucT) Activity The following modified MALDI-TOF assay was used to determine XylT and FucT activity in the transgenic plants described in Example 2 above.
Materials
 HOMOGENIZATION BUFFER: 50 mM HEPES, pH 7.5, 0.25 M sucrose, 2 mM EDTA, 1 mM DTT.
 REACTION BUFFER: 0.1 M Mes, pH 7.0, 10 mM MnCl$_2$, 0.1% (v/v) Triton X-100.
 URIDINE-5'-DIPHOSPHO-D-XYLOSE (UDP-Xyl)
 GUANOSINE-5'-DIPHOSPHO-L-FUCOSE (GDP-Fuc)
 N-ACETYLGLUCOSAMINE
 POLYETHYLENE GLYCOL (PEG) MIXTURE 1000-3000 (10 mg/mL PEG 1000, 2000, and 3000 (4:5:6 ratio) mixed 4:1 with 2 mg/mL sodium iodide).
 [Glu$^1$]-FIBRINOPEPTIDE B (GFP), HUMAN (1 pmol/μL in water)
 DABSYLATED, TETRAPEPTIDE, N-GLYCAN ACCEPTOR (EMD Biosciences)
 CHCA (α-CYANO-4-HYDROXYCINNAMIC ACID) MATRIX (10 mg in 50% [v/v] acetonitrile, 0.05% [v/v] trifluoroacetic acid).
Microsome Preparation
 *L. minor* tissue (100 mg) was ground in 1 mL of cold homogenization buffer in a bead mill at 5× speed for 40 s. The homogenate was spun at 1,000 g for 5 min, 4° C. The supernatant was removed and spun at 18,000 g for 2 h, 4° C. The supernatant was then discarded. The pellet was resuspended in 20 μL of cold reaction buffer and kept on ice or stored at −80° C. until use.
Reaction Conditions
 The reaction mix contains 125 mM N-acetylglucosamine, 6.25 mM UDP-Xyl, 6.25 mM GDP-Fuc, 12.5 mM MnCl$_2$, and 1.5 nmol of dabsylated, tetrapeptide N-glycan acceptor. Microsomes (4 μL) were added to the reaction mix to start the reaction. The reaction was incubated for 30 min at room temperature, and 90 min at 37° C. The reaction was terminated by centrifugation at 18,000 g for 1 min and incubation at 4° C.
MALDI-TOF Analysis
 A portion of the supernatant from each reaction (0.5 μL) was mixed with 0.5 μL of CHCA matrix on a MALDI target plate and allowed to dry. The MALDI instrument was set to reflectron positive ion mode and calibrated with PEG 1000-3000. Combined MS spectra (~200 shots) were taken from 1500-2500 Da using 0.5 pmol GFP as the lock mass. Ion counts of the reference peak (m/z=2222.865) should be above 400. Ion counts of the XylT and FucT products (m/z=2192.854 and 2206.870, respectively) were normalized to the reference peak and the protein concentration of the microsome fraction.

Example 4

Effect of RNAi Inhibition of Expression of *L. minor*
FucT and XylT on Glycosylation Profile of
Monoclonal Antibodies Monoclonal antibodies produced by wild-type (i.e., FucT and XylT expression not silenced) *L. minor* comprising the mAbI01 construct (see FIG. 14) and *L. minor* lines transgenic for the mAbI04 construct (see FIG. 12) or mAbI05 construct (see FIG. 13) were analyzed for their N-glycosylation profile. The following procedures were used.
Purification of mAb from *Lemna*.
 Plant tissue was homogenized with 50 mM Sodium Phosphate, 0.3M Sodium Chloride, and 10 mM EDTA at pH 7.2 using a Silverson High Shear Mixer at a tissue: buffer ratio of 1:8. The homogenate was acidified to pH 4.5 with 1M Citric Acid, and centrifuged at 7,500×g for 30 minutes at 4° C. The supernatant was filtered through a 0.22 μm filter and loaded directly on mAbSelect SuRe resin (GE Healthcare) equilibrated with a solution containing 50 mM Sodium Phosphate, 0.3M Sodium Chloride, and 10 mM EDTA, pH 7.2. After loading, the column was washed to baseline with the equilibration buffer followed by an intermediate wash with 5 column volumes of 0.1M Sodium Acetate, pH 5.0, and finally, bound antibody was eluted with 10 column volumes of 0.1M Sodium Acetate, pH 3.0. The eluate was immediately neutralized with 2M Tris base.

Purification of N-Linked Glycans.

Protein A-purified monoclonal antibodies (1 mg) from wild-type and RNAi *L. minor* plant lines were dialyzed extensively against water and lyophilized to dryness. Samples were resuspended in 100 µL of 5% (v/v) formic acid, brought to 0.05 mg/mL pepsin, and incubated at 37° C. overnight. The samples were heat inactivated at 95° C. for 10 min and dried. Pepsin digests were resuspended in 100 µL of 100 mM sodium acetate, pH 5.0 and incubated with 1 mU of N-glycosidase A at 37° C. overnight. The released N-glycans were isolated using 4 cc Carbograph SPE columns according to Packer et al. (1998) *Glycoconj. J.* 15: 737-747, and dried.

Dried N-glycans were further purified using 1 cc Waters Oasis MCX cartridges. Columns were prepared by washing with 3 column volumes of methanol followed by 3 column volumes of 5% (v/v) formic acid. N-glycans, resuspended in 1 mL of 5% (v/v) formic acid, were loaded onto the prepared columns. The unbound fraction as well as 2 additional column volume washes of 5% (v/v) formic acid were collected, pooled and dried.

Derivatization of Oligosaccharides with 2-aminobenzoic Acid (2-AA).

Purified N-glycans or maltooligosaccharides were labeled with 2-AA and purified using 1 cc Waters Oasis HLB cartridges according to Anumula and Dhume (1998) *Glycobiology* 8: 685-694. Labeled N-glycans and maltooligosaccharides were resuspended in 50 µL of water and analyzed by MALDI-TOF MS and normal phase (NP) HPLC-QTOF MS.

MALDI-TOF Mass Spectrometry.

MALDI-TOF MS was conducted using a Waters MALDI Micro MX (Millford, Mass.). 2-AA labeled N-glycans (0.5 µL) were properly diluted with water, mixed with 0.5 µL of 10 mg/mL DHB matrix in 70% (v/v) acetonitrile, spotted onto a target plate and analyzed in negative reflectron mode.

NP-HPLC-Q-TOF MS Analysis of 2-AA Labeled N-glycans.

2-AA labeled N-glycans or maltooligosaccharides were brought to 80% (v/v) acetonitrile and separated on a Waters 2695 HPLC system fitted with a TSK-Gel Amide-80 (2 mm×25 cm, 5 µm) column (Tosoh Biosciences, Montgomeryville, Pa.). 2-AA labeled carbohydrates were detected and analyzed by fluorescence (230 nm excitation, 425 nm emission) using a Waters 2475 fluorescence detector and a Waters Q-TOF API US quadropole-time of flight (Q-TOF) mass spectrometer (Millford, Mass.) fitted in-line with the HPLC system.

Separations were conducted at 0.2 mL/min, 40° C., using 10 mM ammonium acetate, pH 7.3 (solvent A) and 10 mM ammonium acetate, pH 7.3, 80% (v/v) acetonitrile (solvent B). Sample elution was carried out at 0% A isocratic for 5 min, followed by a linear increase to 10% A at 8 min, and a linear increase to 30% A at 48 min. The column was washed with 100% A for 15 min and equilibrated at 0% A for 15 min prior to the next injection.

Q-TOF analysis was conducted in negative ion mode with source and desolvation temperatures of 100° C. and 300° C., respectively, and capillary and cone voltages of 2,100 and 30 V, respectively. Mass spectra shown are the result of combining ≥50 individual scans per labeled N-glycan.

RP-HPLC-Q-TOF MS Analysis of Intact IgG.

Protein A purified IgG's (50 µg) were desalted using the Waters 2695 HPLC system fitted with a Poros R1-10 column (2 mm×30 mm; Applied Biosystems). IgG's were detected and analyzed using a Waters 2487 dual wavelength UV detector (280 nm) and the Waters Q-TOF API US. Separations were conducted at 0.15 mL/min, 60° C., using 0.05% (v/v) trifluoroacetic acid (TFA; solvent A) and 0.05% (v/v) TFA, 80% (v/v) acetonitrile (solvent B). Sample elution was carried out using a linear increase from 30 to 50% B for 5 min, an increase to 80% B for 5 min. The solvent ratio remained at 80% B for an additional 4 min, followed by a wash with 100% B for 1 min and equilibration of the column with 30% B for 15 min prior to the next run.

Q-TOF analysis was conducted in positive ion mode with source and desolvation temperatures of 100° C. and 300° C., respectively, and capillary and cone voltages of 3.0 and 60 V, respectively. Data are the result of combining ≥100 individual scans and deconvolution to the parent mass spectrum using MaxEnt 1.

See also Triguero et al. (2005) *Plant Biotechnol. J.* 3: 449-457; Takahashi et al. (1998) *Anal. Biochem.* 255: 183-187; Dillon et al. (2004) *J. Chromatogr. A.* 1053: 299-305.

Results.

FIG. 18 shows the structure and molecular weight of derivatized wild-type *L. minor* monoclonal antibody N-glycans.

Figure 19:
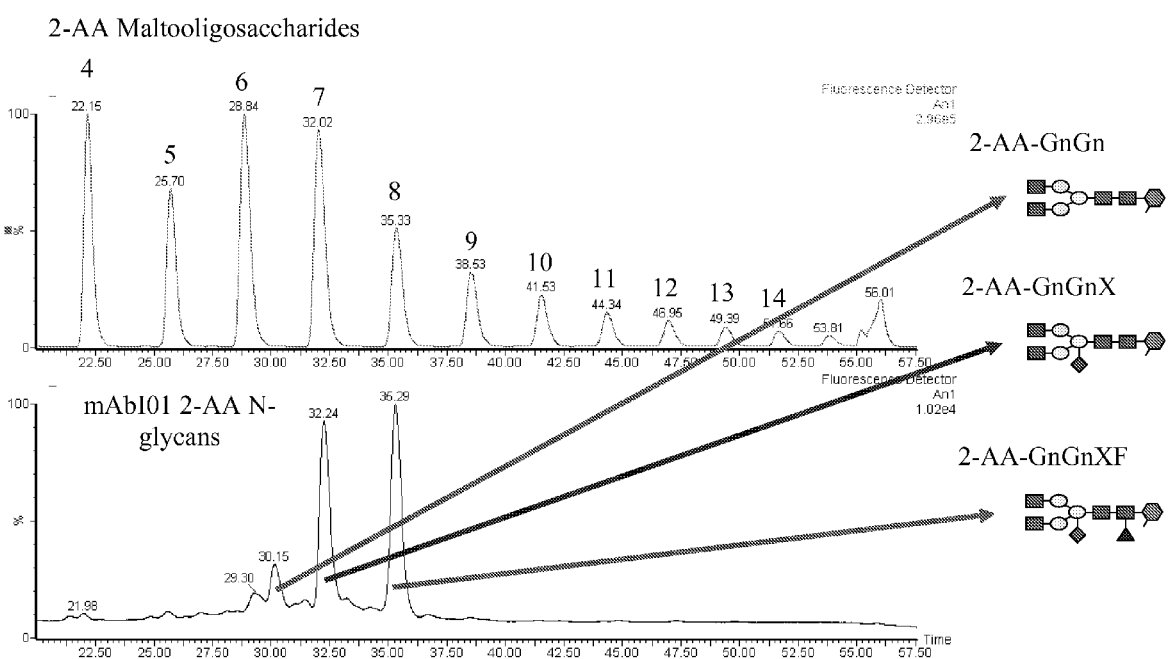
Figure 20:
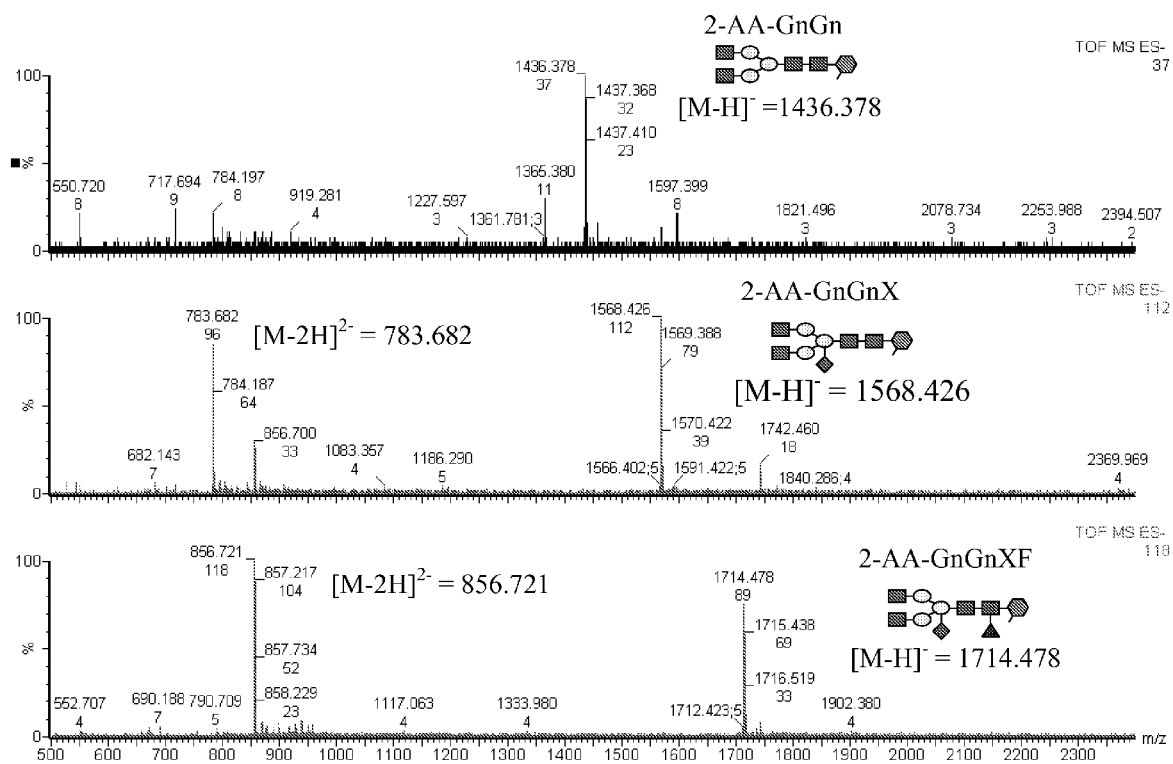
Figure 21:
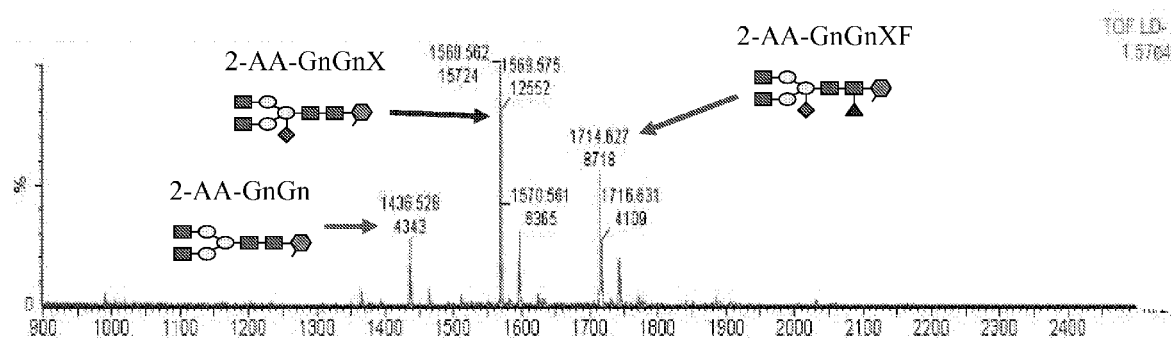

FIG. 19 shows that the wild-type m-AbI01 construct (shown in FIG. 15) providing for expression of the mAbI monoclonal IgG1 antibody in *L. minor*, without RNAi suppression of *L. minor* FucT and XylT, produces an N-glycosylation profile with three major N-glycan species, including one species having the β1,2-linked xylose and one species having both the β1,2-linked xylose and core α1,3-linked fucose residues; this profile is confirmed with liquid chromatography mass spectrometry (LC-MS) (FIG. 20) and MALDI (FIG. 21) analysis.

Figure 22:
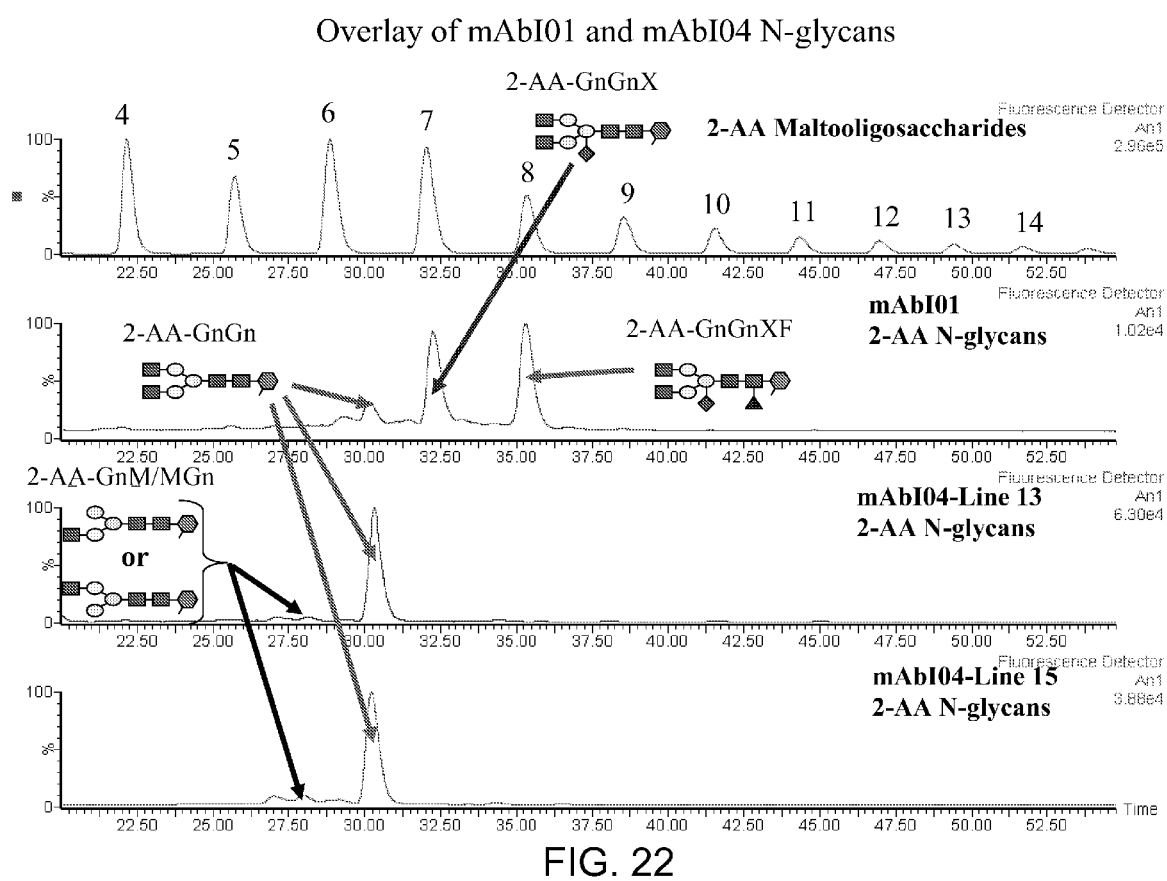
Figure 23:
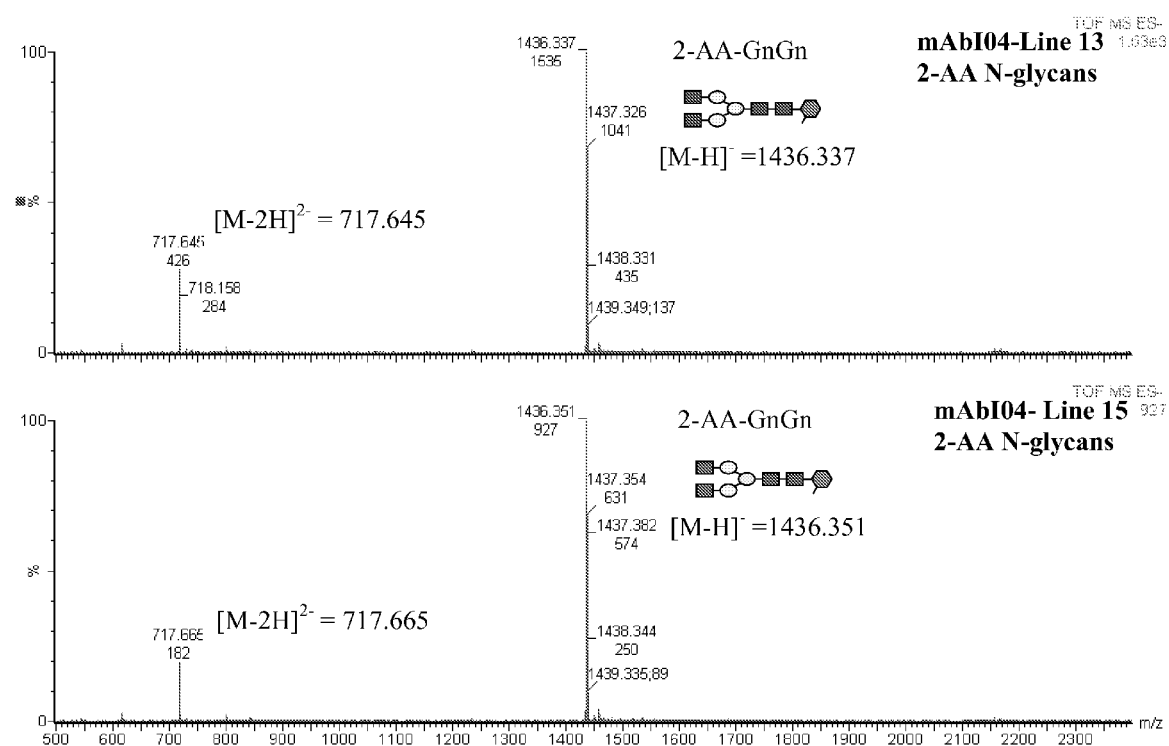
Figure 24:
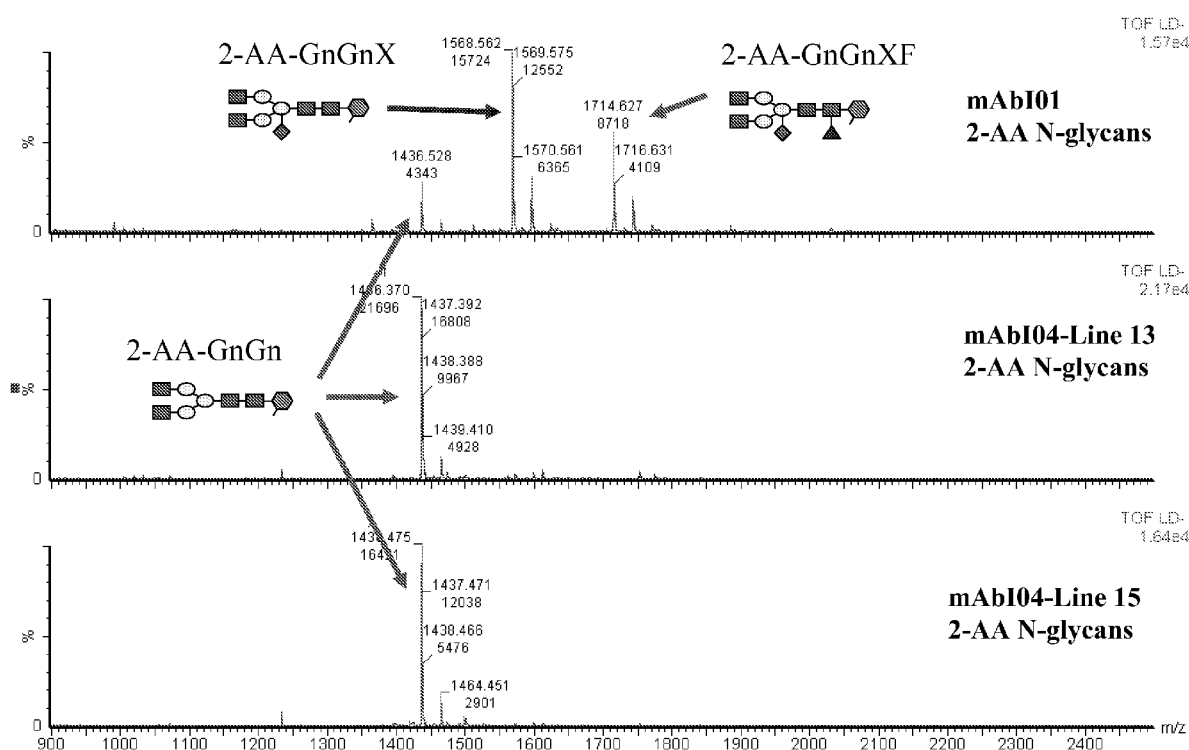

FIG. 22 shows an overlay of the relative amounts of the various N-glycan species of the mAbI produced in the wild-type *L. minor* line comprising the mAbI01 construct (no suppression of FucT or XylT) and in the two transgenic *L. minor* lines comprising the mAbI04 construct of FIG. 12. Note the enrichment of the GnGn (i.e., G0) glycan species, with no β1,2-linked xylose or core α1,3-linked fucose residues attached, and the absence of the species having the β1,2-linked xylose or both the β1,2-linked xylose and core α1,3-linked fucose residues. This profile is confirmed with mass spec (LC-MS) (FIG. 23) and MALDI (FIG. 24) analysis.

Figure 25:
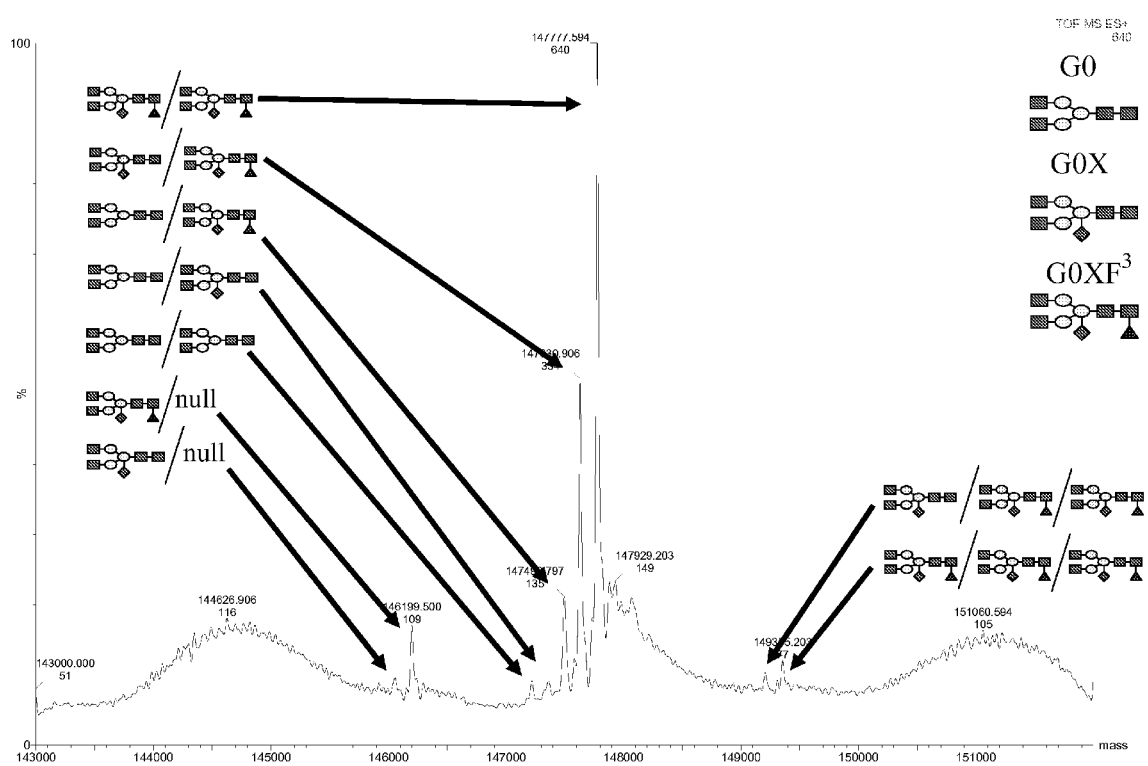

FIG. 25 shows intact mass analysis of the mAbI compositions produced in wild-type *L. minor* (line 20) comprising the mAbI01 construct. When XylT and FucT expression are not suppressed in *L. minor*, the recombinantly produced mAbI composition is heterogeneous, comprising at least 9 different glycoforms, with the G0XF$^3$ glycoform being the predominate species present. Note the very minor peak representing the G0 glycoform.

Figure 26:
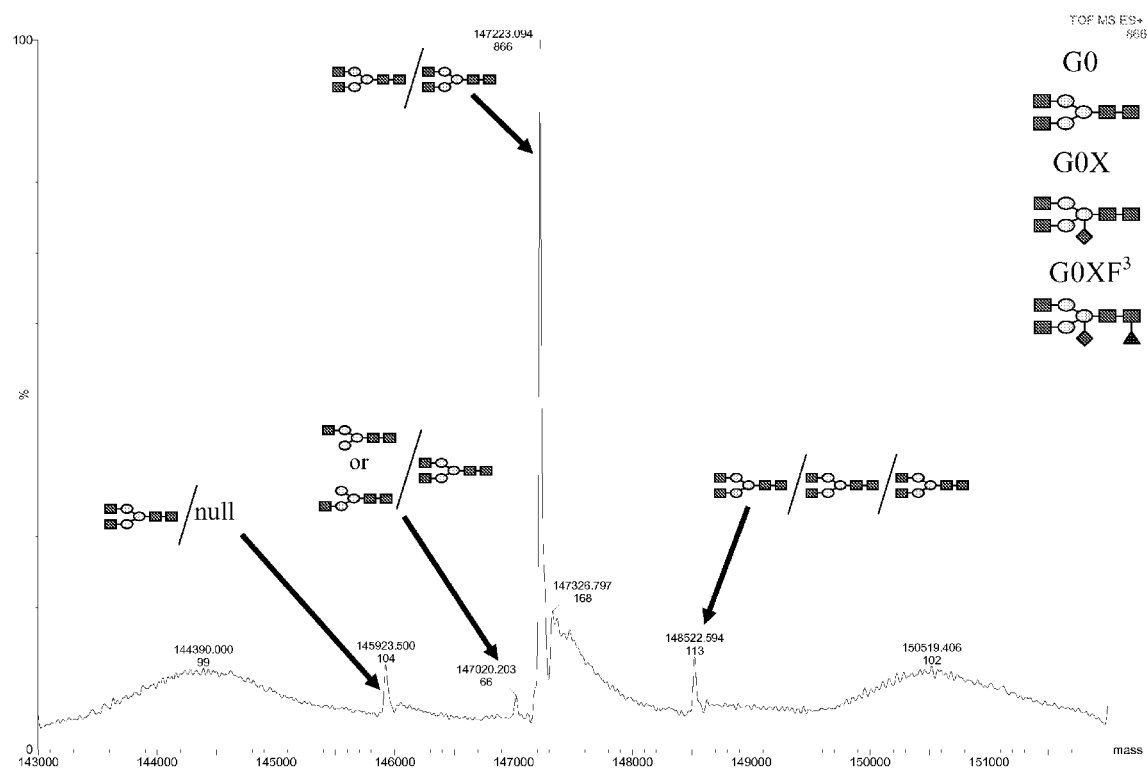

FIG. 26 shows intact mass analysis of the mAbI compositions produced in transgenic *L. minor* (line 15) comprising the mAbI04 construct of FIG. 12. When XylT and FucT expression are suppressed in *L. minor* using this chimeric RNAi construct, the intact mAbI composition is substantially homogeneous for G0 N-glycans, with only trace amounts of precursor N-glycans present (represented by the GnM and MGn precursor glycan species). In addition, the mAbI composition is substantially homogeneous for the G0 glycoform, wherein both glycosylation sites are occupied by the G0 N-glycan species, with three minor peaks reflecting trace amounts of precursor glycoforms (one peak showing mAbI having an Fc region wherein the $C_H{}^2$ domain of one heavy chain has a G0 glycan species attached to Asn 297, and the $C_H{}^2$ domain of the other heavy chain is unglycosylated; another peak showing mAbI having an Fc region wherein the C$_H$2 domain of one heavy chain has a G0 glycan species attached to Asn 297, and the C$_H$2 domain of the other heavy chain has the GnM or MGn precursor glycan attached to Asn 297; and another peak showing mAbI having an Fc region wherein the Asn 297 glycosylation site on each of the C$_H$2 domains has a G0 glycan species attached, with a third G0 glycan species attached to an additional glycosylation site within the mAbI structure).

Figure 27:
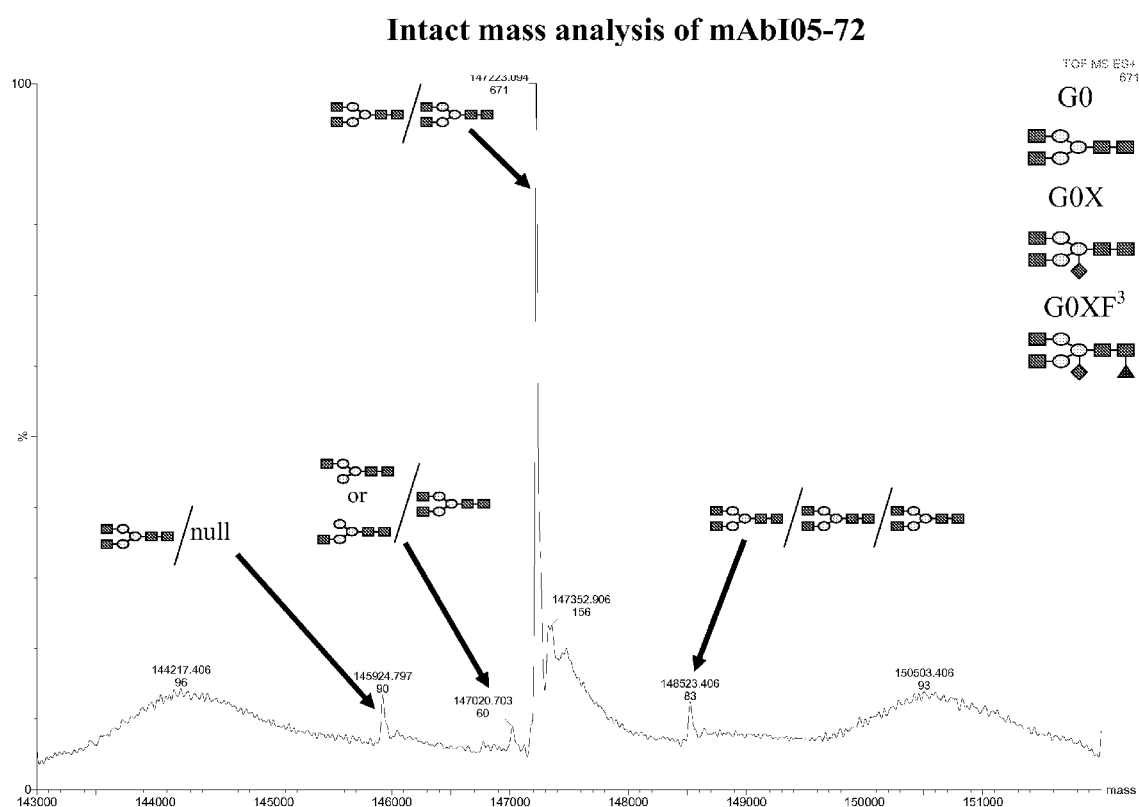

FIG. 27 shows intact mass analysis of the mAbI compositions produced in transgenic *L. minor* (line 72) comprising the mAbI05 construct of FIG. 13. When XylT and FucT expression are suppressed in *L. minor* using this construct, the intact mAbI composition is substantially homogeneous for G0 N-glycans, with only trace amounts of precursor N-glycan species present (represented by the GnM and MGn precursor glycan species). In addition, the mAbI composition is substantially homogeneous (at least 90%) for the G0 glycoform, with the same three minor peaks reflecting precursor glycoforms as obtained with the mAbI04 construct.

The receptor binding activity of the mAbI produced in the wild-type *Lemna* lines comprising the mAbI01 construct (i.e., without inhibition of XylT and FucT expression) and the transgenic *Lemna* lines comprising the mAbI04 or mAbI05 construct (i.e., with XylT and FucT expression inhibited) was compared to the receptor binding activity of the mAbI produced in mammalian cell lines (CHO and SP2/0).

Figure 35:
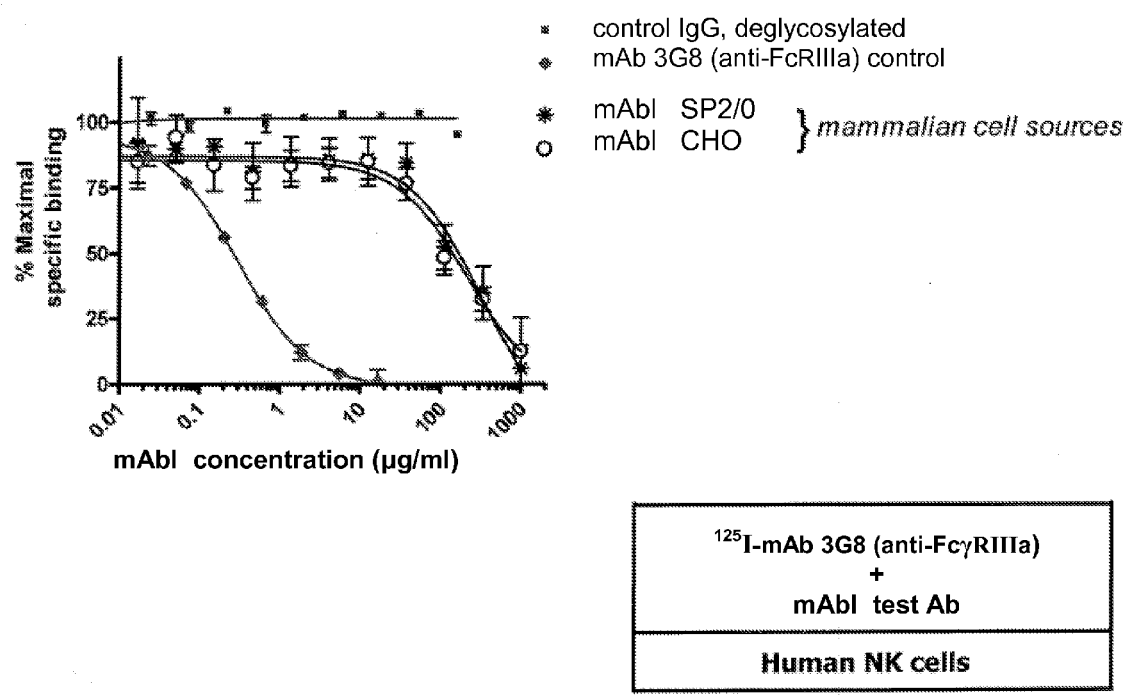
FIG. 35 shows receptor binding activity of the CHO-derived and SP2/0-derived mAbI product for the FcγRIIIa on freshly isolated human NK cells.
Figure 36:
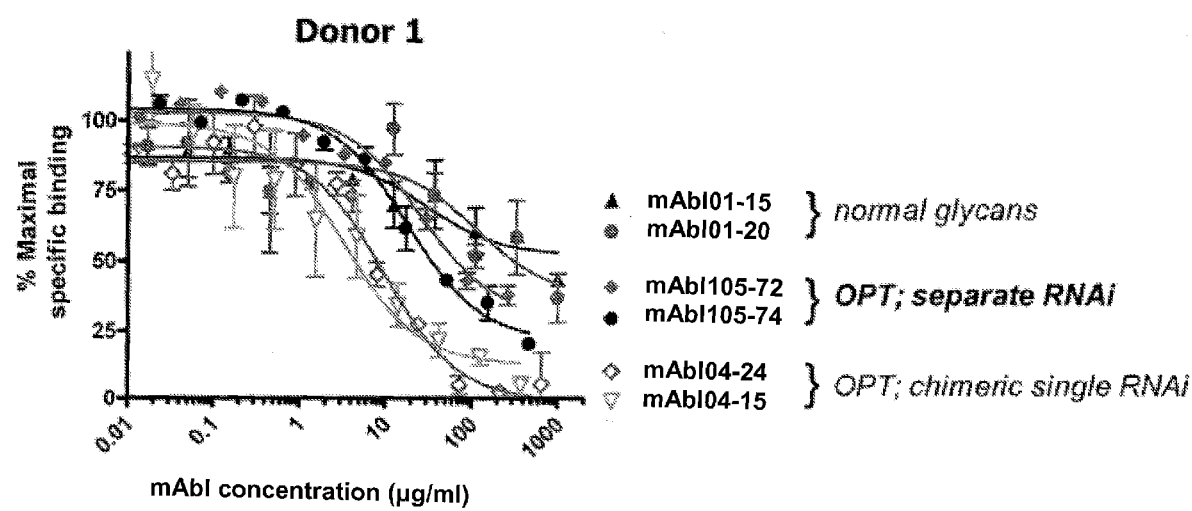
FIG. 36 shows receptor binding activity of the wild-type *Lemna*-derived mAbI product and the transgenic *Lemna*-derived mAbI product for the FcγRIIIa on freshly isolated human NK cells collected from Donor 1.
Figure 37:
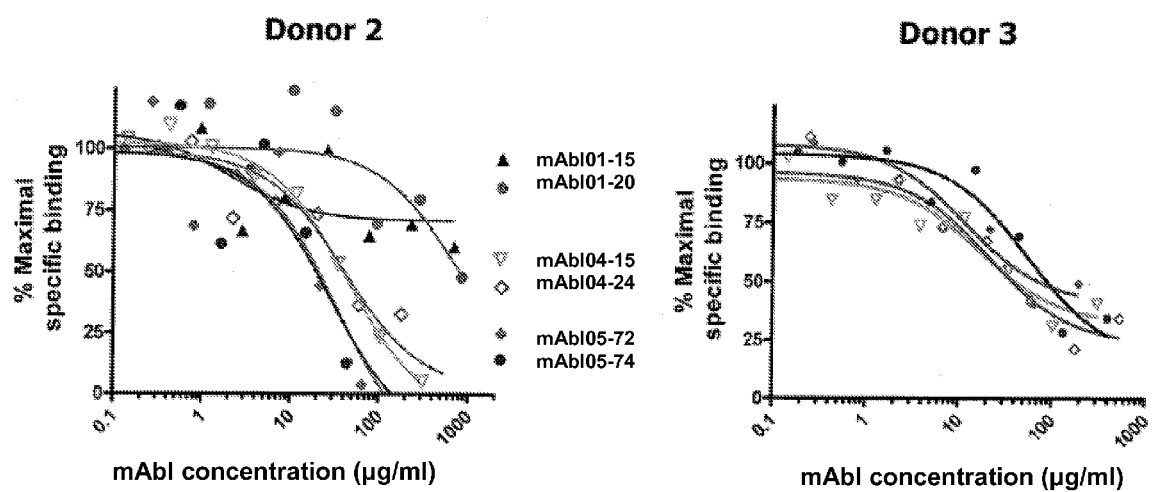
FIG. 37 shows receptor binding activity of the wild-type *Lemna*-derived mAbI product and the transgenic *Lemna*-derived mAbI product for the FcγRIIIa on freshly isolated human NK cells collected from Donors 2 and 3.
Figure 38:
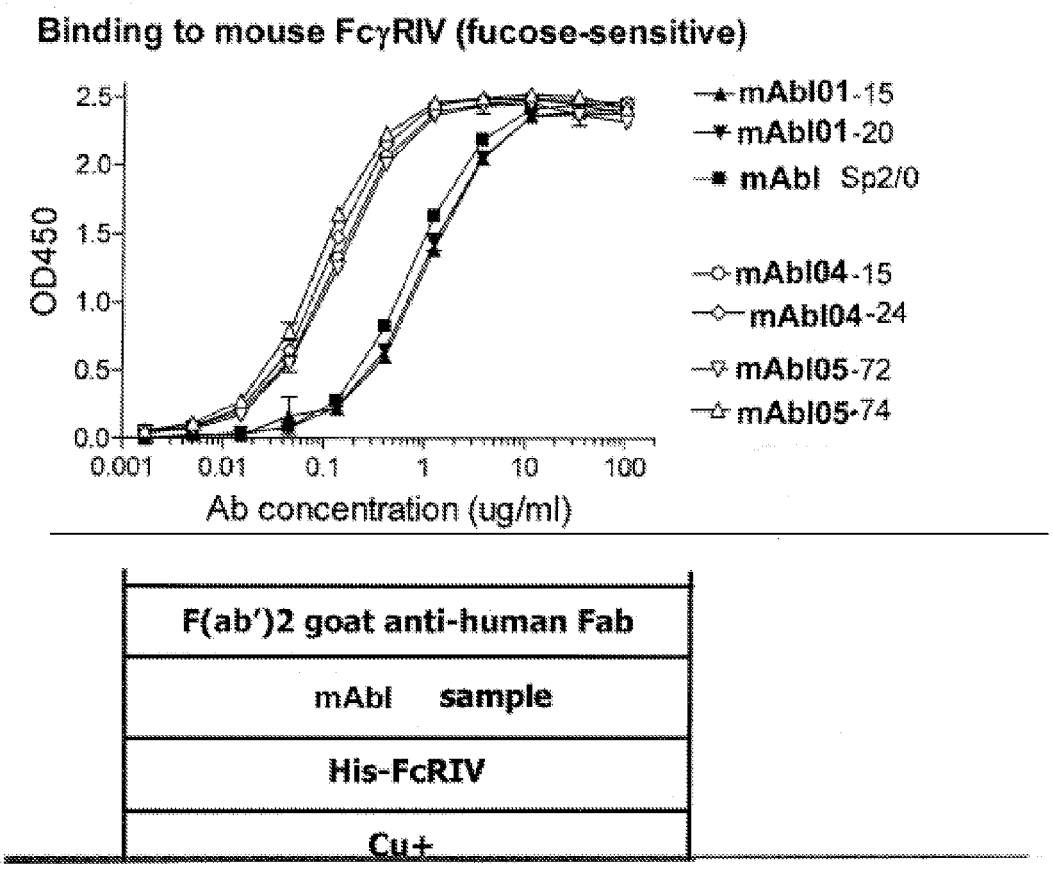
FIG. 38 shows receptor binding activity of the Sp2/0-derived mAbI product, the wild-type *Lemna*-derived mAbI product, and the transgenic *Lemna*-derived mAbI product for the mouse FcγRIV.

Binding to FcFcγRIIIa on freshly isolated human NK cells was assessed for the various mAbI products. Control data collected for CHO-derived mAbI and SP2/0-derived mAbI is shown in FIG. 35. Test data collected for wild-type *Lemna*-produced mAbI having the normal plant N-glycan profile are designated as mAbI01-15 and mabI01-20, wherein the mAbI product has N-linked glycans that include α(1,3)-fucose residues (see FIGS. 36 and 37). Test data collected for transgenic *Lemna*-derived mAbI having an optimized N-glycan profile (OPT) obtained with gene-silencing RNAi constructs that target expression of α1,3-fucosyltransferase are designated as mAbI05-72, mAbI05-74, mAbI04-24, and mAbI04-15 (see FIGS. 36 and 37), wherein the mAbI product has N-linked glycans that are devoid of α(1,3)-fucose residues. Data comparing binding efficacy of mAbI01-15, mAbI01-20, mAbI SP2/0, mAbI04-15, mAbI04-24, mAbI05-72, and mAbI05-74 to recombinant mouse FcγRIV, a receptor that is sensitive to IgG fucose levels and which served as a surrogate for human FcγRIIIa, is shown in FIG. 38.

These data demonstrate that the transgenic *Lemna*-derived mAbI product having the optimized glycan profile (OPT) shows enhanced binding to FcγRIIIa on freshly isolated human NK cells (enhanced about 20 to 50-fold) as well as enhanced binding to recombinant mouse FcγRIV (enhanced about 10-fold) as compared to the wild-type *Lemna*-derived mAbI product.

Example 6

Production of Anti-CD30 Monoclonal Antibody Having Improved Receptor Binding and Increased ADCC Activity This example outlines the expression of human anti-CD30 mAbs in *Lemna*. Optimization of anti-CD30 mAb glycosylation was accomplished by co-expression with an RNAi construct targeting the endogenous expression of α-1,3-fucosyltransferase (FucT) and β-1,2-xylosyltransferase (XylT) genes in a manner similar to that noted in the examples above for mAbI. The resultant anti-CD30 mAb produced in *Lemna* having its native glycosylation machinery engineered to suppress FucT and XylT expression contained a single major N-glycan species without any trace of plant-specific N-glycans. In addition to the N-glycan homogeneity, glyco-optimized anti-CD30 mAbs were also shown to have enhanced antibody-dependent cell-mediated cytotoxicity (ADCC) and effector cell receptor binding activity when compared to CHO-expressed anti-CD30 mAbs.

Methods

Strains and Reagents.

Novablue competent *Escherichia coli* cells were used for all recombinant DNA work (EMD Biosciences, San Diego, Calif.). Restriction endonucleases and DNA modification enzymes were obtained from New England Biolabs (Ipswich, Mass.). Oligonucleotides were obtained from Integrated DNA technologies (Coralville, Iowa). Waters Oasis HLB and MCX columns (1 cc), 2,5-dihydroxybenzoic acid (DHB), and α-cyano-4-hydroxycinnamic acid (CHCA) were from Waters Corporation (Milford, Mass.). Purified dabsylated, tetrapeptide, GnGn N-glycan acceptors (GnGn-dabsyl-peptide) and N-glycosidase A were from EMD Biosciences. Carbograph SPE columns (4 cc) were from Grace Davidson Discovery Sciences (Deerfield, Ill.). Uridine-5'-diphospho-D-xylose (UDP-Xyl) was purchased from Carbosource Services (Athens, Ga.). Acetonitrile (Optima grade) was from Fisher Scientific (Summerville, N.Y.). Ammonium acetate was from MP Biochemicals (Irvine, Calif.). Maltooligosaccharides (MD6-1) were from V-Labs Inc. (Covington, Calif.). Monosaccharide standards were from Dionex (Sunnyvale, Calif.). BATDA (bis(acetoxymethyl)2,2':6',2"-terpyridine-6, 6"-dicarboxylate) and Europium solution were from Perkin-Elmer (Wellesley, Mass.). Guanosine-5'-diphospho-L-fucose (GDP-Fuc), N-acetylglucosamine (GlcNAc), 2-aminobenzoic acid (2-AA) and all other materials were from Sigma (St. Louis, Mo.).

Construction of mAb and RNAi Expression Vectors.

The heavy (H) and light (L) chain variable region cDNA sequences of fully human mAb 1 kappa antibody MDX-060 derived from a transgenic Medarex HuMAb-Mouse® (Borchmann et al. (2003) *Blood* 102:3737-3742) were determined and the full length MDX-060 human mAb1 kappa antibody was produced recombinantly by a Chinese hamster ovary cell line, CHO DG44 (Urlaub et al. (1986) *Cell Mol. Genet.* 12:555-566), using standard techniques. Optimized genes for H and L chains were designed to have *Lemna*-preferred codon usage (63%-67% GC content) and contain the rice α-amylase signal sequence (GenBank M24286) fused to the 5' end of their coding sequences. Restriction endonuclease sites were added for cloning into *Agrobacterium* binary vectors (EcoRI (5')/SacI (3'), H-chain) and (SalI (5')/HindIII (3'), L-chain). Synthetic genes were constructed and provided by Picoscript (Houston, Tex.).

A chimeric hairpin RNA (see FIG. 34) was designed to target silencing of endogenous *Lemna* genes encoding α-1, 3-fucosyltransferase (based on the coding sequence for *L. minor* FucT isoform #1, set forth in SEQ ID NO:2; see also GenBank DQ789145) and β-1,2-xylosyltransferase (based on the coding sequence for *L. minor* XylT isoform #2, nt 1-1275 of SEQ ID NO:19; set forth in SEQ ID NO:20; see also GenBank DQ789146). The chimeric FucT+XylT hairpin RNA was designed to have 602 bp of double stranded FucT sequence, 626 bp of double stranded XylT sequence, and 500 bp of spacer sequence. The sense strand portion of the hairpin RNA cassette encompasses the FucT forward fragment (nt 12-613 of SEQ ID NO:2; equivalent to nt 254-855 of SEQ ID NO:1) and XylT forward fragment (nt 1-626 of SEQ ID NO:19), a spacer sequence (nt 627-1126 of SEQ ID NO:19). The antisense strand portion of the hairpin RNA encompasses the XylT reverse fragment (antisense version of nt 1-626 SEQ ID NO:19) and FucT reverse fragment (antisense version of nt 12-613 of SEQ ID NO:2 or nt 254-855 of SEQ ID NO:1). The chimeric hairpin RNA was constructed by PCR amplifying FucT and XylT forward and reverse gene fragments from *Lemna minor* (8627) cDNA and sequentially cloning them into pT7blue (EMD Biosciences) creating plasmid XF02 in T7-4. The FucT forward gene fragment was amplified with DNA primers BLX 686 (5'-ATGGTCGACTGCT-GCTGGTGCTC TCAAC-3') (SEQ ID NO:22) and BLX690 (5'-ATGTCTAGAATG CAGCAGCAAGTGCACC-3') (SEQ ID NO:23) producing a 620 bp product with terminal SalI (5') and XbaI (3') cloning sites. The XylT forward gene fragment was amplified with DNA primers BLX 700 (5'-ATGAC-TAGTTGC GAAGCCTACTTCGGCAACAGC3') (SEQ ID NO:24) and BLX694 (5'-ATGGGATCCGAATCTCAAGA ACAACTGTCG-3') (SEQ ID NO:25) producing a 1144 bp product with terminal SpeI (5') and BamHI (3') cloning sites. The XylT reverse gene fragment was amplified with DNA primers BLX 695 (5'-ATGGGTACCTGCGAAGCCTACT-TCGGCAA CAGC-3') (SEQ ID NO:26) and BLX696 (5'-ATGGGA TCCACTGGCTGGGAGAAGTTCTT-3') (SEQ ID NO:27) producing a 644 bp product with terminal BamHI (5') and KpnI (3') cloning sites. The FucT reverse gene fragment was amplified with DNA primers BLX 691 (5'-ATG-GAGCTCTGCTGCTGGTGCT CTCAAC-3') (SEQ ID NO:28) and BLX692 (5'-ATGGGTACCATGCAGCAG-CAAGTGCACC-3') (SEQ ID NO:29) producing a 620 bp product with terminal KpnI (5') and SacI (3') cloning sites.

Independent expression cassettes containing promoter, gene of interest, and Nos terminator were created for the optimized MDX-060 H and L chains and the chimeric RNAi. Expression cassettes were cloned into a modification of the *Agrobacterium* binary vector pBMSP3 (obtained from Dr. Stan Gelvin, Purdue University) with the appropriate restriction sites. The H chain was fused to the modified chimeric octopine and mannopine synthase promoter with *Lemna gibba* 5' RbcS leader (Gasdaska et al. (2003) *Bioprocessing J.* 50-56). The L-chain was fused to the high expression, constitutive *Lemna minor* polyubiquitin promoter (LmUbq). The chimeric RNAi cassette, taken from plasmid XF02 in T7-4, was fused to the high expression, constitutive *Spirodela polyrhiza* polyubiquitin promoter (SpUbq). The three expression cassettes were cloned into the modified pBMSP3 binary vector in tandem orientation creating plasmid MDXA04.

Transformation and Plant Line Screening.

Using *Agrobacterium tumefaciens* C58Z707 (Hepburn et al. (1985) *J. Gen. Microbiol.* 131:2961-2969), transgenic plants representing individual clonal lines were generated from rapidly growing *Lemna minor* nodules according to the procedure of Yamamoto et al. (Yamamoto et al. (2001) *In vitro Cell. Dev. Biol.* 37). For transgenic screening, individual clonal lines were preconditioned for 1 week at 150 to 200 $\mu mol\ m^{-2}s^{-2}$ in vented plant growth vessels containing SH media (Schenk and Hildenbrandt (1972) *Can. J. Botany* 50:199-204) without sucrose. Fifteen to twenty preconditioned fronds were then placed into vented containers containing fresh SH media, and allowed to grow for two weeks. Tissue and media samples from each line were frozen and stored at −70° C.

ELISA Analysis of mAb Produced in *Lemna*.

*Lemna* tissue (100 mg) was homogenized using a FastPrep FP120 bead mill (Thermo Electron Corporation). Supernatants were diluted to 1 µg/mL and assayed using the IgG Quantitation ELISA kit (Bethyl Laboratories). For the assay, microtiter plates were coated with goat anti-human IgG at a concentration of 10 µg/mL, and mAb was detected by horseradish peroxidase (HRP)-conjugated goat anti-human IgG diluted 1:100,000. Standard curves were created with Human Reference IgG supplied with the ELISA kit. The sensitivity of the ELISA was 7.8 ng/mL. All samples were analyzed in duplicate.

Preparation of *Lemna* Microsomal Membranes and Assaying for Core β-1,2-xylosyltransferase and α-1,3-fucosyltransferase Activities.

*Lemna* tissue (100 mg) from each line was homogenized in 1 mL of cold homogenization buffer (50 mM 4-[2-hydroxyethyl]-1-piperazineethanesulfonic acid [HEPES], pH 7.5, 0.25 M sucrose, 2 mM ethylenediaminetetraacetic acid [EDTA], 1 mM 1,4-dithiothreitol [DTT]) for 40 s in a Fast-Prep FP120 bead mill (Thermo Electron Corporation, Waltham, Mass.). The homogenate was centrifuged at 1,000 g for 5 min at 4° C. The supernatant was removed and centrifuged at 18,000 g for 90 min at 4° C. The resulting pellet was resuspended in 20 µL of cold reaction buffer (0.1 M 2-[4-morpholino]ethanesulfonic acid [Mes], pH 7.0, 0.1% [v/v] Triton X-100, 10 mM $MnCl_2$) and kept on ice or stored at −80° C. until use.

Core β-1,2-xylosyltransferase and α-1,3-fucosyltransferase activities were measured simultaneously in 4 µL of microsomal membranes prepared from each RNAi line by incubating with 125 mM GlcNAc, 6.25 mM UDP-Xyl, 6.25 mM GDP-Fuc, 12.5 mM $MnCl_2$, and 1.5 nmol of GnGn-dabsyl-peptide acceptor for 2 h at 37° C. as described previously (Leiter et al. (1999) *J. Biol. Chem.* 274:21830-21839). The reaction was terminated by a brief centrifugation and incubation at 4° C. and the products were analyzed by positive reflectron mode MALDI-TOF MS.

Purification of MDX-060 LEX and $LEX^{Opt}$ mAbs.

Plant tissue was homogenized with 50 mM sodium phosphate, 0.3 M sodium chloride, and 10 mM EDTA, pH 7.2 using a Silverson high shear mixer. The homogenate was acidified to pH 4.5 with 1 M citric acid, and centrifuged at 7,500 g for 30 min at 4° C. The pH of the supernatant was adjusted to pH 7.2 with 2 M Tris, prior to filtration using 0.22 µm filters. The material was loaded directly on mAbSelect SuRe protein A resin (GE Healthcare) equilibrated with a solution containing 50 mM sodium phosphate, 0.3 M sodium chloride, and 10 mM EDTA, pH 7.2. After loading, the column was washed to baseline with the equilibration buffer followed by an intermediate wash with 5 column volumes of 0.1 M sodium acetate, pH 5.0. Bound antibody was eluted with 10 column volumes of 0.1 M sodium acetate, pH 3.0. The protein A eluate was immediately neutralized with 2 M 2-amino-2-[hydroxymethyl]-1,3-propanediol (Tris). For aggregate removal, the protein A eluate was adjusted to pH 5.5 and applied to a ceramic hydroxyapatite type I (Bio-Rad) column equilibrated with 25 mM sodium phosphate, pH 5.5. After washing the column with 5 column volumes of equilibration buffer, the antibody was eluted in a single step-elution using 0.25 M sodium phosphate, pH 5.5. Fractions containing antibody by $A_{280}$ were pooled and stored at −80° C.

Tissue extract and protein A flow through samples were prepared for SDS-PAGE under reducing and non-reducing conditions by addition of 2×SDS sample buffer ±5% [v/v] 2-mercaptoethanol. Protein A eluate and hydroxyapatite eluate samples were diluted to a protein concentration of 0.5 mg/mL followed by addition of 2×SDS sample buffer ±5% [v/v] 2-mercaptoethanol. Samples were incubated at 95° C. for 2 minutes prior to electrophoresis using 4-20% Tris-Glycine gradient gels (Invitrogen, Carlsbad, Calif.). Mark12 Molecular weight markers (Invitrogen) and a MDX-060 reference standard were included on the gels. Gels were stained with Colloidal Blue stain.

Purification of N-Linked Glycans.

Protein A purified monoclonal antibodies (1 mg) from wild-type and RNAi *Lemna* plant lines were dialyzed extensively against water and lyophilized to dryness. Samples were resuspended in 100 µL of 5% (v/v) formic acid, brought to 0.05 mg/ml pepsin, and incubated at 37° C. overnight. The samples were heat inactivated at 95° C. for 15 min and dried. Pepsin digests were resuspended in 100 µL of 100 mM sodium acetate, pH 5.0 and incubated with 1 mU of N-glycosidase A at 37° C. overnight. The released N-glycans were isolated using 4 cc Carbograph SPE columns (Packer et al. (1998) *Glycoconj. J.* 19:737-747) and dried.

Dried N-glycans were further purified using 1 cc Waters Oasis MCX cartridges. Columns were prepared by washing with 3 column volumes of methanol followed by 3 column volumes of 5% (v/v) formic acid. N-glycans, resuspended in 1 mL of 5% (v/v) formic acid, were loaded onto the prepared columns. The unbound fraction as well as 2 additional column volume washes of 5% (v/v) formic acid were collected, pooled, and dried.

Derivatization of Oligosaccharides with 2-aminobenzoic Acid (2-AA).

Purified N-glycans or maltooligosaccharides were labeled with 2-AA and purified using 1 cc Waters Oasis HLB cartridges according to Anumula and Dhume, 1998 (Anumula and Dhume (1998) Glycobiology 8:685-694). Labeled N-glycans and maltooligosaccharides were resuspended in 50 µL of water and analyzed by negative mode MALDI-TOF MS and NP-HPLC-QTOF MS.

MALDI-TOF Mass Spectrometry.

MALDI-TOF MS was conducted using a Waters MALDI Micro MX (Millford, Mass.). Analysis of β-1,2-xylosyltransferase/α-1,3-fucosyltransferase reaction products was conducted by mixing 0.5 µL of each reaction supernatant with 0.5 µL of 10 mg/mL CHCA in 0.05% (v/v) TFA, 50% (v/v) acetonitrile on a target plate. Xylosylated ([M+H]$^+$=2192.85 Da) or fucosylated ([M+H]$^+$=2206.87 Da) GnGn-dabsyl-peptide products were detected in positive reflectron mode. Ion counts of 200 combined spectra from each sample were normalized against that of β-1,4-galactosylated, GnGn-dabsyl-peptide ([M+H]$^+$=2222.87 Da) present as a contaminant (<5%) in the original GnGn-dabsyl-peptide mixture from EMD Biosciences.

2-AA labeled N-glycans or maltooligosaccharides (0.5 µL) were diluted with water, mixed with 0.5 µL of 10 mg/ml DHB matrix in 70% (v/v) acetonitrile, spotted onto a target plate and analyzed in negative reflectron mode.

NP-HPLC-Q-TOF MS Analysis of 2-AA Labeled N-glycans.

2-AA labeled N-glycans or maltooligosaccharides were brought to 80% (v/v) acetonitrile and separated on a Waters 2695 HPLC system fitted with a TSK-Gel Amide-80 (2 mm×25 cm, 5 µm) column (Tosoh Biosciences, Montgomeryville, Pa.). 2-AA labeled carbohydrates were detected and analyzed using a Waters 2475 fluorescence detector (230 nm excitation, 425 nm emission) and a Waters Q-TOF API US quadropole-time of flight (QTOF) mass spectrometer fitted on-line with the HPLC system.

Separations were conducted at 0.2 mL/min, 40° C., using 10 mM ammonium acetate, pH 7.3 (solvent A) and 10 mM ammonium acetate, pH 7.3, 80% (v/v) acetonitrile (solvent B). Sample elution was carried out at 0% A isocratic for 5 min, followed by a linear increase to 10% A at 8 min, and a linear increase to 30% A at 48 min. The column was washed with 100% A for 15 min and equilibrated at 0% A for 15 min prior to the next injection.

QTOF analysis was conducted in negative ion mode with source and desolvation temperatures of 100° C. and 300° C., respectively, and capillary and cone voltages of 2,100 and 30 V, respectively. Mass spectra shown are the result of combining ≥40 individual scans per labeled N-glycan.

Monosaccharide Analysis by HPAEC-PAD.

mAb samples (200 µg) were subjected to acid hydrolysis using 2 N TFA at 100° C. for 3 h. Samples were dried by vacuum centrifugation at ambient temperature and reconstituted in 150 µL water prior to analysis by HPAE-PAD (Dionex). An aliquot (25 µL) of the reconstituted sample was applied to a CarboPac PA10 column (4×250 mm) with a pre-column Amino Trap (Dionex). Separation of monosaccharides was accomplished with a mobile phase of 3.5 mM KOH, using an EG40 eluent generator. Monosaccharide peak identity and relative abundance were determined using monosaccharide standards.

Thermal Stability of mAb.

A MicroCal (Northampton, Mass.) VP-Capillary differential scanning calorimetry (DSC) instrument was used to determine thermal stability of glycol-optimized and wild-type mAbs. Purified mAb samples were dialyzed in 20 mM NaH$_2$PO$_4$, pH 7.4, 150 mM NaCl (PBS) overnight. Thermal denaturation data was collected by heating the samples at a concentration of 300 µg/mL from 35 to 95° C. at a scan rate of 1° C./min using PBS as the reference buffer. The feedback and gain were set to low. The baseline-corrected and normalized data was fit to a non-2-state model using Origin v7.0 software.

FcR Binding Activity of mAb.

The experiment was conducted using a BIACORE (Biacore AB, Uppsala, Sweden) instrument using surface plasmon resonance technology. mAbs, 2 µg/mL, were captured on the antigen coated surface (recombinant human CD30). Several concentrations of both the Val[158] and Phe[158] allotypes of FcγRIIIa, starting from 6 µM, were flowed over the captured antibodies for 3 min. The binding signal as a function of FcγRIIIa was fit to a one-site binding model using GraphPad Prism (v4.01) software to obtain the K$_D$ values. HBS-EP buffer (10 mM HEPES, 0.15 M NaCl, 3 mM EDTA and 0.005% (v/v) P20 at pH 7.4) was used throughout the experiment. Binding of the mAbs to buffer or FcγRIIIa to blank surfaces were used as negative controls.

Assay for Antigen Binding Affinity.

CD30-expressing L540 cells (DSMZ Cell Culture Collection # ACC 72) were used as antigen positive cells to assay for binding. Aliquots of 2×10$^5$ cells/well were incubated for 30 min at 4° C. with 100 µL of primary antibody at the indicated concentrations. Cells were washed twice in PBS with 2% (v/v) fetal bovine serum (FBS) before addition of goat anti-human mAb, FITC-labeled secondary antibody (Jackson ImmunoResearch, West Grove, Pa.) at 1:500 dilution in 100 µL/well for 30 min at 4° C. Cells were washed twice in PBS with 2% (v/v) FBS and assayed by flow cytometry using a FACS Calibur instrument (Becton Dickinson, Franklin Lakes, N.J.). EC$_{50}$ values of MDX-060 CHO, LEX and LEX$^{Opt}$ mAb binding to CD30 on L540 cells were determined from binding curves utilizing GraphPad Prism 3.0 software.

ADCC Assay.

Human peripheral blood mononuclear effector cells were purified from heparinized whole blood by standard Ficoll-Paque separation. Cells ($2\times10^6$) were washed in PBS and sent for genotyping. The remaining effector cells were then resuspended at $1\times10^6$ cells/mL in RPMI 1640 medium containing 10% (v/v) FBS and 50 U/mL of human IL-2 (Research Diagnostics, Concord, Mass.) and incubated overnight at 37° C. The effector cells were washed once in culture medium and resuspended at $1\times10^7$ cells/mL prior to use. L540 target cells at $1\times10^6$ cells/mL in RPMI 1640 medium containing 10% (v/v) FBS and 5 mM probenecid were labeled with 20 μM BATDA (bis(acetoxymethyl)2,2':6',2"-terpyridine-6,6"-dicarboxylate) for 20 min at 37° C. Target cells were washed three times in PBS supplemented with 20 mM HEPES and 5 mM probenecid, resuspended at $1\times10^5$ cells/mL and added to effector cells in 96-well plates ($1\times10^4$ target cells and $5\times10^5$ effector cells/well) at a final target to effector ratio of 1:50. Maximal release was obtained by incubation of target cells in 3% (v/v) Lysol and spontaneous release obtained by incubation in cell culture medium alone. After 1 h incubation at 37° C., 20 μL of supernatant was harvested from each well and added to wells containing 180 μL of Europium solution. The reaction was read with a Perkin Elmer Fusion Alpha TRF reader using a 400 μsec delay and 330/80, 620/10 excitation and emission filters respectively. The counts per second were plotted as a function of antibody concentration and the data was analyzed by non-linear regression, sigmoidal dose response (variable slope) using GraphPad Prism 3.0 software. The percent specific lysis was calculated as: (experimental release—spontaneous release)/(maximal release—spontaneous release)$\times$100. In all studies, human mAb1 isotype control was included and compared to MDX-060 CHO, LEX, and LEX$^{Opt}$ mAbs. Other controls included target and effector cells with no mAb, target cells with no effector cells and target and effector cells in the presence of 3% (v/v) Lysol.

Results

Expression of MDX-060 mAb in the LEX System.

MDX-060 is an anti-CD30 antibody (formally known as 5F11) being developed for the treatment of Hodgkins lymphoma and anaplastic large cell lymphoma (Borchmann et al. (2003) *Blood* 102:3737-3742). Two binary vectors were constructed for the expression of MDX-060 in the LEX system. Expression vector MDXA01 contained codon optimized genes encoding heavy (H) and light (L) chains of MDX-060 while vector MDXA04 contained genes encoding H and L chains in addition to a chimeric FucT/XylT RNAi gene (FIG. 39). Independent transgenic lines were generated for both the MDXA01 (165 lines) and MDXA04 (195 lines) expression vectors. For simplicity, MDXA01 derived mAbs (wild-type N-glycosylation), and MDXA04 derived mAbs (containing the FucT/XylT RNAi construct) will be referred to as MDX-060 LEX and MDX-060 LEX$^{Opt}$, respectively, in the discussions below.

Transgenic plant lines were first screened for mAb expression with an IgG ELISA. LEX$^{Opt}$ lines with high levels of mAb expression were assayed further for FucT and XylT activity. Transferase activities in the majority of the high expressing MDX-060 LEX$^{Opt}$ lines were reduced to levels of the negative control indicating effective silencing in the majority of the assayed lines (FIG. 40). MDX-060 LEX$^{Opt}$ lines did not exhibit any morphological or growth differences compared to wild-type *Lemna* plants (data not shown).

Thermal stabilities of the MDX-060 CHO, LEX, and LEX$^{Opt}$ mAbs were determined using differential scanning calorimetry (DSC). All three mAbs exhibited similar melting curve kinetics (data not shown) and melting transition point temperatures (Table 2 below), further demonstrating the structural integrity of the *Lemna*-produced MDX-060 LEX and LEX$^{Opt}$ mAbs compared to the MDX-060 CHO mAb. SDS-PAGE analysis under non-reducing (FIG. 41A) and reducing conditions (FIG. 41B) showed that mAbs from the MDX-060 LEX$^{Opt}$ and MDX-060 CHO lines had similar protein profiles with the mAb appearing as the major component in the protein extract.

TABLE 2

Comparison of the thermal stabilities of MDX-060 CHO, MDX-060 LEX, and glyco-optimized MDX-060 LEX$^{Opt}$ mAbs by differential scanning calorimetry (DSC).

| Antibody | $T_{m1}$ (° C.) | $T_{m2}$ (° C.) | $T_{m3}$ (° C.) |
|---|---|---|---|
| MDX-060 CHO | 72 | 75 | 84 |
| MDX-060 LEX | 71 | 75 | 84 |
| MDX-060 LEX$^{Opt}$ | 72 | 76 | 84 |

N-glycan Structures of MDX-060 CHO, LEX, and LEX$^{Opt}$ mAbs.

The N-glycan profiles of recombinant MDX-060 CHO, MDX-060 LEX, and MDX-060 LEX$^{Opt}$ derived mAbs were determined by negative reflectron mode MALDI-TOF MS and normal phase (NP) HPLC-QTOF MS. The structures of N-glycans referred to in the following discussion are shown in FIG. 53.

MALDI-TOF MS analysis of N-glycans from MDX-060 CHO lines indicated the presence of four major N-glycans with m/z values corresponding to 2-AA labeled GnGnF$^6$ (nomenclature derived from http://www.proglycan.com), Man5, GnA$_{iso}$F$^6$, and AAF$^6$ (FIG. 42). NP-HPLC separated the GnA$_{iso}$F$^6$ N-glycan into its two isoforms (Gal attached to the α-1,6-Man or α-1,3-Man arm) bringing the total number of major N-glycans found on MDX-060 CHO to five (FIG. 43). MS/MS fragmentation of the peaks was not conducted to confirm the identity of each isoform; however, the higher abundance of the earlier peak suggested that Gal was attached to the α-1,6-Man arm of this N-glycan (Shinkawa et al. (2003) *J. Biol. Chem.* 278:3466-3473; Zhu et al. (2005) *Nat. Biotechnol.* 23:1159-1169). On-line negative mode QTOF MS analysis gave m/z values corresponding to doubly charged GnGnF$^6$, Man5, GnA$_{iso}$F$^6$ (both isoforms), and AAF$^6$, confirming the MALDI-TOF MS results (Table 3 below). Peak integration of the fluorescent trace revealed that GnGnF$^6$, Man5, AGnF$^6$, GnAF$^6$, and AAF constituted 50.8, 2.5, 26.1, 10.7 and 6.8%, respectively, of the total N-glycan structures from MDX-060 CHO. The remaining 3.1% of N-glycans were found to be a mixture of GnGn, GnM$_{iso}$F$^6$, GnM$_{iso}$, and MM with no structure higher than 1.2% of the total (data not shown).

TABLE 3

Summary of observed MALDI-TOF and QTOF MS masses of the major 2-AA labeled N-glycans from MDXA-060 mAbs produced by CHO cells (CHO), wild-type Lemna (LEX) or glyco-optimized Lemna lines expressing the RNAi construct (LEX$^{Opt}$).

| N-glycan name[a] | Proposed Structure[b] | Theoretical m/z [M − H]$^-$ | Theoretical m/z [M − 2H]$^{2-}$ | Observed MALDI-TOF[c] [M − H]$^-$ | Observed Q-TOF[c] [M − 2H]$^{2-}$ | % Peak Area[c] |
|---|---|---|---|---|---|---|
| CHO | | | | | | |
| GnGnF$^6$-2AA | | 1582.590 | 790.7911 | 1582.455 | 790.7825 | 50.8 |
| Man5-2AA | | 1354.479 | 676.7436 | 1354.392 | 676.7343 | 2.50 |
| GnA$_{iso}$F$^6$-2AA | or | 1744.642 | 871.8175 | 1744.492 | 871.7970 | 36.8 |
| AAF$^6$-2AA | | 1906.695 | 952.8438 | 1906.567 | 952.8181 | 6.80 |
| LEX | | | | | | |
| GnGn-2AA | | 1436.532 | 717.7622 | 1436.549 | 717.7894 | 8.40 |
| GnGnX-2AA | | 1568.574 | 783.7833 | 1568.581 | 783.8150 | 17.2 |
| GnGnXF$^3$-2AA | | 1714.632 | 856.8122 | 1714.615 | 856.853 | 67.4 |
| LEX$^{Opt}$ | | | | | | |
| GnGn-2AA | | 1436.532 | 717.7622 | 1436.523 | 717.7993 | 95.8 |

[a]N-glycan names are based on Proglycan (http://www.proglycan.com) nomenclature. 2AA, 2-aminobenzoic acid.
[b]The symbols of the proposed N-glycan structures are as follows: ■, N-acetylglucosamine; ○, mannose; ●, galactose; ◆, xylose; ▲, α-1,3-fucose; ▼, α-1,6-fucose; ⬢, 2-aminobenzoic acid.
[c]The m/z values and the % peak area of each N-glycan structure were obtained from FIG. 2.

MALDI-TOF MS analysis of wild-type MDX-060 LEX mAb revealed the presence of three major species with m/z values corresponding to GnGnXF$^3$, GnGnX and GnGn (FIG. 42). NP-HPLC-QTOF MS analysis showed three major fluorescent peaks with m/z values corresponding to doubly charged GnGnXF$^3$, GnGnX and GnGn, again confirming the MALDI-TOF MS results (FIG. 43; Table 3). Integration of the fluorescent peaks indicated that GnGnXF$^3$, GnGnX and GnGn constituted 67.4, 17.2 and 8.4%, respectively, of the total N-glycans derived from the MDX-060 LEX mAb. The remaining 7% of N-glycans were determined to be a mixture of MM, GnM$_{iso}$, MMXF$^3$, GnGnF$^3$, GnM$_{iso}$XF$^3$ Man6, Man7, Gn(FA)$_{iso}$XF$^3$, Man8 and Man9 with no N-glycan greater than 2% of the total. Similar results were seen with mAbs isolated from two independently transformed MDX-060 LEX lines (data not shown). The simple array of N-glycans on LEX mAbs demonstrated here provides an amenable starting point for glyco-optimization.

In contrast to the MDX-060 LEX mAb, N-glycans from the MDX-060 LEX$^{Opt}$ mAb possessed GnGn as the major N-glycan species by both MALD-TOF MS and NP-HPLC-QTOF MS analysis (FIGS. 42 and 43; Table 3). GnGn comprised 95.8% of the total N-glycans with the remaining 4.2% of N-glycans determined to be MM, GnM$_{iso}$, GnA$_{iso}$, Man6, Man7 and Man8 with no one structure greater than 1.2% of the total N-glycans. None of the LEX$^{Opt}$ N-glycans contained fucose (Fuc) or xylose (Xyl). These results demonstrated that co-expression of an RNAi construct targeting Lemna FucT and XylT resulted in the complete elimination of Fuc and Xyl-containing N-glycans from MDX-060 LEX$^{Opt}$ mAbs and produced highly homogeneous mAb glycoforms. The same results were obtained for MDX-060 LEX$^{Opt}$ mAb harvested from an independent transgenic line (line 225) comprising the MDXA04 expression vector, at a different growth scale (300 g tissue for transgenic line 225 versus 1 g tissue for transgenic line 52, which produced the MDX-060 LEX$^{Opt}$ mAb having the N-glycan profile shown in FIGS. 42 and 43. Unlike mammalian cell culture systems where N-glycan heterogeneity can change with culture conditions, growth scale, and growth period (Kanda et al. (2006) *Biotechnol. Bioeng.* 94:680-688), the glycan uniformity observed with LEX$^{Opt}$ mAbs was shown to be consistent under a variety of growth conditions and scales.

The absence of Fuc or Xyl on MDX-060 LEX$^{Opt}$ mAb N-glycans was further confirmed by monosaccharide analysis (Table 4 below). Monosaccharides were released from MDX-060 CHO, LEX and LEX$^{Opt}$ mAbs by acid hydrolysis and analyzed by high performance anion exchange chromatography (HPAEC) coupled to pulsed amperometric detection (PAD). The monosaccharide ratios for Man and GlcNAc residues were similar for CHO and wild-type LEX mAbs and correlated well with expected values. LEX mAbs were significantly decreased in Gal and Fuc content and had a significant increase in Xyl when compared to CHO-derived mAbs. Monosaccharide analysis of *Lemna* derived mAbs revealed that while Fuc and Xyl were present on wild-type LEX N-glycans, they were not detected on LEX$^{Opt}$ mAbs. Collectively, these results demonstrate that co-expression of an RNAi construct targeting *Lemna* XylT and FucT results in the elimination of Fuc and Xyl-containing N-glycans from MDX-060 LEX$^{Opt}$ mAbs and produce highly homogeneous mAb glycoforms. The robustness of this glyco-optimization strategy has been confirmed with multiple independent plant lines expressing the MDX-060 LEX$^{Opt}$ mAb as well as with other mAbs expressed in the LEX System, for example, the mAbI monoclonal antibody discussed in the examples herein above. In these subsequent transformations, glyco-optimized mAb expression levels up to 6% of total soluble protein (TSP) have been obtained.

TABLE 4

Monosaccharides released from MDX-060 CHO, LEX and LEX$^{Opt}$ mAbs by acid hydrolysis and analyzed by HPAEC-PAD. The monosaccharide content from each mAb was determined by normalizing against carbohydrate controls.

| Monosaccharide | MDX-060 CHO pmol (% total) | MDX-060 LEX pmol (% total) | MDX-060 LEX$^{Opt}$ pmol (% total) |
|---|---|---|---|
| Fuc | 254 (20) | 232 (13) | 0 |
| GlcNAc | 605 (47) | 773 (45) | 1,003 (67) |
| Gal | 75 (6) | 0 | 0 |
| Man | 355 (27) | 491 (29) | 501 (33) |
| Xyl | 0 | 226 (13) | 0 |
| Total | 1,289 (100) | 1,722 (100) | 1,504 (100) |

Functional Activity of MDX-060 CHO, LEX and LEX$^{Opt}$ mAbs.

Antigen binding properties of the MDX-060 CHO, MDX-060 LEX, and MDX-060 LEX$^{Opt}$ mAbs were determined using CD30 expressing L540 cells. All three mAbs had nearly identical binding curves (FIG. 43). EC$_{50}$ concentrations were determined to be 0.180 µg/mL, 0.227 µg/mL, and 0.196 µg/mL for MDX-060 CHO, LEX, and LEX$^{Opt}$, respectively (FIG. 44), indicating that antigen binding for all three mAbs were similar.

Fc-receptor-mediated effector cell function has been shown to be important for the in vivo activity of many therapeutic mAbs. Since the FcR expressed on NK cells and macrophages responsible for ADCC activity is FcγRIIIa, binding of the various mAbs to this receptor was compared. FcR binding of CHO, LEX and LEX$^{Opt}$ mAbs was determined by equilibrium binding of the mAbs with effector cells expressing two different human FcRγIIIa allotypes (Phe[158] or Val[158]). MDX-060 LEX had a 1.7-fold increase in FcRγIIaPhe[158] and a 0.4-fold decrease in FcRγIIaVal[158] binding compared to the CHO-derived mAb, demonstrating that receptor binding for CHO and LEX mAbs were similar. In contrast, LEX$^{Opt}$ mAbs had a 27 and 15-fold higher affinity for FcRγIIaPhe[158] and FcRγIIaVal[158], respectively, than CHO mAbs (FIG. 45). These results suggested that RNAi silencing of the *Lemna* FucT and XylT activities in LEX$^{Opt}$ lines produced mAbs with enhanced FcR binding.

ADCC activities of the CHO, LEX and LEX$^{Opt}$ mAbs were determined by incubating mAbs with either homozygous (FcRγIIaPhe[158]) or heterozygous (FcRγIIaPhe/Val[158]) human effector cells and BATDA (bis(acetoxymethyl)2,2':6', 2"-terpyridine-6,6"-dicarboxylate) labeled L540 target cells (FIG. 45). MDX-060 LEX mAbs (31%) had the same maximal percent cell lysis as CHO mAbs (31%) using heterozygous FcRγIIaPhe/Val[158] human effector cells (FIG. 46) with similar EC$_{50}$ values. Maximal percent cell lysis for LEX mAbs (27%) was slightly increased compared to CHO mAbs (15%) using homozygous FcγRIIIa Phe/Phe[158] effector cells. Importantly, LEX$^{Opt}$ mAbs had significantly increased ADCC activity compared to MDX-060 CHO and LEX mAbs, irrespective of the donor genotype. This was assessed by both an increase in potency and efficacy. Maximal percent lysis for MDX-060 Lex$^{Opt}$ was 45% for both experiments, while the EC$_{50}$ value was 3 to 5 times lower than MDX-060 LEX and MDX-060 CHO mAbs, respectively, for FcγRIIIa Val/Phe[158] effector cells and 2 to 3 times lower for the FcγRIIIa Phe/Phe[158] effector cells. These results demonstrate that removal of Fuc and Xyl-containing N-glycans from MDX-060 LEX$^{Opt}$ mAbs caused an enhancement in ADCC activity and hence can improve their therapeutic potential.

RP-HPLC-Q-TOF MS Analysis of Intact IgG for MDX-060 LEX and MDX-060 LE$^{Opt}$.

Protein A purified IgG's (50 µg) were desalted using the Waters 2695 HPLC system fitted with a Poros R1-10 column (2 mm×30 mm; Applied Biosystems). IgG's were detected and analyzed using a Waters 2487 dual wavelength UV detector (280 nm) and the Waters Q-TOF API US. Separations were conducted at 0.15 mL/min, 60° C., using 0.05% (v/v) trifluoroacetic acid (TFA; solvent A) and 0.05% (v/v) TFA, 80% (v/v) acetonitrile (solvent B). Sample elution was carried out using a linear increase from 30 to 50% B for 5 min, an increase to 80% B for 5 min. The solvent ratio remained at 80% B for an additional 4 min, followed by a wash with 100% B for 1 min and equilibration of the column with 30% B for 15 min prior to the next run.

Q-TOF analysis was conducted in positive ion mode with source and desolvation temperatures of 100° C. and 300° C., respectively, and capillary and cone voltages of 3.0 and 60 V, respectively. Data are the result of combining ≥100 individual scans and deconvolution to the parent mass spectrum using MaxEnt 1.

See also Triguero et al. (2005) *Plant Biotechnol. J.* 3: 449-457; Takahashi et al. (1998) *Anal. Biochem.* 255: 183-187; Dillon et al. (2004) *J. Chromatogr. A.* 1053: 299-305.

FIG. 47 shows intact mass analysis of the MDX-060 LEX m-Ab compositions produced in wild-type *L. minor* comprising the MDXA01 construct. When XylT and FucT expression are not suppressed in *L. minor*, the recombinantly produced MDX-060 LEX mAb composition comprises at least 7 different glycoforms, with the G0XF$^3$ glycoform being the predominate species present. Note the absence of a peak representing the G0 glycoform.

FIG. 48 shows glycan mass analysis of the heavy chain of the MDX-060 LEX mAb produced in wild-type *L. minor* comprising the MDXA01 construct. When XylT and FucT expression are not suppressed in *L. minor*, the predominate N-glycan species present is G0XF$^3$, with additional major peaks reflecting the G0X species. Note the minor presence of the G0 glycan species.

FIG. 49 shows intact mass analysis of the MDX-060 LEX-P$^{Opt}$ mAb compositions produced in transgenic *L. minor* comprising the MDXA04 construct. When XylT and FucT expression are suppressed in *L. minor*, the intact mAb composition contains only G0 N-glycans. In addition, the composition is substantially homogeneous for the G0 glycoform (peak 2), wherein both glycosylation sites are occupied by the G0 N-glycan species, with two minor peaks reflecting trace amounts of precursor glycoforms (peak 1, showing mAb having an Fc region wherein the $C_H2$ domain of one heavy chain has a G0 glycan species attached to Asn 297, and the $C_H^2$ domain of the other heavy chain is unglycosylated; and peak 3, showing mAb having an Fc region wherein the Asn 297 glycosylation site on each of the $C_H2$ domains has a G0 glycan species attached, with a third G0 glycan species attached to an additional glycosylation site within the mAb structure).

FIG. 50 shows glycan mass analysis of the heavy chain of the MDX-060 LEX$^{Opt}$ mAb produced in transgenic *L. minor* comprising the MDXA04 construct. When XylT and FucT expression are suppressed in *L. minor*, the only readily detectable N-glycan species attached to the Asn 297 glycosylation sites of the $C_H^2$ domains of the heavy chains is G0.

Discussion

Glyco-optimization of MDX-060 was accomplished by co-expression with an RNAi cassette aimed at silencing the endogenous *Lemna* FucT and XylT genes. This simultaneous silencing of both FucT and XylT genes was achieved using a single RNAi transcript. The absence of Fuc and Xyl on the LEX$^{Opt}$ mAb was confirmed by MALDI-TOF, NP-HPLC-QTOF MS, and monosaccharide analysis of N-glycans purified from the MDX-060 LEX$^{Opt}$ mAb. These analyses corroborate the lack of transferase activity observed in microsomal membranes. Importantly, >95% of the N-glycans released from LEX$^{Opt}$ mAbs were of a single structure, GnGn, indicating that this strategy had the added benefit of producing mAbs with a homogeneous N-glycan profile. MDX-060 LEX and LEX$^{Opt}$ mAbs were found to be indistinguishable with regard to thermal stability and antigen binding compared to MDX-060 CHO. Electrophoretic analysis was also found to be similar for all three mAbs. In fact, the only structural differences detected were in the mAb N-glycan profiles.

Without being bound by theory, the ability of the MDX-060 LEX$^{Opt}$ lines to produce mAbs with a single major N-glycan species may be based on the more uniform mAb glycoform distribution found in wild-type *Lemna*. N-glycans released from mAbs purified from wild-type tobacco (Fujiyama et al. (2006) *J. Biosci. Bioeng.* 101:212-218; Elbers et al. (2001) *Plant Physiol.* 126:1314-1322; Bakker et al. (2001) *Proc. Natl. Acad. Sci.* 98:2899-2904), alfalfa (Bardor et al. (2003) *Plant Biotechnol. J.* 1:451-462), and moss (Koprivova et al. (2003) *Plant Bio.* 5:582-591) show that m-Ab glycoform heterogeneity in plants with wild-type N-glycosylation can range from five (alfalfa) (Bardor et al. (2003) *Plant Biotechnol. J.* 1:451-462) to eight (tobacco) (Fujiyama et al. (2006) *J. Biosci. Bioeng.* 101:212-218) different major structures. MDX-060 LEX possesses only three major N-glycan structures (GnGn, GnGnX and GnGnXF$^3$). This simple array of N-glycans on m-Abs produced by wild-type *Lemna* may provide a more amenable starting point for glyco-optimization leading to greater homogeneity than that observed in other systems.

Fc-receptor mediated effector cell function has been shown to be important for the in vivo activity of many therapeutic m-Abs. In this study, the ADCC activity of MDX-060 CHO, MDX-060 LEX, and MDX-060 LEX$^{Opt}$ mAbs was compared. Since the FcR expressed on NK cells and macrophages responsible for ADCC activity is FcγRIIIa, the binding of the various mAbs to this receptor was also compared. The results discussed above show that MDX-060 LEX$^{Opt}$ mAb has an increased binding affinity (15-25 fold) and maximal binding (4-5 fold) to FcγRIIIa as well as enhanced ADCC activity compared to MDX-060 CHO and MDX-060 LEX mAbs. The removal of α-1,6-linked Fuc from various mAbs produced in other expression systems has been shown previously to increase FcR binding and enhance ADCC function (Shinkawa et al. (2003) *J. Biol. Chem.* 278:3466-3473; Shields et al. (2002) *J. Biol. Chem.* 277:26733-26740; Niwa et al. (2004) *Clin. Cancer Res.* 10:6248-6255). The results presented herein suggest that removal of the α-1,3-linked Fuc from the MDX-060 LEX$^{Opt}$ mAbs has the same effect on mAb function as the removal of α-1,6-linked Fuc.

In this study, two naturally occurring polymorphic isoforms of FcγRIIIa at residue 158[41], Val[158] and Phe[158], were MDX$^{Opt}$ shows higher binding affinity to FcγRIIIa-Val[158] compared to FcγRIIIa-Phe[158] as has been observed with other IgG1 mAbs (Shields et al. (2002) *J. Biol. Chem.* 277:26733-26740). The fact that an increase in binding with MDX-060 LEX$^{Opt}$ was observed with both isoforms is important since differential binding to Val[158] over Phe[158] was found to be predictive of the clinical and immunological responsiveness of certain patient groups receiving anti-CD20 treatment (Cartron et al. (2002) *Blood* 99:754-758; Weng et al. (2003) *J. Clin. Oncol.* 21:3940-3947; Weng et al. (2004) *J. Clin. Oncol.* 22:4717-4724). This increase in binding has been hypothesized to result in a higher percentage of patients responding to treatment that requires Fc functionality.

A similar increase in ADCC activity was also observed. In this study, the MDX-060 LEX$^{Opt}$ mAb showed an increase in cell lysis and a decrease in the EC$_{50}$ value, resulting in an increase in efficacy and potency when compared to MDX-060 CHO. This corresponds to a 20-fold increase in activity, determined by taking the maximum percent lysis of MDX-060 CHO and calculating the concentration of MDX-060 LEX$^{Opt}$ mAb giving rise to the same percent cell lysis. As with the FcγRIIIa binding study, the increase in ADCC activity was observed with both a homozygous FcγRIIIaPhe/Phe[158] and a heterozygous FcγRIIIa Phe/Val[158] effector cell donor. The results presented here suggest that removal of the α-1,3-linked Fuc from the MDX-060 LEX$^{Opt}$ mAbs has the same effect on mAb function as the removal of α-1,6-linked Fuc.

The robustness of this glyco-optimization strategy has been demonstrated with multiple independent *Lemna* plant lines expressing the MDX-060 LEX$^{Opt}$ mAb as well as with other mAbs expressed in the *Lemna* expression system (see, for example, Examples 2-4 above). Furthermore, there is no apparent difference in plant phenotype or growth rate compared with wild-type *Lemna* plants. Unlike mammalian cell culture systems where N-glycan heterogeneity can change with culture conditions, growth scale and growth period[8], the glycan uniformity observed with LEX$^{Opt}$ mAbs has been shown to be consistent under a variety of growth conditions and scales (data not shown).

In conclusion, an RNAi strategy was used to produce a glyco-optimized anti-CD30 antibody in the *Lemna* expression system. The resulting mAb consists of a single, major N-glycan structure, without any evidence of the plant-specific Fuc and Xyl residues. In addition, the resulting optimized mAb has increased ADCC activity and FcγRIIIa binding activity compared to a CHO-derived mAb. The homogeneous glycosylation profile obtained on mAbs produced in a *Lemna* expression system having this FucT+XylT gene knockout strategy makes it is possible to express these mAbs with increased production consistency.

Example 7

Scale-Up Production of Glycan-Optimized mAbI in *Lemna minor*

*L. minor* transgenic line 24 comprising the mAbIO4 construct of FIG. 12 (providing for suppression of FucT and XylT) was generated in a manner similar to that described above. Following its generation, transgenic line 24 was continuously maintained by clonal culture, wherein periodically a subsample of the plant culture was transferred to fresh culture medium for further culturing. This transgenic line was analyzed for the N-glycosylation pattern of the recombinantly produced mAbI antibody following production scale-up from 1 g tissue up to 300 g (0.3 kg) tissue, and further production scale-up to 6.5 kg tissue. The process of scaling production up to 6.5 kg tissue occurred approximately 8 months after transgenic line 24 was generated. Results are shown in FIGS. 51A (MALDI-TOF analysis of N-glycans) and 51B (HPLC fluorescence analysis of N-glycans).

The glycosylation profile for the mAbI antibody produced by transgenic line 24 comprising the mAbIO4 construct remained homogeneous with scale-up in production from 1 g tissue to 0.3 kg tissue, and further scale-up in production to 6.5 kg tissue, and thus was characterized by the presence of a single predominant peak corresponding to the GnGn (i.e., G0) glycan species. Thus, the homogeneity of the glycosylation profile in transgenic *L. minor* comprising the mAbIO4 construct was consistently maintained with an approximately 6,500-fold increase in production scale (i.e., from 1 g up to 6.5 kg). Furthermore, the homogeneity of the glycosylation profile was consistently maintained in this transgenic line at 8 months following its generation.

These data demonstrate that the homogeneity of the glycosylation profile in transgenic *L. minor* comprising the mAbIO4 construct remains consistent with at least a 6,500-fold increase in production scale. Furthermore, the homogeneity of the glycosylation profile in transgenic *L. minor* comprising the mAbIO4 construct is maintained for at least 8 months after the transgenic line is generated. The homogeneity of the glycosylation profile would be expected to be maintained with further increase in production scale, and thus, for example, would be expected to be maintained if production scale was increased by another 4-fold beyond 6.5 kg (e.g., scale-up from 6.5 kg to 26 kg). The homogeneity of the glycosylation profile would also be expected to be maintained with continuous clonal culture of the transgenic line well beyond 8 months after generation of the transgenic line.

Example 8

Glycosylation Pattern for Endogenous Glycoproteins in *Lemna minor* Lines Transgenic for mAbIO4 RNAi Construct The L40 protease is a representative endogenous glycoprotein produced in *L. minor*. In order to assess the impact of the mAbIO4 RNAi construct (FIG. 12) on glycosylation of endogenous proteins, the L40 protein was isolated from a *L. minor* line transgenic for the mAbIO4 RNAi construct using benzamidine affinity chromatography. The N-glycosylation pattern for the isolated L40 protein was analyzed using MALDI-TOF analysis in the manner described above. Results are shown in FIG. 52.

As can be seen from this analysis, suppression of FucT and XylT expression using the chimeric RNAi mAbIO4 construct results in endogenous glycoproteins having a homogeneous glycosylation pattern consistent with that observed for recombinant glycoproteins. Thus, the heterogeneous N-glycan profile for the L40 glycoprotein isolated from *L. minor* having the wild-type glycosylation machinery is represented by a mixture of N-glycans species having the β1,2-linked xylose residue, or both the β1,2-linked xylose and core α1,3-linked fucose residues attached. In contrast, the homogeneous N-glycan profile for L40 isolated from *L. minor* transgenic for the mAbIO4 RNAi construct is represented by a single predominant peak corresponding to the G0 glycan species, and is characterized by the absence of N-glycan species having the β1,2-linked xylose or both the β1,2-linked xylose and core α1,3-linked fucose residues attached.

Example 9

Production of Anti-CD20 and Anti-HER2 Monoclonal Antibody Having Increased ADCC Activity IDEC-C2B8 (IDEC Pharmaceuticals Corp., San Diego, Calif.; commercially available under the tradename Rituxan®, also referred to as rituximab; see U.S. Pat. No. 5,736,137, herein incorporated by reference) is a chimeric anti-CD20 monoclonal antibody containing human IgG1 and kappa constant regions with murine variable regions isolated from a murine anti-CD20 monoclonal antibody, IDEC-2B8 (Reff et al. (1994) *Blood* 83:435-445). Rituximab is licensed for treatment of relapsed B cell low-grade or follicular non-Hodgkin's lymphoma (NHL). The anti-CD20 antibody marketed as rituximab (Rituxan®) is recombinantly produced in CHO cells. The glycosylation pattern of this CHO-expressed anti-CD20 antibody reveals a heterogeneous mixture of glycoforms.

A humanized anti-ERBB2 antibody is commercially available under the tradename Herceptin® (Genentech, Inc., San Francisco, Calif.) (see U.S. Pat. No. 6,165,464, herein incorporated by reference). This recombinant humanized monoclonal antibody has high affinity for p185HER2. Early clinical trials with patients having extensive metastatic breast carcinomas demonstrate the ability of this monoclonal antibody to inhibit growth of breast cancer cells that overexpress HER2 (Baselga et al. (1996) *J. Clin. Oncol.* 14(3):737-744).

A rituximab-sequence antibody and Herceptin® anti-ERBB2-sequence antibody are recombinantly produced in *Lemna* having a wild-type glycosylation pattern, using the mAbI01 construct described above, and in *Lemna* that is genetically modified to suppress expression of both FucT and XylT, using the mAbIO4 chimeric RNAi construct, with the rituximab or anti-ERBB2 heavy and light chain coding sequences replacing those for the mAbI in each of these constructs. The sequences encoding the heavy and light chains are optionally both codon-optimized with *Lemna*-preferred codons. The secreted rituximab-sequence mAb (i.e., having the amino acid sequence of the rituximab antibody) and anti-ERBB2-sequence mAb (i.e., having the amino acid sequence of the Herceptin® anti-ERBB2 mAb) are analyzed for glycosylation pattern as described above in Example 1.

The glycosylation profile for intact rituximab-sequence mAb or anti-ERBB2-sequence mAb produced in the wild-type Lemna comprising the mAbI01-like construct shows a heterogeneous profile with numerous peaks corresponding to multiple glycoforms. In contrast, the glycoyslation profile for intact rituximab-sequence mAb or intact anti-ERBB2-sequence mAb produced in transgenic Lemna comprising the mAbI04-like construct shows a substantially homogeneous glycoprotein composition, with three major glycoform peaks, the largest of which corresponds to the G0 glycoform, and two very minor peaks corresponding to trace amounts of precursor glycoforms, wherein xylose and fucose residues are not attached.

The rituximab-sequence and anti-ERBB2-sequence monoclonal antibody compositions having a glycosylation profile that is substantially homogeneous for the G0 glycoform are tested for ADCC activity and Fcγ receptor IIIa (Fc-γRIIIa) binding on freshly-isolated human NK cells. The rituximab-sequence and anti-ERBB2-sequence mAbs produced from L. minor lines engineered with the mAbI04-like construct exhibit the expected enhanced binding in view of the lack of any fucose residues, relative to the binding observed for the rituximab-sequence and anti-ERBB2-sequence mAbs produced from L. minor lines having the wild-type glycosylation machinery (i.e., no silencing of FucT or XylT). Furthermore, binding affinity is at least strong as for the corresponding mAb produced in CHO cell lines.

ADCC activity of the substantially homogeneous G0 glycoform of rituximab-sequence mAb and of anti-ERBB2-sequence mAb produced in the L. minor line engineered with the mAbI04-like construct is assayed using purified human peripheral blood mononuclear cells as effector cells (see, for example, Shinkawa et al. (2003) *J. Biol. Chem.* 278(5):3466-3473; herein incorporated by reference in its entirety). Activity of the G0 glycoform rituximab-sequence and anti-ERBB2-sequence mAb compositions is improved 50-1000 fold over that exhibited by the respective rituximab-sequence mAb or anti-ERBB2-sequence mAb produced in the L. minor line having the wild-type glycosylation machinery or produced in CHO cells.

CDC activity of the substantially homogeneous G0 glycoform of rituximab-sequence mAb produced in the L. minor line engineered with the mAbI04-like RNAi construct is assayed using standard assays known in the art (see, for example, the complement activation assays described in U.S. Patent Application Publication No. 2004/0167319, herein incorporated by reference in its entirety), and compared to that observed for rituximab. Non-relevant antibody serves as the negative control. In one such assay, CDC activity of the various antibodies against target Daudi cells is measured by assessing elevated membrane permeability using a propidium iodide (PI) exclusion assay, with serum from healthy volunteers serving as a complement source. Serum for complement lysis is prepared by drawing blood from healthy volunteers into autosep gel and clot activator vacutainer tubes (BD Biosciences, Rutherford, N.J.), which are held at room temperature for 30-60 minutes and then centrifuged at 3000 rpm for 5 minutes. Serum is harvested and stored at −80° C.

Briefly, for this CDC activity assay, Daudi cells are washed and resuspended in RPMI-1% BSA at $1 \times 10^6$/ml. Various concentrations of the substantially homogeneous G0 glycoform of rituximab-sequence mAb, rituximab, and negative control mAb are added to the Daudi cells and allowed to bind for 10-15 minutes at room temperature. Thereafter, serum as a source of complement is added to a final concentration of 20% (v/v) and the mixtures are incubated for 45 min at 37° C. The cells are then kept at 4° C. until analysis. Each sample (150 μl) is then added to 10 μl of PI solution (10 μg/ml in PBS) in a FACS tube. The mixture is assessed immediately for cell lysis (number of PI-positive cells) by a FACScalibur flow cytometer and analysed using CellQuest pro software (BD Biosciences, Mountain View, Calif.). At least 5000 events are collected for analysis with cell debris excluded by adjustment of the forward sideward scatter (FCS) threshold.

CDC activity of the substantially homogeneous G0 glycoform rituximab-sequence mAb is decreased relative to that exhibited by rituximab.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A nucleotide construct comprising a first nucleotide sequence that is capable of inhibiting expression of an α1,3-fucosyltransferase (FucT) in a duckweed plant, and a second nucleotide sequence that is capable of inhibiting expression of a β1,2-xylosyltransferase (XylT) in a duckweed plant, wherein said first nucleotide sequence is operably linked to a first promoter that is functional in a plant cell, and wherein said second nucleotide sequence is operably linked to a second promoter that is functional in a plant cell, wherein said first nucleotide sequence comprises in the 5'-to-3' orientation and operably linked:
   (a) a FucT forward fragment, said FucT forward fragment comprising about 500 to about 800 contiguous nucleotides having at least 90% sequence identity to a nucleotide sequence of about 500 to about 800 contiguous nucleotides of SEQ ID NO:1 or SEQ ID NO:2;
   (b) a spacer sequence comprising a nucleotide fragment of the sequence set forth in SEQ ID NO:1; and
   (c) a FucT reverse fragment, said FucT reverse fragment having sufficient length and sufficient complementarity to said FucT forward fragment such that said first nucleotide sequence is transcribed as an RNA molecule capable of forming a hairpin RNA structure.

2. The nucleotide construct of claim 1, wherein said FucT reverse fragment comprises the complement of said FucT forward fragment or a sequence having at least 90% sequence identity to the complement of said FucT forward fragment.

3. The nucleotide construct of claim 1, wherein said FucT forward fragment comprises nucleotides (nt) 255-985 of SEQ ID NO: 1.

4. The nucleotide construct of claim 1, wherein said nucleotide fragment of the sequence set forth in SEQ ID NO:1 comprises about 200 to 700 nucleotides immediately downstream of said FucT forward fragment.

5. The nucleotide construct of claim 4, wherein said spacer sequence comprises (nt) 986-1444 of SEQ ID NO:1.

6. A nucleotide construct comprising a first nucleotide sequence that is capable of inhibiting expression of an α1,3-fucosyltransferase (FucT) in a duckweed plant, and a second nucleotide sequence that is capable of inhibiting expression of a β1,2-xylosyltransferase (XylT) in a duckweed plant, wherein said first nucleotide sequence is operably linked to a first promoter that is functional in a plant cell, and wherein said second nucleotide sequence is operably linked to a second promoter that is functional in a plant cell, wherein said first nucleotide sequence comprises in the 5'-to-3' direction and operably linked:
   (a) a sense nucleotide sequence comprising at least 19 contiguous nucleotides of SEQ ID NO:1; and
   (b) an antisense nucleotide sequence comprising at least 19 contiguous nucleotides of said sense nucleotide sequence;

wherein said first nucleotide sequence is transcribed as a small hairpin RNA having a base-paired stem length shorter than about 200 base pairs.

7. The nucleotide construct of claim 6, wherein said promoter operably linked to said first nucleotide sequence is a type 3 RNA polymerase III promoter.

8. The nucleotide construct of claim 1, wherein said XylT is a polypeptide comprising an amino acid sequence selected from the group consisting of:
   (a) the amino acid sequence set forth in SEQ ID NO:6 or SEQ ID NO:21; and
   (b) an amino acid sequence having at least 90% sequence identity to the amino acid sequence set forth in SEQ ID NO:6 or SEQ ID NO:21.

9. The nucleotide construct of claim 8, wherein said second nucleotide sequence comprises a sequence selected from the group consisting of:
   (a) the nucleotide sequence set forth in SEQ ID NO:4 or SEQ ID NO:19, or a complement thereof;
   (b) the nucleotide sequence set forth in SEQ ID NO:5 or SEQ ID NO:20, or a complement thereof;
   (c) a nucleotide sequence having at least 90% sequence identity to the sequence of preceding item (a) or (b); and
   (d) a fragment of the nucleotide sequence of any one of preceding items (a) through (c), wherein said fragment comprises at least 75 contiguous nucleotides of said nucleotide sequence.

10. The nucleotide construct of claim 8, wherein said second nucleotide sequence comprises in the 5'-to-3' orientation and operably linked:
    (a) a XylT forward fragment, said XylT forward fragment comprising about 500 to about 800 contiguous nucleotides having at least 90% sequence identity to a nucleotide sequence of about 500 to about 800 contiguous nucleotides of SEQ ID NO:4, SEQ ID NO:5, SEQ ID NO:19, or SEQ ID NO:20;
    (b) a spacer sequence comprising about 200 to about 700 nucleotides; and
    (c) a XylT reverse fragment, said XylT reverse fragment having sufficient length and sufficient complementarity to said XylT forward fragment such that said second nucleotide sequence is transcribed as an RNA molecule capable of forming a hairpin RNA structure.

11. The nucleotide construct of claim 10, wherein said XylT reverse fragment comprises the complement of said XylT forward fragment or a sequence having at least 90% sequence identity to the complement of said XylT forward fragment.

12. The nucleotide construct of claim 10 wherein said XylT forward fragment comprises nucleotides (nt) 318-1052 of SEQ ID NO:4 or nt 1-734 of SEQ ID NO:19.

13. The nucleotide construct of claim 10, wherein said spacer sequence within said second nucleotide sequence comprises a nucleotide fragment of the sequence set forth in SEQ ID NO:4 or SEQ ID NO:19.

14. The nucleotide construct of claim 13, wherein said nucleotide fragment of the sequence set forth in SEQ ID NO:4 or SEQ ID NO: 19 comprises about 200 to 700 nucleotides immediately downstream of said XylT forward fragment.

15. The nucleotide construct of claim 14, wherein:
   (a) said XylT forward fragment comprises nt 318-1052 of SEQ ID NO:4 and said spacer sequence comprises nt 1053-1599 of SEQ ID NO:4; or
   (b) said XylT forward fragment comprises nt 1-734 of SEQ ID NO:19 and said spacer sequence comprises nt 735-1282 of SEQ ID NO:19.

16. The nucleotide construct of claim 10, wherein said spacer sequence within said second nucleotide sequence comprises an intron.

17. The nucleotide construct of claim 8, wherein said second nucleotide sequence comprises in the 5'-to-3' direction and operably linked:
   (a) a sense nucleotide sequence comprising at least 19 contiguous nucleotides of SEQ ID NO:4 or SEQ ID NO:19; and
   (b) an antisense nucleotide sequence comprising at least 19 contiguous nucleotides of the complement of said sense nucleotide sequence of preceding item (a);
wherein said second nucleotide sequence is transcribed as a small hairpin RNA having a base-paired stem length shorter than about 200 base pairs.

18. The nucleotide construct of claim 17, wherein said promoter operably linked to said second nucleotide sequence is a type 3 RNA polymerase III promoter.

19. A nucleotide construct comprising a first nucleotide sequence that is capable of inhibiting expression of an α1,3-fucosyltransferase (FucT) in a duckweed plant, and a second nucleotide sequence that is capable of inhibiting expression of a β1,2-xylosyltransferase (XylT) in a duckweed plant, wherein said first nucleotide sequence is operably linked to a first promoter that is functional in a plant cell, and wherein said second nucleotide sequence is operably linked to a second promoter that is functional in a plant cell, wherein said second nucleotide sequence comprises in the 5'-to-3' orientation and operably linked:
   (a) a XylT forward fragment, said XylT forward fragment comprising about 500 to about 800 contiguous nucleotides having at least 90% sequence identity to a nucleotide sequence of about 500 to about 800 contiguous nucleotides of SEQ ID NO:4, SEQ ID NO:5, SEQ ID NO:19, or SEQ ID NO:20;
   (b) a spacer sequence comprising a nucleotide fragment of the sequence set forth in SEQ ID NO:4 or SEQ ID NO:19; and
   (c) a XylT reverse fragment, said XylT reverse fragment having sufficient length and sufficient complementarity to said XylT forward fragment such that said second nucleotide sequence is transcribed as an RNA molecule capable of forming a hairpin RNA structure.

20. The nucleotide construct of claim 19, wherein said XylT reverse fragment comprises the complement of said XylT forward fragment or a sequence having at least 90% sequence identity to the complement of said XylT forward fragment.

21. The nucleotide construct of claim 19, wherein said XylT forward fragment comprises nucleotides (nt) 318-1052 of SEQ ID NO:4 or nt 1-734 of SEQ ID NO:19.

22. The nucleotide construct of claim 19, wherein said nucleotide fragment of the sequence set forth in SEQ ID NO:4 or SEQ ID NO: 19 comprises about 200 to 700 nucleotides immediately downstream of said XylT forward fragment.

23. The nucleotide construct of claim 22 wherein:
   (a) said XylT forward fragment comprises nt 318-1052 of SEQ ID NO:4 and said spacer sequence comprises nt 1053-1599 of SEQ ID NO:4; or
   (b) said XylT forward fragment comprises nt 1-734 of SEQ ID NO:19 and said spacer sequence comprises nt 735-1282 of SEQ ID NO:19.

24. A nucleotide construct comprising a first nucleotide sequence that is capable of inhibiting expression of an α1,3-fucosyltransferase (FucT) in a duckweed plant, and a second nucleotide sequence that is capable of inhibiting expression of a β1,2-xylosyltransferase (XylT) in a duckweed plant, wherein said first nucleotide sequence is operably linked to a first promoter that is functional in a plant cell, and wherein said second nucleotide sequence is operably linked to a second promoter that is functional in a plant cell, wherein said second nucleotide sequence comprises in the 5'-to-3' direction and operably linked:
   (a) a sense nucleotide sequence comprising at least 19 contiguous nucleotides of SEQ ID NO:4 or SEQ ID NO:19; and
   (b) an antisense nucleotide sequence comprising at least 19 contiguous nucleotides of the complement of said sense nucleotide sequence of preceding item (a);
wherein said second nucleotide sequence is transcribed as a small hairpin RNA having a base-paired stem length shorter than about 200 base pairs.

25. The nucleotide construct of claim 24, wherein said promoter operably linked to said second nucleotide sequence is a type 3 RNA polymerase III promoter.

26. The nucleotide construct of claim 19, wherein said FucT is a polypeptide comprising an amino acid sequence selected from the group consisting of:
   (a) the amino acid sequence set forth in SEQ ID NO:3; and
   (b) an amino acid sequence having at least 90% sequence identity to the amino acid sequence set forth in SEQ ID NO:3.

27. The nucleotide construct of claim 26, wherein said first nucleotide sequence comprises a sequence selected from the group consisting of:
   (a) the nucleotide sequence set forth in SEQ ID NO:1 or a complement thereof;
   (b) the nucleotide sequence set forth in SEQ ID NO:2 or a complement thereof;
   (c) a nucleotide sequence having at least 90% sequence identity to the sequence of preceding item (a) or (b); and
   (d) a fragment of the nucleotide sequence of any one of preceding items (a) through (c), wherein said fragment comprises at least 75 contiguous nucleotides of said nucleotide sequence.

28. A nucleotide construct comprising a fusion polynucleotide that is capable of inhibiting expression of an α1,3-fucosyltransferase (FucT) and a β1,2-xylosyltransferase (XylT) in a duckweed plant, wherein said fusion polynucleotide is operably linked to a promoter that is functional in a plant cell, said fusion polynucleotide comprising in the 5'-to-3' orientation and operably linked:
   (a) a chimeric forward fragment, said chimeric forward fragment comprising:
      (i) a first fragment comprising about 500 to about 650 contiguous nucleotides having at least 90% sequence identity to a nucleotide sequence of about 500 to about 650 contiguous nucleotides of SEQ ID NO:1 or SEQ ID NO:2; and (ii) a second fragment comprising about 500 to about 650 contiguous nucleotides having at least 90% sequence identity to a nucleotide sequence of about 500 to about 650 contiguous nucleotides of a polynucleotide encoding said XylT;

(b) a spacer sequence comprising a fragment of said polynucleotide encoding said XylT, said fragment being about 200 to about 700 nucleotides in length; and (c) a reverse fragment, said reverse fragment having sufficient length and sufficient complementarity to said chimeric forward fragment such that said fusion polynucleotide is transcribed as an RNA molecule capable of forming a hairpin RNA structure;

wherein said polynucleotide encoding said XylT is selected from the group consisting of:

(1) a polynucleotide comprising SEQ ID NO:4, SEQ ID NO:5, SEQ ID NO:19, or SEQ ID NO:20;

(2) a polynucleotide encoding the polypeptide set forth in SEQ ID NO:6 or SEQ ID NO:21; and (3) a polynucleotide encoding a polypeptide having at least 90% sequence identity to the polypeptide set forth in SEQ ID NO:6 or SEQ ID NO:21.

29. The nucleotide construct of claim 28, wherein said reverse fragment comprises the complement of said chimeric forward fragment or a sequence having at least 90% sequence identity to the complement of said chimeric forward fragment.

30. The nucleotide construct of claim 28, wherein said spacer sequence comprises about 200 to 700 nucleotides immediately downstream of the second fragment of said chimeric forward fragment.

31. The nucleotide construct of claim 28, wherein said FucT is a polypeptide comprising the amino acid sequence set forth in SEQ ID NO:3.

32. The nucleotide construct of claim 28, wherein said XylT is a polypeptide comprising the amino acid sequence set forth in SEQ ID NO:6 or SEQ ID NO:21.

33. The nucleotide construct of claim 28, wherein said first fragment comprises about 500 to about 650 contiguous nucleotides of SEQ ID NO: 1; and said second fragment comprises about 500 to about 650 contiguous nucleotides of SEQ ID NO:4 or SEQ ID NO:19.

34. The nucleotide construct of claim 33, wherein said reverse fragment comprises the complement of said chimeric forward fragment or a sequence having at least 90% sequence identity to the complement of said chimeric forward fragment.

35. The nucleotide construct of claim 33, wherein said chimeric forward fragment comprises:

(a) nucleotides (nt) 254-855 of SEQ ID NO:1 and nt 318-943 of SEQ ID NO:4; or (b) nucleotides (nt) 254-855 of SEQ ID NO:1 and nt 1-626 of SEQ ID NO:19.

36. The nucleotide construct of claim 33, wherein said spacer sequence comprises about 200 to 700 nucleotides immediately downstream of the second fragment of said chimeric forward fragment.

37. The nucleotide construct of claim 36, wherein:

(a) said chimeric forward fragment comprises nt 254-855 of SEQ ID NO:1 and nt 318-943 of SEQ ID NO:4 and said spacer sequence comprises nt 944-1443 of SEQ ID NO:4; or (b) said chimeric forward fragment comprises nt 254-855 of SEQ ID NO:1 and nt 1-626 of SEQ ID NO: 19 and said spacer sequence comprises nt 627-1126 of SEQ ID NO:19.

38. A nucleotide construct comprising a fusion polynucleotide that is capable of inhibiting expression of an α1,3-fucosyltransferase (FucT) and a β1,2-xylosyltransferase (XylT) in a duckweed plant, wherein said fusion polynucleotide is operably linked to a promoter that is functional in a plant cell, said fusion polynucleotide comprising in the 5'-to-3' orientation and operably linked:

(a) a chimeric forward fragment, said chimeric forward fragment comprising:

(i) a first fragment comprising about 500 to about 650 contiguous nucleotides having at least 90% sequence identity to a nucleotide sequence of about 500 to about 650 contiguous nucleotides of SEQ ID NO:4, SEQ ID NO:5, SEQ ID NO:19, or SEQ ID NO:20; and (ii) a second fragment comprising about 500 to about 650 contiguous nucleotides having at least 90% sequence identity to a nucleotide sequence of about 500 to about 650 contiguous nucleotides of a polynucleotide encoding said FucT;

(b) a spacer sequence comprising a fragment of said polynucleotide encoding said FucT, said fragment being about 200 to about 700 nucleotides in length; and c) a reverse fragment, said reverse fragment having sufficient length and sufficient complementarity to said chimeric forward fragment such that said fusion polynucleotide is transcribed as an RNA molecule capable of forming a hairpin RNA structure;

wherein said polynucleotide encoding said FucT is selected from the group consisting of:

(1) a polynucleotide comprising SEQ ID NO:1 or SEQ ID NO:2;

(2) a polynucleotide encoding the polypeptide set forth in SEQ ID NO:3; and (3) a polynucleotide encoding a polypeptide having at least 90% sequence identity to the polypeptide set forth in SEQ ID NO:3.

39. The nucleotide construct of claim 38, wherein said reverse fragment comprises the complement of said chimeric forward fragment or a sequence having at least 90% sequence identity to the complement of said chimeric forward fragment.

40. The nucleotide construct of claim 38, wherein said spacer sequence comprises about 200 to 700 nucleotides immediately downstream of the second fragment of said chimeric forward fragment.

41. The nucleotide construct of claim 38, wherein said FucT is a polypeptide comprising the amino acid sequence set forth in SEQ ID NO:3.

42. The nucleotide construct of claim 38, wherein said XylT is a polypeptide comprising the amino acid sequence set forth in SEQ ID NO:6 or SEQ ID NO:21.

43. The nucleotide construct of claim 38, wherein said first fragment comprises about 500 to about 650 contiguous nucleotides of SEQ ID NO:4 or SEQ ID NO: 19; and said second fragment comprises about 500 to about 650 contiguous nucleotides of SEQ ID NO:1.

44. The nucleotide construct of claim 43, wherein said reverse fragment comprises the complement of said chimeric forward fragment or a sequence having at least 90% sequence identity to the complement of said chimeric forward fragment.

45. The nucleotide construct of claim 43, wherein said spacer sequence comprises about 200 to 700 nucleotides immediately downstream of the second fragment of said chimeric forward fragment.

46. A nucleotide construct comprising a first polynucleotide sequence that is capable of inhibiting expression of an α1,3-fucosyltransferase (FucT) in a duckweed plant, wherein said first polynucleotide sequence comprises in the 5'-to-3' orientation and operably linked:
  (a) a FucT forward fragment, said FucT forward fragment comprising about 500 to about 800 contiguous nucleotides having at least 90% sequence identity to a nucleotide sequence of about 500 to about 800 contiguous nucleotides of SEQ ID NO:1 or SEQ ID NO:2;
  (b) a spacer sequence comprising a fragment of said polynucleotide encoding said FucT, said fragment being about 200 to about 700 nucleotides in length; and
  (c) a FucT reverse fragment, said FucT reverse fragment having sufficient length and sufficient complementarity to said FucT forward fragment such that said first polynucleotide sequence is transcribed as an RNA molecule capable of forming a hairpin RNA structure;
  wherein said first polynucleotide sequence is operably linked to a promoter that is functional in a plant cell.

47. The nucleotide construct of claim 46, wherein said FucT reverse fragment comprises the complement of said FucT forward fragment or a sequence having at least 90% sequence identity to the complement of said FucT forward fragment.

48. The nucleotide construct of claim 46, wherein said spacer sequence within said first polynucleotide sequence comprises about 200 to 700 nucleotides immediately downstream of said FucT forward fragment.

49. The nucleotide construct of claim 46, wherein said FucT is a polypeptide comprising the amino acid sequence set forth in SEQ ID NO:3.

50. The nucleotide construct of claim 49, wherein said FucT forward fragment comprises about 500 to about 800 contiguous nucleotides of SEQ ID NO:1 or SEQ ID NO:2.

51. The nucleotide construct of claim 50, wherein said FucT reverse fragment comprises the complement of said FucT forward fragment or a sequence having at least 90% sequence identity to the complement of said FucT forward fragment.

52. The nucleotide construct of claim 50, wherein said FucT forward fragment comprises nucleotides (nt) 255-985 of SEQ ID NO:1.

53. The nucleotide construct of claim 50, wherein said spacer sequence comprises about 200 to 700 nucleotides immediately downstream of said FucT forward fragment.

54. The nucleotide construct of claim 53, wherein said spacer sequence comprises nt 986-1444 of SEQ ID NO:1.

55. A nucleotide construct comprising a first polynucleotide sequence that is capable of inhibiting expression of a β1,2-xylosyltransferase (XylT) in a duckweed plant, wherein said first polynucleotide sequence comprises in the 5'-to-3' orientation and operably linked:
  (a) a XylT forward fragment, said XylT forward fragment comprising about 500 to about 800 contiguous nucleotides having at least 90% sequence identity to a nucleotide sequence of about 500 to about 800 contiguous nucleotides of SEQ ID NO:4, SEQ ID NO:5, SEQ ID NO:19, or SEQ ID NO:20;
  (b) a spacer sequence comprising a fragment of said polynucleotide encoding said XylT, said fragment being about 200 to about 700 nucleotides in length; and
  (c) a XylT reverse fragment, said XylT reverse fragment having sufficient length and sufficient complementarity to said XylT forward fragment such that said first polynucleotide sequence is transcribed as an RNA molecule capable of forming a hairpin RNA structure;
  wherein said first polynucleotide sequence is operably linked to a promoter that is functional in a plant cell.

56. The nucleotide construct of claim 55, wherein said XylT reverse fragment comprises the complement of said XylT forward fragment or a sequence having at least 90% sequence identity to the complement of said XylT forward fragment.

57. The nucleotide construct of claim 55, wherein said spacer sequence within said first polynucleotide sequence comprises about 200 to 700 nucleotides immediately downstream of said XylT forward fragment.

58. The nucleotide construct of claim 55, wherein said XylT is a polypeptide comprising the amino acid sequence set forth in SEQ ID NO:6 or SEQ ID NO:21.

59. The nucleotide construct of claim 58, wherein said XylT forward fragment comprises about 500 to about 800 contiguous nucleotides of SEQ ID NO:4, SEQ ID NO:5, SEQ ID NO:19, or SEQ ID NO:20.

60. The nucleotide construct of claim 59, wherein said XylT reverse fragment comprises the complement of said XylT forward fragment or a sequence having at least 90% sequence identity to the complement of said XylT forward fragment.

61. The nucleotide construct of claim 59, wherein said XylT forward fragment comprises nucleotides nt 318-1052 of SEQ ID NO:4 or nt 1-734 of SEQ ID NO:19.

62. The nucleotide construct of claim 59, wherein said spacer sequence comprises about 200 to 700 nucleotides immediately downstream of said XylT forward fragment.

63. The nucleotide construct of claim 62, wherein:
  (a) said XylT forward fragment comprises nt 318-1052 of SEQ ID NO:4 and said spacer sequence comprises nt 1053-1599 of SEQ ID NO:4; or
  (b) said XylT forward fragment comprises nt 1-734 of SEQ ID NO:19 and said spacer sequence comprises nt 735-1282 of SEQ ID NO:19.

64. The nucleotide construct of claim 28, further comprising at least one polynucleotide encoding a polypeptide of interest, wherein said polynucleotide encoding said polypeptide of interest is operably linked to a promoter that is functional in a plant cell.

65. The nucleotide construct of claim 64, wherein said polypeptide of interest is a mammalian polypeptide.

66. The nucleotide construct of claim 65, wherein said mammalian polypeptide is a monoclonal antibody.

67. The nucleotide construct of claim 65, wherein said mammalian polypeptide is selected from the group consisting of an interferon, erythropoietin (EPO), tissue plasminogen activator (tPA), plasminogen, blood coagulation factors, granulocyte-macrophage colony stimulating factor (GM-CSF), and therapeutic immunoglobulins.

68. A vector comprising a nucleotide construct according to claim 28.

69. A duckweed plant or duckweed plant cell or nodule comprising a nucleotide construct according to claim 28 stably integrated into its genome.

70. The duckweed plant or duckweed plant cell or nodule of claim 69, wherein said duckweed is from a genus selected from the group consisting of the genus *Spirodela*, genus *Wolffia*, genus *Wolfiella*, genus *Landoltia*, and genus *Lemna*.

71. The duckweed plant or duckweed plant cell or nodule of claim 70, wherein said duckweed is a member of a species selected from the group consisting of *Lemna minor*, *Lemna miniscula*, *Lemna aequinoctialis*, and *Lemna gibba*.

72. A method for stably transforming a duckweed plant to express glycoproteins having an altered N-glycosylation pattern, said method comprising introducing into said duckweed plant the nucleotide construct according to claim 28.

73. The method of claim 72, wherein said duckweed plant expresses at least one heterologous polypeptide of interest.

74. The method of claim 73, wherein said heterologous polypeptide of interest is a mammalian polypeptide or biologically active variant thereof.

75. The method of claim 74, wherein said mammalian polypeptide is selected from the group consisting of an interferon, erythropoietin (EPO), tissue plasminogen activator (tPA), plasminogen, blood coagulation factors, granulocyte-macrophage colony stimulating factor (GM-CSF), and therapeutic immunoglobulins.

76. A method for stably transforming a duckweed plant to express a heterologous polypeptide of interest having an altered N-glycosylation pattern, said method comprising introducing into said duckweed plant the nucleotide construct according to claim 64.

77. The method of claim 76, wherein the N-glycosylation pattern is characterized by a reduction in the attachment of α1,3-fucose residues to N-glycans attached to said heterologous polypeptide, a reduction in the attachment of β1,2-xylose residues to N-glycans attached to said heterologous polypeptide, or a reduction in the attachment of α1,3-fucose residues and β1,2-xylose residues to N-glycans attached to said heterologous polypeptide.

78. A method for producing a heterologous mammalian glycoprotein in a duckweed plant, wherein said heterologous mammalian glycoprotein has a reduction in the attachment of α1,3-fucose and β1,2-xylose residues to N-glycans of said glycoprotein compared to said glycoprotein when produced in a control duckweed plant that has not been genetically modified to inhibit expression of α1,3-fucosyltransferase (FucT) and β1,2-xylosyltransferase (XylT) in said control duckweed plant, said method comprising:
  (a) introducing into said duckweed plant an expression cassette comprising a sequence encoding a mammalian polypeptide that is post-translationally processed as said glycoprotein, and a polynucleotide comprising the nucleotide construct of claim 28; and
  (b) culturing said duckweed plant under conditions suitable for expression of said glycoprotein.

79. The method of claim 78, wherein said mammalian polypeptide is selected from the group consisting of an interferon, erythropoietin (EPO), tissue plasminogen activator (tPA), plasminogen, blood coagulation factors, granulocyte-macrophage colony stimulating factor (GM-CSF), and therapeutic immunoglobulins.

80. A method for reducing heterogeneity of the N-glycosylation profile of a glycoprotein produced in a duckweed plant when compared to the heterogeneity of the N-glycosylation profile of said glycoprotein when produced in a control duckweed plant that has not been genetically modified to inhibit expression of α1,3-fucosyltransferase (FucT) and β1,2-xylosyltransferase (XylT) in said control duckweed plant, said method comprising introducing into said duckweed plant the nucleotide construct according to claim 28, and culturing said duckweed plant under conditions suitable for expression of said glycoprotein.

81. The method of claim 80, wherein said glycoprotein is an endogenous glycoprotein.

82. The method of claim 80, wherein said glycoprotein is a heterologous glycoprotein.

83. The method of claim 82, wherein said heterologous glycoprotein is a mammalian glycoprotein.

84. The method of claim 83, wherein said mammalian glycoprotein is selected from the group consisting of an interferon, erythropoietin (EPO), tissue plasminogen activator (tPA), plasminogen, blood coagulation factors, granulocyte-macrophage colony stimulating factor (GM-CSF), and therapeutic immunoglobulins.

85. The method of claim 80, wherein at least 90% of the N-glycans within said profile are GlcNAc2Man3GlcNAc2 (G0), and wherein said profile is devoid of N-glycan species having fucose, xylose, or both fucose and xylose attached thereto.

86. The method of claim 85, wherein at least 95% of the N-glycans within said profile are G0.

87. The method according to claim 80, wherein the reduced heterogeneity of said N-glycosylation profile is maintained with scale-up in production of said duckweed plant, wherein production scale is increased by at least 6,500-fold.

88. The method according to claim 80, wherein the reduced heterogeneity of said N-glycosylation profile is maintained with continuous clonal culture of said duckweed plant.

89. The method of claim 88, wherein the reduced heterogeneity of said N-glycosylation profile is maintained with continuous clonal culture of said duckweed plant for at least 8 months.

90. A method for altering the N-glycosylation pattern of a heterologous polypeptide produced in a duckweed plant or duckweed plant cell or nodule, said method comprising:
  (a) introducing into said duckweed plant or duckweed plant cell or nodule a nucleotide construct comprising a first nucleotide sequence that is capable of inhibiting expression of an α1,3-fucosyltransferase (FucT) in said duckweed plant or duckweed plant cell or nodule, and wherein said first nucleotide sequence is operably linked to a promoter that is functional in a plant cell, said first nucleotide sequence comprising in the 5'-to-3' orientation and operably linked:
    (i) a FucT forward fragment, said FucT forward fragment comprising about 500 to about 800 contiguous nucleotides having at least 90% sequence identity to a nucleotide sequence of about 500 to about 800 contiguous nucleotides of SEQ ID NO:1 or SEQ ID NO:2;
    (ii) a spacer sequence comprising about 200 to about 700 nucleotides immediately downstream of said FucT forward fragment; and
    (iii) a FucT reverse fragment, said FucT reverse fragment having sufficient length and sufficient complementarity to said FucT forward fragment such that said first nucleotide sequence is transcribed as an RNA molecule capable of forming a hairpin RNA structure; and
  (b) culturing said duckweed plant or duckweed plant cell or nodule under conditions suitable for expression of said heterologous polypeptide.

91. The method of claim 90, wherein said FucT reverse fragment comprises the complement of said FucT forward fragment or a sequence having at least 90% sequence identity to the complement of said FucT forward fragment.

92. The method of claim 90, wherein said FucT forward fragment comprises nucleotides (nt) 255-985 of SEQ ID NO:1 and said spacer sequence comprises nt 986-1444 of SEQ ID NO:1.

93. A method for altering the N-glycosylation pattern of a heterologous polypeptide produced in a duckweed plant or duckweed plant cell or nodule, said method comprising:
  (a) introducing into said duckweed plant or duckweed plant cell or nodule a nucleotide construct comprising a first nucleotide sequence that is capable of inhibiting expression of an α1,3-fucosyltransferase (FucT) in said duckweed plant or duckweed plant cell or nodule, and wherein said first nucleotide sequence is operably linked to a promoter that is functional in a plant cell, said first nucleotide sequence comprising in the 5'-to-3' orientation and operably linked:
  (i) a sense nucleotide sequence comprising at least 19 contiguous nucleotides of SEQ ID NO:1 or SEQ ID NO:2; and
  (ii) an antisense nucleotide sequence comprising at least 19 contiguous nucleotides of the complement of said sense nucleotide sequence; wherein said first nucleotide sequence is transcribed as a small hairpin RNA having a base-paired stem length shorter than about 200 base pairs; and
  (b) culturing said duckweed plant or duckweed plant cell or nodule under conditions suitable for expression of said heterologous polypeptide.

94. The method of claim 93, wherein said promoter operably linked to said first nucleotide sequence is a type 3 RNA polymerase III promoter.

95. The method of claim 90, further comprising inhibiting expression of a β1,2-xylosyltransferase (XylT) in said duckweed plant or duckweed plant cell or nodule.

96. The method of claim 95, wherein the expression of said XylT is inhibited by a method selected from the group consisting of:
  (a) introducing a polynucleotide into said duckweed plant or duckweed plant cell or nodule, wherein said polynucleotide inhibits expression of said XylT in said duckweed plant or duckweed plant cell or nodule;
  (b) eliminating a gene in said duckweed plant or duckweed plant cell or nodule, wherein said gene encodes said XylT; and
  (c) mutating a gene in said duckweed plant or duckweed plant cell or nodule, wherein said gene encodes said XylT.

97. The method of claim 96, comprising introducing into said duckweed plant or duckweed plant cell or nodule a nucleotide construct comprising a nucleotide sequence that is capable of inhibiting expression of said XylT in said duckweed plant or duckweed plant cell or nodule, wherein said nucleotide sequence that is capable of inhibiting expression of said XylT is operably linked to a promoter that is functional in a plant cell.

98. The method of claim 97, wherein said nucleotide sequence that is capable of inhibiting expression of said XylT comprises in the 5'-to-3' orientation and operably linked:
  (a) a XylT forward fragment, said XylT forward fragment comprising about 500 to about 800 contiguous nucleotides having at least 90% sequence identity to a nucleotide sequence of about 500 to about 800 contiguous nucleotides of a polynucleotide encoding said XylT;
  (b) a spacer sequence comprising about 200 to about 700 nucleotides immediately downstream of said XylT forward fragment; and
  (c) a XylT reverse fragment, said XylT reverse fragment having sufficient length and sufficient complementarity to said XylT forward fragment such that said nucleotide sequence that is capable of inhibiting expression of said XylT is transcribed as an RNA molecule capable of forming a hairpin RNA structure;
  wherein said polynucleotide encoding said XylT is selected from the group consisting of:
  (1) a polynucleotide comprising SEQ ID NO:4, SEQ ID NO:5, SEQ ID NO:19, or SEQ ID NO:20;
  (2) a polynucleotide encoding the polypeptide set forth in SEQ ID NO:6 or SEQ ID NO:21; and
  (3) a polynucleotide encoding a polypeptide having at least 90% sequence identity to the polypeptide set forth in SEQ ID NO:6 or SEQ ID NO:21.

99. The method of claim 98, wherein said XylT reverse fragment comprises the complement of said XylT forward fragment or a sequence having at least 90% sequence identity to the complement of said XylT forward fragment.

100. The method of claim 98, wherein:
  (a) said XylT forward fragment comprises nucleotides (nt) 318-1052 of SEQ ID NO:4 and wherein said spacer sequence comprises nt 1053-1599 of SEQ ID NO:4; or
  (b) said XylT forward fragment comprises nt 1-734 of SEQ ID NO:19 and said spacer sequence comprises nt 735-1282 of SEQ ID NO: 19.

101. The method of claim 97, wherein said nucleotide sequence that is capable of inhibiting expression of said XylT comprises in the 5'-to-3' direction and operably linked:
  (a) a sense nucleotide sequence comprising at least 19 contiguous nucleotides of SEQ ID NO:4 or SEQ ID NO:19; and
  (b) an antisense nucleotide sequence comprising at least 19 contiguous nucleotides of the complement of said sense nucleotide sequence of preceding item (a);
wherein said nucleotide sequence that is capable of inhibiting expression of said XylT is transcribed as a small hairpin RNA having a base-paired stem length shorter than about 200 base pairs.

102. The method of claim 101, wherein said promoter operably linked to said nucleotide sequence that is capable of inhibiting expression of said XylT is a type 3 RNA polymerase III promoter.

103. A method for altering the N-glycosylation pattern of a heterologous polypeptide produced in a duckweed plant or duckweed plant cell or nodule, said method comprising:
  (a) introducing into said duckweed plant or duckweed plant cell or nodule a nucleotide construct comprising a first nucleotide sequence that is capable of inhibiting expression of a β1,2-xylosyltransferase (XylT) in said duckweed plant or duckweed plant cell or nodule, and wherein said first nucleotide sequence is operably linked to a promoter that is functional in a plant cell, said first nucleotide sequence comprising in the 5'-to-3' orientation and operably linked:
    (i) a XylT forward fragment, said XylT forward fragment comprising about 500 to about 800 contiguous nucleotides having at least 90% sequence identity to a nucleotide sequence of about 500 to about 800 contiguous nucleotides of SEQ ID NO:4, SEQ ID NO:5, SEQ ID NO:19, or SEQ ID NO:20;
    (ii) a spacer sequence comprising about 200 to about 700 nucleotides immediately downstream of said XylT forward fragment; and
    (iii) a XylT reverse fragment, said XylT reverse fragment having sufficient length and sufficient complementarity to said XylT forward fragment such that said first nucleotide sequence is transcribed as an RNA molecule capable of forming a hairpin RNA structure; and
  (b) culturing said duckweed plant or duckweed plant cell or nodule under conditions suitable for expression of said heterologous polypeptide.

104. The method of claim 103, wherein said XylT reverse fragment comprises the complement of said XylT forward fragment or a sequence having at least 90% sequence identity to the complement of said XylT forward fragment.

105. The method of claim 103, wherein:
(a) said XylT forward fragment comprises nucleotides (nt) 318-1052 of SEQ ID NO:4 and wherein said spacer sequence comprises nt 1053-1599 of SEQ ID NO:4; or
(b) said XylT forward fragment comprises nt 1-734 of SEQ ID NO:19 and wherein said spacer sequence comprises nt 735-1282 of SEQ ID NO: 19.

106. A method for altering the N-glycosylation pattern of a heterologous polypeptide produced in a duckweed plant or duckweed plant cell or nodule, said method comprising:
(a) introducing into said duckweed plant or duckweed plant cell or nodule a nucleotide construct comprising a first nucleotide sequence that is capable of inhibiting expression of a β1,2-xylosyltransferase (XylT) in said duckweed plant or duckweed plant cell or nodule, and wherein said first nucleotide sequence is operably linked to a promoter that is functional in a plant cell, said first nucleotide sequence comprising in the 5'-to-3' orientation and operably linked:
(i) a sense nucleotide sequence comprising at least 19 contiguous nucleotides of SEQ ID NO:4 or SEQ ID NO: 19; and
(ii) an antisense nucleotide sequence comprising at least 19 contiguous nucleotides of the complement of said sense nucleotide sequence of preceding item (a); wherein said nucleotide sequence that is capable of inhibiting expression of said XylT is transcribed as a small hairpin RNA having a base-paired stem length shorter than about 200 base pairs; and
(b) culturing said duckweed plant or duckweed plant cell or nodule under conditions suitable for expression of said heterologous polypeptide.

107. The method of claim 106, wherein said promoter operably linked to said first nucleotide sequence is a type 3 RNA polymerase III promoter.

108. The method of claim 103, further comprising inhibiting expression of an α1,3-fucosyltransferase (FucT) in said duckweed plant or duckweed plant cell or nodule.

109. The method of claim 108, wherein the expression of said FucT is inhibited by a method selected from the group consisting of:
(a) introducing a polynucleotide into said duckweed plant or duckweed plant cell or nodule, wherein said polynucleotide inhibits expression of said FucT in said duckweed plant or duckweed plant cell or nodule;
(b) eliminating a gene in said duckweed plant or duckweed plant cell or nodule, wherein said gene encodes said FucT; and
(c) mutating a gene in said duckweed plant or duckweed plant cell or nodule, wherein said gene encodes said FucT.

110. A method for altering the N-glycosylation pattern of a heterologous polypeptide produced in a duckweed plant or duckweed plant cell or nodule, said method comprising:
(a) introducing into said duckweed plant or duckweed plant cell or nodule a nucleotide construct comprising a fusion polynucleotide that is capable of inhibiting expression of an α1,3-fucosyltransferase (FucT) and a β1,2-xylosyltransferase (XylT) in said duckweed plant or duckweed plant cell or nodule, wherein said fusion polynucleotide is operably linked to a promoter that is functional in a plant cell, said fusion polynucleotide comprising in the 5'-to-3' orientation and operably linked:
(i) a chimeric forward fragment, said chimeric forward fragment comprising:
(a) a first fragment comprising about 500 to about 650 contiguous nucleotides having at least 90% sequence identity to a nucleotide sequence of about 500 to about 650 contiguous nucleotides of SEQ ID NO: 1 or SEQ ID NO:2; and
(b) a second fragment comprising about 500 to about 650 contiguous nucleotides having at least 90% sequence identity to a nucleotide sequence of about 500 to about 650 contiguous nucleotides of a polynucleotide encoding said XylT;
(ii) a spacer sequence comprising about 200 to about 700 nucleotides immediately downstream of said second fragment of said chimeric forward fragment; and
(iii) a reverse fragment, said reverse fragment having sufficient length and sufficient complementarity to said chimeric forward fragment such that said fusion polynucleotide is transcribed as an RNA molecule capable of forming a hairpin RNA structure; and
(b) culturing said duckweed plant or duckweed plant cell or nodule under conditions suitable for expression of said heterologous polypeptide;
wherein said polynucleotide encoding said XylT is selected from the group consisting of:
(1) a polynucleotide comprising SEQ ID NO:4, SEQ ID NO:5, SEQ ID NO:19, or SEQ ID NO:20;
(2) a polynucleotide encoding the polypeptide set forth in SEQ ID NO:6 or SEQ ID NO:21; and
(3) a polynucleotide encoding a polypeptide having at least 90% sequence identity to the polypeptide set forth in SEQ ID NO:6 or SEQ ID NO:21.

111. The method of claim 110, wherein said first fragment comprises about 500 to about 650 contiguous nucleotides of SEQ ID NO: 1; and said second fragment comprises about 500 to about 650 contiguous nucleotides of SEQ ID NO:4 or SEQ ID NO:19.

112. The method of claim 111, wherein said reverse fragment comprises the complement of said chimeric forward fragment or a sequence having at least 90% sequence identity to the complement of said chimeric forward fragment.

113. The method of claim 111, wherein:
(a) said chimeric forward fragment comprises nucleotides (nt) 254-855 of SEQ ID NO:1 and nt 318-943 of SEQ ID NO:4, and wherein said spacer sequence comprises nt 944-1443 of SEQ ID NO:4; or
(b) said chimeric forward fragment comprises nucleotides (nt) 254-855 of SEQ ID NO:1 and nt 1-626 of SEQ ID NO: 19, and wherein said spacer sequence comprises nt 627-1126 of SEQ ID NO:19.

114. A method for altering the N-glycosylation pattern of a heterologous polypeptide produced in a duckweed plant or duckweed plant cell or nodule, said method comprising:
(a) introducing into said duckweed plant or duckweed plant cell or nodule a nucleotide construct comprising a fusion polynucleotide that is capable of inhibiting expression of an α1,3-fucosyltransferase (FucT) and a β1,2-xylosyltransferase (XylT) in said duckweed plant or duckweed plant cell or nodule, wherein said fusion polynucleotide is operably linked to a promoter that is functional in a plant cell, said fusion polynucleotide comprising in the 5'-to-3' orientation and operably linked:
(i) a chimeric forward fragment, said chimeric forward fragment comprising:
(a) a first fragment comprising about 500 to about 650 contiguous nucleotides having at least 90% sequence identity to a nucleotide sequence of about 500 to about 650 contiguous nucleotides of SEQ ID NO:4, SEQ ID NO:5, SEQ ID NO:19, or SEQ ID NO:20; and (b) a second fragment comprising about 500 to about 650 contiguous nucleotides having at least 90% sequence identity to a nucleotide sequence of about 500 to about 650 contiguous nucleotides of a polynucleotide encoding said FucT;

(ii) a spacer sequence comprising about 200 to about 700 nucleotides immediately downstream of said second fragment of said chimeric forward fragment; and (iii) a reverse fragment, said reverse fragment having sufficient length and sufficient complementarity to said chimeric forward fragment such that said fusion polynucleotide is transcribed as an RNA molecule capable of forming a hairpin RNA structure; and (b) culturing said duckweed plant or duckweed plant cell or nodule under conditions suitable for expression of said heterologous polypeptide;

wherein said polynucleotide encoding said FucT is selected from the group consisting of:

(1) a polynucleotide comprising SEQ ID NO:1 or SEQ ID NO:2;

(2) a polynucleotide encoding the polypeptide set forth in SEQ ID NO:3; and (3) a polynucleotide encoding a polypeptide having at least 90% sequence identity to the polypeptide set forth in SEQ ID NO:3.

115. The method of claim 114, wherein said reverse fragment comprises the complement of said chimeric forward fragment or a sequence having at least 90% sequence identity to the complement of said chimeric forward fragment.

116. The method of claim 114, wherein said first fragment comprises about 500 to about 650 contiguous nucleotides of SEQ ID NO:4 or SEQ ID NO: 19; and said second fragment comprises about 500 to about 650 contiguous nucleotides of SEQ ID NO:1.

117. The method of claim 116, wherein said reverse fragment comprises the complement of said chimeric forward fragment or a sequence having at least 90% sequence identity to the complement of said chimeric forward fragment.

* * * * *

SEQUENCE LISTING

```
<160> NUMBER OF SEQ ID NOS: 41

<210> SEQ ID NO 1
<211> LENGTH: 1865
<212> TYPE: DNA
<213> ORGANISM: Lemna minor
<220> FEATURE:
<221> NAME/KEY: CDS
<222> LOCATION: (243)...(1715)

<400> SEQUENCE: 1 acgcggggg aagtggttga gtagctcagt ggaaaattgg aaatgtctat tagaggggga      60
agaggggagg gatccgaggg gaacgaggaa ggtgtgccga attctcgtag atttcttcaa     120
ttcctgcaga tctcgtcttc tctctgattt cttcccgagc tccgcccgta ggaactcaat    180
cggactcgat ccaagttgac gaggcctacy gaggaaggcg attttccgaa gcccctgcgat    240 cg atg gcc acc tct gct gct ggt gct ctc aac gcc ggt ggc agg gtc        287
   Met Ala Thr Ser Ala Ala Gly Ala Leu Asn Ala Gly Gly Arg Val
```

```
              1               5              10              15
ggg ggc agg agg agt tgg gtc aga ttg ctt ccc ttc ttt gtg ttg atg       335
Gly Gly Arg Arg Ser Trp Val Arg Leu Leu Pro Phe Phe Val Leu Met
                       20              25              30 ctg gtg gta ggg gag atc tgg ttc ctc ggg cgg ctg gat gtg gtc aag       383
Leu Val Val Gly Glu Ile Trp Phe Leu Gly Arg Leu Asp Val Val Lys
                35              40              45 aac gcc gct atg gtt caa aac tgg act tcc tcc cac ttg ttt ttc tta       431
Asn Ala Ala Met Val Gln Asn Trp Thr Ser Ser His Leu Phe Phe Leu
            50              55              60 cca gtt tct tcc tac acg tgg tcc gag acc gtc aag gag gaa gag gat       479
Pro Val Ser Ser Tyr Thr Trp Ser Glu Thr Val Lys Glu Glu Glu Asp
        65              70              75 tgc aag gac tgg ctg gaa aga gta gat gcg gtc gat tac aag aga gat       527
Cys Lys Asp Trp Leu Glu Arg Val Asp Ala Val Asp Tyr Lys Arg Asp
 80              85              90              95 ttc cgt gtg gaa ccc gtt ctg gta aat gac gct gaa cag gat tgg agt       575
Phe Arg Val Glu Pro Val Leu Val Asn Asp Ala Glu Gln Asp Trp Ser
                100             105             110 tca tgt tca gtg ggc tgt aag ttc gga tca ttc ccc gga aga acg cct       623
Ser Cys Ser Val Gly Cys Lys Phe Gly Ser Phe Pro Gly Arg Thr Pro
                115             120             125 gat gct aca ttt ggt ttc tct cag aat cca tca aca gtc agt gtc cat       671
Asp Ala Thr Phe Gly Phe Ser Gln Asn Pro Ser Thr Val Ser Val His
            130             135             140 cga tcc atg gaa tca tcc cat tat tat ttg gag aat aat ctt gat aat       719
Arg Ser Met Glu Ser Ser His Tyr Tyr Leu Glu Asn Asn Leu Asp Asn
        145             150             155 gca cga cgg aaa ggc tat caa att gtg atg aca act agt ctc ttg tca       767
Ala Arg Arg Lys Gly Tyr Gln Ile Val Met Thr Thr Ser Leu Leu Ser
160             165             170             175 gat gtg cct gtc ggt tat ttc tca tgg gct gaa tat gat atc atg gcg       815
Asp Val Pro Val Gly Tyr Phe Ser Trp Ala Glu Tyr Asp Ile Met Ala
                180             185             190 cct ctt cag ccg aaa act gct ggt gca ctt gct gct gca ttt ata tct       863
Pro Leu Gln Pro Lys Thr Ala Gly Ala Leu Ala Ala Ala Phe Ile Ser
                195             200             205 aat tgc gga gca cgt aat ttc cgc ttg cag gcc ctt gat atg ctc gaa       911
Asn Cys Gly Ala Arg Asn Phe Arg Leu Gln Ala Leu Asp Met Leu Glu
            210             215             220 aag tcg aat att aag att gat tca tat ggt gct tgc cat cgc aac caa       959
Lys Ser Asn Ile Lys Ile Asp Ser Tyr Gly Ala Cys His Arg Asn Gln
        225             230             235 gac ggt aaa gtg gac aag gta caa act ttg aag cgg tat aag ttc agc      1007
Asp Gly Lys Val Asp Lys Val Gln Thr Leu Lys Arg Tyr Lys Phe Ser
240             245             250             255 tta gct ttt gaa aac tcg aac gag gat gac tat gtt act gag aag ttc      1055
Leu Ala Phe Glu Asn Ser Asn Glu Asp Asp Tyr Val Thr Glu Lys Phe
                260             265             270 ttt caa tct ctt gtc gct gga gct att cct gtt gtc gtc gga gcc ccc      1103
Phe Gln Ser Leu Val Ala Gly Ala Ile Pro Val Val Val Gly Ala Pro
                275             280             285 aac att caa aat ttt gcg cca tct tct gat tca att ctg cac atc agg      1151
Asn Ile Gln Asn Phe Ala Pro Ser Ser Asp Ser Ile Leu His Ile Arg
            290             295             300 gag ccc aag gat gtc agt tca gtc gct gag aga atg aaa ttt ctc gct      1199
Glu Pro Lys Asp Val Ser Ser Val Ala Glu Arg Met Lys Phe Leu Ala
        305             310             315 tca aat cca gaa gca tat aac caa tca ctg agg tgg aag ttt gag ggc      1247
Ser Asn Pro Glu Ala Tyr Asn Gln Ser Leu Arg Trp Lys Phe Glu Gly
```

```
                320                 325                 330                 335 cct tct aac tcc ttc aaa gcc ctg gtg gac atg gca gca gtt cac tcc    1295
Pro Ser Asn Ser Phe Lys Ala Leu Val Asp Met Ala Ala Val His Ser
            340                 345                 350 tcc tgc cgc cta tgc att cac att gcc acc aag atc aga gag aag gaa    1343
Ser Cys Arg Leu Cys Ile His Ile Ala Thr Lys Ile Arg Glu Lys Glu
            355                 360                 365 gag aga aac ccg aat ttc aag act cgc cct tgc aag tgc acc cgc aat    1391
Glu Arg Asn Pro Asn Phe Lys Thr Arg Pro Cys Lys Cys Thr Arg Asn
            370                 375                 380 ggg tct acc tta tat cac tta tac gcc cgc gaa aga ggc acc ttt gac    1439
Gly Ser Thr Leu Tyr His Leu Tyr Ala Arg Glu Arg Gly Thr Phe Asp
            385                 390                 395 ttc tta tca atc ttc atg aga tcg gat aat cta tca ctg aaa gcg ctg    1487
Phe Leu Ser Ile Phe Met Arg Ser Asp Asn Leu Ser Leu Lys Ala Leu
400                 405                 410                 415 ggg tca aca gtt ctt gag aaa ttc agt tct ttg aag cac gtg ccg att    1535
Gly Ser Thr Val Leu Glu Lys Phe Ser Ser Leu Lys His Val Pro Ile
            420                 425                 430 tgg aag aag gag agg cca gag agt ctg aaa gga ggg agc aag ctg gat    1583
Trp Lys Lys Glu Arg Pro Glu Ser Leu Lys Gly Gly Ser Lys Leu Asp
            435                 440                 445 ctt tac aga atc tat cca gtg ggc att act cag aga gaa gct ctc ttc    1631
Leu Tyr Arg Ile Tyr Pro Val Gly Ile Thr Gln Arg Glu Ala Leu Phe
            450                 455                 460 tct ttc cag ttc aac act gac aaa gaa ctt caa atc tac ctt gaa tcc    1679
Ser Phe Gln Phe Asn Thr Asp Lys Glu Leu Gln Ile Tyr Leu Glu Ser
            465                 470                 475 cat cca tgt gcg aag ttt gaa gtc atc ttt att tga tccctgaggt         1725
His Pro Cys Ala Lys Phe Glu Val Ile Phe Ile  *
480                 485                 490 aattaggtca cgaattcagc taatttggtt aattatgctt caagcccaca tggtatttca  1785
tatcattaat tgaaggcata gttagttgat attgacattt tcgtctagga tcattctaaa  1845
gtctatccca atgaacttaa                                              1865

<210> SEQ ID NO 2
<211> LENGTH: 1473
<212> TYPE: DNA
<213> ORGANISM: Lemna minor
<220> FEATURE:
<221> NAME/KEY: CDS
<222> LOCATION: (1)...(1473)
<223> OTHER INFORMATION: Encodes alpha-1, 3-fucosyltransferase

<400> SEQUENCE: 2 atg gcc acc tct gct gct ggt gct ctc aac gcc ggt ggc agg gtc ggg      48
Met Ala Thr Ser Ala Ala Gly Ala Leu Asn Ala Gly Gly Arg Val Gly
 1               5                  10                  15 ggc agg agg agt tgg gtc aga ttg ctt ccc ttc ttt gtg ttg atg ctg      96
Gly Arg Arg Ser Trp Val Arg Leu Leu Pro Phe Phe Val Leu Met Leu
                20                  25                  30 gtg gta ggg gag atc tgg ttc ctc ggg cgg ctg gat gtg gtc aag aac     144
Val Val Gly Glu Ile Trp Phe Leu Gly Arg Leu Asp Val Val Lys Asn
            35                  40                  45 gcc gct atg gtt caa aac tgg act tcc tcc cac ttg ttt ttc tta cca     192
Ala Ala Met Val Gln Asn Trp Thr Ser Ser His Leu Phe Phe Leu Pro
        50                  55                  60 gtt tct tcc tac acg tgg tcc gag acc gtc aag gag gaa gag gat tgc     240
Val Ser Ser Tyr Thr Trp Ser Glu Thr Val Lys Glu Glu Glu Asp Cys
65                  70                  75                  80
```

```
aag gac tgg ctg gaa aga gta gat gcg gtc gat tac aag aga gat ttc      288
Lys Asp Trp Leu Glu Arg Val Asp Ala Val Asp Tyr Lys Arg Asp Phe
             85                  90                  95 cgt gtg gaa ccc gtt ctg gta aat gac gct gaa cag gat tgg agt tca      336
Arg Val Glu Pro Val Leu Val Asn Asp Ala Glu Gln Asp Trp Ser Ser
        100                 105                 110 tgt tca gtg ggc tgt aag ttc gga tca ttc ccc gga aga acg cct gat      384
Cys Ser Val Gly Cys Lys Phe Gly Ser Phe Pro Gly Arg Thr Pro Asp
        115                 120                 125 gct aca ttt ggt ttc tct cag aat cca tca aca gtc agt gtc cat cga      432
Ala Thr Phe Gly Phe Ser Gln Asn Pro Ser Thr Val Ser Val His Arg
        130                 135                 140 tcc atg gaa tca tcc cat tat tat ttg gag aat aat ctt gat aat gca      480
Ser Met Glu Ser Ser His Tyr Tyr Leu Glu Asn Asn Leu Asp Asn Ala
145                 150                 155                 160 cga cgg aaa ggc tat caa att gtg atg aca act agt ctc ttg tca gat      528
Arg Arg Lys Gly Tyr Gln Ile Val Met Thr Thr Ser Leu Leu Ser Asp
                165                 170                 175 gtg cct gtc ggt tat ttc tca tgg gct gaa tat gat atc atg gcg cct      576
Val Pro Val Gly Tyr Phe Ser Trp Ala Glu Tyr Asp Ile Met Ala Pro
        180                 185                 190 ctt cag ccg aaa act gct ggt gca ctt gct gct gca ttt ata tct aat      624
Leu Gln Pro Lys Thr Ala Gly Ala Leu Ala Ala Ala Phe Ile Ser Asn
        195                 200                 205 tgc gga gca cgt aat ttc cgc ttg cag gcc ctt gat atg ctc gaa aag      672
Cys Gly Ala Arg Asn Phe Arg Leu Gln Ala Leu Asp Met Leu Glu Lys
        210                 215                 220 tcg aat att aag att gat tca tat ggt gct tgc cat cgc aac caa gac      720
Ser Asn Ile Lys Ile Asp Ser Tyr Gly Ala Cys His Arg Asn Gln Asp
225                 230                 235                 240 ggt aaa gtg gac aag gta caa act ttg aag cgg tat aag ttc agc tta      768
Gly Lys Val Asp Lys Val Gln Thr Leu Lys Arg Tyr Lys Phe Ser Leu
                245                 250                 255 gct ttt gaa aac tcg aac gag gat gac tat gtt act gag aag ttc ttt      816
Ala Phe Glu Asn Ser Asn Glu Asp Asp Tyr Val Thr Glu Lys Phe Phe
        260                 265                 270 caa tct ctt gtc gct gga gct att cct gtt gtc gtc gga gcc ccc aac      864
Gln Ser Leu Val Ala Gly Ala Ile Pro Val Val Val Gly Ala Pro Asn
        275                 280                 285 att caa aat ttt gcg cca tct tct gat tca att ctg cac atc agg gag      912
Ile Gln Asn Phe Ala Pro Ser Ser Asp Ser Ile Leu His Ile Arg Glu
        290                 295                 300 ccc aag gat gtc agt tca gtc gct gag aga atg aaa ttt ctc gct tca      960
Pro Lys Asp Val Ser Ser Val Ala Glu Arg Met Lys Phe Leu Ala Ser
305                 310                 315                 320 aat cca gaa gca tat aac caa tca ctg agg tgg aag ttt gag ggc cct     1008
Asn Pro Glu Ala Tyr Asn Gln Ser Leu Arg Trp Lys Phe Glu Gly Pro
                325                 330                 335 tct aac tcc ttc aaa gcc ctg gtg gac atg gca gca gtt cac tcc tcc     1056
Ser Asn Ser Phe Lys Ala Leu Val Asp Met Ala Ala Val His Ser Ser
        340                 345                 350 tgc cgc cta tgc att cac att gcc acc aag atc aga gag aag gaa gag     1104
Cys Arg Leu Cys Ile His Ile Ala Thr Lys Ile Arg Glu Lys Glu Glu
        355                 360                 365 aga aac ccg aat ttc aag act cgc cct tgc aag tgc acc cgc aat ggg     1152
Arg Asn Pro Asn Phe Lys Thr Arg Pro Cys Lys Cys Thr Arg Asn Gly
        370                 375                 380 tct acc tta tat cac tta tac gcc cgc gaa aga ggc acc ttt gac ttc     1200
Ser Thr Leu Tyr His Leu Tyr Ala Arg Glu Arg Gly Thr Phe Asp Phe
385                 390                 395                 400
```

```
tta tca atc ttc atg aga tcg gat aat cta tca ctg aaa gcg ctg ggg      1248
Leu Ser Ile Phe Met Arg Ser Asp Asn Leu Ser Leu Lys Ala Leu Gly
            405                 410                 415 tca aca gtt ctt gag aaa ttc agt tct ttg aag cac gtg ccg att tgg      1296
Ser Thr Val Leu Glu Lys Phe Ser Ser Leu Lys His Val Pro Ile Trp
        420                 425                 430 aag aag gag agg cca gag agt ctg aaa gga ggg agc aag ctg gat ctt      1344
Lys Lys Glu Arg Pro Glu Ser Leu Lys Gly Gly Ser Lys Leu Asp Leu
    435                 440                 445 tac aga atc tat cca gtg ggc att act cag aga gaa gct ctc ttc tct      1392
Tyr Arg Ile Tyr Pro Val Gly Ile Thr Gln Arg Glu Ala Leu Phe Ser
450                 455                 460 ttc cag ttc aac act gac aaa gaa ctt caa atc tac ctt gaa tcc cat      1440
Phe Gln Phe Asn Thr Asp Lys Glu Leu Gln Ile Tyr Leu Glu Ser His
465                 470                 475                 480 cca tgt gcg aag ttt gaa gtc atc ttt att tga                          1473
Pro Cys Ala Lys Phe Glu Val Ile Phe Ile *
                485                 490

<210> SEQ ID NO 3
<211> LENGTH: 490
<212> TYPE: PRT
<213> ORGANISM: Lemna minor

<400> SEQUENCE: 3

Met Ala Thr Ser Ala Ala Gly Ala Leu Asn Ala Gly Gly Arg Val Gly
 1               5                  10                  15

Gly Arg Arg Ser Trp Val Arg Leu Leu Pro Phe Phe Val Leu Met Leu
             20                  25                  30

Val Val Gly Glu Ile Trp Phe Leu Gly Arg Leu Asp Val Val Lys Asn
         35                  40                  45

Ala Ala Met Val Gln Asn Trp Thr Ser Ser His Leu Phe Phe Leu Pro
     50                  55                  60

Val Ser Ser Tyr Thr Trp Ser Glu Thr Val Lys Glu Glu Glu Asp Cys
 65                  70                  75                  80

Lys Asp Trp Leu Glu Arg Val Asp Ala Val Asp Tyr Lys Arg Asp Phe
                 85                  90                  95

Arg Val Glu Pro Val Leu Val Asn Asp Ala Glu Gln Asp Trp Ser Ser
            100                 105                 110

Cys Ser Val Gly Cys Lys Phe Gly Ser Phe Pro Gly Arg Thr Pro Asp
        115                 120                 125

Ala Thr Phe Gly Phe Ser Gln Asn Pro Ser Thr Val Ser Val His Arg
    130                 135                 140

Ser Met Glu Ser Ser His Tyr Tyr Leu Glu Asn Asn Leu Asp Asn Ala
145                 150                 155                 160

Arg Arg Lys Gly Tyr Gln Ile Val Met Thr Thr Ser Leu Leu Ser Asp
                165                 170                 175

Val Pro Val Gly Tyr Phe Ser Trp Ala Glu Tyr Asp Ile Met Ala Pro
            180                 185                 190

Leu Gln Pro Lys Thr Ala Gly Ala Leu Ala Ala Phe Ile Ser Asn
        195                 200                 205

Cys Gly Ala Arg Asn Phe Arg Leu Gln Ala Leu Asp Met Leu Glu Lys
    210                 215                 220

Ser Asn Ile Lys Ile Asp Ser Tyr Gly Ala Cys His Arg Asn Gln Asp
225                 230                 235                 240

Gly Lys Val Asp Lys Val Gln Thr Leu Lys Arg Tyr Lys Phe Ser Leu
                245                 250                 255
```

```
Ala Phe Glu Asn Ser Asn Glu Asp Asp Tyr Val Thr Glu Lys Phe Phe
            260                 265                 270

Gln Ser Leu Val Ala Gly Ala Ile Pro Val Val Gly Ala Pro Asn
        275                 280                 285

Ile Gln Asn Phe Ala Pro Ser Ser Asp Ser Ile Leu His Ile Arg Glu
    290                 295                 300

Pro Lys Asp Val Ser Ser Val Ala Glu Arg Met Lys Phe Leu Ala Ser
305                 310                 315                 320

Asn Pro Glu Ala Tyr Asn Gln Ser Leu Arg Trp Lys Phe Glu Gly Pro
                325                 330                 335

Ser Asn Ser Phe Lys Ala Leu Val Asp Met Ala Ala Val His Ser Ser
        340                 345                 350

Cys Arg Leu Cys Ile His Ile Ala Thr Lys Ile Arg Glu Lys Glu Glu
    355                 360                 365

Arg Asn Pro Asn Phe Lys Thr Arg Pro Cys Lys Cys Thr Arg Asn Gly
    370                 375                 380

Ser Thr Leu Tyr His Leu Tyr Ala Arg Glu Arg Gly Thr Phe Asp Phe
385                 390                 395                 400

Leu Ser Ile Phe Met Arg Ser Asp Asn Leu Ser Leu Lys Ala Leu Gly
                405                 410                 415

Ser Thr Val Leu Glu Lys Phe Ser Ser Leu Lys His Val Pro Ile Trp
            420                 425                 430

Lys Lys Glu Arg Pro Glu Ser Leu Lys Gly Gly Ser Lys Leu Asp Leu
        435                 440                 445

Tyr Arg Ile Tyr Pro Val Gly Ile Thr Gln Arg Glu Ala Leu Phe Ser
    450                 455                 460

Phe Gln Phe Asn Thr Asp Lys Glu Leu Gln Ile Tyr Leu Glu Ser His
465                 470                 475                 480

Pro Cys Ala Lys Phe Glu Val Ile Phe Ile
                485                 490

<210> SEQ ID NO 4
<211> LENGTH: 1860
<212> TYPE: DNA
<213> ORGANISM: Lemna minor
<220> FEATURE:
<221> NAME/KEY: CDS
<222> LOCATION: (63)...(1592)

<400> SEQUENCE: 4
ggcttccaac cggaggatct cgagctgaag aatcttcatg actgaagaat tcatgtgatc         60 cc atg gct ttg gtg aac tcg cga ggg agc agg gtc aga cgc atc gcg          107
   Met Ala Leu Val Asn Ser Arg Gly Ser Arg Val Arg Arg Ile Ala
   1               5                  10                  15 aag ccc acc ttc gtt ttc ctc ttg atc aac gta gtc tgt ctc ctg tac        155
Lys Pro Thr Phe Val Phe Leu Leu Ile Asn Val Val Cys Leu Leu Tyr
                20                  25                  30 ttt ttc cgt cag aac cct aat ccc att ccc gac gct tgt ctt cac ggg        203
Phe Phe Arg Gln Asn Pro Asn Pro Ile Pro Asp Ala Cys Leu His Gly
            35                  40                  45 gaa tgc gac aaa ccc ccg att tta gtg act ccc cgg cga tgg aac ttg        251
Glu Cys Asp Lys Pro Pro Ile Leu Val Thr Pro Arg Arg Trp Asn Leu
        50                  55                  60 aag cca tgg ccg att ctt cct tcc ttt ctg cca tgg gtg ccg agc tcc        299
Lys Pro Trp Pro Ile Leu Pro Ser Phe Leu Pro Trp Val Pro Ser Ser
    65                  70                  75 cac cct gcc cag ggc tcc tgc gaa gcc tac ttc ggc aac agc ttc aac        347
His Pro Ala Gln Gly Ser Cys Glu Ala Tyr Phe Gly Asn Ser Phe Asn
```

```
              80                  85                  90                  95 cgc cgg acg gag atg ctg aag aag gta gag gga aga gga tgg ttc cag       395
Arg Arg Thr Glu Met Leu Lys Lys Val Glu Gly Arg Gly Trp Phe Gln
                    100                 105                 110 tgc ctg tac agc gat act ctt cga agt tct gtt tgc cag gga ggg aat       443
Cys Leu Tyr Ser Asp Thr Leu Arg Ser Ser Val Cys Gln Gly Gly Asn
                    115                 120                 125 ttg cgg atg gac ccg gaa agg att agg atg tcg aaa ggg ggg gaa gat       491
Leu Arg Met Asp Pro Glu Arg Ile Arg Met Ser Lys Gly Gly Glu Asp
                    130                 135                 140 cta gag gag gtg atg aag aga gag gag gaa gaa gaa ttg ccc aaa ttc       539
Leu Glu Glu Val Met Lys Arg Glu Glu Glu Glu Glu Leu Pro Lys Phe
                    145                 150                 155 gag gag ggg tcg ttc cag att gaa tct ggt tat gga agc gga ggg gaa       587
Glu Glu Gly Ser Phe Gln Ile Glu Ser Gly Tyr Gly Ser Gly Gly Glu
160                 165                 170                 175 gtt gga gag aga att gcg act gac gag gtc ctc gat aat gtt gtg ccg       635
Val Gly Glu Arg Ile Ala Thr Asp Glu Val Leu Asp Asn Val Val Pro
                    180                 185                 190 aaa ggc gct gtt cat gta cat acc atg cgc aat ctc atc agt tcg att       683
Lys Gly Ala Val His Val His Thr Met Arg Asn Leu Ile Ser Ser Ile
                    195                 200                 205 cag att gtt ggt ccc ggg cat ctt caa tgc tct cag tgg atc gac gaa       731
Gln Ile Val Gly Pro Gly His Leu Gln Cys Ser Gln Trp Ile Asp Glu
                    210                 215                 220 ccg gtt ctt ctt gtc aca cgc ttc gaa tac gcc aat ctc ttt cac acc       779
Pro Val Leu Leu Val Thr Arg Phe Glu Tyr Ala Asn Leu Phe His Thr
                    225                 230                 235 gtc acc gac tgg tac agc gcc tac gca agc tcg agg att gcc aac ttg       827
Val Thr Asp Trp Tyr Ser Ala Tyr Ala Ser Ser Arg Ile Ala Asn Leu
240                 245                 250                 255 cct tct cgc cct cac tta att ttc gtc gat ggc cat tgc agg gcg gaa       875
Pro Ser Arg Pro His Leu Ile Phe Val Asp Gly His Cys Arg Ala Glu
                    260                 265                 270 cag tta gag gac atg tgg aga gcc ctg ttc tcg acc gtc cga tac tcc       923
Gln Leu Glu Asp Met Trp Arg Ala Leu Phe Ser Thr Val Arg Tyr Ser
                    275                 280                 285 aag aac ttc tcc cag cca atc tgc ttc cgc cac gtc gtc ctc tca cct       971
Lys Asn Phe Ser Gln Pro Ile Cys Phe Arg His Val Val Leu Ser Pro
                    290                 295                 300 ctg ggc tat gag acg gct ctc ttc aaa ggc cta tca gag agc ttc agc      1019
Leu Gly Tyr Glu Thr Ala Leu Phe Lys Gly Leu Ser Glu Ser Phe Ser
                    305                 310                 315 tgt gag gga gct ccg gcc aat cgg ctc aaa gtc aac ccc gat gac cag      1067
Cys Glu Gly Ala Pro Ala Asn Arg Leu Lys Val Asn Pro Asp Asp Gln
320                 325                 330                 335 aag act gca aga ctg gct gaa ttc gga gag atg atc aga gcc gcc ttt      1115
Lys Thr Ala Arg Leu Ala Glu Phe Gly Glu Met Ile Arg Ala Ala Phe
                    340                 345                 350 gac ttt cct gtc gtt gac ccg tcc att gac ccg ttg acc aaa tcc atc      1163
Asp Phe Pro Val Val Asp Pro Ser Ile Asp Pro Leu Thr Lys Ser Ile
                    355                 360                 365 ctc ttc gtg cgg cgg gaa gat tac gtg gcg cac cca cgc cac agt ggg      1211
Leu Phe Val Arg Arg Glu Asp Tyr Val Ala His Pro Arg His Ser Gly
                    370                 375                 380 aga gtg gag tcg cgg ctg acc aac gag caa gag gtg ttt gac ttt ctg      1259
Arg Val Glu Ser Arg Leu Thr Asn Glu Gln Glu Val Phe Asp Phe Leu
                    385                 390                 395 cac aat tgg gca agt cat cac aga ggc agg tgc aac atc agt atg gtc      1307
His Asn Trp Ala Ser His His Arg Gly Arg Cys Asn Ile Ser Met Val
```

-continued

```
                 400                 405                 410                 415
aac ggg ctt ttc gcg cac atg gga atg aag gaa cag ttg aag gcg att      1355
Asn Gly Leu Phe Ala His Met Gly Met Lys Glu Gln Leu Lys Ala Ile
                     420                 425                 430 atg gaa gct tcg gtg gtg gtg ggg gcc cac ggg gct ggt ttg acc cat      1403
Met Glu Ala Ser Val Val Val Gly Ala His Gly Ala Gly Leu Thr His
                 435                 440                 445 ctg gtg gca gca agg tca acg aca gtt gtt ctt gag att ctg agt agt      1451
Leu Val Ala Ala Arg Ser Thr Thr Val Val Leu Glu Ile Leu Ser Ser
             450                 455                 460 caa tac cgt aga ccg cac ttt caa ctg att tct cgg tgg aaa ggg ttg      1499
Gln Tyr Arg Arg Pro His Phe Gln Leu Ile Ser Arg Trp Lys Gly Leu
465                 470                 475 gac tac cat gca att aat ctt gcc ggg tca ttt gct gac cct cgg gag      1547
Asp Tyr His Ala Ile Asn Leu Ala Gly Ser Phe Ala Asp Pro Arg Glu
480                 485                 490                 495 gtg gtc gag aaa ttg act ggc ata gtt gac agg ctt gga tgt tga          1592
Val Val Glu Lys Leu Thr Gly Ile Val Asp Arg Leu Gly Cys *
                 500                 505 agagaagtga aagtcaacat ttggaatttt aactttaagg ggtggttaac aattgagcgg    1652
cattgtcaac gggtttggat gctgggaaaa gtgaaaatca cacttggag ttctgacatt    1712 gaaggcaaga cgtggaattt tgatggtgtt gaggatattt ggatgtggag ttctgatgaa    1772
ttaaagcagg ggttgatcat ttgccagtgg aattatgttg gtgtaagaga aaggggggag    1832
aataaacagt gttagagagc tatgctgg                                       1860

<210> SEQ ID NO 5
<211> LENGTH: 1530
<212> TYPE: DNA
<213> ORGANISM: Lemna minor
<220> FEATURE:
<221> NAME/KEY: CDS
<222> LOCATION: (1)...(1530)
<223> OTHER INFORMATION: XyIT isoform #1; Encodes beta-1,
      2-xylosyltransferase

<400> SEQUENCE: 5 atg gct ttg gtg aac tcg cga ggg agc agg gtc aga cgc atc gcg aag      48
Met Ala Leu Val Asn Ser Arg Gly Ser Arg Val Arg Arg Ile Ala Lys
1               5                   10                  15 ccc acc ttc gtt ttc ctc ttg atc aac gta gtc tgt ctc ctg tac ttt      96
Pro Thr Phe Val Phe Leu Leu Ile Asn Val Val Cys Leu Leu Tyr Phe
                20                  25                  30 ttc cgt cag aac cct aat ccc att ccc gac gct tgt ctt cac ggg gaa      144
Phe Arg Gln Asn Pro Asn Pro Ile Pro Asp Ala Cys Leu His Gly Glu
            35                  40                  45 tgc gac aaa ccc ccg att tta gtg act ccc cgg cga tgg aac ttg aag      192
Cys Asp Lys Pro Pro Ile Leu Val Thr Pro Arg Arg Trp Asn Leu Lys
        50                  55                  60 cca tgg ccg att ctt cct tcc ttt ctg cca tgg gtg ccg agc tcc cac      240
Pro Trp Pro Ile Leu Pro Ser Phe Leu Pro Trp Val Pro Ser Ser His
65                  70                  75                  80 cct gcc cag ggc tcc tgc gaa gcc tac ttc ggc aac agc ttc aac cgc      288
Pro Ala Gln Gly Ser Cys Glu Ala Tyr Phe Gly Asn Ser Phe Asn Arg
                85                  90                  95 cgg acg gag atg ctg aag aag gta gag gga aga gga tgg ttc cag tgc      336
Arg Thr Glu Met Leu Lys Lys Val Glu Gly Arg Gly Trp Phe Gln Cys
            100                 105                 110 ctg tac agc gat act ctt cga agt tct gtt tgc cag gga ggg aat ttg      384
Leu Tyr Ser Asp Thr Leu Arg Ser Ser Val Cys Gln Gly Gly Asn Leu
        115                 120                 125
```

```
cgg atg gac ccg gaa agg att agg atg tcg aaa ggg ggg gaa gat cta      432
Arg Met Asp Pro Glu Arg Ile Arg Met Ser Lys Gly Gly Glu Asp Leu
    130                 135                 140 gag gag gtg atg aag aga gag gag gaa gaa ttg ccc aaa ttc gag          480
Glu Glu Val Met Lys Arg Glu Glu Glu Glu Leu Pro Lys Phe Glu
145                 150                 155                 160 gag ggg tcg ttc cag att gaa tct ggt tat gga agc gga ggg gaa gtt      528
Glu Gly Ser Phe Gln Ile Glu Ser Gly Tyr Gly Ser Gly Gly Glu Val
                165                 170                 175 gga gag aga att gcg act gac gag gtc ctc gat aat gtt gtg ccg aaa      576
Gly Glu Arg Ile Ala Thr Asp Glu Val Leu Asp Asn Val Val Pro Lys
            180                 185                 190 ggc gct gtt cat gta cat acc atg cgc aat ctc atc agt tcg att cag      624
Gly Ala Val His Val His Thr Met Arg Asn Leu Ile Ser Ser Ile Gln
        195                 200                 205 att gtt ggt ccc ggg cat ctt caa tgc tct cag tgg atc gac gaa ccg      672
Ile Val Gly Pro Gly His Leu Gln Cys Ser Gln Trp Ile Asp Glu Pro
    210                 215                 220 gtt ctt ctt gtc aca cgc ttc gaa tac gcc aat ctc ttt cac acc gtc      720
Val Leu Leu Val Thr Arg Phe Glu Tyr Ala Asn Leu Phe His Thr Val
225                 230                 235                 240 acc gac tgg tac agc gcc tac gca agc tcg agg att gcc aac ttg cct      768
Thr Asp Trp Tyr Ser Ala Tyr Ala Ser Ser Arg Ile Ala Asn Leu Pro
                245                 250                 255 tct cgc cct cac tta att ttc gtc gat ggc cat tgc agg gcg gaa cag      816
Ser Arg Pro His Leu Ile Phe Val Asp Gly His Cys Arg Ala Glu Gln
            260                 265                 270 tta gag gac atg tgg aga gcc ctg ttc tcg acc gtc cga tac tcc aag      864
Leu Glu Asp Met Trp Arg Ala Leu Phe Ser Thr Val Arg Tyr Ser Lys
        275                 280                 285 aac ttc tcc cag cca atc tgc ttc cgc cac gtc gtc ctc tca cct ctg      912
Asn Phe Ser Gln Pro Ile Cys Phe Arg His Val Val Leu Ser Pro Leu
    290                 295                 300 ggc tat gag acg gct ctc ttc aaa ggc cta tca gag agc ttc agc tgt      960
Gly Tyr Glu Thr Ala Leu Phe Lys Gly Leu Ser Glu Ser Phe Ser Cys
305                 310                 315                 320 gag gga gct ccg gcc aat cgg ctc aaa gtc aac ccc gat gac cag aag     1008
Glu Gly Ala Pro Ala Asn Arg Leu Lys Val Asn Pro Asp Asp Gln Lys
                325                 330                 335 act gca aga ctg gct gaa ttc gga gag atg atc aga gcc gcc ttt gac     1056
Thr Ala Arg Leu Ala Glu Phe Gly Glu Met Ile Arg Ala Ala Phe Asp
            340                 345                 350 ttt cct gtc gtt gac ccg tcc att gac ccg ttg acc aaa tcc atc ctc     1104
Phe Pro Val Val Asp Pro Ser Ile Asp Pro Leu Thr Lys Ser Ile Leu
        355                 360                 365 ttc gtg cgg cgg gaa gat tac gtg gcg cac cca cgc cac agt ggg aga     1152
Phe Val Arg Arg Glu Asp Tyr Val Ala His Pro Arg His Ser Gly Arg
    370                 375                 380 gtg gag tcg cgg ctg acc aac gag caa gag gtt ttt gac ttt ctg cac     1200
Val Glu Ser Arg Leu Thr Asn Glu Gln Glu Val Phe Asp Phe Leu His
385                 390                 395                 400 aat tgg gca agt cat cac aga ggc agg tgc aac atc agt atg gtc aac     1248
Asn Trp Ala Ser His His Arg Gly Arg Cys Asn Ile Ser Met Val Asn
                405                 410                 415 ggg ctt ttc gcg cac atg gga atg aag gaa cag ttg aag gcg att atg     1296
Gly Leu Phe Ala His Met Gly Met Lys Glu Gln Leu Lys Ala Ile Met
            420                 425                 430 gaa gct tcg gtg gtg gtg ggg gcc cac ggg gct ggt ttg acc cat ctg     1344
Glu Ala Ser Val Val Val Gly Ala His Gly Ala Gly Leu Thr His Leu
        435                 440                 445
```

```
gtg gca gca agg tca acg aca gtt gtt ctt gag att ctg agt agt caa    1392
Val Ala Ala Arg Ser Thr Thr Val Val Leu Glu Ile Leu Ser Ser Gln
    450                 455                 460 tac cgt aga ccg cac ttt caa ctg att tct cgg tgg aaa ggg ttg gac    1440
Tyr Arg Arg Pro His Phe Gln Leu Ile Ser Arg Trp Lys Gly Leu Asp
465                 470                 475                 480 tac cat gca att aat ctt gcc ggg tca ttt gct gac cct cgg gag gtg    1488
Tyr His Ala Ile Asn Leu Ala Gly Ser Phe Ala Asp Pro Arg Glu Val
                485                 490                 495 gtc gag aaa ttg act ggc ata gtt gac agg ctt gga tgt tga            1530
Val Glu Lys Leu Thr Gly Ile Val Asp Arg Leu Gly Cys *
            500                 505
```

<210> SEQ ID NO 6
<211> LENGTH: 509
<212> TYPE: PRT
<213> ORGANISM: Lemna minor

<400> SEQUENCE: 6

```
Met Ala Leu Val Asn Ser Arg Gly Ser Arg Val Arg Arg Ile Ala Lys
 1               5                  10                  15

Pro Thr Phe Val Phe Leu Leu Ile Asn Val Val Cys Leu Leu Tyr Phe
             20                  25                  30

Phe Arg Gln Asn Pro Asn Pro Ile Pro Asp Ala Cys Leu His Gly Glu
         35                  40                  45

Cys Asp Lys Pro Pro Ile Leu Val Thr Pro Arg Arg Trp Asn Leu Lys
     50                  55                  60

Pro Trp Pro Ile Leu Pro Ser Phe Leu Pro Trp Val Pro Ser Ser His
 65                  70                  75                  80

Pro Ala Gln Gly Ser Cys Glu Ala Tyr Phe Gly Asn Ser Phe Asn Arg
                 85                  90                  95

Arg Thr Glu Met Leu Lys Lys Val Glu Gly Arg Gly Trp Phe Gln Cys
            100                 105                 110

Leu Tyr Ser Asp Thr Leu Arg Ser Ser Val Cys Gln Gly Gly Asn Leu
        115                 120                 125

Arg Met Asp Pro Glu Arg Ile Arg Met Ser Lys Gly Gly Glu Asp Leu
    130                 135                 140

Glu Glu Val Met Lys Arg Glu Glu Glu Leu Pro Lys Phe Glu
145                 150                 155                 160

Glu Gly Ser Phe Gln Ile Glu Ser Gly Tyr Gly Ser Gly Gly Glu Val
                165                 170                 175

Gly Glu Arg Ile Ala Thr Asp Glu Val Leu Asp Asn Val Val Pro Lys
            180                 185                 190

Gly Ala Val His Val His Thr Met Arg Asn Leu Ile Ser Ser Ile Gln
        195                 200                 205

Ile Val Gly Pro Gly His Leu Gln Cys Ser Gln Trp Ile Asp Glu Pro
    210                 215                 220

Val Leu Leu Val Thr Arg Phe Glu Tyr Ala Asn Leu Phe His Thr Val
225                 230                 235                 240

Thr Asp Trp Tyr Ser Ala Tyr Ala Ser Ser Arg Ile Ala Asn Leu Pro
                245                 250                 255

Ser Arg Pro His Leu Ile Phe Val Asp Gly His Cys Arg Ala Glu Gln
            260                 265                 270

Leu Glu Asp Met Trp Arg Ala Leu Phe Ser Thr Val Arg Tyr Ser Lys
        275                 280                 285

Asn Phe Ser Gln Pro Ile Cys Phe Arg His Val Val Leu Ser Pro Leu
```

```
                290                  295                 300
Gly Tyr Glu Thr Ala Leu Phe Lys Gly Leu Ser Glu Ser Phe Ser Cys
305                 310                 315                 320

Glu Gly Ala Pro Ala Asn Arg Leu Lys Val Asn Pro Asp Asp Gln Lys
                325                 330                 335

Thr Ala Arg Leu Ala Glu Phe Gly Glu Met Ile Arg Ala Ala Phe Asp
                340                 345                 350

Phe Pro Val Val Asp Pro Ser Ile Asp Pro Leu Thr Lys Ser Ile Leu
                355                 360                 365

Phe Val Arg Arg Glu Asp Tyr Val Ala His Pro Arg His Ser Gly Arg
370                 375                 380

Val Glu Ser Arg Leu Thr Asn Glu Gln Glu Val Phe Asp Phe Leu His
385                 390                 395                 400

Asn Trp Ala Ser His His Arg Gly Arg Cys Asn Ile Ser Met Val Asn
                405                 410                 415

Gly Leu Phe Ala His Met Gly Met Lys Glu Gln Leu Lys Ala Ile Met
                420                 425                 430

Glu Ala Ser Val Val Gly Ala His Gly Ala Gly Leu Thr His Leu
                435                 440                 445

Val Ala Ala Arg Ser Thr Thr Val Val Leu Glu Ile Leu Ser Ser Gln
450                 455                 460

Tyr Arg Arg Pro His Phe Gln Leu Ile Ser Arg Trp Lys Gly Leu Asp
465                 470                 475                 480

Tyr His Ala Ile Asn Leu Ala Gly Ser Phe Ala Asp Pro Arg Glu Val
                485                 490                 495

Val Glu Lys Leu Thr Gly Ile Val Asp Arg Leu Gly Cys
                500                 505

<210> SEQ ID NO 7
<211> LENGTH: 2160
<212> TYPE: DNA
<213> ORGANISM: Lemna minor

<400> SEQUENCE: 7
agtcgagtga tatgaaatct tggtgaagaa ggatcggaga acggaccggg tgaggcaagg      60
ataattctgc tgttaaattc gagagcaaga cacctgcaat tcaagaatcg agtggcaatt     120
aatatagcag gatgatctgg aaggtagatc ctgcccatcg aatgatccaa acatcaacac     180
taggatcata ccgttaacaa taatgaatga aaaagtagaa gatgacgaag ttgaagtgat     240
gaccaaaaac tttgaaaatt ccaaccgtat ggccggaatc agtgtgaaga aaatcgaaat     300
caaatactct aatggatcgg attgttattc tggaggcaaa tctgaaactt cgaggatagg     360
atttaatcca cgcaagtaat aatttgaaac tcagaaggag aaaaaaaaac taaaatagag     420
aagaagagat ctcaaagaag ccgtgagcac gagacgaacg agaagaggta agcaccagt     480 cagaggaaaa caccaaaatt agagaaatag cacgaacatt aaagcacaga tccgcgccgc     540
aaacccgaaa gacgaaaaat agagccaaac gaaaccctaa taatcgatct gcacaaaaaa     600
aaaaaaaaaa aactttgaga gagccgcga aattacccta gaatcctcag aactggccgg     660
acgagagaag cgctcgatcg aaacccaaca taaaacccct tccaacggca aattactccg     720 caaacccga aaataaaca aaatcaacga tcacgagaag gtgcaagggc aaaagaggc       780 agtgcgatcg agagtctacc tgaatcgtcg gcgcaaaagg cgagcccacc gacgaacgct     840
ccctctagaa cctggagatg cggcgagaga gaaggaaaga tcttcggtgg gtgatgctcg     900
ctatttatcg caagagagtt agagagatct tcttcggcgg cggatttctg gcatctagcg     960
```

-continued

```
tttaacctca ccgcccagtg ctcacatcct tcttctcata tttgaatatt taattaacaa    1020
atgaatcagt cattttcctt taattttaa ttcccggaga gggcaatgtt ggtatcaaaa    1080
attatttagg aaaaattaat tacacgaata atcggatttt tcccttttt taattaattt    1140
ctaattttgg aaaggaaag aaaaatttta ggggtatgga gggcaagaat gaaatattac    1200
aaaattaggg gttttgcgt aatttattat atttaataaa gaaagtcgaa tattcccatc    1260
cgattggtag ttgaaagggg ccgaaaggcc tcggggtttc tagagatttc tacattattc    1320
tcgttttgt cgccaagaag gtgggcaatt atgtttcatg ccttaacttc ttcttttgt    1380
gggaatactc ttattcttag tacaaaagaa aagagtatat gcataaataa gatgaaaaat    1440
gggtttattc gagatttcta cgtcatgtgt gactcgctta ggaaatatcg ccgaaaccta    1500
acaaaggcgg tacgctcctc tcccccgacc tataaataga gaccttttgcc tcgtctttct    1560
caactcaagc atttctgtat gatccttctc tttccgcgga agctctcgcg ccagttgatc    1620
gcaaggtatg cgtctttcct ccttgtgatt cgatctttct gttggctaga tctggtctat    1680
tgatctgctc tattgatctg gtctatttat cgctgcatcg ggatctattg atccgtatgt    1740
tgatttggga tccgtaggtt ggtttggatc ggagactgcg atttgattct tgtgatttcg    1800
cttggatttc ggaaatcggt gtggttgaag tcgtgcgatc ttttagatct gctcctttt    1860
ttatttgcta ttttatattt acgttgttta tgatcgcgga ttattttgat tcgtttattc    1920
gagatccatg ccgtttaact cgttctttgt gctccgatct ttgcgatacg tcggtcgttc    1980
tagatccgtt cactaggtta gttttaagtt ctttgagctt gattatatg gatttgctgt    2040
tttccaggaa aaatttatgc gcgattctta cgcccgtttc cccatttac tttaggtcgt    2100
gaattctttt gatctgagaa tgatgaatct gacatgtacc ttccggtttg taatttgcag    2160
```

<210> SEQ ID NO 8
<211> LENGTH: 2021
<212> TYPE: DNA
<213> ORGANISM: Spirodela polyrrhiza

<400> SEQUENCE: 8

```
caaataaaga gatggacaga taatgagatg aattagaaaa aaaaaattcg tgttgtaaga     60
tagaatactt gctatctact gatgaatgca gttcagtttt cctcacgatc ttaaagatcg    120
cgcactatcc tcagcttcac tctggaaatt ttgattctct tcttctgctc agcagcctcg    180
actctgtcta gggtttcgta caatcggacg ccattctaca tgaatcgagc acagggaatg    240
aagacaatta ggagatcctc gatgtcctcc gacttacttg catgacttga cggggaagat    300
ctcgagcagg gaagcgacgc ctctccggag gactcgcctc ccgagagga cctcctccgc    360
gacacggacc atggcctcca cggggtagaa gctggccctg ttctttattc tcttgaggat    420
catcggccga agcctccgca aatccatccc cgaggagtag aatctcgcct gcaggaagca    480
tctgtcgaga tcctcgccga gcggcggag ataccctcgcc ggcgccgcca tggcgccggg    540
gacggagcac caccacgag aagaagaacc ctaacccaag gcattaacga agttgcgcag    600
attatacaaa agccctcaaa tatctttcat tttctatttc actgatacat tttcattatt    660
gtatatgagt gttatttaa attattccgt attagaaaag cacctccaga acccgacaaa    720
atagggtgac gtcatcatgg tgtcatgacc gcccaacagc cgcagattta aaatcggtgg    780
atgagtgcgg ccacgccacg aaagcgatgg gccttcgtcg atgccgtgag aatccatctg    840
acataaagta aacggcgccg tcagtattga cggcgtatga cacgtggaaa gaagctattg    900
gttcacgcat cggtggttcc gctagcctcc gtcgaccgct agtactataa atacggtccc    960
```

```
gaggcctcct caccactcgc acatatcctc tttgttttcc tctccgtgaa agaagcgagg    1020
aagcgcgtcg tctctcccaa ggtaaggagc agatctcttt gatcgttttt gttcttcttt    1080
tgttttgttt ttttttttctg cggatcttcg gttgcatcat gccttggctg tttttattag    1140
tttaggatat cctcgtttgg atctgagccg atcatatatg ttaaaggttg tgttcgatct    1200
ctttgttcat tttcgcatga aaaggatgta tccttttgat gtgaggcgat cttctatggt    1260
taagactttg ttcggtctat tgatcatttc tgttcttcgt ttttgagttt ttttctgcgg    1320
atatcgcatc atccctaggt ttttgctttg gttaggatgc atcctttgga tttgagccga    1380
tctcccttgg ttaaggctgt gtctgttgca gaggagaaag tctgtcgagg tccttatgca    1440
ggctttgtcc agatgcgcgt gctctctcat gctatgaatt tatgttttga gaactcctcc    1500
cggtttttct agatccggat ttgaagtatt cattgcggtt cccttcggt tttatgtatt     1560 tctcgagttg atttggtcca tgatcgtgtt ctgtccagat ctctcttgat atggatgaga    1620
tattcgttac ctcttcaaa catcggtgga tgttctttt agtcttggct caccttatc      1680 tagaaattaa ttttcggttt gaaacccctg cttgttaagg tgatgtattc cttctttata    1740
gatttcggtg tgttatttct taacggtgat ctgtccgatc catgtgttgc acctcttgtt    1800
ttctgtgtaa tcctctgtga attataatta tgttttgaaa acgtacttaa gtaaggggca    1860
tgttccccgt ttaaaacttt tgttctatca atttgtggtt aatagatcct gatttgtggt    1920
cgccttattc tgtctttaat cgtggatttt atttatcttg agcgcgtcct tttctttttaa   1980 aatcatgtgt ttaacctttc agtcgtcata tgttccatca g                        2021

<210> SEQ ID NO 9
<211> LENGTH: 2068
<212> TYPE: DNA
<213> ORGANISM: Lemna aequinoctialis

<400> SEQUENCE: 9
agtgtaccaa tattttaaac cctacattta tcattcttta ttcattattg ccataagtta     60
atgaatattg aaattcaaat acgcgcaaga tgtcaatatc gatcgaatat gaataccaga    120
tataaaatca aaaatcaaat atcaaattaa taaagatata aaatattgaa tccaaaagca    180
ataaagaata tcactattaa tatcaaaata tcgatttgaa gttcaaaaat tgggtccatt    240
aggagccaag accgatcatg atccgatact gatatcaata tctgtagctc agtggctagg    300
cccctcaatt tgcctggccg aaggcagtgt acaaaacctg gctctcgcaa gggcaaagaa    360
agagtctttc ccaaaaaaaa aaaaatcgaa cccatttgta gtatccaata tttggattga    420
cataagatac caaaacataa agtactaacc acccaatctt ataattaatc aagatttata    480
tcacatccaa tatcaagatc cgatatcaat acctagaccg gtaaaaccta atttactctt    540 ccccccctcta aaaatttcca ataaatatct ccacatattt aactattaaa aaattgataa    600
gagataggcc ctagccctaa gtcctaacat ataaccactc tctatgaaaa gtcctattaa    660
atgacgtcat ttatttattt attgccggtt ggctgctcca cagccgcaat ttaatggatg    720
gctgacacgg cacgaaaccg acgggcggtg ccgtgggaat aattctagag taaacctaac    780
ggcgccgtta actttgacgg tggcgaagac gcgtggggat aggtggttgg tccgcgtgac    840
ggcggcggtt cagcccgtcg accttgagcc gagactataa atcgaggcga agggatgagc    900
tttgccattg cgttcttctt ctgttcatct ctgaaattcg gcggaatcc ttcttcttct     960 caaggtatgg gcctcgatct ttctgtttca atcgagtttt gatcttcgtt ttggcggcga    1020
tcggtgtttt ctttgtattg tgaataaatc cttgataaga aaaccctagg ttttgtgacc    1080
```

```
tgttgacgga tgcgtgcgga tctgttattt gtcttttagg cgattttctc ttgtttgtaa   1140
tagtttatca taaccagatg aacatggatc aagtcgattt gacttatttt ttctgtgaaa   1200
ttaggccgaa atcctttttt ttggtttgag ccttgatatt tctatataat tcgatttgat   1260
tttttgtttt cttctgcgtc tgatgctttc tcttgactcc tgattaaatt tttgctacgg   1320
aaaccctaga tgtcgagatc tgttgacaga ttctggcaaa tctgttttta tcataatcag   1380
atgaacgcaa attaagtcga tttggttttt ctctgaaatt agggggaaa ctccttatag    1440 tatgagcctc gatatttcta taatagtcga tttgattttc tcttgcctcc tgattcaatt   1500
tttggtgcgg aaaccctaga tattgtaatc tgtttacgga tgcttgcgga tctgattttt   1560
aatattgtga tctattgacg gatgctcgta gatctggttg ttttgatttc ttcatgcctt   1620
atacggcgat ttgattcggc gattaaaaat tttcaattct tttaaaaaaa atattaagat   1680
tttcaacgtt tcaaattatt tcatagatcg gcacaaatac ttttcatcag attcctcctg   1740
atgtgatggt ttgtgtttaa aatctgttga agatatcaga ttctattagg tcaccgatat   1800
aatcttctct gtttattctg cgatcggtgc ttacaaaccc tatttcctac ggtgattaat   1860
tatttttaat ctcctagcta gcgtaaatat atatttttt aatttgatct ttgcattagt    1920
ttcctccttt tatttgctat taattgtaac cgatgctaca aaacatcaga ttttttttcc   1980
caattcgttg tcatcattat agaaaacttt tatctgatat ttttaatcgt cattaatata   2040
attttcaatt tattattttc ccttgcag                                      2068

<210> SEQ ID NO 10
<211> LENGTH: 1625
<212> TYPE: DNA
<213> ORGANISM: Lemna minor

<400> SEQUENCE: 10
agtcgagtga tatgaaatct tggtgaagaa ggatcggaga acggaccggg tgaggcaagg     60
ataattctgc tgttaaattc gagagcaaga cacctgcaat tcaagaatcg agtggcaatt    120
aatatagcag gatgatctgg aaggtagatc ctgcccatcg aatgatccaa acatcaacac    180
taggatcata ccgttaacaa taatgaatga aaaagtagaa gatgacgaag ttgaagtgat    240
gaccaaaaac tttgaaaatt ccaaccgtat ggccggaatc agtgtgaaga aaatcgaaat    300
caaatactct aatggatcgg attgttattc tggaggcaaa tctgaaactt cgaggatagg    360
atttaatcca cgcaagtaat aatttgaaac tcagaaggag aaaaaaaaac taaaatagag    420
aagaagagat ctcaaagaag ccgtgagcac gagacgaacg agaagaggta aagcaccagt    480
cagaggaaaa caccaaaatt agagaaatag cacgaacatt aaagcacaga tccgcgccgc    540
aaacccgaaa gacgaaaaat agagccaaac gaaaccctaa taatcgatct gcacaaaaaa    600
aaaaaaaaaa aactttgaga gagccgcgaa aattaccccta gaatcctcag aactggccgg   660
acgagagaag cgctcgatcg aaacccaaca taaaacccct tccaacggca aattactccg    720
caaaacccga aaataaaca aaatcaacga tcacgagaag gtgcaagggc aaaaagaggc     780
agtgcgatcg agagtctacc tgaatcgtcg gcgcaaaagg cgagcccacc gacgaacgct    840
ccctctagaa cctggagatg cggcgagaga gaaggaaaga tcttcggtgg gtgatgctcg    900
ctatttatcg caagagagtt agagagatct tcttcggcgg cggatttctg gcatctagcg    960
tttaacctca ccgcccagtg ctcacatcct tcttctcata tttgaatatt taattaacaa   1020
atgaatcagt cattttctctt taattttta ttcccggaga gggcaatgtt ggtatcaaaa    1080
attatttagg aaaaattaat tacacgaata atcggatttt tcccttttttt taattaattt   1140
```

```
ctaattttgg aaaaggaaag aaaaatttta ggggtatgga gggcaagaat gaaatattac    1200
aaaattaggg gttttttgcgt aatttattat atttaataaa gaaagtcgaa tattcccatc    1260
cgattggtag ttgaaagggg ccgaaaggcc tcggggtttc tagagatttc tacattattc    1320
tcgtttttgt cgccaagaag gtgggcaatt atgtttcatg ccttaacttc ttctttttgt    1380
gggaatactc ttattcttag tacaaaagaa aagagtatat gcataaataa gatgaaaaat    1440
gggtttattc gagatttcta cgtcatgtgt gactcgctta ggaaatatcg ccgaaaccta    1500
acaaaggcgg tacgctcctc tcccccgacc tataaataga gacctttgcc tcgtctttct    1560
caactcaagc atttctgtat gatccttctc tttccgcgga agctctcgcg ccagttgatc    1620
gcaag                                                                 1625

<210> SEQ ID NO 11
<211> LENGTH: 1041
<212> TYPE: DNA
<213> ORGANISM: Spirodela polyrrhiza

<400> SEQUENCE: 11
caaataaaga gatggacaga taatgagatg aattagaaaa aaaaaattcg tgttgtaaga      60
tagaatactt gctatctact gatgaatgca gttcagtttt cctcacgatc ttaaagatcg     120
cgcactatcc tcagcttcac tctggaaatt ttgattctct tcttctgctc agcagcctcg     180
actctgtcta gggtttcgta caatcggacg ccattctaca tgaatcgagc acagggaatg     240
aagacaatta ggagatcctc gatgtcctcc gacttacttg catgacttga cggggaagat     300
ctcgagcagg gaagcgacgc ctctccggag gactcgcctc gccgagagga cctcctccgc     360
gacacggacc atggcctcca cggggtagaa gctggccctg ttctttattc tcttgaggat     420
catcggccga agcctccgca aatccatccc cgaggagtag aatctcgcct gcaggaagca     480
tctgtcgaga tcctcgccga gcggcggag atacctcgcc ggcgccgcca tggcgccggg     540
gacggagcac caccacggag aagaagaacc ctaacccaag gcattaacga agttgcgcag     600
attatacaaa agccctcaaa tatctttcat tttctatttc actgatacat tttcattatt     660
gtatatgagt gtttatttaa attattccgt attagaaaag cacctccaga acccgacaaa     720 ataggggtgac gtcatcatgg tgtcatgacc gcccaacagc cgcagattta aaatcggtgg    780
atgagtgcgg ccacgccacg aaagcgatgg gccttcgtcg atgccgtgag aatccatctg    840
acataaagta aacggcgccg tcagtattga cggcgtatga cacgtggaaa gaagctattg     900
gttcacgcat cggtggttcc gctagcctcc gtcgaccgct agtactataa atacggtccc    960
gaggcctcct caccactcgc acatatcctc tttgttttcc tctccgtgaa agaagcgagg   1020
aagcgcgtcg tctctcccaa g                                             1041

<210> SEQ ID NO 12
<211> LENGTH: 964
<212> TYPE: DNA
<213> ORGANISM: Lemna aequinoctialis

<400> SEQUENCE: 12
agtgtaccaa tattttaaac cctacattta tcattcttta ttcattattg ccataagtta     60
atgaatattg aaattcaaat acgcgcaaga tgtcaatatc gatcgaatat gaataccaga    120
tataaaatca aaaatcaaat atcaaattaa taagatata aatattgaa tccaaaagca      180 ataaagaata tcactattaa tatcaaaata tcgatttgaa gttcaaaaat tgggtccatt    240
aggagccaag accgatcatg atccgatact gatatcaata tctgtagctc agtggctagg    300
```

```
cccctcaatt tgcctggccg aaggcagtgt acaaaacctg gctctcgcaa gggcaaagaa    360
agagtctttc ccaaaaaaaa aaaaatcgaa cccatttgta gtatccaata tttggattga    420
cataagatac caaaacataa agtactaacc acccaatctt ataattaatc aagatttata    480
tcacatccaa tatcaagatc cgatatcaat acctagaccg gtaaaccctg atttactctt    540
cccccctcta aaatttccaa ataaatatct ccacatattt aactattaaa aaattgataa    600
gagataggcc ctagccctaa gtcctaacat ataaccactc tctatgaaaa gtcctattaa    660
atgacgtcat ttatttattt attgccggtt ggctgctcca cagccgcaat ttaatggatg    720
gctgacacgg cacgaaaccg acgggcggtg ccgtgggaat aattctagag taaacctaac    780
ggcgccgtta actttgacgg tggcgaagac gcgtggggat aggtggttgg tccgcgtgac    840
ggcggcggtt cagcccgtcg accttgagcc gagactataa atcgaggcga agggatgagc    900
tttgccattg cgttcttctt ctgttcatct ctgaaattcg ggcggaatcc ttcttcttct    960
caag                                                                964

<210> SEQ ID NO 13
<211> LENGTH: 535
<212> TYPE: DNA
<213> ORGANISM: Lemna minor

<400> SEQUENCE: 13
gtatgcgtct ttcctccttg tgattcgatc tttctgttgg ctagatctgg tctattgatc     60
tgctctattg atctggtcta tttatcgctg catcgggatc tattgatccg tatgttgatt    120
tgggatccgt aggttggttt ggatcggaga ctgcgatttg attcttgtga tttcgcttgg    180
atttcggaaa tcggtgtggt tgaagtcgtg cgatctttta gatctgctcc tttttttatt    240
tgctatttta tatttacgtt gtttatgatc gcggattatt ttgattcgtt tattcgagat    300
ccatgccgtt taactcgttc tttgtgctcc gatctttgcg atacgtcggt cgttctagat    360
ccgttcacta ggttagtttt aagttctttg agcttgattt atatggattt gctgttttcc    420
aggaaaaatt tatgcgcgat tcttacgccc gtttccccat tttactttag gtcgtgaatt    480
cttttgatct gagaatgatg aatctgacat gtaccttccg gtttgtaatt tgcag         535

<210> SEQ ID NO 14
<211> LENGTH: 980
<212> TYPE: DNA
<213> ORGANISM: Spirodela polyrrhiza

<400> SEQUENCE: 14
gtaaggagca gatctctttg atcgtttttg ttcttctttt gttttgtttt tttttttctgc    60 ggatcttcgg ttgcatcatg ccttggctgt ttttattagt ttaggatatc ctcgtttgga    120
tctgagccga tcatatatgt taaaggttgt gttcgatctc tttgttcatt ttcgcatgaa    180
aaggatgtat cctttttgatg tgaggcgatc ttctatggtt aagactttgt tcggtctatt    240
gatcatttct gttcttcgtt tttgagtttt tttctgcgga tatcgcatca tccctaggtt    300
tttgctttgg ttaggatgca tccttttggat ttgagccgat ctcccttggt taaggctgtg    360
tctgttgcag aggagaaagt ctgtcgaggt ccttatgcag gctttgtcca gatgcgcgtg    420
ctctctcatg ctatgaattt atgttttgag aactcctccc ggttttttcta gatccggatt    480 tgaagtattc attgcggttc cccttggtt ttatgtattt ctcgagttga tttggtccat    540
gatcgtgttc tgtccagatc tctccttgata tggatgagat attcgttacc tctttcaaac    600
atcggtggat gttctttttta gtcttggctc acctttatct agaaattaat tttcggtttg    660
```

```
aaaccctgc ttgttaaggt gatgtattcc ttctttatag atttcggtgt gttatttctt    720
aacggtgatc tgtccgatcc atgtgttgca cctcttgttt tctgtgtaat cctctgtgaa    780
ttataattat gttttgaaaa cgtacttaag taagggcat gttccccgtt taaaactttt    840
gttctatcaa tttgtggtta atagatcctg atttgtggtc gccttattct gtctttaatc    900
gtggatttta tttatcttga gcgcgtcctt ttcttttaaa atcatgtgtt taacctttca    960
gtcgtcatat gttccatcag                                                980

<210> SEQ ID NO 15
<211> LENGTH: 1104
<212> TYPE: DNA
<213> ORGANISM: Lemna aequinoctialis

<400> SEQUENCE: 15
gtatgggcct cgatctttct gtttcaatcg agttttgatc ttcgttttgg cggcgatcgg     60
tgttttcttt gtattgtgaa taaatcctg ataagaaaac cctaggtttt gtgacctgtt    120
gacggatgcg tgcggatctg ttatttgtct tttaggcgat tttctcttgt ttgtaatagt    180
ttatcataac cagatgaaca tggatcaagt cgatttgact tattttttct gtgaaattag    240
gccgaaatcc ttttttttgg tttgagcctt gatatttcta tataattcga tttgatttt     300 tgttttcttc tgcgtctgat gcttctctt gactcctgat taaattttg ctacggaaac     360 cctagatgtc gagatctgtt gacagattct ggcaaatctg tttttatcat aatcagatga    420
acgcaaatta agtcgatttg ttttttctct gaaattaggg gggaaactcc ttatagtatg    480
agcctcgata tttctataat agtcgatttg attttctctt gcctcctgat tcaattttg     540 gtgcggaaac cctagatatt gtaatctgtt tacggatgct tgcggatctg attttaata     600 ttgtgatcta ttgacggatg ctcgtagatc tggttgtttt gatttcttca tgccttatac    660
ggcgatttga ttcggcgatt aaaattttc aattctttta aaaaaatat taagattttc      720 aacgtttcaa attatttcat agatcggcac aaatactttt catcagattc ctcctgatgt    780
gatggtttgt gttaaaaatc tgttgaagat atcagattct attaggtcac cgatataatc    840
ttctctgttt attctgcgat cggtgcttac aaaccctatt cctacggtg attaattatt     900 tttaatctcc tagctagcgt aaatatatat ttttttaatt tgatctttgc attagtttcc    960 tcctttatt tgctattaat tgtaaccgat gctacaaaac atcagatttt ttttcccaat    1020
tcgttgtcat cattatagaa acttttatc tgatattttt aatcgtcatt aatataattt    1080
tcaatttatt attttcccttt gcag                                         1104

<210> SEQ ID NO 16
<211> LENGTH: 64
<212> TYPE: DNA
<213> ORGANISM: Lemna gibba

<400> SEQUENCE: 16
aagcacgagc tgagcgagaa ttcggggagg ctgagtcgaa gaggaagaga gaagtaggta     60
cgcc                                                                 64

<210> SEQ ID NO 17
<211> LENGTH: 58
<212> TYPE: DNA
<213> ORGANISM: Lemna gibba

<400> SEQUENCE: 17
actcgcaagt ggagagagga tccgagcgtc cagtgagagg aagagagagg gaggcgcg      58
```

<210> SEQ ID NO 18
<211> LENGTH: 62
<212> TYPE: DNA
<213> ORGANISM: Lemna gibba

<400> SEQUENCE: 18

```
aaactcccga ggtgagcaag gatccggagt cgagcgcgaa gaagagaaag agggaaagcg    60
cg                                                                  62
```

<210> SEQ ID NO 19
<211> LENGTH: 1282
<212> TYPE: DNA
<213> ORGANISM: Lemna minor
<220> FEATURE:
<221> NAME/KEY: CDS
<222> LOCATION: (1)...(1275)

<400> SEQUENCE: 19

```
tgc gaa gcc tac ttc ggc aac agc ttc aac cgc cgg acg gag atg ctg      48
Cys Glu Ala Tyr Phe Gly Asn Ser Phe Asn Arg Arg Thr Glu Met Leu
 1               5                  10                  15 aag aag gta gag gga aga gga tgg ttc cag tgc ctg tac agc gat act      96
Lys Lys Val Glu Gly Arg Gly Trp Phe Gln Cys Leu Tyr Ser Asp Thr
            20                  25                  30 ctt cga agt tct gtt tgc cag gga ggg aat ttg cgg atg gac ccg gaa     144
Leu Arg Ser Ser Val Cys Gln Gly Gly Asn Leu Arg Met Asp Pro Glu
        35                  40                  45 agg att agg atg tcg aaa ggg ggg gaa gat cta gag gag gtg atg aag     192
Arg Ile Arg Met Ser Lys Gly Gly Glu Asp Leu Glu Glu Val Met Lys
    50                  55                  60 aga gag gag gaa gaa gaa ttg ccc aaa ttc gag gag ggg tcg ttc cag     240
Arg Glu Glu Glu Glu Glu Leu Pro Lys Phe Glu Glu Gly Ser Phe Gln
65                  70                  75                  80 att gaa tct ggt tat gga agc gga ggg gaa gtt gga gag aga att gcg     288
Ile Glu Ser Gly Tyr Gly Ser Gly Gly Glu Val Gly Glu Arg Ile Ala
                85                  90                  95 act gac gag gtc ctc gat aat gtt gtg ccg aaa ggc gct gtt cat gta     336
Thr Asp Glu Val Leu Asp Asn Val Val Pro Lys Gly Ala Val His Val
            100                 105                 110 cat acc atg cgc aat ctc atc agt tcg att cag att gtt ggt ccc ggg     384
His Thr Met Arg Asn Leu Ile Ser Ser Ile Gln Ile Val Gly Pro Gly
        115                 120                 125 cat ctt caa tgc tct cag tgg atc gac gaa ccg gtt ctt ctt gtc aca     432
His Leu Gln Cys Ser Gln Trp Ile Asp Glu Pro Val Leu Leu Val Thr
    130                 135                 140 cgc ttc gaa tac gcc aat ctc ttt cac acc gtc acc gac tgg tac agc     480
Arg Phe Glu Tyr Ala Asn Leu Phe His Thr Val Thr Asp Trp Tyr Ser
145                 150                 155                 160 gcc tac gca agc tcg agg att gcc aac ttg ccc tct cgc cct cac ttg     528
Ala Tyr Ala Ser Ser Arg Ile Ala Asn Leu Pro Ser Arg Pro His Leu
                165                 170                 175 att ttc gtc gat ggc cat tgc agg gca gaa cag tta gag gac acg tgg     576
Ile Phe Val Asp Gly His Cys Arg Ala Glu Gln Leu Glu Asp Thr Trp
            180                 185                 190 cga gcc ctg ttc tca acc gtc cga tac gcc aag aac ttc tcc cag cca     624
Arg Ala Leu Phe Ser Thr Val Arg Tyr Ala Lys Asn Phe Ser Gln Pro
        195                 200                 205 gtc tgc ttc cgc cac gcc gtc ctc tcc cct ctt ggc tat gag aca gct     672
Val Cys Phe Arg His Ala Val Leu Ser Pro Leu Gly Tyr Glu Thr Ala
    210                 215                 220
```

```
ctc ttc aaa ggc cta tca gag agc ttc agc tgt gag gga gtg ccg gcc      720
Leu Phe Lys Gly Leu Ser Glu Ser Phe Ser Cys Glu Gly Val Pro Ala
225                 230                 235                 240 aat cag ctc aaa gtc aac cct gat gac cag aag act gcg aga ctg gct      768
Asn Gln Leu Lys Val Asn Pro Asp Asp Gln Lys Thr Ala Arg Leu Ala
                245                 250                 255 gaa ttc gga gag atg atc agg gct gcc ttt gac ttt cct gtc gtt gac      816
Glu Phe Gly Glu Met Ile Arg Ala Ala Phe Asp Phe Pro Val Val Asp
                    260                 265                 270 ccg ccc gtt gac ccg ttg acc aaa tcc atc ctc ttt gtg cgg cgg gaa      864
Pro Pro Val Asp Pro Leu Thr Lys Ser Ile Leu Phe Val Arg Arg Glu
            275                 280                 285 gat tac gtg gcg cac cca cgc cac agt ggg aga gtg gag tcg cgg ttg      912
Asp Tyr Val Ala His Pro Arg His Ser Gly Arg Val Glu Ser Arg Leu
        290                 295                 300 acc aat gag caa gag gtg ttt gac ttt ctg cac aaa tgg gca agt caa      960
Thr Asn Glu Gln Glu Val Phe Asp Phe Leu His Lys Trp Ala Ser Gln
305                 310                 315                 320 cac aga agc agg tgc aac gtc agt gtg gtc aac ggg ctt ttc gcg cac      1008
His Arg Ser Arg Cys Asn Val Ser Val Val Asn Gly Leu Phe Ala His
                325                 330                 335 atg gga atg aag gaa cag gtg aag gca att atg gaa gct tcg gtg gtg      1056
Met Gly Met Lys Glu Gln Val Lys Ala Ile Met Glu Ala Ser Val Val
                340                 345                 350 gtc ggg gcc cac ggg gct ggt ttg act cat ctg gtg gca gca agg tca      1104
Val Gly Ala His Gly Ala Gly Leu Thr His Leu Val Ala Ala Arg Ser
            355                 360                 365 acg aca gtt gtt ctt gag att ctg agc agt caa tat cgt aga ccg cac      1152
Thr Thr Val Val Leu Glu Ile Leu Ser Ser Gln Tyr Arg Arg Pro His
        370                 375                 380 ttt caa ctg att tca cgg tgg aaa ggg ttg gac tac cac gca att aat      1200
Phe Gln Leu Ile Ser Arg Trp Lys Gly Leu Asp Tyr His Ala Ile Asn
385                 390                 395                 400 ctt gcc ggg tcg tat gct gat cct cgg gag gtg gtc gag aaa ttg act      1248
Leu Ala Gly Ser Tyr Ala Asp Pro Arg Glu Val Val Glu Lys Leu Thr
                405                 410                 415 ggc ata gtc gat ggg ctt gga tgt tga a gataag                          1282
Gly Ile Val Asp Gly Leu Gly Cys  *
                420
```

<210> SEQ ID NO 20
<211> LENGTH: 1275
<212> TYPE: DNA
<213> ORGANISM: Lemna minor
<220> FEATURE:
<221> NAME/KEY: CDS
<222> LOCATION: (1)...(1275)
<220> FEATURE:
<221> NAME/KEY: misc_feature
<222> LOCATION: (0)...(0)
<223> OTHER INFORMATION: XylT isoform #2; Encodes partial-length beta-1,
      2-xylosyltransferase

<400> SEQUENCE: 20

```
tgc gaa gcc tac ttc ggc aac agc ttc aac cgc cgg acg gag atg ctg      48
Cys Glu Ala Tyr Phe Gly Asn Ser Phe Asn Arg Arg Thr Glu Met Leu
1               5                   10                  15 aag aag gta gag gga aga gga tgg ttc cag tgc ctg tac agc gat act      96
Lys Lys Val Glu Gly Arg Gly Trp Phe Gln Cys Leu Tyr Ser Asp Thr
                20                  25                  30 ctt cga agt tct gtt tgc cag gga ggg aat ttg cgg atg gac ccg gaa      144
Leu Arg Ser Ser Val Cys Gln Gly Gly Asn Leu Arg Met Asp Pro Glu
            35                  40                  45
```

| | | |
|---|---|---|
| agg att agg atg tcg aaa ggg ggg gaa gat cta gag gag gtg atg aag<br>Arg Ile Arg Met Ser Lys Gly Gly Glu Asp Leu Glu Glu Val Met Lys<br>50  55  60 | | 192 |
| aga gag gag gaa gaa gaa ttg ccc aaa ttc gag gag ggg tcg ttc cag<br>Arg Glu Glu Glu Glu Glu Leu Pro Lys Phe Glu Glu Gly Ser Phe Gln<br>65  70  75  80 | | 240 |
| att gaa tct ggt tat gga agc gga ggg gaa gtt gga gag aga att gcg<br>Ile Glu Ser Gly Tyr Gly Ser Gly Gly Glu Val Gly Glu Arg Ile Ala<br>85  90  95 | | 288 |
| act gac gag gtc ctc gat aat gtt gtg ccg aaa ggc gct gtt cat gta<br>Thr Asp Glu Val Leu Asp Asn Val Val Pro Lys Gly Ala Val His Val<br>100  105  110 | | 336 |
| cat acc atg cgc aat ctc atc agt tcg att cag att gtt ggt ccc ggg<br>His Thr Met Arg Asn Leu Ile Ser Ser Ile Gln Ile Val Gly Pro Gly<br>115  120  125 | | 384 |
| cat ctt caa tgc tct cag tgg atc gac gaa ccg gtt ctt ctt gtc aca<br>His Leu Gln Cys Ser Gln Trp Ile Asp Glu Pro Val Leu Leu Val Thr<br>130  135  140 | | 432 |
| cgc ttc gaa tac gcc aat ctc ttt cac acc gtc acc gac tgg tac agc<br>Arg Phe Glu Tyr Ala Asn Leu Phe His Thr Val Thr Asp Trp Tyr Ser<br>145  150  155  160 | | 480 |
| gcc tac gca agc tcg agg att gcc aac ttg ccc tct cgc cct cac ttg<br>Ala Tyr Ala Ser Ser Arg Ile Ala Asn Leu Pro Ser Arg Pro His Leu<br>165  170  175 | | 528 |
| att ttc gtc gat ggc cat tgc agg gca gaa cag tta gag gac acg tgg<br>Ile Phe Val Asp Gly His Cys Arg Ala Glu Gln Leu Glu Asp Thr Trp<br>180  185  190 | | 576 |
| cga gcc ctg ttc tca acc gtc cga tac gcc aag aac ttc tcc cag cca<br>Arg Ala Leu Phe Ser Thr Val Arg Tyr Ala Lys Asn Phe Ser Gln Pro<br>195  200  205 | | 624 |
| gtc tgc ttc cgc cac gcc gtc ctc tcc cct ctt ggc tat gag aca gct<br>Val Cys Phe Arg His Ala Val Leu Ser Pro Leu Gly Tyr Glu Thr Ala<br>210  215  220 | | 672 |
| ctc ttc aaa ggc cta tca gag agc ttc agc tgt gag gga gtg ccg gcc<br>Leu Phe Lys Gly Leu Ser Glu Ser Phe Ser Cys Glu Gly Val Pro Ala<br>225  230  235  240 | | 720 |
| aat cag ctc aaa gtc aac cct gat gac cag aag act gcg aga ctg gct<br>Asn Gln Leu Lys Val Asn Pro Asp Asp Gln Lys Thr Ala Arg Leu Ala<br>245  250  255 | | 768 |
| gaa ttc gga gag atg atc agg gct gcc ttt gac ttt cct gtc gtt gac<br>Glu Phe Gly Glu Met Ile Arg Ala Ala Phe Asp Phe Pro Val Val Asp<br>260  265  270 | | 816 |
| ccg ccc gtt gac ccg ttg acc aaa tcc atc ctc ttt gtg cgg cgg gaa<br>Pro Pro Val Asp Pro Leu Thr Lys Ser Ile Leu Phe Val Arg Arg Glu<br>275  280  285 | | 864 |
| gat tac gtg gcg cac cca cgc cac agt ggg aga gtg gag tcg cgg ttg<br>Asp Tyr Val Ala His Pro Arg His Ser Gly Arg Val Glu Ser Arg Leu<br>290  295  300 | | 912 |
| acc aat gag caa gag gtg ttt gac ttt ctg cac aaa tgg gca agt caa<br>Thr Asn Glu Gln Glu Val Phe Asp Phe Leu His Lys Trp Ala Ser Gln<br>305  310  315  320 | | 960 |
| cac aga agc agg tgc aac gtc agt gtg gtc aac ggg ctt ttc gcg cac<br>His Arg Ser Arg Cys Asn Val Ser Val Val Asn Gly Leu Phe Ala His<br>325  330  335 | | 1008 |
| atg gga atg aag gaa cag gtg aag gca att atg gaa gct tcg gtg gtg<br>Met Gly Met Lys Glu Gln Val Lys Ala Ile Met Glu Ala Ser Val Val<br>340  345  350 | | 1056 |
| gtc ggg gcc cac ggg gct ggt ttg act cat ctg gtg gca gca agg tca<br>Val Gly Ala His Gly Ala Gly Leu Thr His Leu Val Ala Ala Arg Ser<br>355  360  365 | | 1104 |

| | | | | | | | | | | | | | | |
|---|---|---|---|---|---|---|---|---|---|---|---|---|---|---|
| acg | aca | gtt | gtt | ctt | gag | att | ctg | agc | agt | caa | tat | cgt | aga | ccg | cac | 1152
| Thr | Thr | Val | Val | Leu | Glu | Ile | Leu | Ser | Ser | Gln | Tyr | Arg | Arg | Pro | His |
| | 370 | | | | 375 | | | | | 380 | | | | | |

| | | | | | | | | | | | | | | | | |
|---|---|---|---|---|---|---|---|---|---|---|---|---|---|---|---|---|
| ttt | caa | ctg | att | tca | cgg | tgg | aaa | ggg | ttg | gac | tac | cac | gca | att | aat | 1200 |
| Phe | Gln | Leu | Ile | Ser | Arg | Trp | Lys | Gly | Leu | Asp | Tyr | His | Ala | Ile | Asn | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| ctt | gcc | ggg | tcg | tat | gct | gat | cct | cgg | gag | gtg | gtc | gag | aaa | ttg | act | 1248 |
| Leu | Ala | Gly | Ser | Tyr | Ala | Asp | Pro | Arg | Glu | Val | Val | Glu | Lys | Leu | Thr | |
| | | | | 405 | | | | | 410 | | | | | 415 | | |

| | | | | | | | |
|---|---|---|---|---|---|---|---|
| ggc | ata | gtc | gat | ggg | ctt | gga | tgt | tga | 1275 |
| Gly | Ile | Val | Asp | Gly | Leu | Gly | Cys | * | |
| | | | 420 | | | | | | |

<210> SEQ ID NO 21
<211> LENGTH: 424
<212> TYPE: PRT
<213> ORGANISM: Lemna minor

<400> SEQUENCE: 21

Cys Glu Ala Tyr Phe Gly Asn Ser Phe Asn Arg Arg Thr Glu Met Leu
 1               5                  10                  15

Lys Lys Val Glu Gly Arg Gly Trp Phe Gln Cys Leu Tyr Ser Asp Thr
            20                  25                  30

Leu Arg Ser Ser Val Cys Gln Gly Gly Asn Leu Arg Met Asp Pro Glu
        35                  40                  45

Arg Ile Arg Met Ser Lys Gly Gly Glu Asp Leu Glu Glu Val Met Lys
    50                  55                  60

Arg Glu Glu Glu Glu Leu Pro Lys Phe Glu Gly Ser Phe Gln
65                  70                  75                  80

Ile Glu Ser Gly Tyr Gly Ser Gly Gly Glu Val Gly Glu Arg Ile Ala
                85                  90                  95

Thr Asp Glu Val Leu Asp Asn Val Val Pro Lys Gly Ala Val His Val
            100                 105                 110

His Thr Met Arg Asn Leu Ile Ser Ile Gln Ile Val Gly Pro Gly
        115                 120                 125

His Leu Gln Cys Ser Gln Trp Ile Asp Glu Pro Val Leu Leu Val Thr
    130                 135                 140

Arg Phe Glu Tyr Ala Asn Leu Phe His Thr Val Thr Asp Trp Tyr Ser
145                 150                 155                 160

Ala Tyr Ala Ser Ser Arg Ile Ala Asn Leu Pro Ser Arg Pro His Leu
                165                 170                 175

Ile Phe Val Asp Gly His Cys Arg Ala Glu Gln Leu Glu Asp Thr Trp
            180                 185                 190

Arg Ala Leu Phe Ser Thr Val Arg Tyr Ala Lys Asn Phe Ser Gln Pro
        195                 200                 205

Val Cys Phe Arg His Ala Val Leu Ser Pro Leu Gly Tyr Glu Thr Ala
    210                 215                 220

Leu Phe Lys Gly Leu Ser Glu Ser Phe Ser Cys Glu Gly Val Pro Ala
225                 230                 235                 240

Asn Gln Leu Lys Val Asn Pro Asp Asp Gln Lys Thr Ala Arg Leu Ala
                245                 250                 255

Glu Phe Gly Glu Met Ile Arg Ala Ala Phe Asp Phe Pro Val Val Asp
            260                 265                 270

Pro Pro Val Asp Pro Leu Thr Lys Ser Ile Leu Phe Val Arg Arg Glu
        275                 280                 285

Asp Tyr Val Ala His Pro Arg His Ser Gly Arg Val Glu Ser Arg Leu
    290                 295                 300

```
Thr Asn Glu Gln Glu Val Phe Asp Phe Leu His Lys Trp Ala Ser Gln
305                 310                 315                 320

His Arg Ser Arg Cys Asn Val Ser Val Val Asn Gly Leu Phe Ala His
            325                 330                 335

Met Gly Met Lys Glu Gln Val Lys Ala Ile Met Glu Ala Ser Val Val
        340                 345                 350

Val Gly Ala His Gly Ala Gly Leu Thr His Leu Val Ala Ala Arg Ser
    355                 360                 365

Thr Thr Val Val Leu Glu Ile Leu Ser Ser Gln Tyr Arg Arg Pro His
370                 375                 380

Phe Gln Leu Ile Ser Arg Trp Lys Gly Leu Asp Tyr His Ala Ile Asn
385                 390                 395                 400

Leu Ala Gly Ser Tyr Ala Asp Pro Arg Glu Val Val Glu Lys Leu Thr
                405                 410                 415

Gly Ile Val Asp Gly Leu Gly Cys
            420
```

<210> SEQ ID NO 22
<211> LENGTH: 28
<212> TYPE: DNA
<213> ORGANISM: Artificial Sequence
<220> FEATURE:
<223> OTHER INFORMATION: primer

<400> SEQUENCE: 22
atggtcgact gctgctggtg ctctcaac                                  28

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23
atgtctagaa tgcagcagca agtgcacc                                  28

<210> SEQ ID NO 24
<211> LENGTH: 33
<212> TYPE: DNA
<213> ORGANISM: Artificial Sequence
<220> FEATURE:
<223> OTHER INFORMATION: primer

<400> SEQUENCE: 24
atgactagtt gcgaagccta cttcggcaac agc                            33

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
atgggatccg aatctcaaga acaactgtcg                                30

<210> SEQ ID NO 26
<211> LENGTH: 33
<212> TYPE: DNA
<213> ORGANISM: Artificial Sequence
<220> FEATURE:
<223> OTHER INFORMATION: primer -continued

<400> SEQUENCE: 26
atgggtacct gcgaagccta cttcggcaac agc                                    33

<210> SEQ ID NO 27
<211> LENGTH: 29
<212> TYPE: DNA
<213> ORGANISM: Artificial Sequence
<220> FEATURE:
<223> OTHER INFORMATION: primer

<400> SEQUENCE: 27
atgggatcca ctggctggga gaagttctt                                         29

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
atggagctct gctgctggtg ctctcaac                                          28

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29
atgggtacca tgcagcagca agtgcacc                                          28

<210> SEQ ID NO 30
<211> LENGTH: 487
<212> TYPE: PRT
<213> ORGANISM: Triticum aestivum

<400> SEQUENCE: 30

```
Met Lys Gly Ser His Ser Gln Ser Gln Ala Ala Ser Arg Arg Arg Arg
 1               5                  10                  15

Cys Gly Trp Leu Leu Pro Leu Val Gly Val Ala Phe Val Gly Glu
            20                  25                  30

Ile Ala Phe Leu Gly Arg Leu Asp Met Ser Lys Asn Ala Ala Val
        35                  40                  45

Glu Ser Trp Thr Thr Ser Phe Tyr Arg Leu Ser Ser Thr Trp Gly Ala
 50                  55                  60

Asp Ala Pro Pro Gly Ser Gly Asp Asp Asp Glu Cys Glu Arg
 65                  70                  75                  80

Leu Glu Arg Glu Asp Ala Val Pro Tyr Asp Arg Asp Phe Glu Arg Asp
                85                  90                  95

Pro Val Leu Val Gly Gly Ala Ala Lys Asp Trp Asn Arg Cys Ser Val
            100                 105                 110

Gly Cys Glu Phe Gly Phe Pro Ala Ser Lys Thr Pro Asp Ala Thr Phe
        115                 120                 125

Gly Ile Ala Pro Asp Pro Ser Val Glu Ser Ile Leu Arg Ser Met Glu
    130                 135                 140

Ser Ser Gln Tyr Tyr Ser Glu Asn Asn Ile Asn Ala Ala Arg Gly Arg
145                 150                 155                 160

Gly Tyr Gln Ile Val Met Thr Thr Ser Leu Ser Ser Asp Val Pro Val
```

```
            165                 170                 175
Gly Tyr Phe Ser Trp Ala Glu Tyr Asp Ile Met Ala Pro Val Pro Pro
                180                 185                 190

Lys Thr Glu Glu Ala Leu Ala Ala Phe Ile Ser Asn Cys Gly Ala
            195                 200                 205

Arg Asn Phe Arg Leu Gln Ala Leu Glu Met Leu Glu Ser Leu Asp Val
210                 215                 220

Lys Ile Asp Ser Tyr Gly Ser Cys His Arg Asn Arg Asp Gly Lys Val
225                 230                 235                 240

Asp Lys Val Glu Thr Leu Lys Arg Tyr Lys Phe Ser Leu Ala Phe Glu
                245                 250                 255

Asn Ser Gly Glu Glu Asp Tyr Val Thr Glu Lys Phe Phe Gln Ser Leu
                260                 265                 270

Val Thr Gly Ala Ile Pro Val Val Gly Ala Pro Asn Ile Gln Glu
            275                 280                 285

Phe Ser Pro Gly Glu Gly Ala Ile Leu His Ile Lys Glu Leu Asp Asp
        290                 295                 300

Val Ile Ser Val Ala Lys Thr Met Lys His Ile Ala Ser Asn Pro Asp
305                 310                 315                 320

Ala Phe Asn Gln Ser Leu Arg Trp Lys Tyr Asp Gly Pro Ser Asp Ser
                325                 330                 335

Phe Lys Ala Leu Ile Asp Met Ala Val His Ser Ser Cys Arg Leu
            340                 345                 350

Cys Ile His Ile Ala Thr Lys Ile His Glu Lys Glu Arg Thr Pro
        355                 360                 365

Lys Phe Met Asn Arg Ser Cys Ser Cys Ser Ser Lys Arg Gly Thr Val
        370                 375                 380

Tyr His Leu Phe Val Arg Glu Arg Gly Arg Phe Lys Thr Glu Ser Ile
385                 390                 395                 400

Tyr Leu Arg Ser Asp Gln Leu Thr Leu Gly Ala Leu Glu Ser Ala Val
                405                 410                 415

His Gly Lys Phe Arg Ser Leu Lys His Val Pro Val Trp Lys Asp Glu
            420                 425                 430

Arg Pro Ser Ser Ile Arg Gly Gly Asp Glu Leu Lys Val Tyr Lys Ile
            435                 440                 445

Tyr Pro Ile Gly Leu Thr Glu Arg Gln Ala Leu Tyr Lys Phe Gln Phe
        450                 455                 460

Ser Asp Asp Ala Glu Val Ala Arg Tyr Ile Lys Gly His Pro Cys Ala
465                 470                 475                 480

Lys Leu Glu Val Ile Phe Val
                485

<210> SEQ ID NO 31
<211> LENGTH: 486
<212> TYPE: PRT
<213> ORGANISM: Hordeum vulgare

<400> SEQUENCE: 31

Met Gly Ser His Ser Leu Thr Gln Ala Ala Ser Arg Arg Arg Cys
1               5                   10                  15

Gly Trp Leu Leu Pro Leu Val Val Gly Val Ala Phe Leu Gly Glu Ile
                20                  25                  30

Ala Phe Leu Gly Arg Leu Asp Met Ser Lys Asn Ala Ala Ala Val Glu
            35                  40                  45

Ser Trp Thr Thr Ser Phe His Arg Leu Ser Ser Thr Trp Gly Ala Asp
```

```
             50                  55                  60
Ala Pro Pro Gly Ser Gly Asp Asp Glu Glu Cys Glu Glu Arg Leu
 65                  70                  75                  80

Glu Arg Asp Asp Ala Val Pro Tyr Asp Arg Asp Phe Glu Arg His Pro
                 85                  90                  95

Val Leu Val Gly Gly Ala Ala Lys Asp Trp Asn Arg Cys Ser Val Gly
                100                 105                 110

Cys Glu Phe Gly Phe Pro Ala Ser Lys Thr Pro Asp Ala Thr Phe Gly
                115                 120                 125

Ile Ala Pro Asp Pro Ser Val Glu Ser Ile Leu Arg Ser Met Glu Ser
130                 135                 140

Ser Gln Tyr Tyr Ser Glu Asn Asn Ile Asn Ala Ala Arg Gly Arg Gly
145                 150                 155                 160

Tyr Gln Ile Val Met Thr Thr Ser Leu Ser Ser Asp Val Pro Val Gly
                165                 170                 175

Tyr Phe Ser Trp Ala Glu Tyr Asp Ile Met Ala Pro Val Pro Pro Lys
                180                 185                 190

Thr Glu Glu Ala Leu Ala Ala Ala Phe Ile Ser Asn Cys Gly Ala Arg
                195                 200                 205

Asn Phe Arg Leu Gln Ala Leu Glu Met Leu Glu Ser Leu Asp Val Lys
210                 215                 220

Ile Asp Ser Tyr Gly Ser Cys His Arg Asn Arg Asp Gly Lys Val Asp
225                 230                 235                 240

Lys Val Glu Thr Leu Lys Gly Tyr Lys Phe Ser Leu Ala Phe Glu Asn
                245                 250                 255

Ser Asn Glu Glu Asp Tyr Val Thr Glu Lys Phe Phe Gln Ser Leu Val
                260                 265                 270

Thr Gly Ala Ile Pro Val Val Gly Ala Pro Asn Ile Gln Glu Phe
                275                 280                 285

Ser Pro Gly Glu Asp Ala Ile Leu His Ile Lys Glu Leu Asp Asp Val
                290                 295                 300

Ile Ser Val Ala Lys Thr Met Lys His Ile Ala Ser Asn Pro Asp Ala
305                 310                 315                 320

Phe Asn Gln Ser Leu Arg Trp Lys Tyr Asp Gly Pro Ser Asp Ser Phe
                325                 330                 335

Lys Ala Leu Ile Asp Met Ala Ala Val His Ser Ser Cys Arg Leu Cys
                340                 345                 350

Ile His Ile Ala Thr Lys Ile His Glu Lys Glu Lys Thr Pro Lys
                355                 360                 365

Phe Met Asn Arg Ser Cys Ser Cys Ser Ser Lys Arg Gly Thr Val Tyr
370                 375                 380

His Leu Phe Val Arg Glu Arg Gly Arg Phe Lys Thr Glu Asn Ile Tyr
385                 390                 395                 400

Leu Arg Ser Asp Gln Leu Thr Leu Gly Ala Leu Lys Ser Ala Val His
                405                 410                 415

Asp Lys Phe Ser Ser Leu Lys His Val Pro Ile Trp Lys Asp Glu Arg
                420                 425                 430

Pro Ser Ser Ile Arg Gly Gly Asp Glu Leu Lys Val Tyr Lys Ile Tyr
                435                 440                 445

Pro Ile Gly Leu Thr Glu Arg Gln Ala Leu Tyr Lys Phe Gln Phe Ser
                450                 455                 460

Asp Asp Ala Glu Val Ala Arg Tyr Ile Lys Gly His Pro Cys Ala Lys
465                 470                 475                 480
```

-continued

```
Leu Glu Val Ile Phe Val
            485

<210> SEQ ID NO 32
<211> LENGTH: 513
<212> TYPE: PRT
<213> ORGANISM: Oryza sativa

<400> SEQUENCE: 32

Met Lys Gly Ser His Ser Gln Ser Gln Ala Gln Ala Gln Ser Gln Ala
1               5                   10                  15

Gly Arg Arg Arg Cys Gly Trp Leu Leu Pro Leu Leu Val Gly Ala
            20                  25                  30

Ala Phe Leu Ala Glu Ile Ala Phe Leu Gly Arg Leu Asp Met Ala Lys
        35                  40                  45

Asn Ala Ala Val Glu Ser Trp Thr Thr Ser Phe Tyr Ala Arg Ser
    50                  55                  60

Ser Ala Pro Ala Arg Asp Gly Lys Ala Ala Val Val Pro Gly Ala
65              70                  75                  80

Asp Ala Asp Ala Pro Pro Gly Gly Glu Val Val Glu Asp
                85                  90                  95

Asp Gly Asp Ile Arg Leu Cys Glu Glu Arg Leu Glu Arg Glu Asp Gly
                100                 105                 110

Val Pro His Asp Arg Asp Phe Asp Lys Asp Pro Val Leu Val Gly Gly
            115                 120                 125

Ala Ala Lys Asp Trp Asn Lys Cys Ser Val Gly Cys Glu Phe Gly Phe
        130                 135                 140

Ser Ala Thr Lys Thr Pro Asp Ala Thr Phe Gly Ile Ala Pro Asp Pro
145                 150                 155                 160

Thr Val Glu Ser Ile Leu Arg Ser Met Glu Ser Ser Gln Tyr Tyr Ser
                165                 170                 175

Glu Asn Asn Ile Ala Val Ala Arg Gly Arg Gly Tyr Lys Ile Val Met
            180                 185                 190

Thr Thr Ser Leu Ser Ser Asp Val Pro Val Gly Tyr Phe Ser Trp Ala
        195                 200                 205

Glu Tyr Asp Ile Met Ala Pro Val Pro Pro Lys Thr Glu Glu Ala Leu
    210                 215                 220

Ala Ala Ala Phe Ile Ser Asn Cys Gly Ala Arg Asn Phe Arg Leu Gln
225                 230                 235                 240

Ala Leu Glu Met Leu Glu Ser Leu Asp Val Lys Ile Asp Ser Tyr Gly
                245                 250                 255

Ser Cys His Arg Asn His Asp Gly Lys Val Asp Lys Val Glu Thr Leu
            260                 265                 270

Lys Arg Tyr Lys Phe Ser Leu Ala Phe Glu Asn Ser Asn Glu Glu Asp
        275                 280                 285

Tyr Val Thr Glu Lys Phe Phe Gln Ser Leu Val Thr Gly Ala Ile Pro
    290                 295                 300

Val Val Ile Gly Ala Pro Asn Ile Gln Glu Phe Ser Pro Gly Glu Gly
305                 310                 315                 320

Ala Ile Leu His Ile Lys Glu Leu Asp Asp Val Pro Ser Ile Ala Lys
                325                 330                 335

Thr Met Lys His Ile Ala Ser Asn Gln Glu Ala Phe Asn Gln Ser Leu
            340                 345                 350

Arg Trp Lys Tyr Asp Gly Pro Ser Asp Ser Phe Lys Ala Leu Ile Asp
        355                 360                 365
```

```
Met Ala Ala Val His Ser Ser Cys Arg Leu Cys Ile His Val Ala Thr
        370                 375                 380
Lys Ile His Glu Lys Glu Arg Thr Pro Lys Phe Met Asn Arg Pro
385                 390                 395                 400
Cys Ser Cys Ser Ser Lys Arg Gly Lys Val Tyr His Leu Phe Val Arg
                405                 410                 415
Glu Arg Gly Arg Phe Lys Thr Glu Ser Ile Phe Leu Arg Ser Asp Gln
                420                 425                 430
Leu Thr Met Gly Ala Leu Glu Ser Ala Val Leu Ala Lys Phe Arg Ser
        435                 440                 445
Leu Asn His Val Pro Val Trp Lys Asp Glu Arg Pro Pro Ser Ile Arg
450                 455                 460
Gly Gly Asp Glu Leu Lys Val Tyr Lys Ile Tyr Pro Ile Gly Leu Thr
465                 470                 475                 480
Gln Arg Gln Ala Leu Tyr Gln Phe Arg Phe Arg Asp Asp Ala Asp Leu
                485                 490                 495
Asp Lys Tyr Ile Lys Asp His Pro Cys Ala Lys Leu Glu Val Ile Phe
                500                 505                 510
Val

<210> SEQ ID NO 33
<211> LENGTH: 506
<212> TYPE: PRT
<213> ORGANISM: Medicago sativa

<400> SEQUENCE: 33

Met Gly Leu Val Ser Arg Thr Thr Thr Thr Thr Gln Glu Gly Leu
1               5                   10                  15
Pro Val Ser Val Ser Val Ser Thr Thr Val Pro Lys Lys Lys Trp Ser
                20                  25                  30
Asn Leu Met Pro Leu Phe Val Ala Leu Val Val Ile Ala Glu Ile Ala
            35                  40                  45
Phe Leu Gly Arg Leu Asp Met Ala Lys Asn Ala Ala Met Val Ala Asp
        50                  55                  60
Leu Phe Tyr Arg Ser Arg Ala Val Val Glu Gly Asp Asp Phe Gly Leu
65                  70                  75                  80
Glu Thr Val Gly Gly Asp Lys Asn Leu Glu Leu Glu Arg Glu Thr Cys
                85                  90                  95
Glu Glu Trp Leu Glu Arg Glu Asp Ala Val Thr Tyr Ser Arg Asn Phe
                100                 105                 110
Asn Lys Glu Pro Val Phe Val Ser Gly Ala Glu Gln Glu Trp Lys Ser
            115                 120                 125
Cys Ser Val Gly Cys Lys Phe Gly Phe Asn Gly Asp Arg Lys Pro Glu
        130                 135                 140
Ala Ala Phe Gly Leu Pro Gln Gln Ala Gly Thr Ala Ser Val Leu Arg
145                 150                 155                 160
Ser Met Glu Ser Ala Gln Tyr Tyr Ala Glu Asn Asn Leu Ala Met Ala
                165                 170                 175
Arg Arg Arg Gly Tyr His Ile Val Met Thr Thr Ser Leu Ser Ser Asp
                180                 185                 190
Val Pro Val Gly Tyr Phe Ser Trp Ala Glu Tyr Asp Ile Met Ala Pro
            195                 200                 205
Ile Lys Pro Lys Thr Glu Lys Ala Leu Ala Ala Phe Ile Ser Asn
        210                 215                 220
Cys Gly Ala Arg Asn Phe Arg Leu Gln Ala Leu Glu Ala Leu Glu Lys
```

```
                      225                 230                 235                 240

Thr Asn Ile Ser Ile Asp Ser Tyr Gly Ser Cys His Arg Asn Arg Asp
                        245                 250                 255

Gly Arg Val Asp Lys Leu Glu Thr Leu Thr Arg Tyr Lys Phe Ser Leu
                        260                 265                 270

Ala Phe Glu Asn Ser Asn Glu Glu Asp Tyr Val Thr Glu Lys Phe Phe
                        275                 280                 285

Gln Ser Leu Val Ala Gly Thr Ile Pro Val Val Gly Pro Pro Asn
                        290                 295                 300

Ile Gln Asp Phe Ala Pro Ser Pro Asp Ser Phe Leu Tyr Ile Lys Glu
        305                 310                 315                 320

Leu Glu Asp Val Glu Ser Val Ala Lys Ser Met Arg Tyr Leu Ala Glu
                        325                 330                 335

Asn Pro Glu Ala Tyr Asn His Ser Leu Arg Trp Lys Tyr Glu Gly Pro
                        340                 345                 350

Ser Asp Ser Phe Lys Ala Leu Val Asp Met Ala Ala Val His Ser Ser
                        355                 360                 365

Cys Arg Leu Cys Ile His Leu Ala Thr Lys Ser Arg Glu Lys Glu Glu
                        370                 375                 380

Lys Ser Pro Asp Phe Lys Lys Arg Pro Cys Lys Cys Thr Arg Gly Ser
        385                 390                 395                 400

Glu Thr Val Tyr His Ile Tyr Val Arg Glu Arg Gly Thr Phe Glu Met
                        405                 410                 415

Glu Ser Ile Tyr Leu Arg Ser Ser Asn Leu Thr Leu Glu Ser Phe Lys
                        420                 425                 430

Thr Ala Val Leu Thr Lys Phe Thr Ser Leu Asn His Val Pro Val Trp
                        435                 440                 445

Lys Pro Glu Arg Pro Glu Ile Leu Lys Gly Gly Asp Lys Leu Lys Val
        450                 455                 460

Tyr Lys Ile Ile Pro Ala Gly Leu Thr Gln Arg Gln Ala Leu Tyr Thr
        465                 470                 475                 480

Phe Gln Phe Asn Gly Asp Val Asp Phe Arg Ser His Leu Glu Ser Asn
                        485                 490                 495

Pro Cys Ala Lys Phe Glu Val Ile Phe Val
                        500                 505

<210> SEQ ID NO 34
<211> LENGTH: 513
<212> TYPE: PRT
<213> ORGANISM: Arabidopsis thaliana

<400> SEQUENCE: 34

Met Gly Val Phe Ser Asn Leu Arg Gly Pro Arg Ala Gly Ala Thr His
         1               5                  10                  15

Asp Glu Phe Pro Ala Thr Asn Gly Ser Pro Ser Ser Ser Ser Ser Pro
                        20                  25                  30

Ser Ser Ser Ile Lys Arg Lys Leu Ser Asn Leu Leu Pro Leu Cys Val
                        35                  40                  45

Ala Leu Val Val Ile Ala Glu Ile Gly Phe Leu Gly Arg Leu Asp Lys
                        50                  55                  60

Val Ala Leu Val Asp Thr Leu Asp Phe Phe Thr Gln Ser Pro Ser
        65                  70                  75                  80

Leu Ser Gln Ser Pro Pro Ala Arg Ser Asp Arg Lys Lys Ile Gly Leu
                        85                  90                  95

Phe Thr Asp Arg Ser Cys Glu Glu Trp Leu Met Arg Glu Asp Ser Val
```

```
                100             105             110
Thr Tyr Ser Arg Asp Phe Thr Lys Asp Pro Ile Phe Ile Ser Gly Gly
            115                 120             125

Glu Lys Asp Phe Gln Trp Cys Ser Val Asp Cys Thr Phe Gly Asp Ser
        130                 135             140

Ser Gly Lys Thr Pro Asp Ala Ala Phe Gly Leu Gly Gln Lys Pro Gly
145                 150                 155                 160

Thr Leu Ser Ile Ile Arg Ser Met Glu Ser Ala Gln Tyr Tyr Pro Glu
            165                 170                 175

Asn Asp Leu Ala Gln Ala Arg Arg Gly Tyr Asp Ile Val Met Thr
        180                 185                 190

Thr Ser Leu Ser Ser Asp Val Pro Val Gly Tyr Phe Ser Trp Ala Glu
        195                 200                 205

Tyr Asp Ile Met Ser Pro Val Gln Pro Lys Thr Glu Arg Ala Ile Ala
        210                 215                 220

Ala Ala Phe Ile Ser Asn Cys Gly Ala Arg Asn Phe Arg Leu Gln Ala
225                 230                 235                 240

Leu Glu Ala Leu Met Lys Thr Asn Ile Lys Ile Asp Ser Tyr Gly Gly
            245                 250                 255

Cys His Arg Asn Arg Asp Gly Lys Val Asp Lys Val Glu Ala Leu Lys
            260                 265                 270

Arg Tyr Lys Phe Ser Leu Ala Phe Glu Asn Thr Asn Glu Glu Asp Tyr
        275                 280                 285

Val Thr Glu Lys Phe Phe Gln Ser Leu Val Ala Gly Ser Val Pro Val
        290                 295                 300

Val Val Gly Pro Pro Asn Ile Glu Glu Phe Ala Pro Ala Ser Asp Thr
305                 310                 315                 320

Phe Leu His Ile Lys Thr Met Glu Asp Val Glu Pro Val Ala Lys Arg
            325                 330                 335

Met Lys Tyr Leu Ala Ala Asn Pro Ala Ala Tyr Asn Gln Thr Leu Arg
            340                 345                 350

Trp Lys Tyr Glu Gly Pro Ser Asp Ser Phe Lys Ala Leu Val Asp Met
            355                 360                 365

Ala Ala Val His Ser Ser Cys Arg Leu Cys Ile Phe Leu Ala Thr Arg
        370                 375                 380

Val Arg Glu Gln Glu Glu Ser Pro Asn Phe Lys Lys Arg Pro Cys
385                 390                 395                 400

Lys Cys Ser Arg Gly Gly Ser Asp Thr Val Tyr His Val Phe Val Arg
            405                 410                 415

Glu Arg Gly Arg Phe Glu Met Glu Ser Val Phe Leu Arg Gly Lys Ser
            420                 425                 430

Val Thr Gln Glu Ala Leu Glu Ser Ala Val Leu Ala Lys Phe Lys Ser
        435                 440                 445

Leu Lys His Glu Ala Val Trp Lys Lys Glu Arg Pro Gly Asn Leu Lys
        450                 455                 460

Gly Asp Lys Glu Leu Lys Ile His Arg Ile Tyr Pro Leu Gly Leu Thr
465                 470                 475                 480

Gln Arg Gln Ala Leu Tyr Asn Phe Lys Phe Glu Gly Asn Ser Ser Leu
            485                 490                 495

Ser Ser His Ile Gln Asn Asn Pro Cys Ala Lys Phe Glu Val Val Phe
            500                 505                 510

Val
```

<210> SEQ ID NO 35
<211> LENGTH: 475
<212> TYPE: PRT
<213> ORGANISM: Artificial Sequence
<220> FEATURE:
<223> OTHER INFORMATION: Consensus Sequence

<400> SEQUENCE: 35

```
Gly Ser His Ser Ser Ala Ala Ala Ser Arg Arg Arg Cys Gly
 1               5                  10                  15

Trp Leu Leu Pro Leu Leu Val Gly Leu Ala Val Ile Ala Glu Ile Ala
                 20                  25                  30

Phe Leu Gly Arg Leu Asp Met Ala Lys Asn Ala Ala Val Glu Ser
             35                  40                  45

Trp Thr Thr Ser Phe Tyr Ala Leu Ser Ser Gly Ala Asp Ala Pro Pro
     50                  55                  60

Gly Ser Gly Asp Asp Glu Glu Cys Glu Glu Trp Leu Glu Arg Glu Asp
 65                  70                  75                  80

Ala Val Pro Tyr Asp Arg Asp Phe Glu Lys Asp Pro Val Leu Val Gly
                 85                  90                  95

Gly Ala Glu Lys Asp Trp Asn Arg Cys Ser Val Gly Cys Glu Phe Gly
                100                 105                 110

Phe Ala Ser Lys Thr Pro Asp Ala Thr Phe Gly Ile Ala Gln Asp Pro
             115                 120                 125

Ser Val Glu Ser Ile Leu Arg Ser Met Glu Ser Ser Gln Tyr Tyr Ser
130                 135                 140

Glu Asn Asn Ile Ala Ala Arg Arg Gly Tyr Gln Ile Val Met Thr
145                 150                 155                 160

Thr Ser Leu Ser Ser Asp Val Pro Val Gly Tyr Phe Ser Trp Ala Glu
                165                 170                 175

Tyr Asp Ile Met Ala Pro Val Pro Pro Lys Thr Glu Glu Ala Leu Ala
             180                 185                 190

Ala Ala Phe Ile Ser Asn Cys Gly Ala Arg Asn Phe Arg Leu Gln Ala
         195                 200                 205

Leu Glu Met Leu Glu Ser Leu Asn Ile Lys Ile Asp Ser Tyr Gly Ser
210                 215                 220

Cys His Arg Asn Arg Asp Gly Lys Val Asp Lys Val Glu Thr Leu Lys
225                 230                 235                 240

Arg Tyr Lys Phe Ser Leu Ala Phe Glu Asn Ser Asn Glu Glu Asp Tyr
                245                 250                 255

Val Thr Glu Lys Phe Phe Gln Ser Leu Val Thr Gly Ala Ile Pro Val
             260                 265                 270

Val Val Gly Ala Pro Asn Ile Gln Glu Phe Ala Pro Gly Glu Asp Ala
         275                 280                 285

Ile Leu His Ile Lys Glu Leu Asp Asp Val Ser Val Ala Lys Thr Met
290                 295                 300

Lys His Ile Ala Ser Asn Pro Glu Ala Phe Asn Gln Ser Leu Arg Trp
305                 310                 315                 320

Lys Tyr Asp Gly Pro Ser Asp Ser Phe Lys Ala Leu Ile Asp Met Ala
                325                 330                 335

Ala Val His Ser Ser Cys Arg Leu Cys Ile His Ile Ala Thr Lys Ile
             340                 345                 350

Arg Glu Lys Glu Glu Arg Thr Pro Lys Phe Met Asn Arg Pro Cys Ser
         355                 360                 365

Cys Ser Ser Lys Arg Gly Thr Val Tyr His Leu Phe Val Arg Glu Arg
370                 375                 380
```

```
Gly Arg Phe Lys Thr Glu Ser Ile Phe Leu Arg Ser Asp Gln Leu Thr
385                 390                 395                 400

Leu Gly Ala Leu Glu Ser Ala Val Leu Ala Lys Phe Ser Ser Leu Lys
            405                 410                 415

His Val Pro Val Trp Lys Asp Glu Arg Pro Ser Ile Lys Gly Gly Asp
        420                 425                 430

Glu Leu Lys Val Tyr Lys Ile Tyr Pro Ile Gly Leu Thr Gln Arg Gln
    435                 440                 445

Ala Leu Tyr Phe Gln Phe Asp Asp Ala Glu Leu Ala Arg Tyr Ile Lys
450                 455                 460

His Pro Cys Ala Lys Leu Glu Val Ile Phe Val
465                 470                 475

<210> SEQ ID NO 36
<211> LENGTH: 511
<212> TYPE: PRT
<213> ORGANISM: Medicago sativa

<400> SEQUENCE: 36

Met Asn Lys Lys Val Gln Ile Leu Leu Phe Leu Phe Ile Phe Asn Ser
1               5                   10                  15

Phe Ser Leu Cys Leu Tyr Phe Ile His His Pro Ser Phe Leu Asn Pro
            20                  25                  30

Thr Pro Ser Pro Asn Pro Asp Ile Lys Ile Phe Thr Lys Asp Ser Pro
        35                  40                  45

Phe Arg Arg Pro Phe Ile Glu Lys His Lys Thr His Ile Leu Lys Pro
    50                  55                  60

Trp Pro Ile Leu Pro Ser Tyr Ser Pro Trp Ser Gln Pro Ser Asn Ser
65                  70                  75                  80

Thr Pro Leu Arg Ser Cys Glu Gly Tyr Phe Gly Asn Gly Phe Thr Arg
                85                  90                  95

Leu Val Asp Val Phe Ser Ser Arg Ala Glu Gly Arg Gly Gly Gly Trp
            100                 105                 110

Phe Arg Cys Trp Tyr Ser Glu Thr Leu Arg Ser Ser Val Cys Glu Gly
        115                 120                 125

Gly Arg Val Arg Met Val Val Glu Arg Ile Lys Met Ala Lys Gly Gly
    130                 135                 140

Glu Ser Leu Gly Asp Val Ile Gly Arg Ser Glu Asp Glu Glu Leu Pro
145                 150                 155                 160

Leu Phe Glu Asp Gly Ala Phe Glu Val Asp Gly Val Gly Phe Lys
                165                 170                 175

Gly Gly Lys Met Val Val Asp Glu Gly Phe Leu Asp Arg Tyr Val Pro
            180                 185                 190

Arg Gly Glu Ile Met Arg His Thr Met Arg Asp Leu Ile Gly Lys Met
        195                 200                 205

Lys Val Val Gly Arg Lys Glu Phe Lys Cys Asp Lys Trp Ile Glu Glu
    210                 215                 220

Pro Thr Leu Leu Val Thr Arg Phe Glu Tyr Ala Asn Leu Phe His Thr
225                 230                 235                 240

Val Thr Asp Trp Tyr Ser Ala Tyr Val Ser Ser Arg Val Thr Gly Leu
                245                 250                 255

Pro Ser Arg Pro His Leu Ile Phe Val Asp Gly His Cys Lys Ala Pro
            260                 265                 270

Leu Glu Glu Thr Trp Lys Ala Leu Phe Ser Ser Val Arg Tyr Ala Lys
        275                 280                 285
```

```
Asn Phe Thr Gly Thr Val Cys Phe Arg His Ala Ile Leu Ser Pro Leu
    290                 295                 300

Gly Tyr Glu Thr Ala Leu Phe Lys Gly Leu Thr Glu Asp Ile Phe Cys
305                 310                 315                 320

Asp Gly Ala Ser Ala Gln Glu Leu Trp Arg Lys Pro Asn Glu Lys
                325                 330                 335

Thr Ala Arg Ile Ser Glu Phe Gly Glu Met Ile Arg Ala Ser Phe Gly
                340                 345                 350

Leu Pro Leu Asn Leu Asn His Val Gly Lys Pro Ile Phe Gly Gly His
                355                 360                 365

Asn Ala Leu Phe Val Arg Arg Glu Asp Tyr Leu Ala His Pro Arg His
    370                 375                 380

Gly Gly Lys Val Glu Ser Arg Leu Thr Asn Glu Ala Glu Val Phe Glu
385                 390                 395                 400

Ser Leu Lys Ser Trp Ala Ala Asn Tyr Lys Gly Cys Lys Ile Asn Leu
                405                 410                 415

Val Asn Gly Leu Phe Ala His Met Ser Met Lys Glu Gln Val Arg Ala
                420                 425                 430

Ile Gln Asp Ala Ser Val Ile Gly Ala His Gly Ala Gly Leu Thr
    435                 440                 445

His Ile Val Ser Ala Leu Pro Lys Thr Val Ile Leu Glu Ile Ser
    450                 455                 460

Ser Gln Phe Arg Arg Pro His Phe Ala Tyr Ile Ala Arg Trp Lys Gly
465                 470                 475                 480

Leu Glu Tyr His Ala Ile Asn Leu Asp Gly Ser Tyr Ala Asn Pro Glu
                485                 490                 495

Thr Val Ile Asn Ala Leu Val Ser Ile Met Lys Ser Leu Arg Cys
                500                 505                 510

<210> SEQ ID NO 37
<211> LENGTH: 533
<212> TYPE: PRT
<213> ORGANISM: Oryza sativa

<400> SEQUENCE: 37

Met Met Pro Val Arg Thr Tyr His His His His His Asn Asn Ser
1               5                   10                  15

Asn Asn His Arg Leu Arg Arg Ile Ile Pro Arg Val Leu Leu Ala Val
                20                  25                  30

Phe Ala Ile Tyr Ala Val Ser Phe Ala Ala Tyr Leu Leu Arg His Gln
                35                  40                  45

Ser Pro His Pro His Pro His Pro Ala Ala Asp Pro Glu Arg Asp Ala
    50                  55                  60

Val Asp Ala Ala Gly Gly Gly Gly Gly Gly Ala Val Asp Arg Val
65                  70                  75                  80

Arg Val Glu Ala Pro Ser Ser Gln Lys Pro Trp Pro Arg Leu Pro Ser
                85                  90                  95

Phe Leu Pro Trp Thr Ser Ala Ser Val Arg Pro Pro Lys His Ser
                100                 105                 110

Cys Glu Gly Tyr Phe Gly Asn Gly Phe Ser Arg Leu Val Asp Val Leu
                115                 120                 125

Pro Ala Arg Gly Gly Gly Gly Gly Trp Phe Arg Cys His His Ser
    130                 135                 140

Glu Thr Leu Arg Ser Ser Ile Cys Glu Gly Gly Arg Val Arg Leu Asp
145                 150                 155                 160
```

Pro Gly Leu Ile Ala Met Ser Arg Gly Glu Pro Leu Asp Gln Val
            165                 170                 175

Met Gly Arg Ala Glu Glu Glu Leu Pro Lys Tyr Glu Pro Gly Ala
            180                 185                 190

Leu Gln Val Glu Ala Ala Lys Arg Thr Gly Pro Leu Val Glu Ala
            195                 200                 205

Gly Phe Leu Asp Ala Tyr Val Pro Thr Gly Ile Gly Met His Thr
            210                 215                 220

Met Arg Ser Leu Leu Asp Ser Gly Arg Val Val Pro Pro Gly Glu Leu
225                 230                 235                 240

His Cys Ser Gln Trp Val Glu Pro Thr Leu Leu Val Thr Arg Phe
            245                 250                 255

Glu Tyr Ala Asn Leu Phe His Thr Ile Thr Asp Trp Tyr Ser Ala Tyr
            260                 265                 270

Val Ser Ser Arg Val Thr Asp Leu Pro Asn Arg Pro Asn Val Val Phe
            275                 280                 285

Val Asp Gly His Cys Lys Ala Gln Leu Glu Gln Thr Trp Glu Ala Leu
            290                 295                 300

Phe Ser Asn Val Thr Tyr Val Lys Asn Phe Ser Gly Pro Val Cys Phe
305                 310                 315                 320

Arg His Ala Ile Leu Ser Pro Leu Gly Tyr Glu Thr Ala Leu Phe Lys
            325                 330                 335

Gly Leu Ser Glu Ser Phe Ser Cys Glu Gly Ala Ser Ala Glu Ser Leu
            340                 345                 350

Arg Glu Lys Pro Asp His Gln Lys Thr Ala Arg Leu Ser Glu Phe Gly
            355                 360                 365

Glu Met Ile Leu Ala Ser Phe Asp Leu Leu Arg Asp Asp Ile Leu Ser
            370                 375                 380

Ser Lys Thr Ser Asn Gly Leu Asn Val Leu Phe Val Arg Arg Glu Asp
385                 390                 395                 400

Tyr Leu Ala His Pro Arg His Ser Gly Lys Val Glu Ser Arg Leu Ser
            405                 410                 415

Asn Glu Lys Glu Val Tyr Asp Ala Ile Glu Gly Trp Ala Lys Gly Gln
            420                 425                 430

Lys Cys Lys Ile Asn Val Ile Asn Gly Leu Phe Ala His Met Asn Met
            435                 440                 445

Lys Glu Gln Leu Arg Ala Ile Gln Glu Ala Ser Val Val Ile Gly Ala
            450                 455                 460

His Gly Ala Gly Leu Thr His Leu Val Ser Ala Thr Pro Asp Thr Lys
465                 470                 475                 480

Val Leu Glu Ile Ile Ser Ser Met Tyr Arg Arg Pro His Phe Ala Leu
            485                 490                 495

Ile Ser His Trp Lys Ser Leu Glu Tyr His Ala Ile Asn Leu Pro Gly
            500                 505                 510

Ser Tyr Ala Arg Val Thr Asp Val Ile Asn Glu Leu Ser Asn Ile Leu
            515                 520                 525

Lys Gly Phe Gly Cys
            530

<210> SEQ ID NO 38
<211> LENGTH: 534
<212> TYPE: PRT
<213> ORGANISM: Arabidopsis thaliana

<400> SEQUENCE: 38

-continued

```
Met Ser Lys Arg Asn Pro Lys Ile Leu Lys Ile Phe Leu Tyr Met Leu
 1               5                  10                  15
Leu Leu Asn Ser Leu Phe Leu Ile Ile Tyr Phe Val Phe His Ser Ser
             20                  25                  30
Ser Phe Ser Pro Glu Gln Ser Gln Pro His Ile Tyr His Val Ser
         35                  40                  45
Val Asn Asn Gln Ser Ala Ile Gln Lys Pro Trp Pro Ile Leu Pro Ser
 50                  55                  60
Tyr Leu Pro Trp Thr Pro Pro Gln Arg Asn Leu Pro Thr Gly Ser Cys
 65                  70                  75                  80
Glu Gly Tyr Phe Gly Asn Gly Phe Thr Lys Arg Val Asp Phe Leu Lys
                 85                  90                  95
Pro Arg Ile Gly Gly Gly Glu Gly Ser Trp Phe Arg Cys Phe Tyr
                100                 105                 110
Ser Glu Thr Leu Gln Ser Ser Ile Cys Glu Gly Arg Asn Leu Arg Met
             115                 120                 125
Val Pro Asp Arg Ile Val Met Ser Arg Gly Gly Glu Lys Leu Glu Glu
130                 135                 140
Val Met Gly Arg Lys Glu Glu Glu Leu Pro Ala Phe Arg Gln Gly
145                 150                 155                 160
Ala Phe Glu Val Ala Glu Glu Val Ser Ser Arg Leu Gly Phe Lys Arg
                165                 170                 175
His Arg Arg Phe Gly Gly Gly Glu Gly Gly Ser Ala Val Ser Arg Arg
             180                 185                 190
Leu Val Asn Asp Glu Met Leu Asn Glu Tyr Met Gln Glu Gly Gly Ile
             195                 200                 205
Asp Arg His Thr Met Arg Asp Leu Val Ala Ser Ile Arg Ala Val Asp
             210                 215                 220
Thr Asn Asp Phe Val Cys Glu Glu Trp Val Glu Pro Thr Leu Leu
225                 230                 235                 240
Val Thr Arg Phe Glu Tyr Ala Asn Leu Phe His Thr Val Thr Asp Trp
                245                 250                 255
Tyr Ser Ala Tyr Val Ser Ser Arg Val Thr Gly Leu Pro Asn Arg Pro
             260                 265                 270
His Val Val Phe Val Asp Gly His Cys Thr Thr Gln Leu Glu Glu Thr
             275                 280                 285
Trp Thr Ala Leu Phe Ser Gly Ile Arg Tyr Ala Lys Asn Phe Thr Lys
290                 295                 300
Pro Val Cys Phe Arg His Ala Ile Leu Ser Pro Leu Gly Tyr Glu Thr
305                 310                 315                 320
Ala Leu Phe Lys Gly Leu Ser Gly Glu Ile Asp Cys Lys Gly Asp Ser
                325                 330                 335
Ala His Asn Leu Trp Gln Asn Pro Asp Asp Lys Arg Thr Ala Arg Ile
             340                 345                 350
Ser Glu Phe Gly Glu Met Ile Arg Ala Ala Phe Gly Leu Pro Val Asn
             355                 360                 365
Arg His Arg Ser Leu Glu Lys Pro Leu Ser Ser Ser Ser Ser Ala
             370                 375                 380
Ser Val Tyr Asn Val Leu Phe Arg Arg Glu Asp Tyr Leu Ala His
385                 390                 395                 400
Pro Arg His Gly Gly Lys Val Gln Ser Arg Leu Ile Asn Glu Glu Glu
                405                 410                 415
Val Phe Asp Ser Leu His His Trp Val Ala Thr Gly Ser Thr Gly Leu
```

```
                         420                 425                 430
Thr Lys Cys Gly Ile Asn Leu Val Asn Gly Leu Leu Ala His Met Ser
                435                 440                 445

Met Lys Asp Gln Val Arg Ala Ile Gln Asp Ala Ser Val Ile Ile Gly
    450                 455                 460

Ala His Gly Ala Gly Leu Thr His Ile Val Ser Ala Thr Pro Asn Thr
465                 470                 475                 480

Thr Ile Phe Glu Ile Ile Ser Val Glu Phe Gln Arg Pro His Phe Glu
                485                 490                 495

Leu Ile Ala Lys Trp Lys Gly Leu Glu Tyr His Ala Met His Leu Ala
                500                 505                 510

Asn Ser Arg Ala Glu Pro Thr Ala Val Ile Glu Lys Leu Thr Glu Ile
            515                 520                 525

Met Lys Ser Leu Gly Cys
    530

<210> SEQ ID NO 39
<211> LENGTH: 515
<212> TYPE: PRT
<213> ORGANISM: Saccharum officinarum

<400> SEQUENCE: 39

Met Met Ala Gly Arg Ala His Gly His Arg Asn Arg Leu Arg Arg Leu
1               5                   10                  15

Ile Pro Arg Leu Leu Leu Val Phe Ala Val Tyr Ala Ala Ser Phe
            20                  25                  30

Ala Ile Tyr Leu Leu Leu Gln Ser Pro Gln Ser Glu Ser His His Gln
            35                  40                  45

Ser Pro Pro Asp Pro Thr Pro Arg Thr Glu Ala Arg Asp Gly Val Gly
    50                  55                  60

Ala Pro Pro Tyr Ser His Lys Pro Trp Pro Arg Leu Pro Ser Cys Leu
65                  70                  75                  80

Pro Trp Val Tyr Ser Ala Ala Pro Pro His Thr Cys Glu Ala Tyr Phe
                85                  90                  95

Gly Asn Gly Phe Ser Arg Arg Val Asp Val Leu Pro Ala Gly Arg Gly
                100                 105                 110

Gly Gly Gly Gly Trp Phe Arg Cys His His Ser Glu Thr Leu Gly Ser
            115                 120                 125

Ser Ile Cys Glu Gly Ala Arg Val Arg Leu Asp Pro Ala Leu Ile Ala
    130                 135                 140

Met Ser Arg Gly Gly Glu Pro Leu Glu Gln Val Met Gly Arg Ala Glu
145                 150                 155                 160

Glu Glu Glu Leu Pro Lys Tyr Glu Pro Ser Ala Leu Gln Val Glu Gly
                165                 170                 175

Pro Ala Ala Gly Lys Thr Ala Pro Leu Val Asp Ala Gly Phe Leu Asn
            180                 185                 190

Asp Tyr Val Pro Asn Gly Gly Ile Arg Met His Thr Met Arg Ala Leu
            195                 200                 205

Leu Asp Ser Ala Arg Val Val Pro Pro Gly Glu Leu His Cys Ser Gln
    210                 215                 220

Trp Val Glu Glu Pro Thr Leu Leu Val Thr Arg Phe Glu Tyr Ala Asn
225                 230                 235                 240

Leu Phe His Thr Ile Thr Asp Trp Tyr Ser Ala Tyr Val Ser Ser Arg
                245                 250                 255

Val Thr Asn Leu Pro Asp Arg Pro Asn Val Val Phe Val Asp Gly His
```

```
                    260                 265                 270
Cys Lys Ala Pro Leu Glu Gln Thr Trp Glu Ala Leu Phe Ser Asn Val
        275                 280                 285
Thr Tyr Ile Lys Ser Phe Ser Gly Pro Val Cys Phe Arg Arg Ala Val
        290                 295                 300
Leu Ser Pro Leu Gly Tyr Glu Thr Ala Leu Phe Lys Gly Leu Ser Glu
305                 310                 315                 320
Ser Phe Ser Cys Glu Gly Ala Ser Ala Gln Ser Leu Arg Asn Arg Pro
                325                 330                 335
Asp His Gln Lys Thr Ala Arg Leu Ser Glu Phe Gly Glu Met Ile Ile
                340                 345                 350
Ala Ser Phe Asp Leu Leu Glu Asp Gly Ile Val Pro Ser Lys Lys Thr
                355                 360                 365
Ser Thr Gly Leu Lys Val Leu Phe Val Arg Arg Glu Asp Tyr Leu Ala
        370                 375                 380
His Pro Arg His Ser Gly Lys Val Glu Ser Arg Leu Ser Asn Glu Gln
385                 390                 395                 400
Glu Val Phe Gly Ala Val Glu Lys Trp Ala Lys Gly Gln Lys Cys
                405                 410                 415
Lys Ile Asn Val Val Asn Gly Leu Phe Ala His Met Ser Met Lys Glu
                420                 425                 430
Gln Leu Gln Ala Ile Leu Glu Ala Ser Val Ile Ile Gly Ala His Gly
                435                 440                 445
Ala Gly Leu Thr His Leu Val Ser Ala Thr Pro Asp Thr Lys Val Leu
        450                 455                 460
Glu Ile Ile Ser Ser Phe Tyr Arg Arg Pro His Phe Ala Leu Ile Ser
465                 470                 475                 480
His Trp Lys Ala Leu Glu Tyr His Ala Ile Asn Leu Pro Gly Ser Tyr
                485                 490                 495
Ala Ser Ile Pro Asp Val Thr Ser Glu Leu Ser Asn Ile Leu Lys Gly
                500                 505                 510
Leu Gly Cys
        515

<210> SEQ ID NO 40
<211> LENGTH: 523
<212> TYPE: PRT
<213> ORGANISM: Nicotiana tabacum

<400> SEQUENCE: 40

Met Asn Lys Lys Lys Leu Lys Phe Leu Val Ser Leu Phe Ala Leu Asn
1               5                   10                  15
Ser Ile Thr Leu Tyr Leu Tyr Phe Ser Ser His Ser Asp His Phe Arg
                20                  25                  30
His Lys Ser Pro Gln Asn His Phe Pro Asn Thr Gln Asn His Tyr Ser
        35                  40                  45
Leu Ser Glu Asn His His Asp Asn Phe His Ser Ser Val Thr Ser Gln
    50                  55                  60
Tyr Thr Lys Pro Trp Pro Ile Leu Pro Ser Tyr Leu Pro Trp Ser Gln
65                  70                  75                  80
Asn Pro Asn Val Ser Leu Arg Ser Cys Glu Gly Tyr Phe Gly Asn Gly
                85                  90                  95
Phe Thr Leu Lys Val Asp Leu Leu Lys Thr Ser Pro Glu Leu His Gln
                100                 105                 110
Lys Phe Gly Glu Asn Thr Val Ser Gly Asp Gly Gly Trp Phe Arg Cys
```

```
            115                 120                 125
Phe Phe Ser Glu Thr Leu Gln Ser Ser Ile Cys Glu Gly Gly Ala Ile
130                 135                 140

Arg Met Asn Pro Asp Glu Ile Leu Met Ser Arg Gly Gly Glu Lys Leu
145                 150                 155                 160

Glu Ser Val Ile Gly Arg Ser Glu Asp Asp Glu Leu Pro Val Phe Lys
                165                 170                 175

Asn Gly Ala Phe Gln Ile Lys Val Thr Asp Lys Leu Lys Ile Gly Lys
            180                 185                 190

Lys Leu Val Asp Glu Lys Ile Leu Asn Lys Tyr Leu Pro Glu Gly Ala
        195                 200                 205

Ile Ser Arg His Thr Met Arg Glu Leu Ile Asp Ser Ile Gln Leu Val
    210                 215                 220

Gly Ala Asp Glu Phe His Cys Ser Glu Trp Ile Glu Glu Pro Ser Leu
225                 230                 235                 240

Leu Ile Thr Arg Phe Glu Tyr Ala Asn Leu Phe His Thr Val Thr Asp
                245                 250                 255

Trp Tyr Ser Ala Tyr Val Ala Ser Arg Val Thr Gly Leu Pro Ser Arg
            260                 265                 270

Pro His Leu Val Phe Val Asp Gly His Cys Glu Thr Gln Leu Glu Glu
        275                 280                 285

Thr Trp Lys Ala Leu Phe Ser Ser Leu Thr Tyr Ala Lys Asn Phe Ser
    290                 295                 300

Gly Pro Val Cys Phe Arg His Ala Val Leu Ser Pro Leu Gly Tyr Glu
305                 310                 315                 320

Thr Ala Leu Phe Lys Gly Leu Thr Glu Thr Ile Asp Cys Asn Gly Ala
                325                 330                 335

Ser Ala His Asp Leu Trp Gln Asn Pro Asp Asp Lys Arg Thr Ala Arg
            340                 345                 350

Leu Ser Glu Phe Gly Glu Met Ile Arg Ala Ala Phe Gly Phe Pro Val
        355                 360                 365

Asp Arg Gln Asn Ile Pro Arg Thr Val Thr Gly Pro Asn Val Leu Phe
    370                 375                 380

Val Arg Arg Glu Asp Tyr Leu Ala His Pro Arg His Gly Gly Lys Val
385                 390                 395                 400

Gln Ser Arg Leu Ser Asn Glu Glu Gln Val Phe Asp Ser Ile Lys Ser
                405                 410                 415

Trp Ala Leu Asn His Ser Glu Cys Lys Leu Asn Val Ile Asn Gly Leu
            420                 425                 430

Phe Ala His Met Ser Met Lys Glu Gln Val Arg Ala Ile Gln Asp Ala
        435                 440                 445

Ser Val Ile Val Gly Ala His Gly Ala Gly Leu Thr His Ile Val Ser
    450                 455                 460

Ala Ala Pro Lys Ala Val Ile Leu Glu Ile Ser Ser Glu Tyr Arg
465                 470                 475                 480

Arg Pro His Phe Ala Leu Ile Ala Gln Trp Lys Gly Leu Glu Tyr His
                485                 490                 495

Pro Ile Tyr Leu Glu Gly Ser Tyr Ala Asp Pro Val Val Ile Asp
            500                 505                 510

Arg Leu Ser Ser Ile Leu Arg Ser Leu Gly Cys
        515                 520

<210> SEQ ID NO 41
<211> LENGTH: 443
```

```
<212> TYPE: PRT
<213> ORGANISM: Artificial Sequence
<220> FEATURE:
<223> OTHER INFORMATION: Consensus Sequence

<400> SEQUENCE: 41

Arg Leu Arg Lys Ile Leu Lys Ile Leu Leu Phe Ala Ile Asn Ser
 1               5                  10                  15

Val Ser Leu Ile Tyr Phe Leu His Ser Ser Pro Ser Lys Pro Trp
             20                  25                  30

Pro Ile Leu Pro Ser Tyr Leu Pro Trp Ser Ser Pro Ser Cys Glu
             35                  40                  45

Gly Tyr Phe Gly Asn Gly Phe Thr Arg Arg Val Asp Val Leu Lys Ala
             50                  55                  60

Gly Gly Gly Gly Trp Phe Arg Cys Phe Tyr Ser Glu Thr Leu Arg
 65                  70                  75                  80

Ser Ser Ile Cys Glu Gly Gly Arg Val Arg Met Asp Pro Asp Arg Ile
                 85                  90                  95

Met Ser Arg Gly Gly Glu Leu Glu Val Met Gly Arg Ala Glu Glu
                100                 105                 110

Glu Leu Pro Lys Phe Glu Gly Ala Phe Gln Val Glu Gly Ala Lys
            115                 120                 125

Gly Lys Arg Leu Val Asp Asp Gly Phe Leu Asn Tyr Val Pro Gly Gly
    130                 135                 140

Ile Arg His Thr Met Arg Asp Leu Ile Asp Ser Ile Arg Val Val Gly
145                 150                 155                 160

Pro Gly Glu Leu His Cys Ser Gln Trp Ile Glu Pro Thr Leu Leu
                165                 170                 175

Val Thr Arg Phe Glu Tyr Ala Asn Leu Phe His Thr Val Thr Asp Trp
                180                 185                 190

Tyr Ser Ala Tyr Val Ser Ser Arg Val Thr Gly Leu Pro Ser Arg Pro
            195                 200                 205

His Leu Val Phe Val Asp Gly His Cys Lys Ala Gln Leu Glu Glu Thr
    210                 215                 220

Trp Lys Ala Leu Phe Ser Ser Val Thr Tyr Ala Lys Asn Phe Ser Gly
225                 230                 235                 240

Pro Val Cys Phe Arg His Ala Ile Leu Ser Pro Leu Gly Tyr Glu Thr
                245                 250                 255

Ala Leu Phe Lys Gly Leu Ser Glu Ser Ile Ser Cys Glu Gly Ala Ser
            260                 265                 270

Ala Gln Leu Trp Gln Asn Pro Asp Asp Gln Lys Thr Ala Arg Leu Ser
    275                 280                 285

Glu Phe Gly Glu Met Ile Arg Ala Ala Phe Gly Leu Pro Val Asp Ile
290                 295                 300

Lys Lys Thr Ser Ser Gly Asn Val Leu Phe Val Arg Arg Glu Asp Tyr
305                 310                 315                 320

Leu Ala His Pro Arg His Ser Gly Lys Val Glu Ser Arg Leu Ser Asn
            325                 330                 335

Glu Glu Val Phe Asp Ser Leu Trp Ala Ala Gly Lys Cys Lys Ile Asn
                340                 345                 350

Val Val Asn Gly Leu Phe Ala His Met Ser Met Lys Glu Gln Leu Arg
            355                 360                 365

Ala Ile Gln Asp Ala Ser Val Ile Ile Gly Ala His Gly Ala Gly Leu
    370                 375                 380

Thr His Ile Val Ser Ala Thr Pro Thr Val Ile Leu Glu Ile Ile Ser
```

-continued

```
          385           390           395           400
Ser Tyr Arg Arg Pro His Phe Ala Leu Ile Ala Arg Trp Lys Gly Leu
                405                     410               415

Glu Tyr His Ala Ile Asn Leu Gly Ser Tyr Ala Asp Pro Asp Val Ile
            420                 425                 430

Glu Lys Leu Ser Ile Leu Lys Ser Leu Gly Cys
            435             440
```